US012692273B2

(12) United States Patent
Shokat et al.

(10) Patent No.: US 12,692,273 B2
(45) Date of Patent: Jul. 28, 2026

(54) p53 MODULATORS AND USES THEREOF

(71) Applicant: The Regents of the University of California, Oakland, CA (US)

(72) Inventors: Kevan Shokat, San Francisco, CA (US); Keelan Guiley, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1004 days.

(21) Appl. No.: 17/772,948

(22) PCT Filed: Oct. 29, 2020

(86) PCT No.: PCT/US2020/057934

§ 371 (c)(1),
(2) Date: Apr. 28, 2022

(87) PCT Pub. No.: WO2021/087096

PCT Pub. Date: May 6, 2021

(65) Prior Publication Data

US 2023/0145782 A1 May 11, 2023

Related U.S. Application Data

(60) Provisional application No. 62/929,489, filed on Nov. 1, 2019.

(51) Int. Cl.

| | |
|---|---|
| ***C07D 209/42*** | (2006.01) |
| ***A61K 45/06*** | (2006.01) |
| ***A61P 35/00*** | (2006.01) |
| ***A61P 35/02*** | (2006.01) |
| ***C07D 209/08*** | (2006.01) |
| ***C07D 209/12*** | (2006.01) |
| ***C07D 209/26*** | (2006.01) |
| ***C07D 209/86*** | (2006.01) |
| ***C07D 209/88*** | (2006.01) |
| ***C07D 401/14*** | (2006.01) |
| ***C07D 403/04*** | (2006.01) |
| ***C07D 403/14*** | (2006.01) |
| ***C07D 409/04*** | (2006.01) |
| ***C07D 413/14*** | (2006.01) |
| ***C07D 487/04*** | (2006.01) |
| ***C07D 495/14*** | (2006.01) |
| ***C07D 498/04*** | (2006.01) |
| ***C07J 43/00*** | (2006.01) |

(52) U.S. Cl.

CPC ......... *C07D 495/14* (2013.01); *C07D 209/42* (2013.01); *C07D 209/86* (2013.01); *C07D 209/88* (2013.01); *C07D 403/04* (2013.01); *C07D 413/14* (2013.01); *C07D 487/04* (2013.01); *C07D 498/04* (2013.01); *C07J 43/003* (2013.01)

(58) Field of Classification Search

None

See application file for complete search history.

(56) References Cited

U.S. PATENT DOCUMENTS

| | | | | |
|---|---|---|---|---|
| 11,666,661 | B2 * | 6/2023 | Nomura .................. | A61P 35/00 424/133.1 |
| 2002/0025991 | A1 | 2/2002 | Crivello | |
| 2005/0004104 | A1 | 1/2005 | Cali et al. | |
| 2005/0215548 | A1 | 9/2005 | Wang et al. | |
| 2016/0193214 | A1 * | 7/2016 | Amaro ................ | C07D 405/04 514/366 |
| 2018/0237454 | A1 | 8/2018 | Bradner et al. | |

FOREIGN PATENT DOCUMENTS

| | | | | |
|---|---|---|---|---|
| CN | 103 012 241 | A | 4/2013 | |
| CN | 108358894 | A * | 8/2018 | ........... C07D 401/14 |
| CN | 110 467 640 | A | 11/2019 | |
| EP | 1 990 335 | A1 | 11/2008 | |
| GB | 1 187 903 | A | 4/1970 | |
| WO | WO-2007/084625 | A2 | 7/2007 | |
| WO | WO-2007/084625 | A3 | 7/2007 | |
| WO | WO-2008/019357 | A2 | 2/2008 | |
| WO | WO-2008/019357 | A3 | 2/2008 | |
| WO | WO-2018/221679 | A1 | 12/2018 | |
| WO | WO-2019/075386 | A1 | 4/2019 | |
| WO | WO-2019/118851 | A1 | 6/2019 | |

OTHER PUBLICATIONS

STN (STN, CAS Registry No. 2499-65-2 Registry Entered STN: Nov. 16, 1984 (Year: 1984).*
CN_108358894_A_I_english translation (Year: 2018).*
Boeckler et al., Targeted rescue of a destabilized mutant of p53 by an in silico screened drug, PNAS, Jul. 29, 2008, vol. 105, No. 30, 10360-10365 (Year: 2008).*
Bauer et al., A structure-guided molecular chaperone approach for restoring the transcriptional activity of the p53 cancer mutant Y220C, Future Med. Chem. (2019) 11(19), 2491-2504 (Year: 2019).*
Adeniyi et al., Expert Opin. Drug Discov. (2016) 11(1):79-90 (Year: 2016).*
Basse, N. et al. (Jan. 29, 2010). "Toward the Rational Design of p53-Stabilizing Drugs: Probing the Surface of the Oncogenic Y220C Mutant," *Chem. Biol.* 17(1):46-56.

(Continued)

*Primary Examiner* — Kortney L. Klinkel
*Assistant Examiner* — Alison Azar Hasting
(74) *Attorney, Agent, or Firm* — Mintz, Levin, Cohn, Ferris, Glovsky and Popeo, P.C.

(57) ABSTRACT

Described herein, inter alia, are p53 modulator compounds and methods of using the same. In an aspect is provided a p53 protein covalently bonded to a compound described herein. In an aspect is provided a pharmaceutical composition including a compound described herein and a pharmaceutically acceptable excipient. In an aspect is provided a method of treating cancer in a subject in need of such treatment, including administering to the subject an effective amount of a compound described herein.

14 Claims, 47 Drawing Sheets

Specification includes a Sequence Listing.

(56) References Cited

OTHER PUBLICATIONS

Baud, M. G. J. et al. (May 25, 2018). "Aminobenzothiazole derivatives stabilize the thermolabile p53 cancer mutant Y220C and show anticancer activity in p53-Y220C cell lines," *Eur J Med Chem* 152:101-114.
Bauer, M. R. et al. (Aug. 19, 2016). "Harnessing Fluorine-Sulfur Contacts and Multipolar Interactions for the Design of p53 Mutant Y220C Rescue Drugs," *ACS Chem Biol* 11(8):2265-2274.
Bauer, M. R. et al. (Sep. 6, 2016, e-published Aug. 22, 2016). "2-Sulfonylpyrimidines: Mild alkylating agents with anticancer activity toward p53-compromised cells," *PNAS USA* 113(36):E5271-E5280.
Bauer, M. R. et al. (Oct. 2019). "A structure-guided molecular chaperone approach for restoring the transcriptional activity of the p53 cancer mutant Y220C," *Future Med. Chem.* 11(19):2491-2504.
Boeckler, F. M. et al. (Jul. 29, 2008). "Targeted rescue of a destabilized mutant of p53 by an in silico screened drug," *PNAS USA* 105(30):10360-10365.
Boettcher, S. et al. (Aug. 9, 2019). "A dominant-negative effect drives selection of TP53 missense mutations in myeloid malignancies," *Science* 365(6453):599-604.
Bullock, A. N. et al. (Mar. 2, 2000). "Quantitative analysis of residual folding and DNA binding in mutant p53 core domain: Definition of mutant states for rescue in cancer therapy," *Oncogene* 19(10):1245-1256.
Bykov, V. J. N. et al. (Mar. 2002). "Restoration of the tumor suppressor function to mutant p53 by a low-molecular-weight compound," *Nature Medicine* 8(3):282-288.
Chiarella, A. M. et al. (Jan. 2020). "Dose-dependent activation of gene expression is achieved using CRISPR and small molecules that recruit endogenous chromatin machinery," *Nat Biotechnol* 38(1):50-55.
Dong, L. et al. (Sep. 1, 2014). "Sulfur(VI) fluoride exchange (SuFEx): another good reaction for click chemistry," *Angew. Chem. Int. Ed. Engl.* 53(36):9430-9448.
Erwin, G. S. et al. (Dec. 22, 2017). "Synthetic transcription elongation factors license transcription across repressive chromatin," *Science* 358(6370):1617-1622.
Hammitzsch, A. (Aug. 25, 2015). "CBP30, a selective CBP/p300 bromodomain inhibitor, suppresses human Th17 responses," *PNAS* 112(34):10768-10773.
International Search Report mailed on Mar. 22, 2021 for PCT Application No. PCT/US2020/057934, filed Oct. 29, 2020, 6 pages.
Joerger, A. C. et al. (Oct. 10, 2006). "Structural basis for understanding oncogenic p53 mutations and designing rescue drugs," *PNAS USA* 103(41):15056-15061.
Kolb, H. C. et al. (Jun. 1, 2001). "Click Chemistry: Diverse Chemical Function from a Few Good Reactions," *Angew. Chem. Int. Ed.* 40(11):2004-2021.
Latif, A-L. et al. (Sep. 16, 2020). "BRD4-mediated repression of p53 is a target for combination therapy in AML," *bioRxiv* pp. 1-48.
Latif, A-L. et al. (Jan. 11, 2021). "BRD4-mediated repression of p53 is a target for combination therapy in AML," *Nat Commun* 12(1):241.
Van Goor, F. et al. (Nov. 15, 2011). "Correction of the F508del-CFTR protein processing defect in vitro by the investigational drug VX-809," *PNAS USA* 108(46):18843-18848.
Ventura, A. et al. (Feb. 8, 2007). "Restoration of p53 function leads to tumour regression in vivo," *Nature* 445(7128):661-665.
Wang, P. L. et al. (Apr. 26, 2001). "The 'wildtype' conformation of p53: epitope mapping using hybrid proteins," *Oncogene* 20(18):2318-2324.
Wilcken, R. et al. (Apr. 18, 2012). "Halogen-Enriched Fragment Libraries as Leads for Drug Rescue of Mutant p53," *J. Am. Chem. Soc.* 134(15):6810-6818.
Written Opinion mailed on Mar. 22, 2021 for PCT Application No. PCT/US2020/057934, filed Oct. 29, 2020, 5 pages.
Xue, W. et al. (Feb. 8, 2007). "Senescence and tumour clearance is triggered by p53 restoration in murine liver carcinomas," *Nature* 445(7128):656-660.
Bi, M.-X. et al. (Apr. 8, 2020). "Cascade trifluoromethylthiolation and cyclization of N-[(3-aryl)propioloyl]indoles," *Beilstein J Org Chem* 16:657-662.
Black, D.S. et al. (1993). "Nitrones and Oxaziridines. XLVI. Formation of Pyrrolo[3,2,1-ij]Quinolines by Intramolecular Nitrone Cycloaddition," *Aust J Chem* 46(6):843-862.
Extended European Search Report mailed on Feb. 26, 2024, for EP Patent Application No. EP20881246.1, 30 pages.
Huang, H. et al. (Feb. 16, 2018). "Sustainable Radical Cascades to Synthesize Difluoroalkylated Pyrrolo[1,2-a]indoles," *J Org Chem* 84(4):2425-2437.
Irwin, L.C. et al. (Sep. 21, 2017). "One-Pot Michael Addition/Radical Cyclization Reaction of N-Acryloyl Indoles," *Synlett* 28(20):2859-2864.
Liu, H.-M. et al. (Aug. 1, 2019). "Discovery and synthesis of novel indole derivatives-containing 3-methylenedihydrofuran-2(3H)-one as irreversible LSD1 inhibitors," *Eur J Med Chem* 175:357-372.
Wei, Y.-L. et al. (May 25, 2019). Synthesis of indolo[2,1-a]isoquinoline derivatives via visible-light-induced radical cascade cyclization reactions, *Chem Commun* 55(42):5922-5925.
Yamamoto, H. et al. (Jan. 1969). "1-Acylindoles. IX. Syntheses of 1-cinnamoyl-5-methoxy-2-methyl-3-indolylaliphatic acids as potential antiinflammatory agents," *J Med Chem* 12(1):176-178.
Yang, X. et al. (Sep. 10, 2019). "Palladium-Catalyzed Cascade Cyclization of Alkene-Tethered Aryl Halides with o-Bromobenzoic Acids: Access to Diverse Fused Indolo[2,1-a]isoquinolines," *Organic Letters* 21(18):7284-7288.
Zeng, F.-L. et al. (Nov. 19, 2019). "Metal-Free Visible-Light Promoted Radical Cyclization to Access Perfluoroalkyl-Substituted Benzimidazo[2, 1-a]isoquinolin-6(5H)-ones and Indolo[2, 1-a]isoquinolin-6(5H)-ones," *Adv Synth Catal* 361(22):5176-5181.
Gorre, R. et al. (Feb. 21, 2020). "Visible-light-driven metal-free aerobic synthesis of highly diastereoselective phosphinoylpyrroloindoles," *Org Biomol Chem* 18(7):1354-1358.
Popescu, M.V. et al. (Dec. 14, 2020). "Visible-Light-Mediated Heterocycle Functionalization via Geometrically Interrupted [2+2] Cycloaddition," *Angew Chem Int Ed* 59(51):23020-23024.

* cited by examiner

Donehower, et. al., *Nature Reviews*, 2009

Bernard X., et. al., *PLosONE*, 2011

KG1

KG2

KG3_76

| | % Labeled | | | | |
|---|---|---|---|---|---|
| 1a  | 97% | 2a  | 79% | 3a  | 61% |
| 1b  | 94% | 2b  | 90% | 3b  | 96% |
| 1c  | 72% | 2c  | 68% | 3c  | 89% |

KG1

KG78 p53 MODULATORS AND USES THEREOF

CROSS-REFERENCES TO RELATED APPLICATIONS

This application is the national stage filing under 35 U.S.C. § 371 of International Application No. PCT/US2020/057934 filed Oct. 29, 2020, which claims the benefit of U.S. Provisional Application No. 62/929,489, filed Nov. 1, 2019, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048536-669N01US Sequence Listing ST25.TXT, created Apr. 25, 2022, 47, 367 bytes, machine format IBM-PC, MS Windows operating system, is hereby incorporated by reference.

BACKGROUND

Cancer is a genetic disease caused broadly by mutations in two classes of genes called oncogenes and tumor suppressors. Using the car as an analogy, an oncogene is the gas pedal and a tumor suppressor is the brake of the car. Most tumor cells have an activating mutation in an oncogene to push harder on the gas pedal and an in-activating mutation in a tumor suppressor to "take the brakes off" cell growth. In the last 20 years we have seen an explosion in the numbers of drugs to block the proteins which serve as the accelerators, but we have not figured out how to re-engage our cell's own brakes on cancer after mutations have inactivated them. In 2018 an estimated 1.7 million patients in the US will be diagnosed with cancer, of these roughly 1.5% will have the p53(Y220C) mutation, or >25,000 patients per year. Disclosed herein, inter alia, are solutions to these and other problems in the art.

BRIEF SUMMARY

In an aspect is provided a compound, or a pharmaceutically acceptable salt thereof, having the formula:

(I)

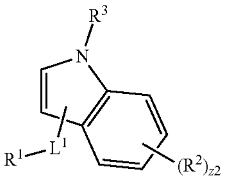

or (II)

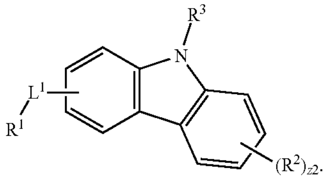

$L^1$ is a bond or covalent linker. $R^1$ is a transcriptional coactivator binding moiety. $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $-L^2-R^{23}$; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl. $X^2$ is independently $-F$, $-Cl$, $-Br$, or $-I$. The symbol n2 is independently an integer from 0 to 4. The symbols m2 and v2 are independently 1 or 2. The symbol z2 is an integer from 0 to 7. $L^2$ is independently a bond or covalent linker. $R^{23}$ is independently a detectable moiety. $R^3$ is a covalent cysteine modifier moiety.

In embodiments, the compound, or a pharmaceutically acceptable salt thereof, has the formula:

(I)

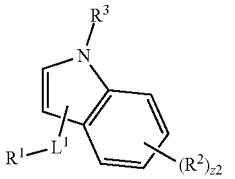

or (II)

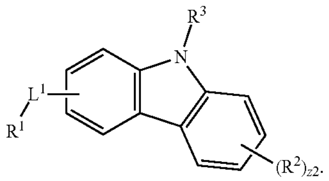

$L^1$ is a bond or covalent linker. $R^1$ is a transcriptional coactivator binding moiety. In embodiments, $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl. $X^2$ is independently —F, —Cl, —Br, or —I. The symbol n2 is independently an integer from 0 to 4. The symbols m2 and v2 are independently 1 or 2. The symbol z2 is an integer from 0 to 7. $R^3$ is a covalent cysteine modifier moiety.

In an aspect is provided a compound having the formula:

(III)

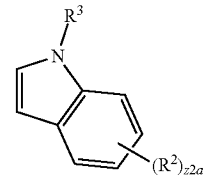

or (IV)

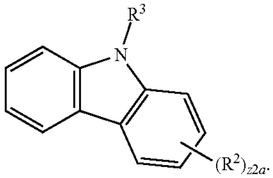

$R^2$ and $R^3$ are as described herein, including in embodiments. The symbol z2a is an integer from 0 to 8.

In an aspect is provided a p53 protein covalently bonded to a compound described herein.

In an aspect is provided a pharmaceutical composition including a compound described herein and a pharmaceutically acceptable excipient.

In an aspect is provided a method of treating cancer in a subject in need of such treatment, including administering to the subject an effective amount of a compound described herein.

In an aspect is provided a method of increasing the level of a protein in a cell, wherein the level of the protein is regulated by p53, the method including contacting the cell with a compound described herein.

BRIEF DESCRIPTION OF THE DRAWINGS

FIG. 1A: Structural representation of p53 DNA-binding domain (DBD) hotspot mutations (PDB 1TUP). FIG. 1B: The frequency of top p53 hotspot mutations in all tumor samples of The Cancer Genome Atlas (TCGA) (1).

FIG. 2A: WT p53 (PDB: 1TUP) positions Y220 between two proline rich loops. FIG. 2B: The p53 mutation Y220C creates a gap between the loops destabilizing the protein fold. KG1 covalently labels the mutagenic cysteine filling this crevice in the mutant with a carbazole scaffold and stabilizes the fold (this is an unpublished crystal structure).

FIG. 3A: Mass spectrum of the covalent adduct between p53 (Y220C) and KG1. FIG. 3B: Differential scanning fluorimetry (DSF) spectrum of p53 WT DBD, Y220C, Y220C-KG1, Y220C-KG37, and Y220C-KG78. The mutation Y220C reduces the Tm of p53 from 41.5° C. to 33.0° C. The addition of KG1 to p53 (Y220C) increases the Tm from 33.0° C. to 34.5° C. showing partial stabilization. FIG. 3C: The carbazole is synthesized with either the R1 groups or the R2 groups indicated. FIG. 3D: Western blot for MCF10A (WT), BxPC-3 (Y220C), or Calu-1 (null) cells treated with DMSO, nutlin-3a, or KG2.

FIG. 4A: Structure of bivalent KG1-JQ1 molecule (JQ1PEG6KG1). FIG. 4B: The p53 mutant Y220C is partially stabilized when bound to KG1 and elicits full transcriptional activation when bound to KG1-JQ1. FIG. 4C: Western blot analysis of p21 induction by p53 in BxPC-3 (Y220C) cells treated with DMSO, JQ1, KG1, JQ1PEG6KG1 or JQ1PEG4KG1 for 24 hours. Arrow on the p53 blot shows migration position of p53 suggestive of target engagement (gel shift to higher MW).

```
Human:
                                          (SEQ ID NO: 1)
RQNPCGSKACRRLFGPVDSEQLSRDCDALMAGCIQEARERWNFDFVTET
PLEG-DFAWERVRGLGLPKLYLPTGPRR;

Mouse:
                                          (SEQ ID NO: 2)
RPVPHRSKVCRCLFGPVDSEQLRRDCDALMAGCLQEARERWNFDFVTET
PLEG-NFVWERVRSLGLPKVYLSPGSR;

Chicken:
                                          (SEQ ID NO: 3)
GPMPCSSKACRNLFGPVDHEQIQNDFEQLLRQQLEEAQRRWNFNFETET
PLEG-HFKWERVLLAEQPPWEAFSLA;

Frog:
                                          (SEQ ID NO: 4)
QASGNKEKSCRMLFGPVDHEQLRADFDEFMQKSNEEAKAKWNFGFATET
PLEG-QYDWVKVENNTLNGS;

Zebrafish:
                                          (SEQ ID NO: 5)
LRSLGNGPTRRSLFGPVDREQLQREYRAALRRDLEDASRRWSFDFASEK
PLEGGDFHWEGVSGVRVPLLYRACQEKQ.
```

Figure 8:
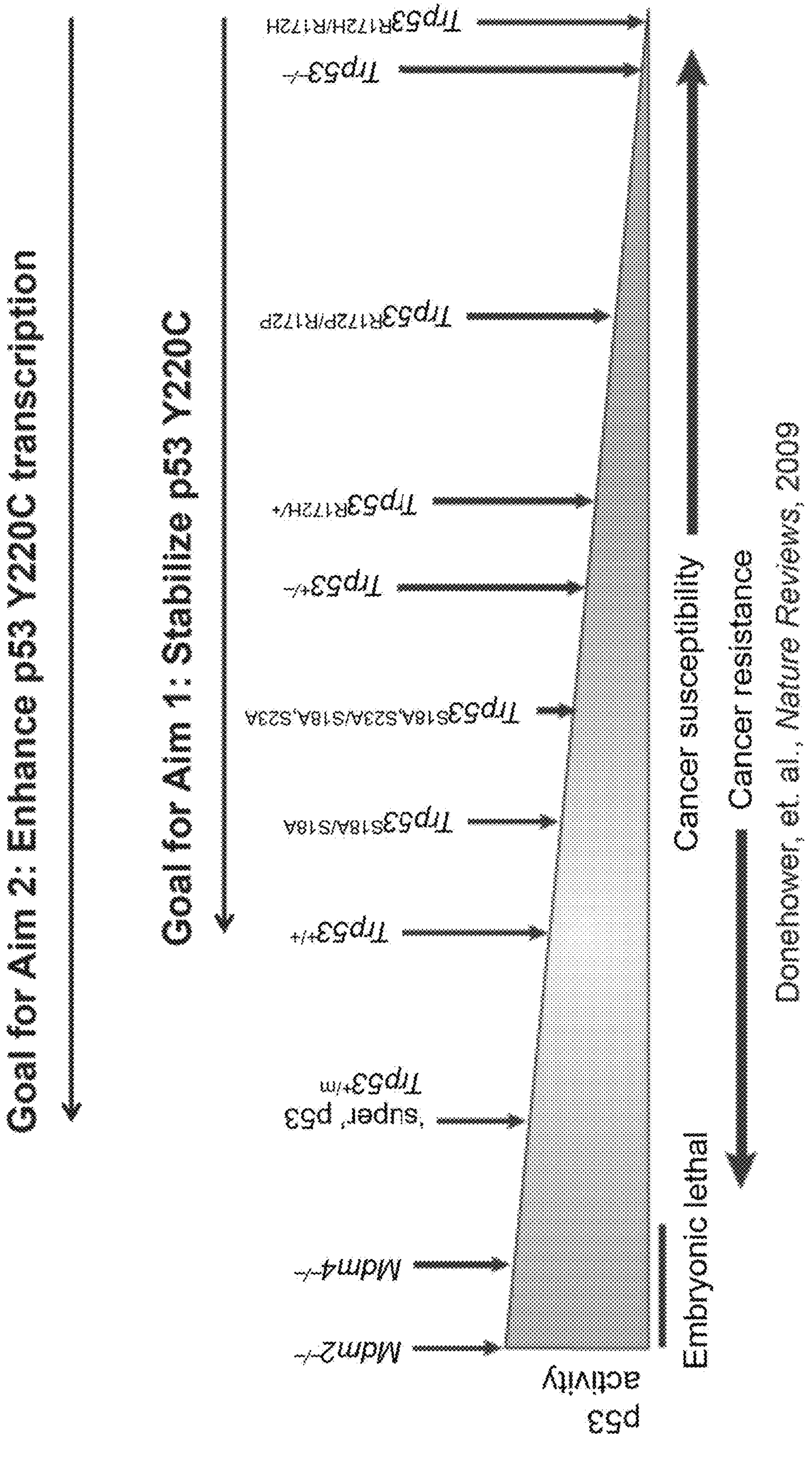

FIG. 8. Mouse models for p53.

Figure 9:
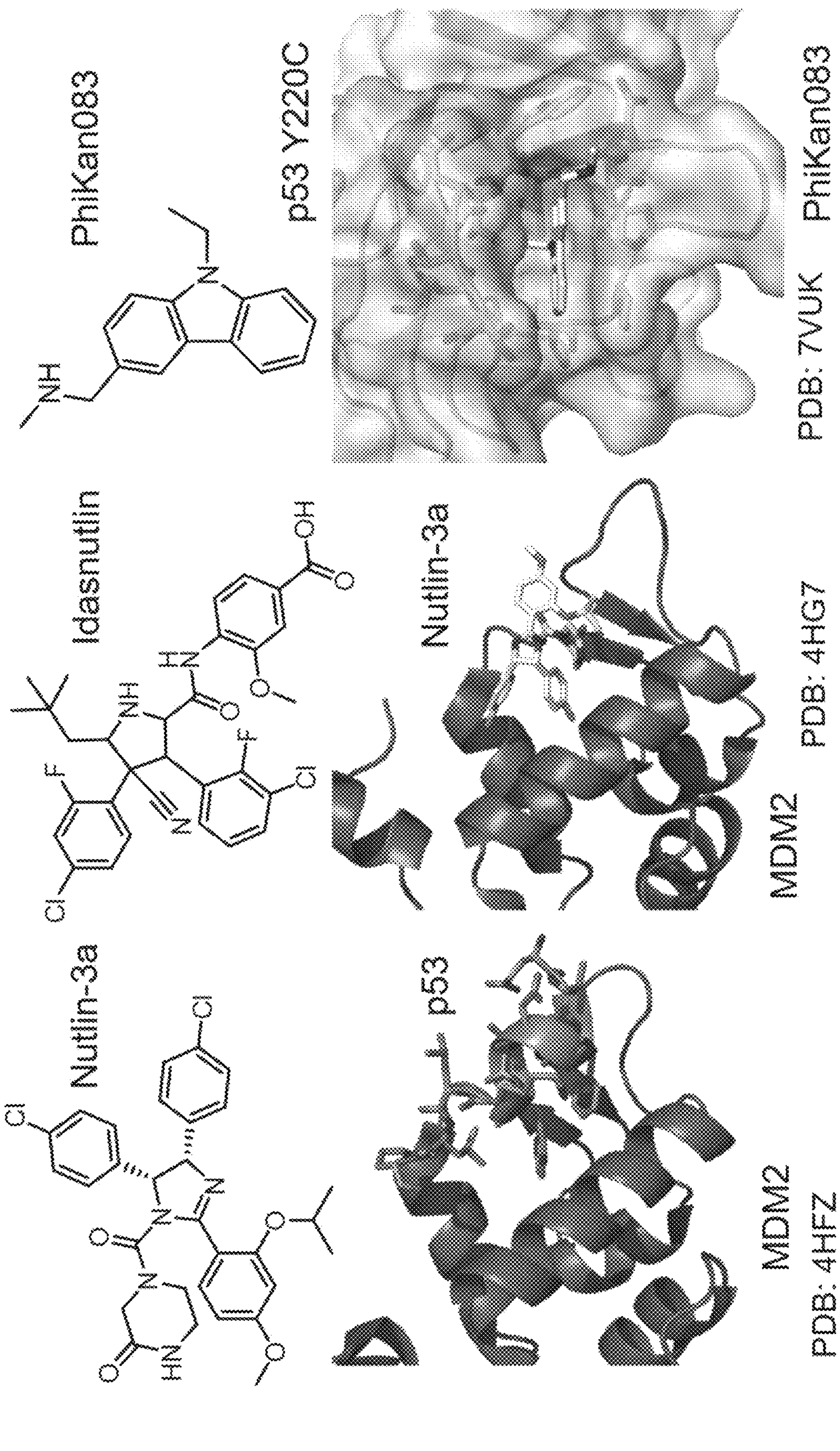

FIG. 9. Nutlin and Phikan083 as promising therapeutic strategies.

Figure 10:
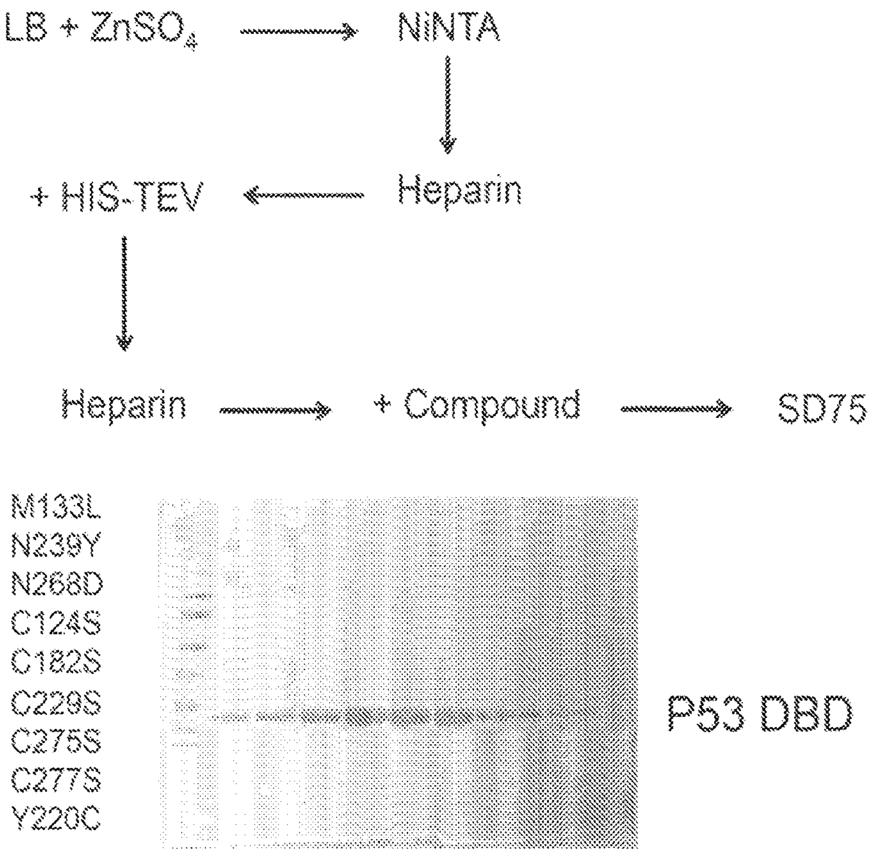

FIG. 10. Purification of "cys light" p53 Y220C DBD.

Figure 11:
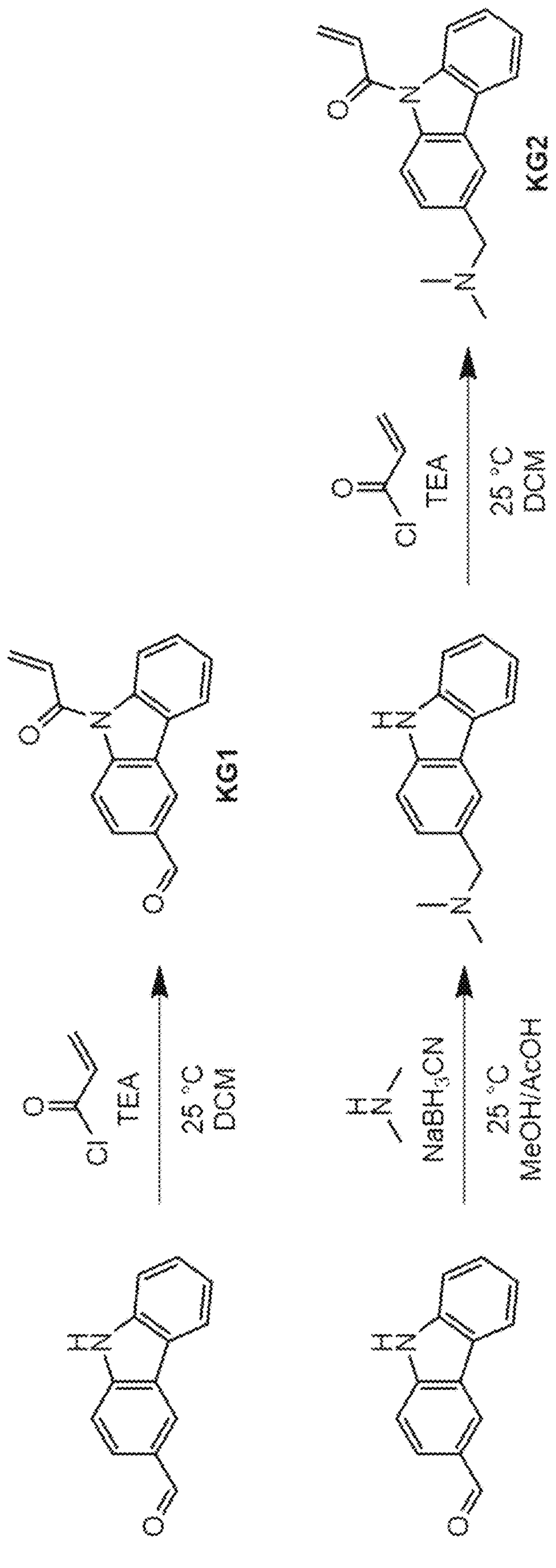
Figure 11:
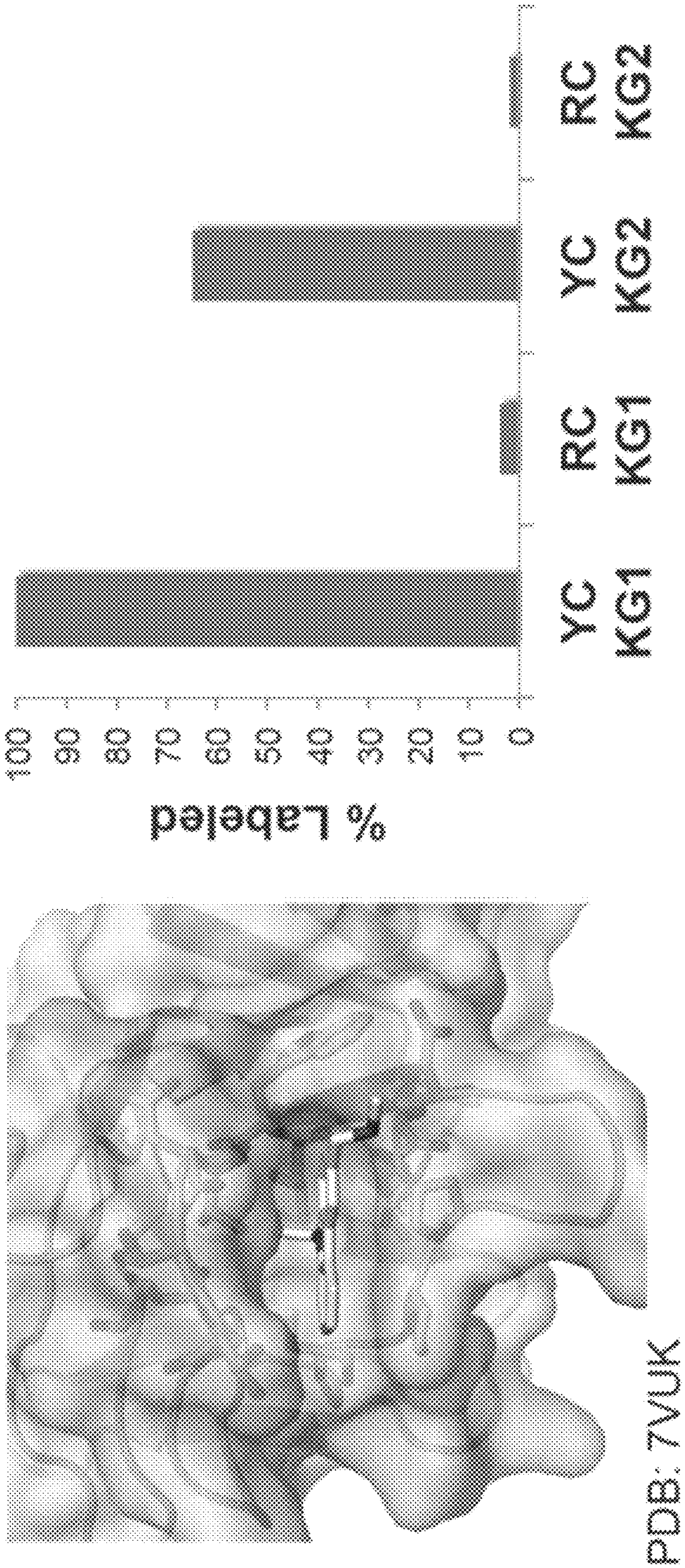

FIG. 11. Generating a covalent probe.

Figure 12:
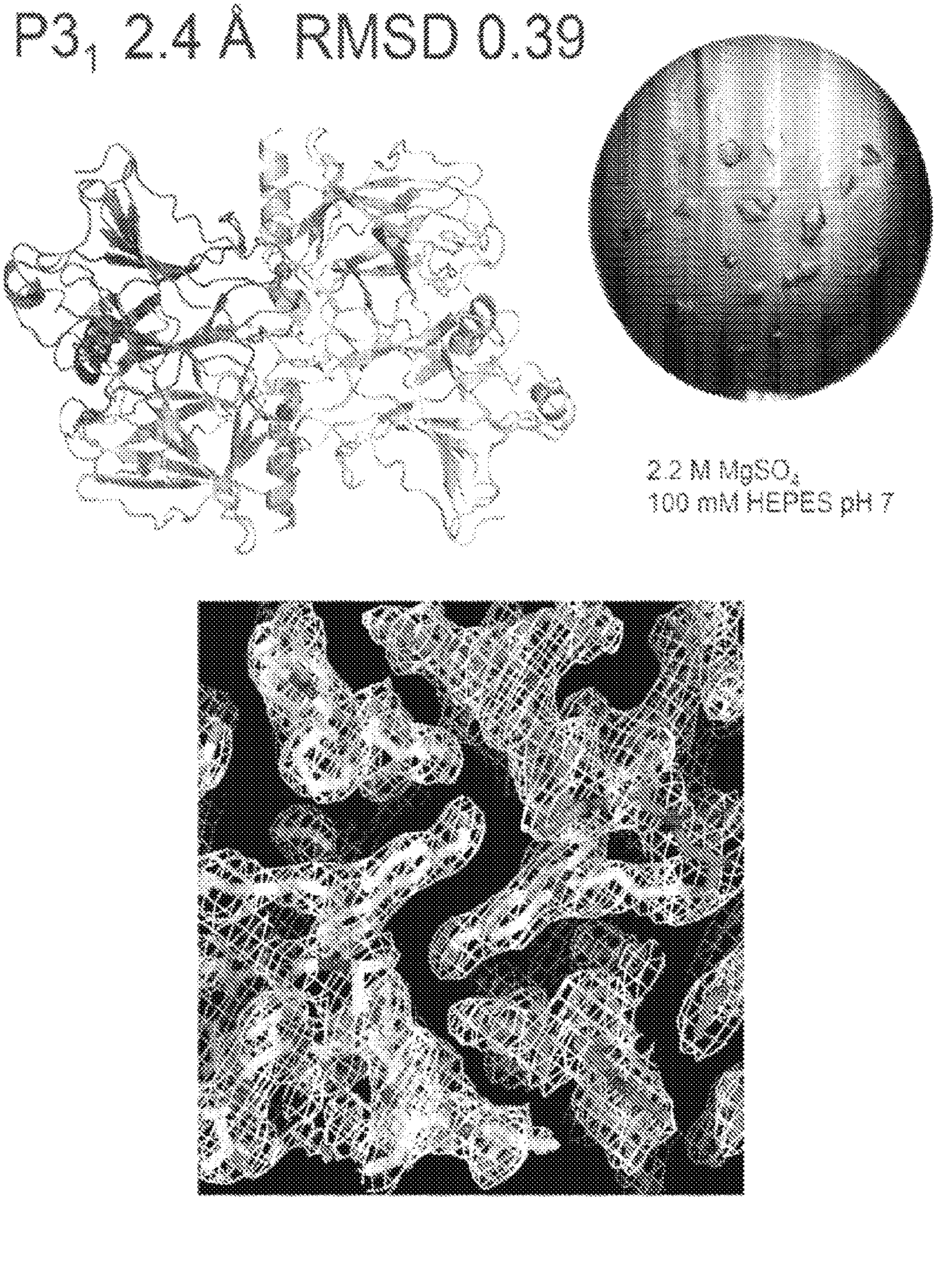

FIG. 12. KG1 crystals are pyramidal and perfectly twinned. Compound density is well-defined and demonstrates a covalent adduct.

Figure 13:
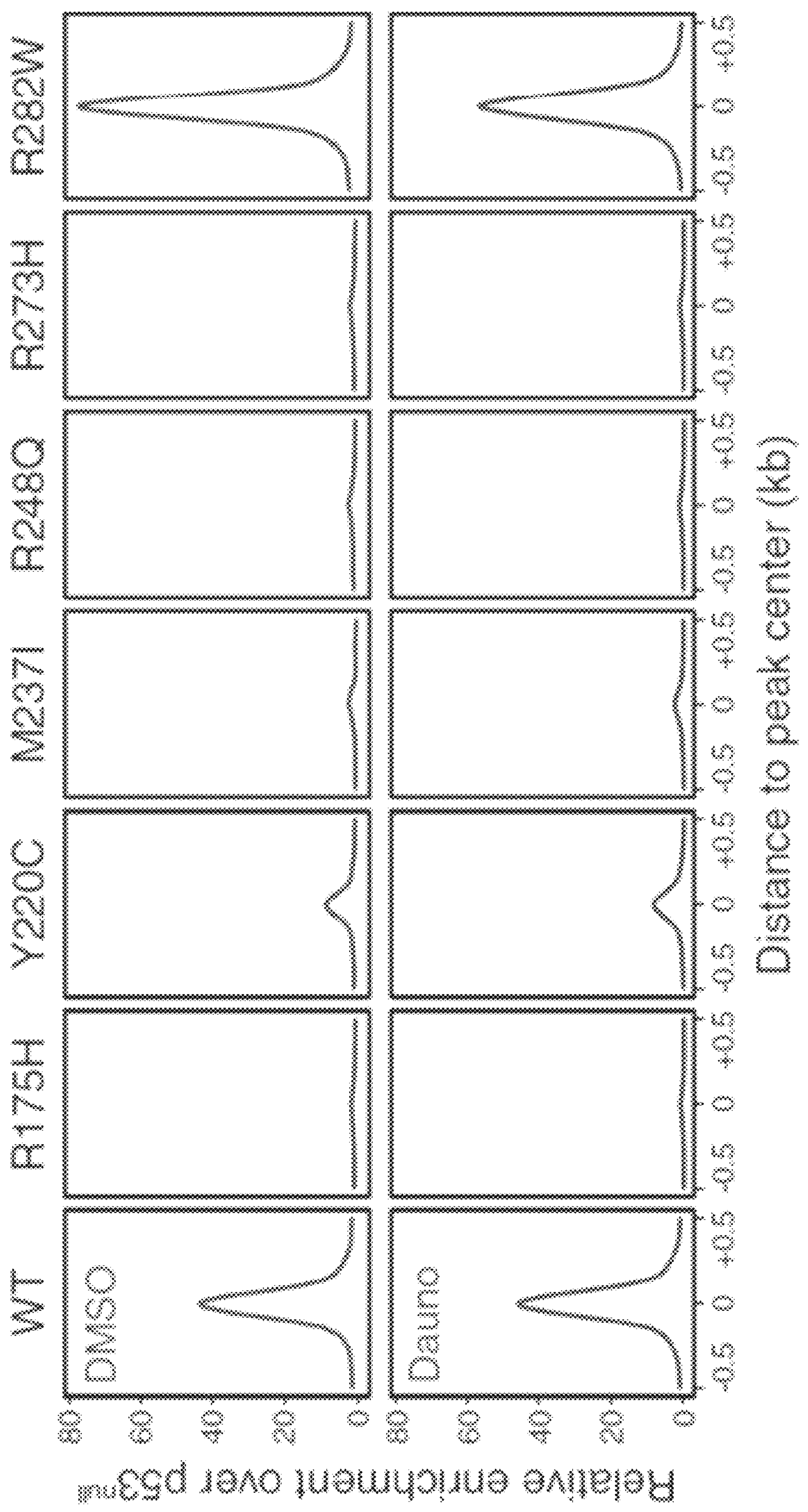
Figure 13:
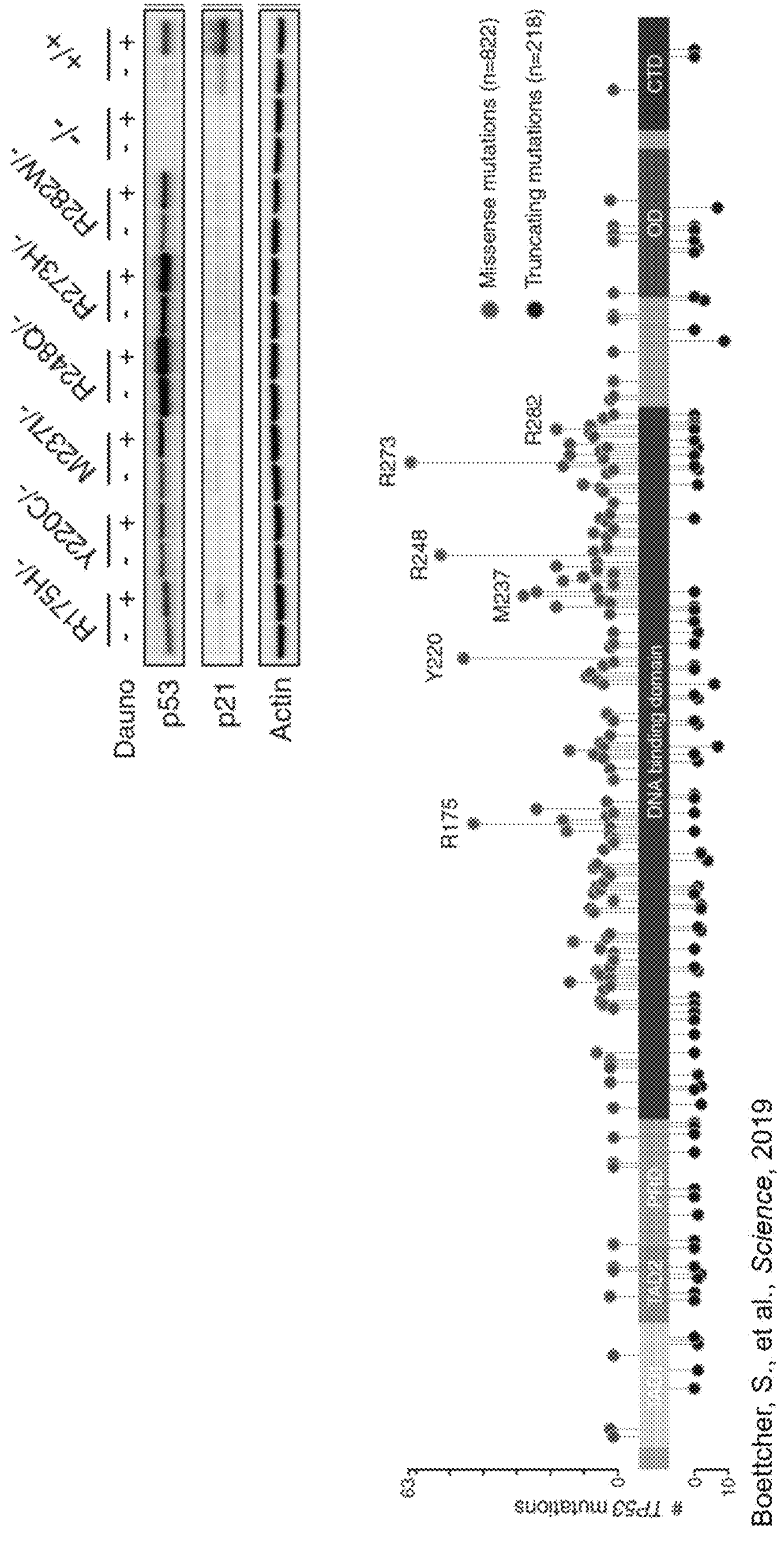

FIG. 13. Y220C still binds to DNA but does not activate p21.

Figure 14:
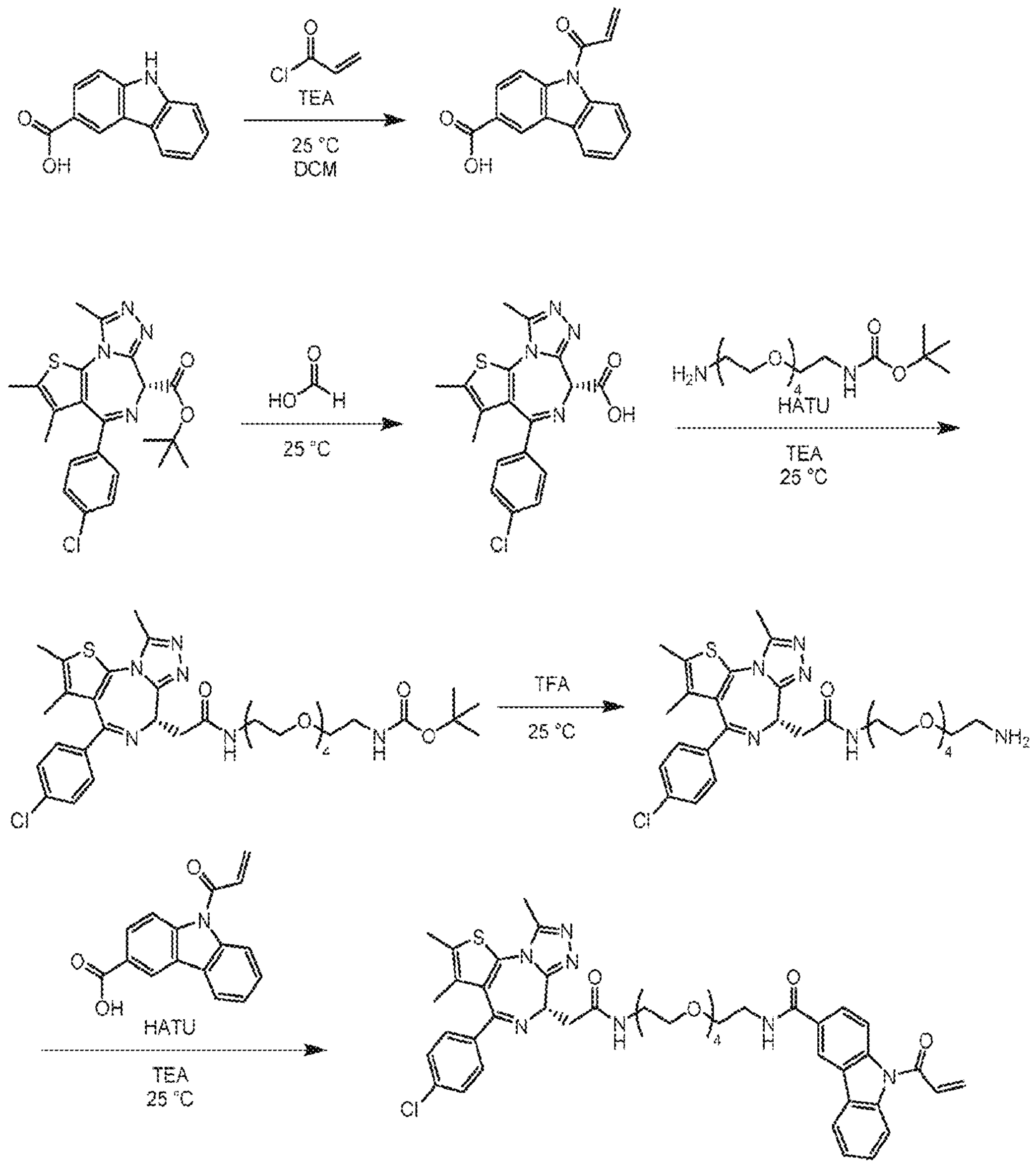

FIG. 14. Synthesis of KG1-PEG4/6-JQ1.

Figure 15:
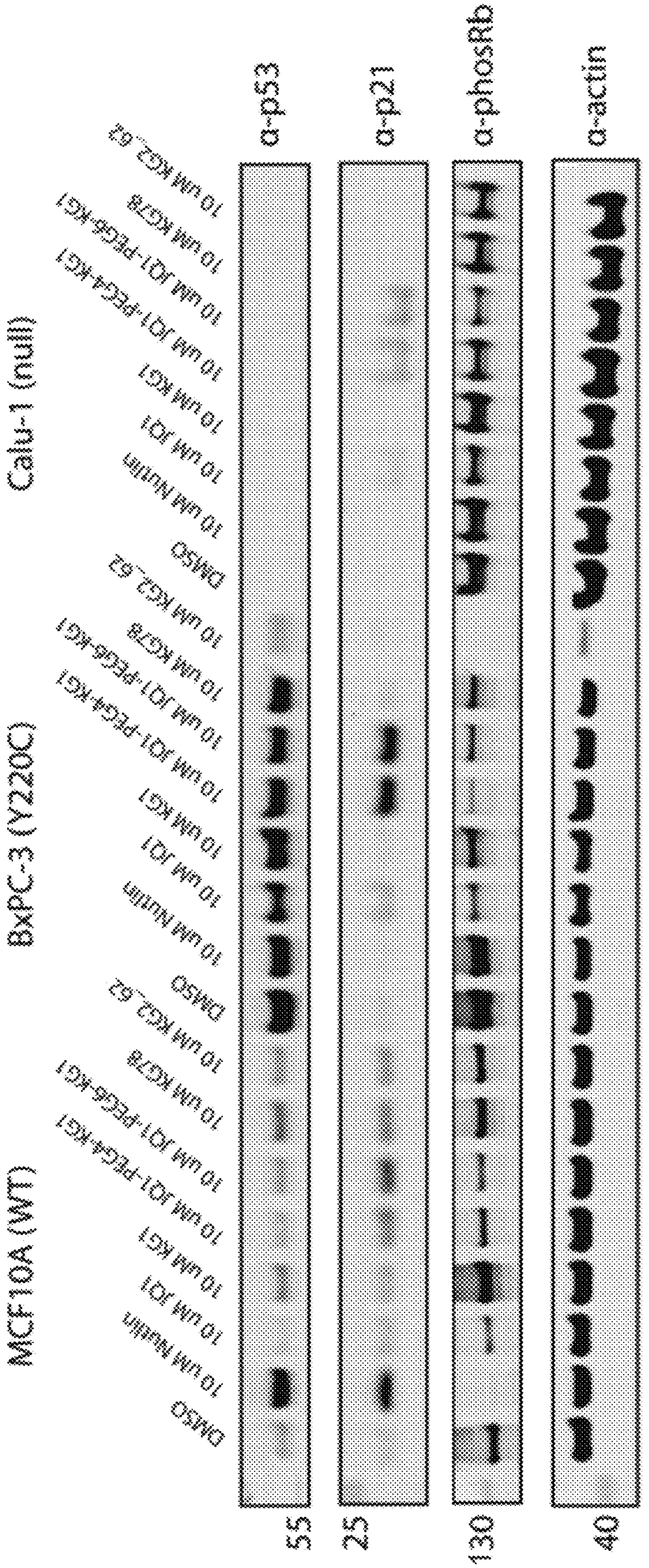

FIG. 15. KG1-PEG4-JQ1 shows selectivity in Y220C cells.

Figure 16:
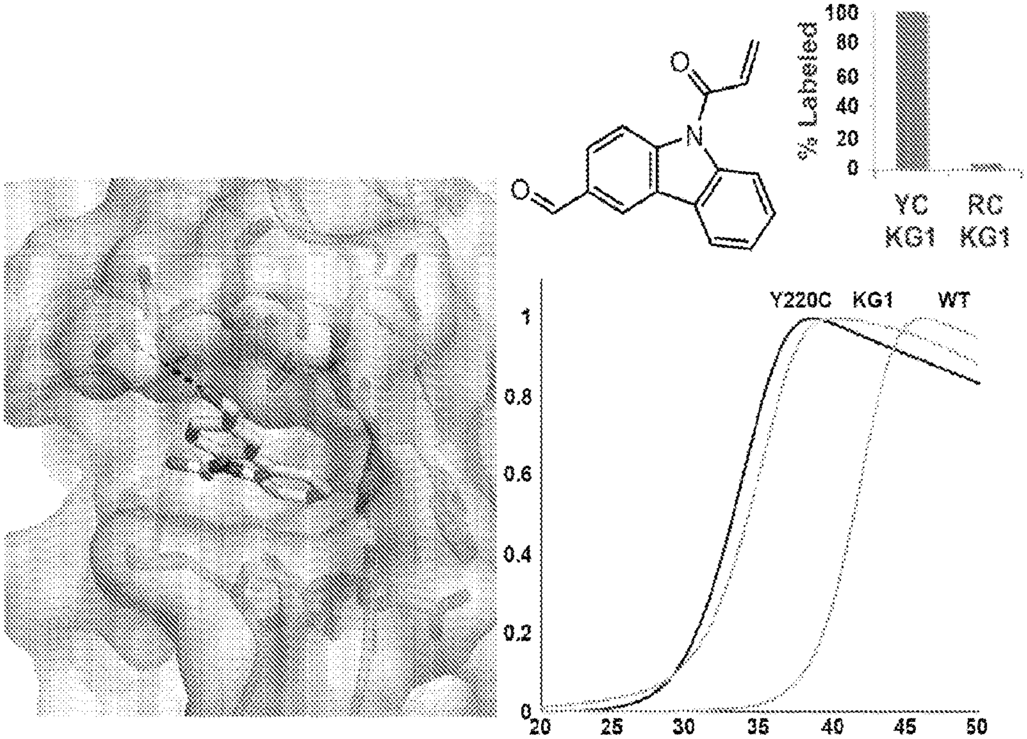

FIG. 16. KG1 partially stabilizes Y220C 1.5° C.

Figure 17:
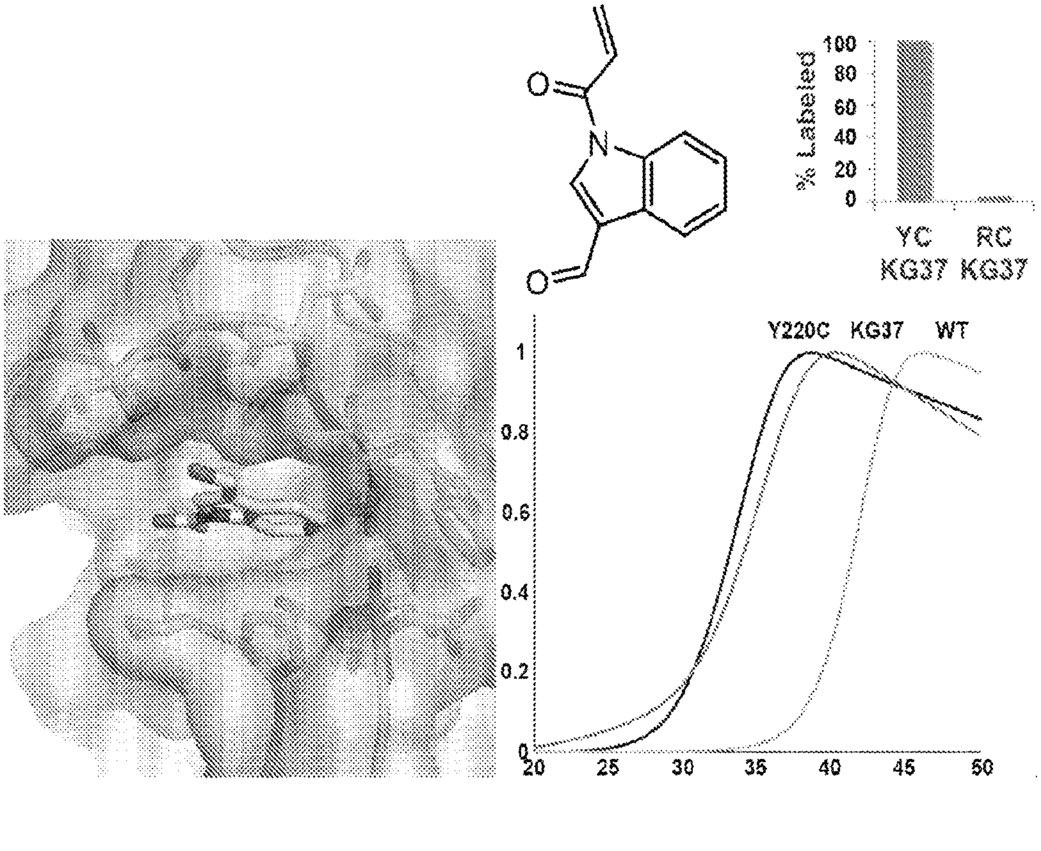

FIG. 17. Indole stabilizes Y220C similar to carbazole.

Figure 18:
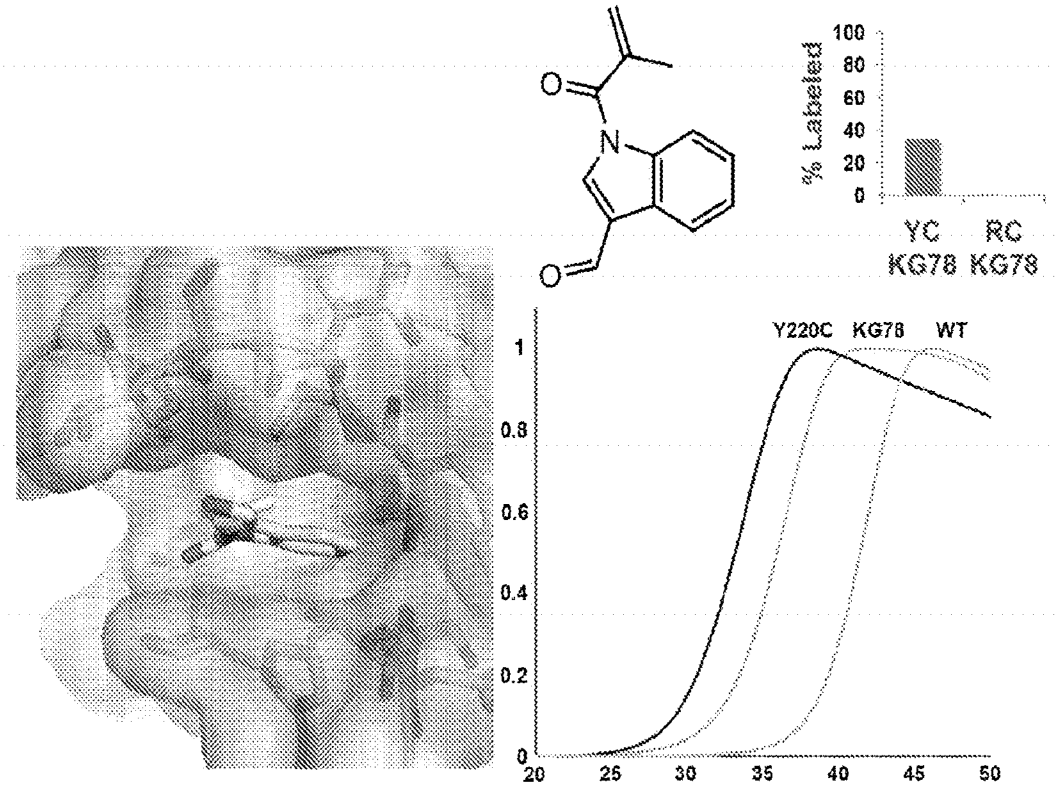

FIG. 18. Methacrylamide indole stabilizes Y220C 3° C.

Figure 19:
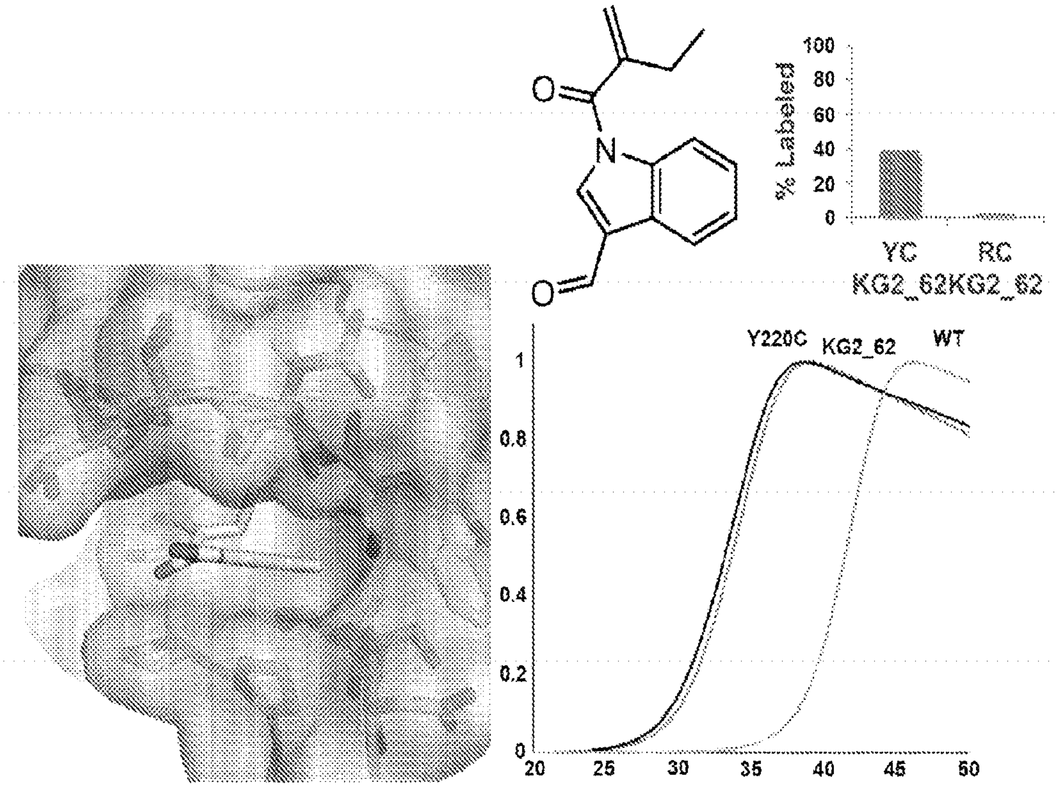

FIG. 19. 2-Ethylacrylamide did not stabilize Y220C in the assay tested.

Figure 20:
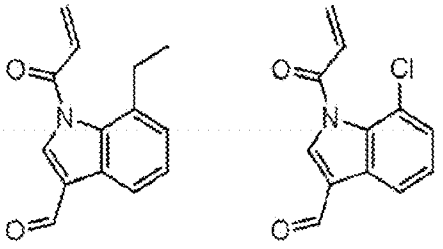

FIG. 20. Compounds that did not sufficiently label Y220C for differential scanning fluorimetry (DSF) in the assay tested.

Figure 21:
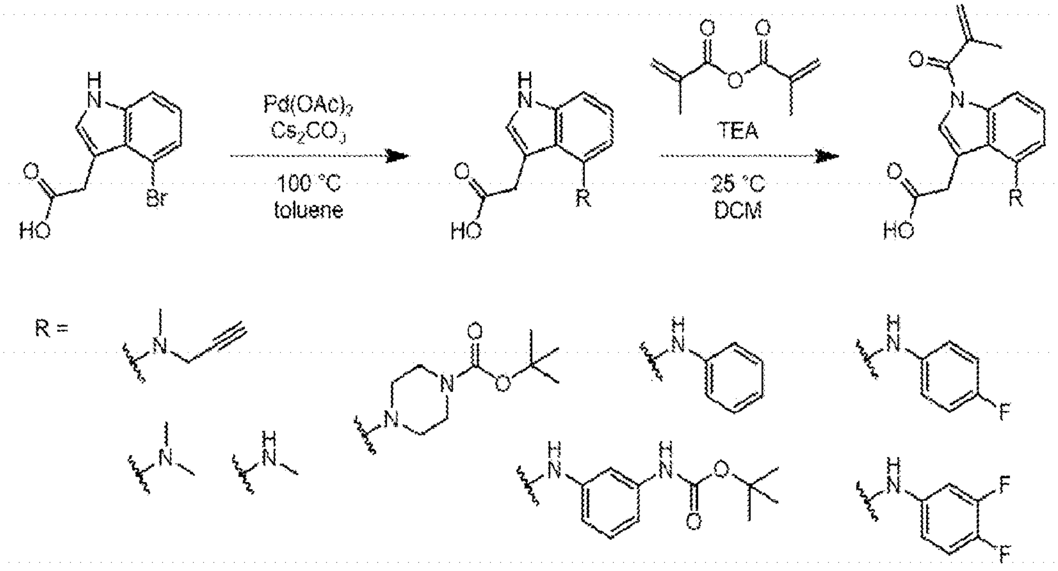
Figure 21:
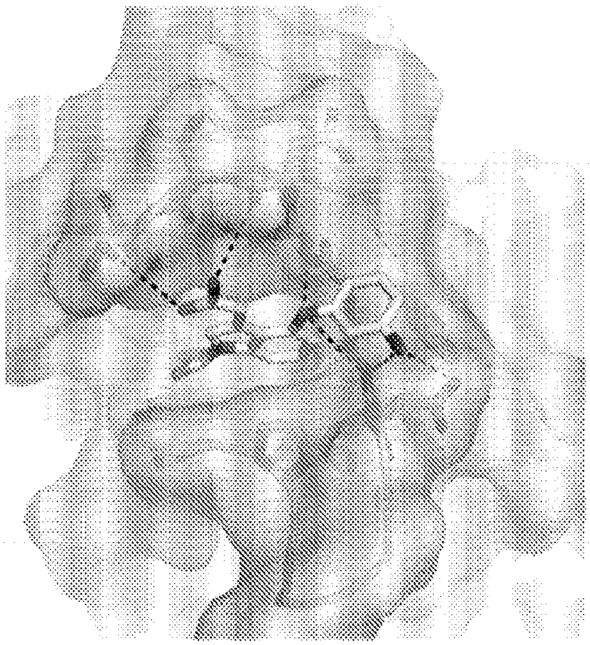

FIG. 21. KG78 optimization.

Figure 22:
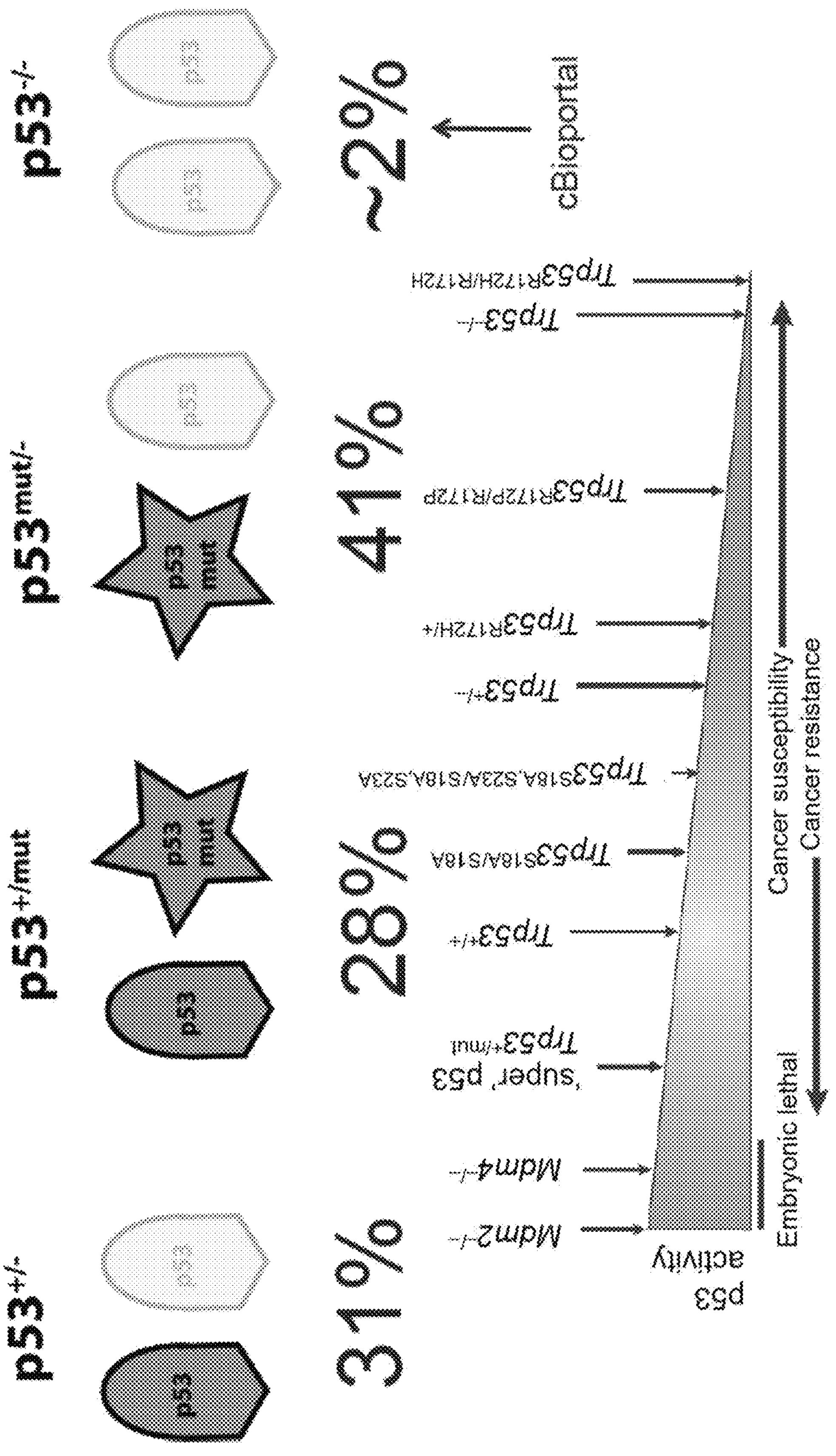

FIG. 22. ~50% of cancers have altered p53. Boettcher, S., et al., *Nature* 2016; Donehower, L., et al., *Nature Rev.,* 2009.

Figure 23:
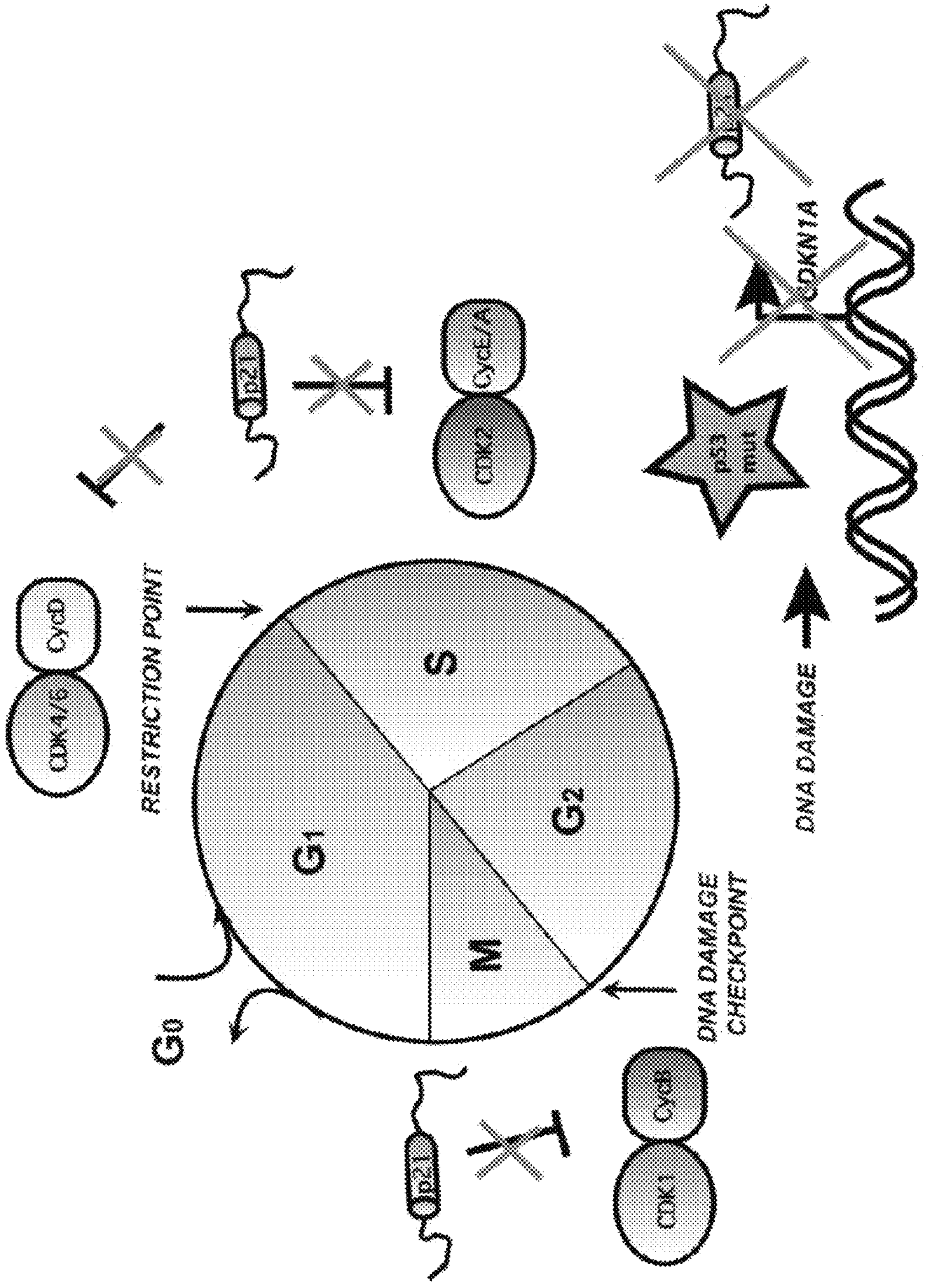

FIG. 23. Mutant p53 results in loss of CDK/cell cycle regulation. Sherr, C., *Cell,* 2004.

Figure 24:
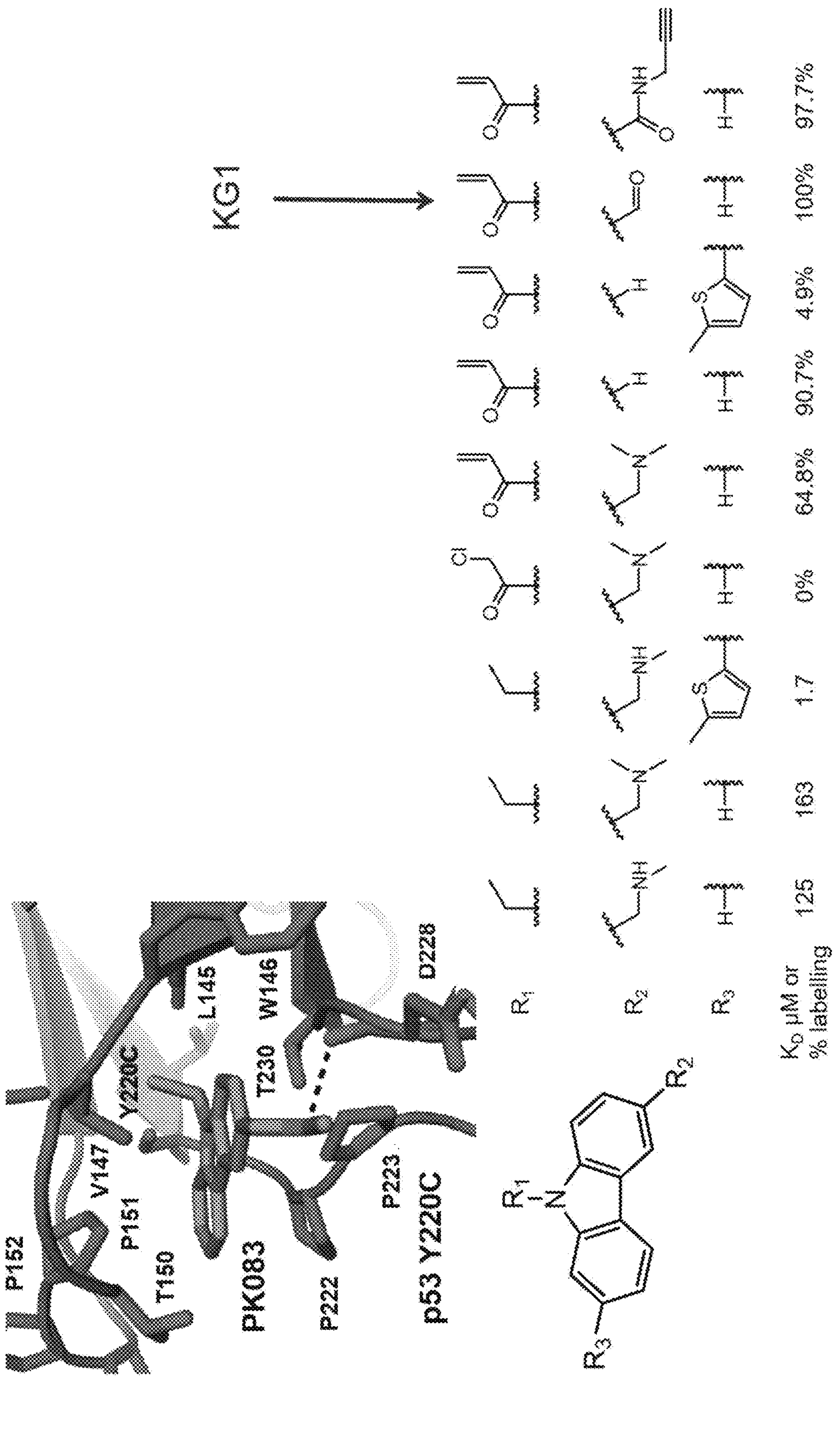

FIG. 24. Labelling studies suggest covalent carbazoles have alternative binding mode to PhiKan series.

Figure 25:
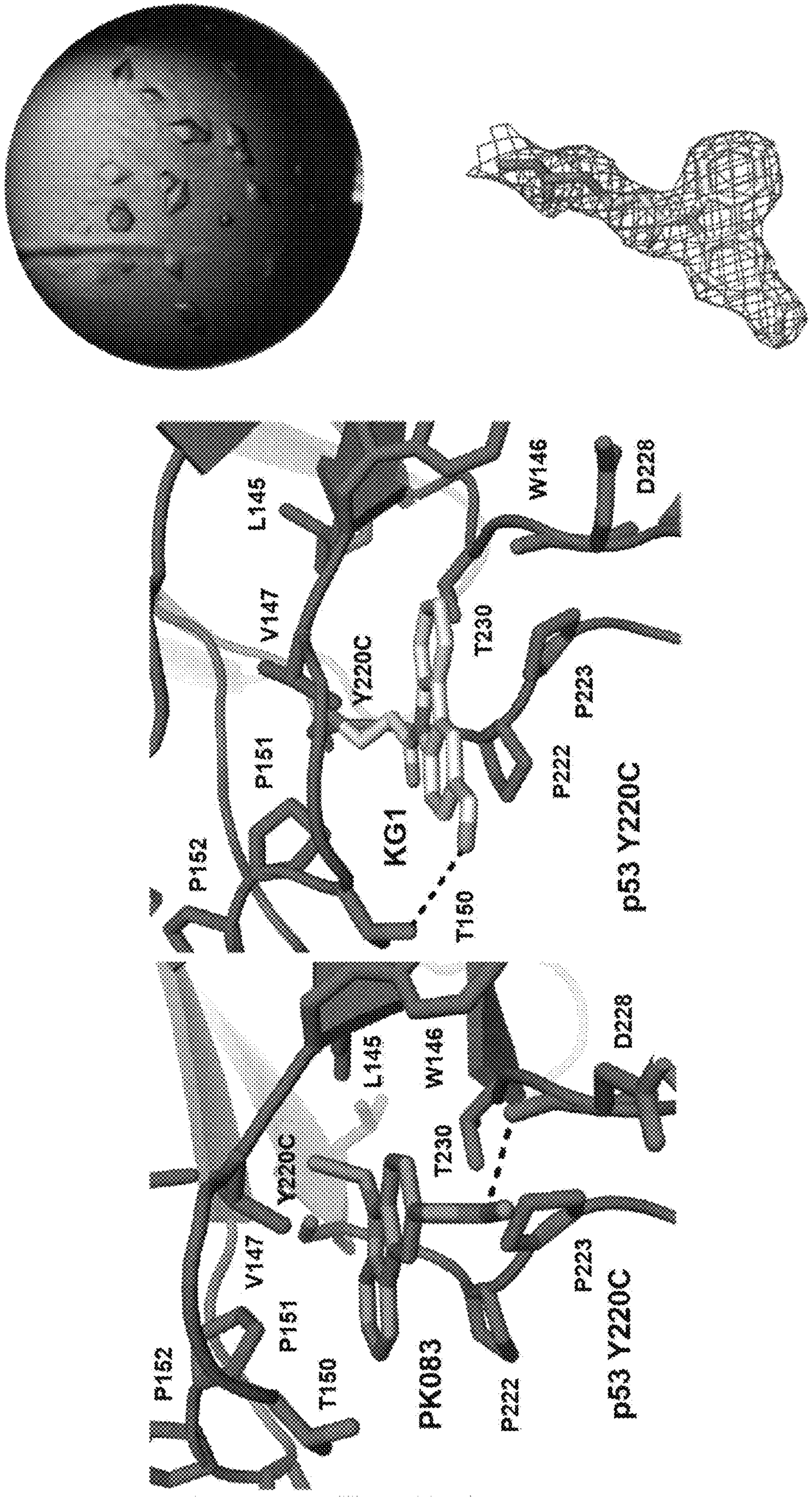

FIG. 25. KG1 crystal structure reveals alternate binding mode.

Figure 26:
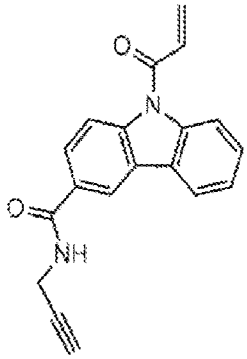
Figure 26:
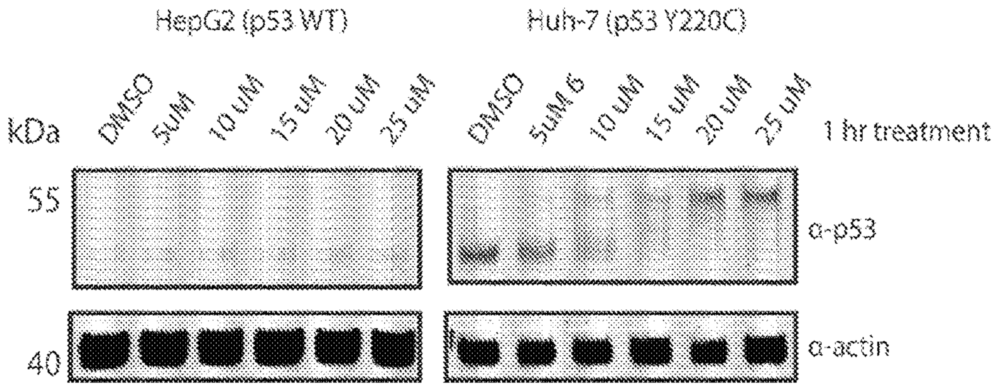

FIG. 26. Covalent carbazole engages p53 Y220C between 5-25 μM in 1 hour.

Figure 27:
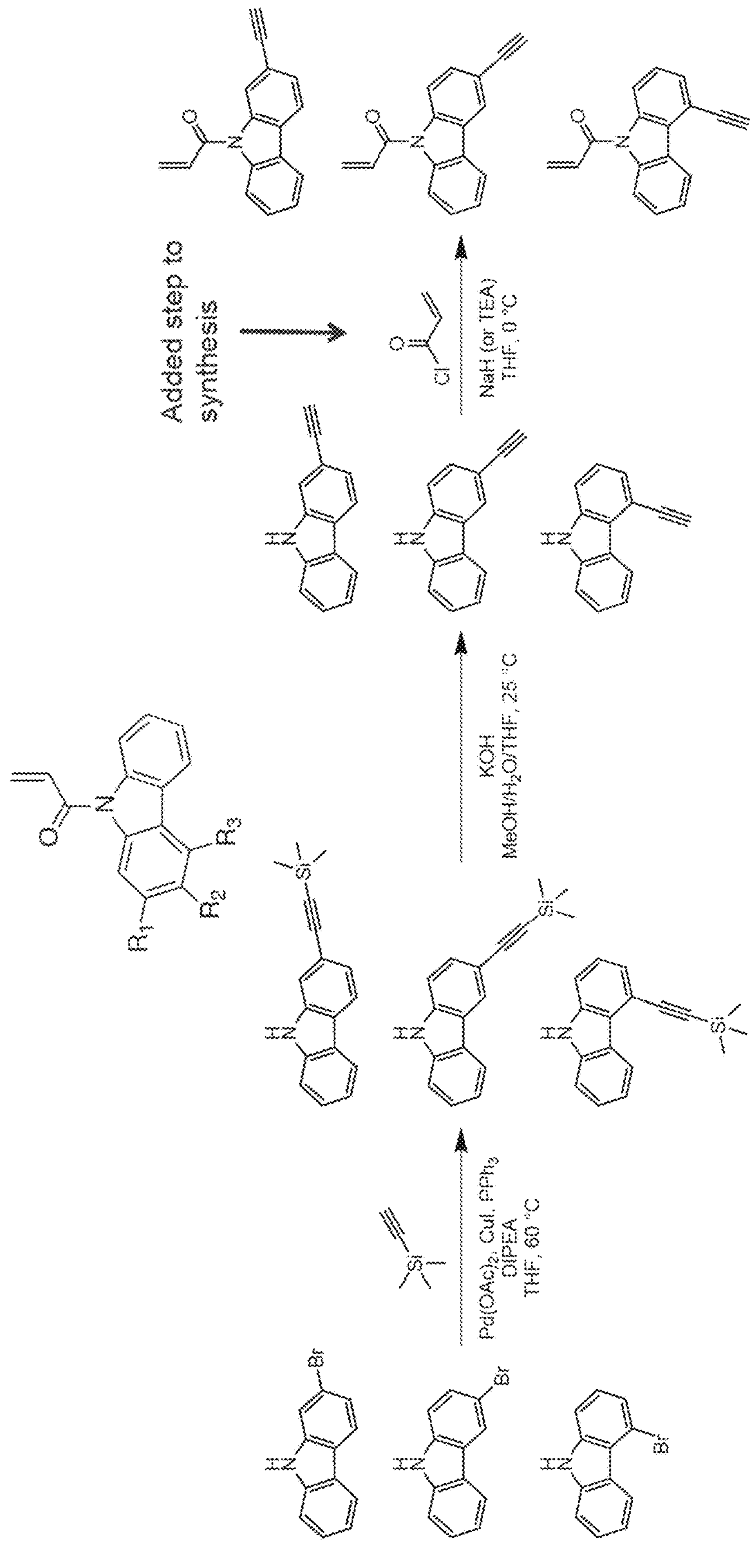

FIG. 27. Alkyne compounds designed to diversify and improve covalent carbazole. Reference: Al-Balushi, R., *Inorganic Chemistry,* 2004.

Figure 28:
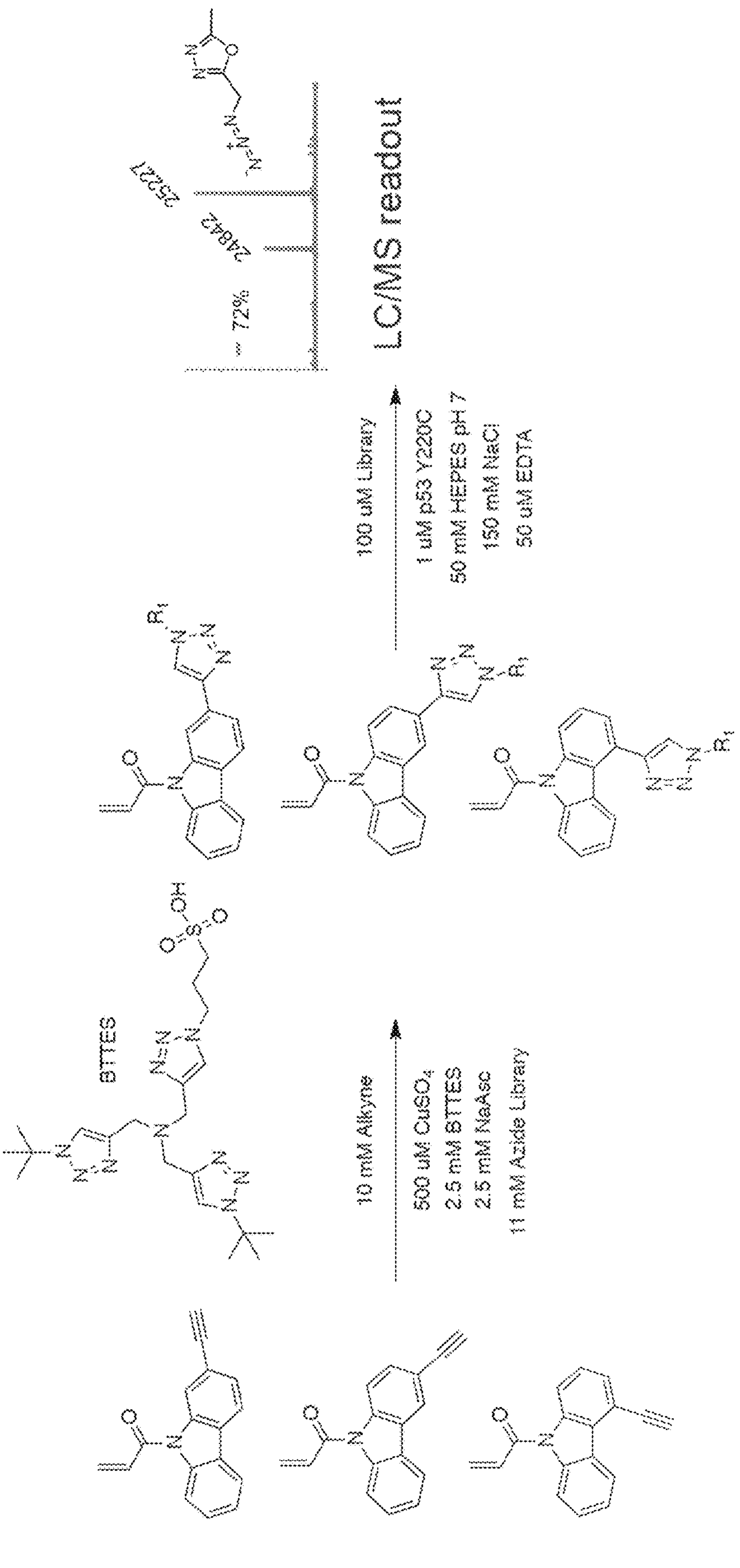

FIG. 28. High-throughput 96-well copper click chemistry library improves carbazole labelling.

Figure 29A:
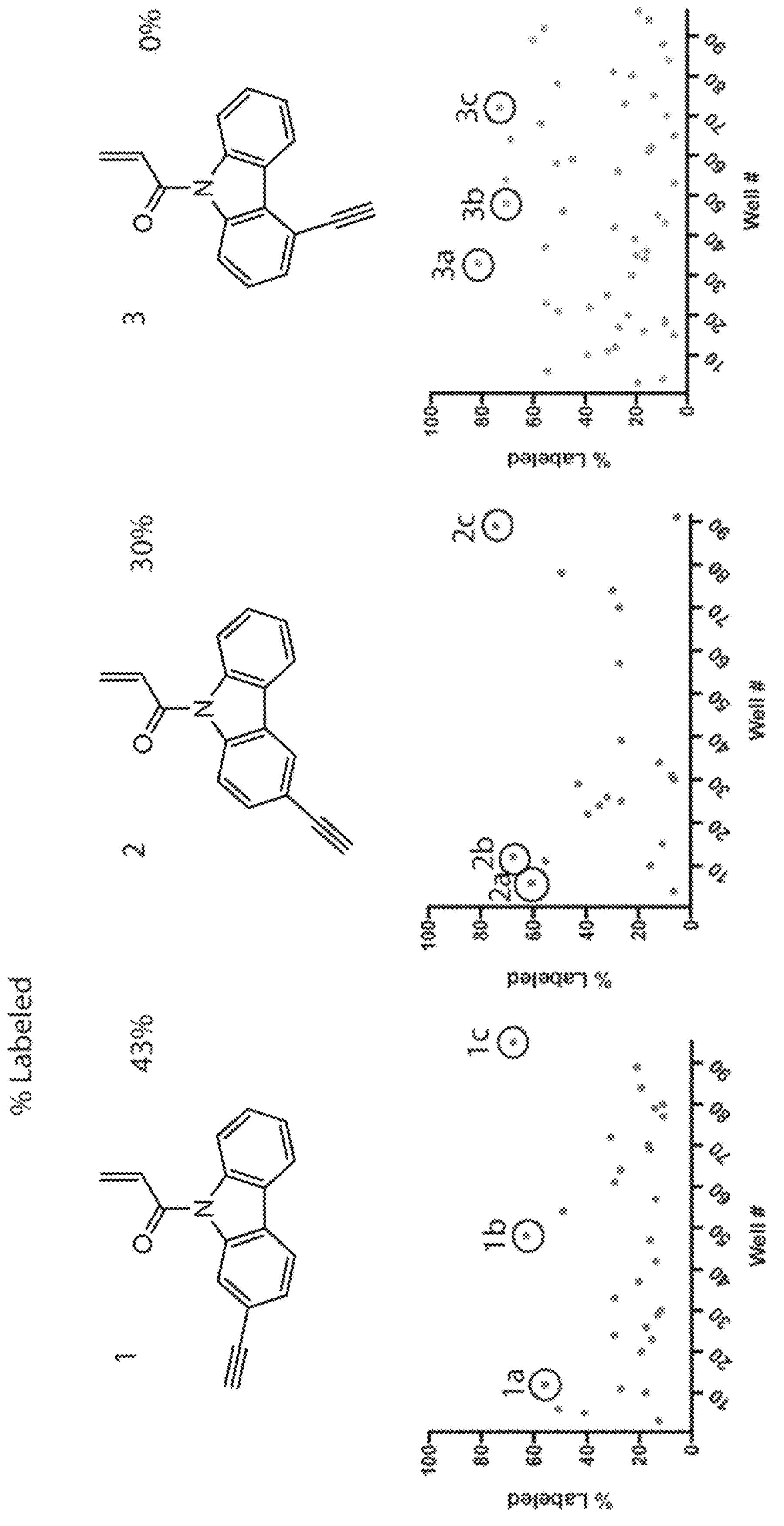
Figure 29B:
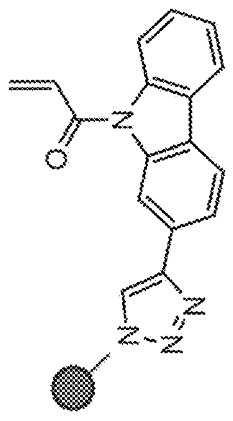
Figure 29B:
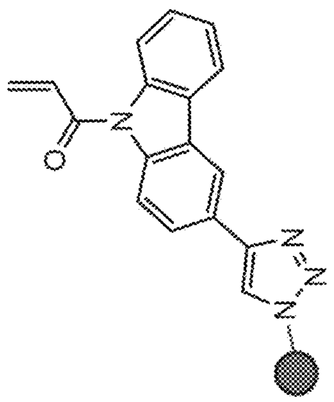
Figure 29B:
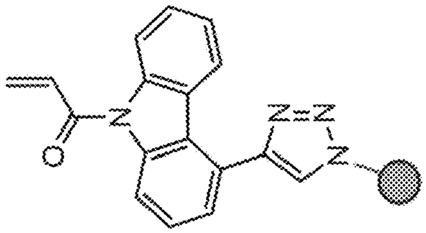
Figure 29B:
Figure 29B:
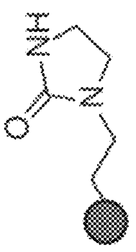
Figure 29B:
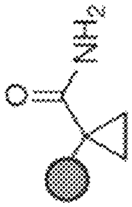
Figure 29B:
Figure 29B:
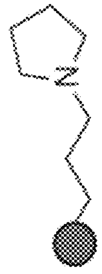
Figure 29B:
Figure 29B:
Figure 29B:
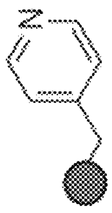
Figure 29B:
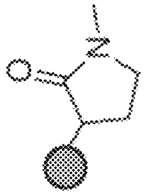

FIGS. 29A-29B. 4' position of carbazole produces most hits. Top hits are pyrrolidines.

Figure 30:
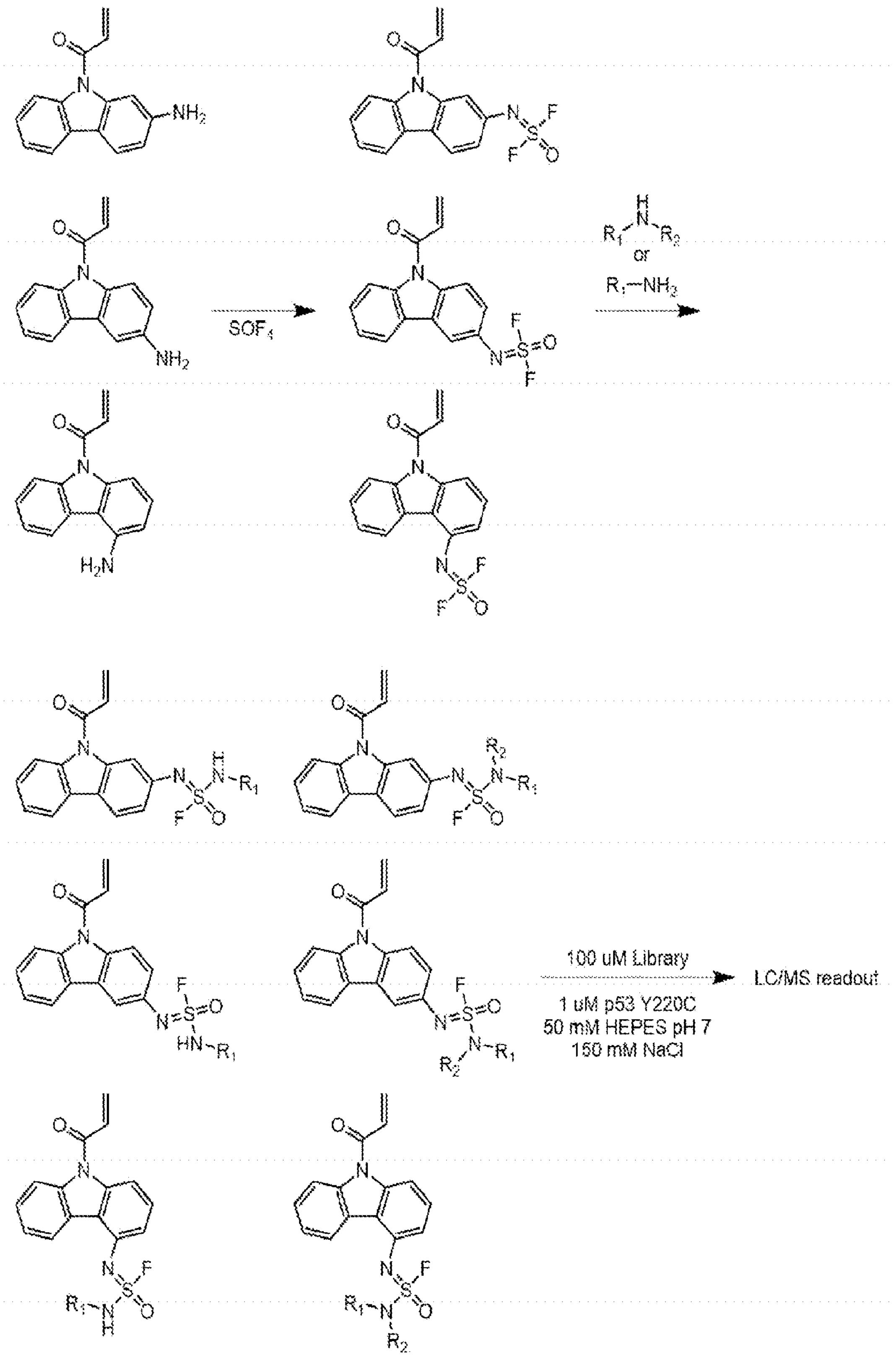

FIG. 30. Synthesis of SuFEx click chemistry library. SuFEx review article: Barrow, A., *Chem. Soc. Rev.,* 2019.

Figure 31:
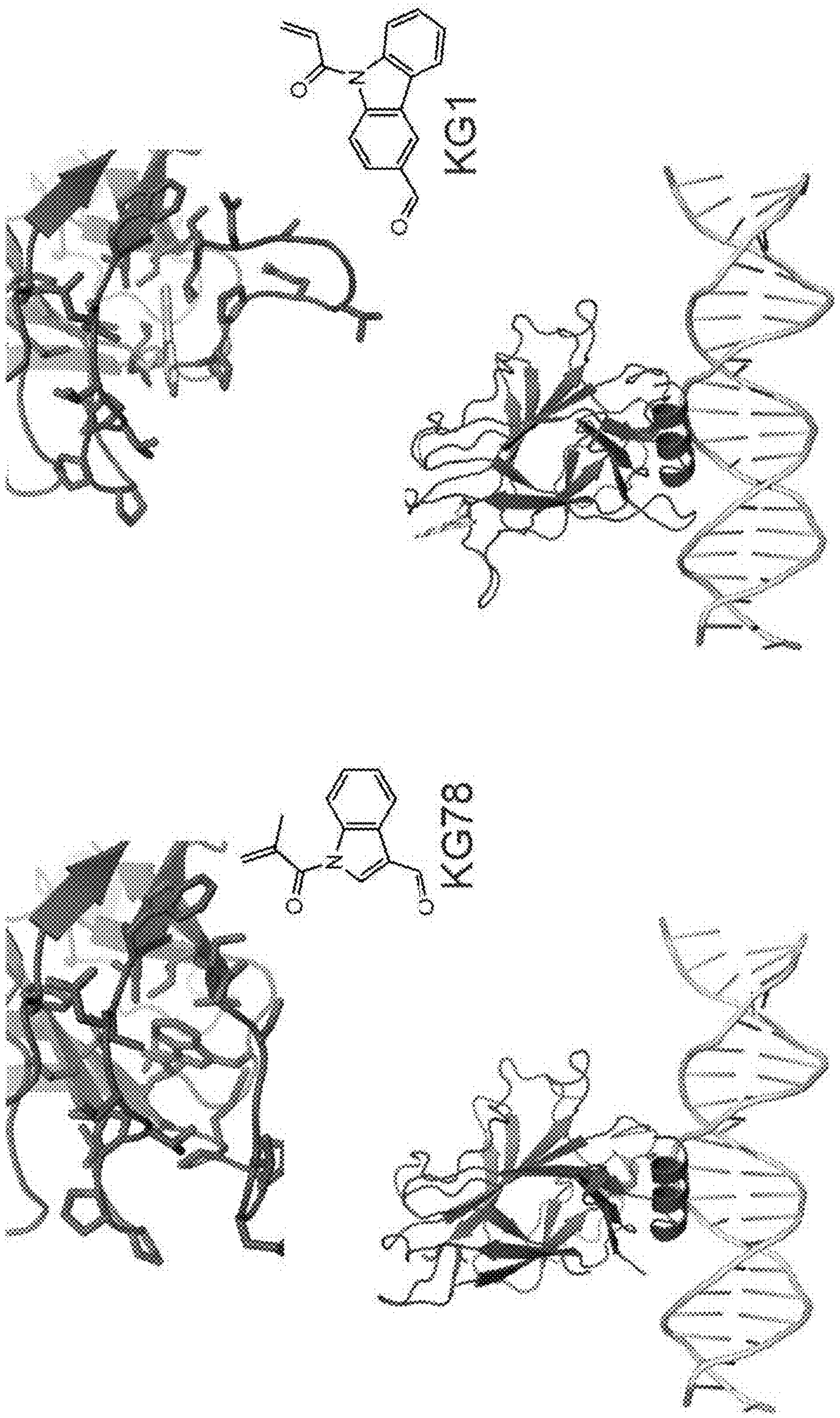

FIG. 31. Crystal structure of KG78 reveals unexpected binding mode.

Figure 32:
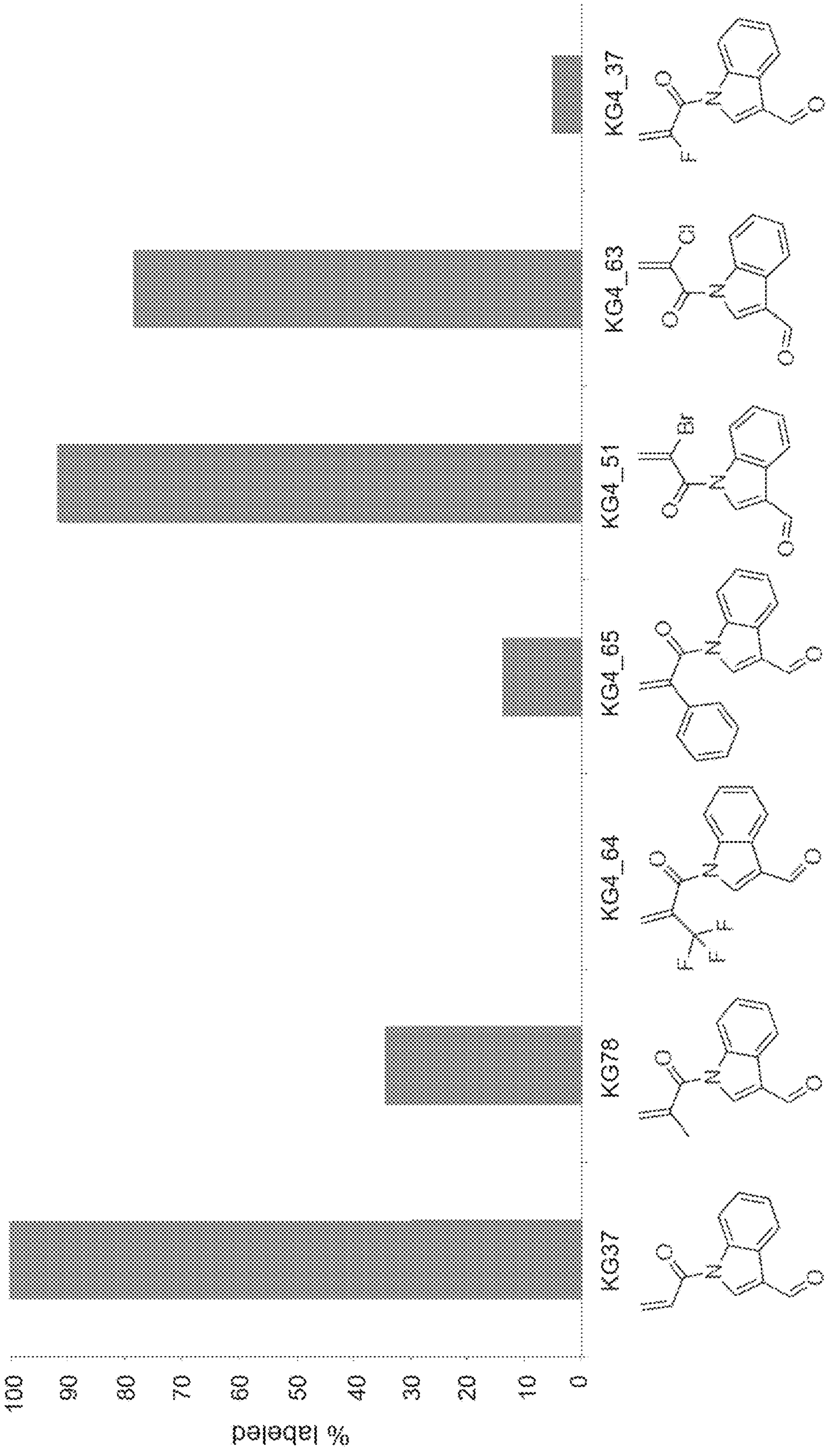

FIG. 32. Warhead substitutions suggest Br, Cl as replacements for methyl group.

Figure 33:
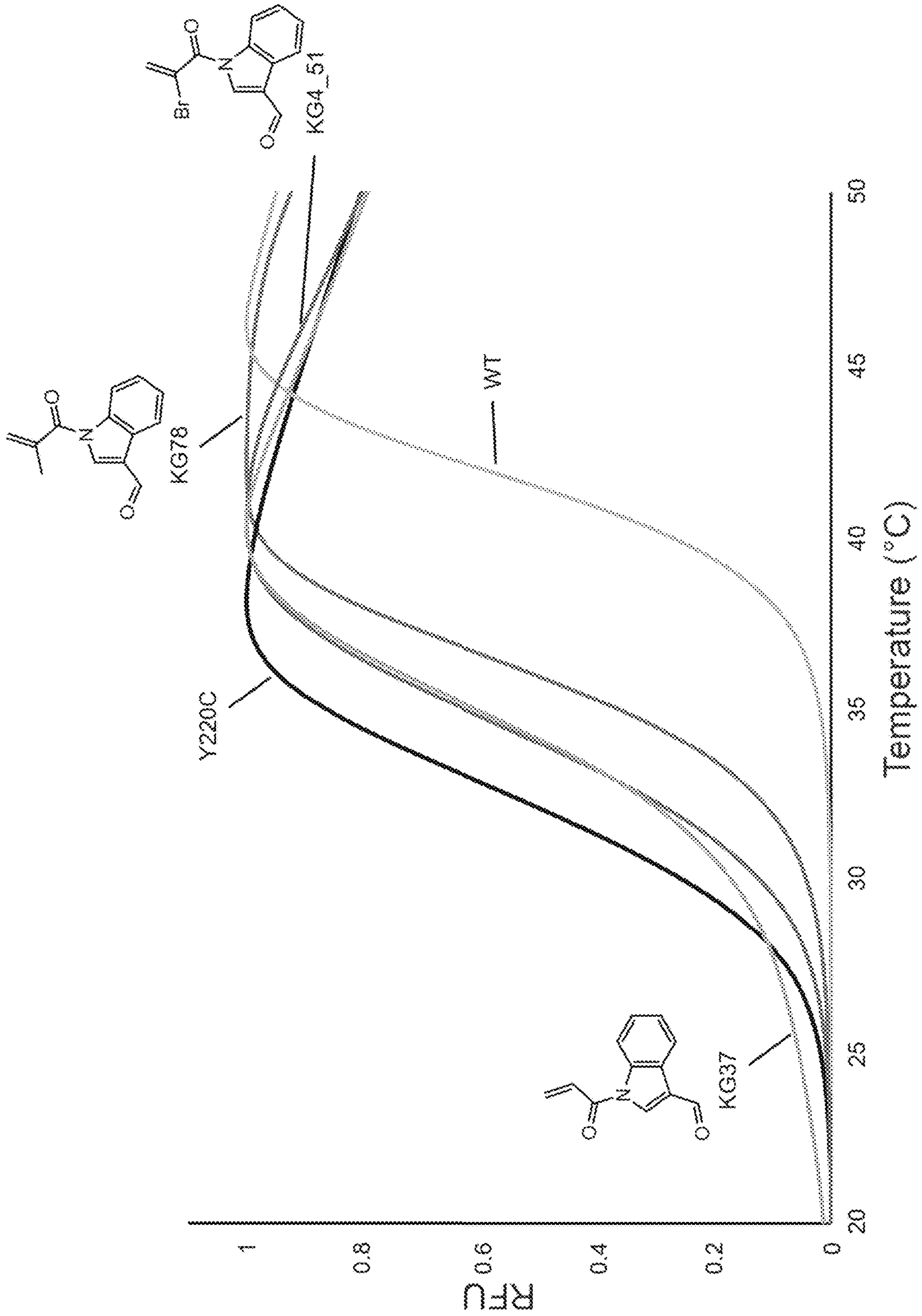

FIG. 33. Methacrylamide is the best stabilizer in the assay tested.

Figure 34:
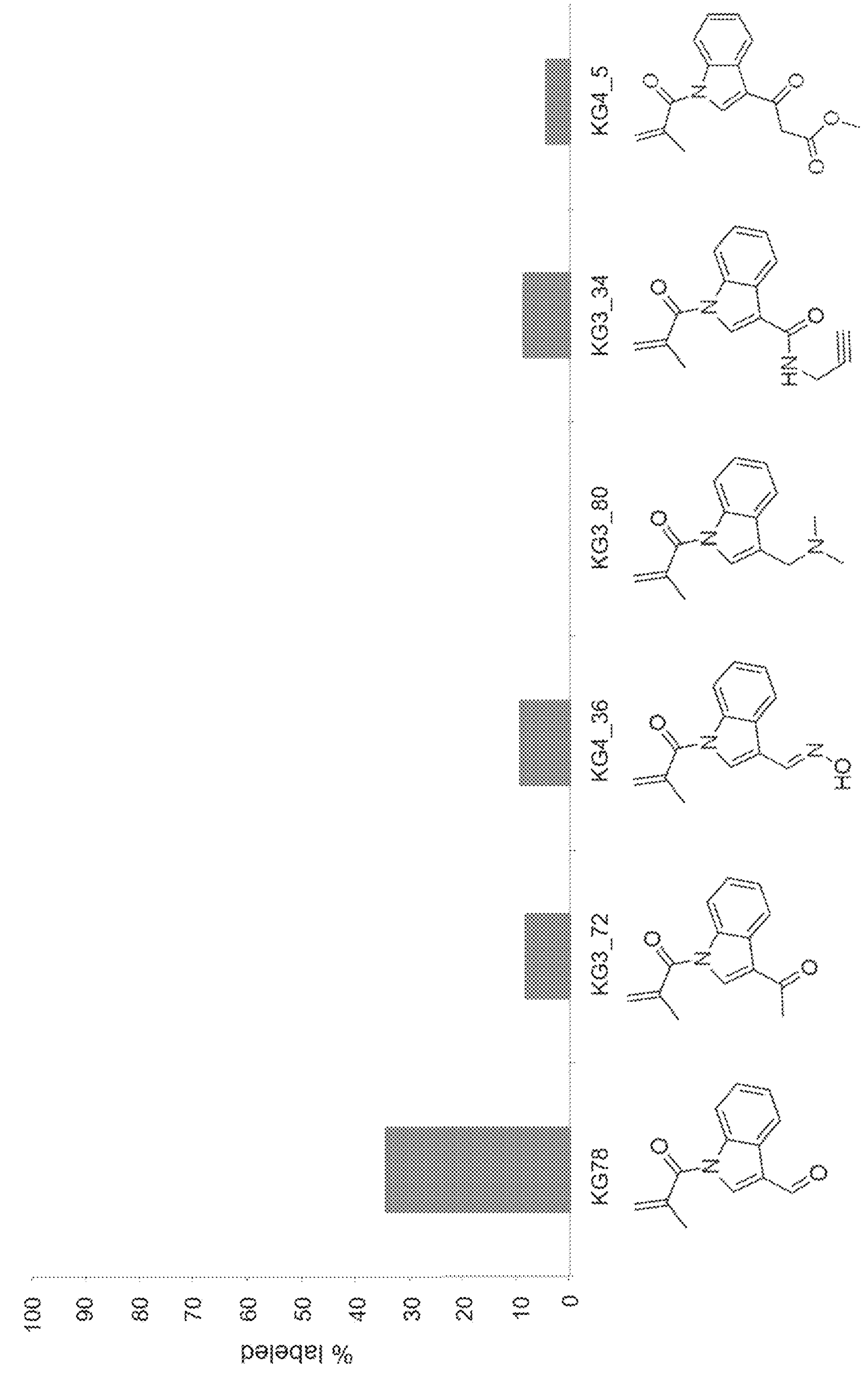

FIG. 34. Replacing the aldehyde decreased % labelling in the assay tested.

Figure 35:
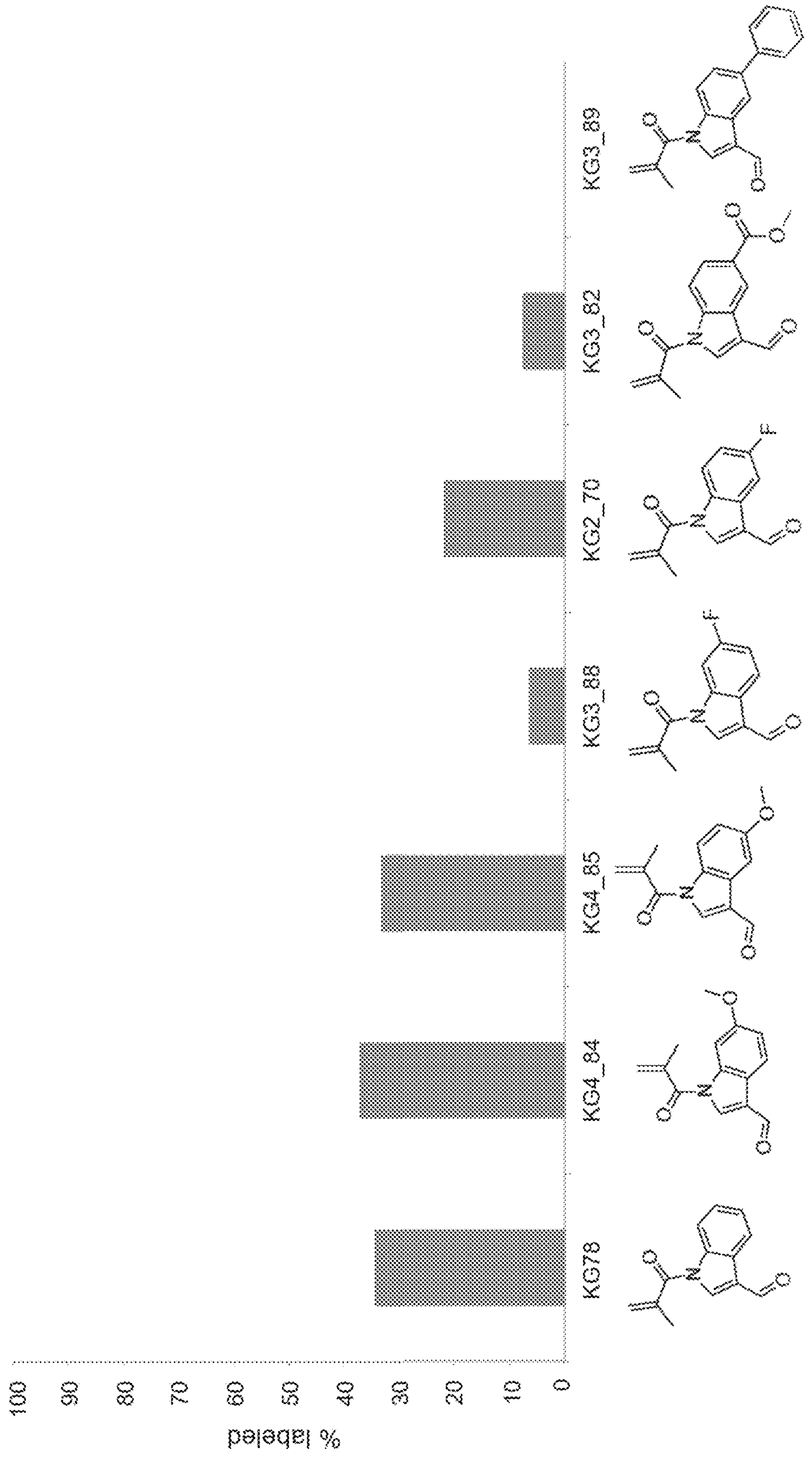

FIG. 35. Ethers may contribute to binding.

Figure 36:
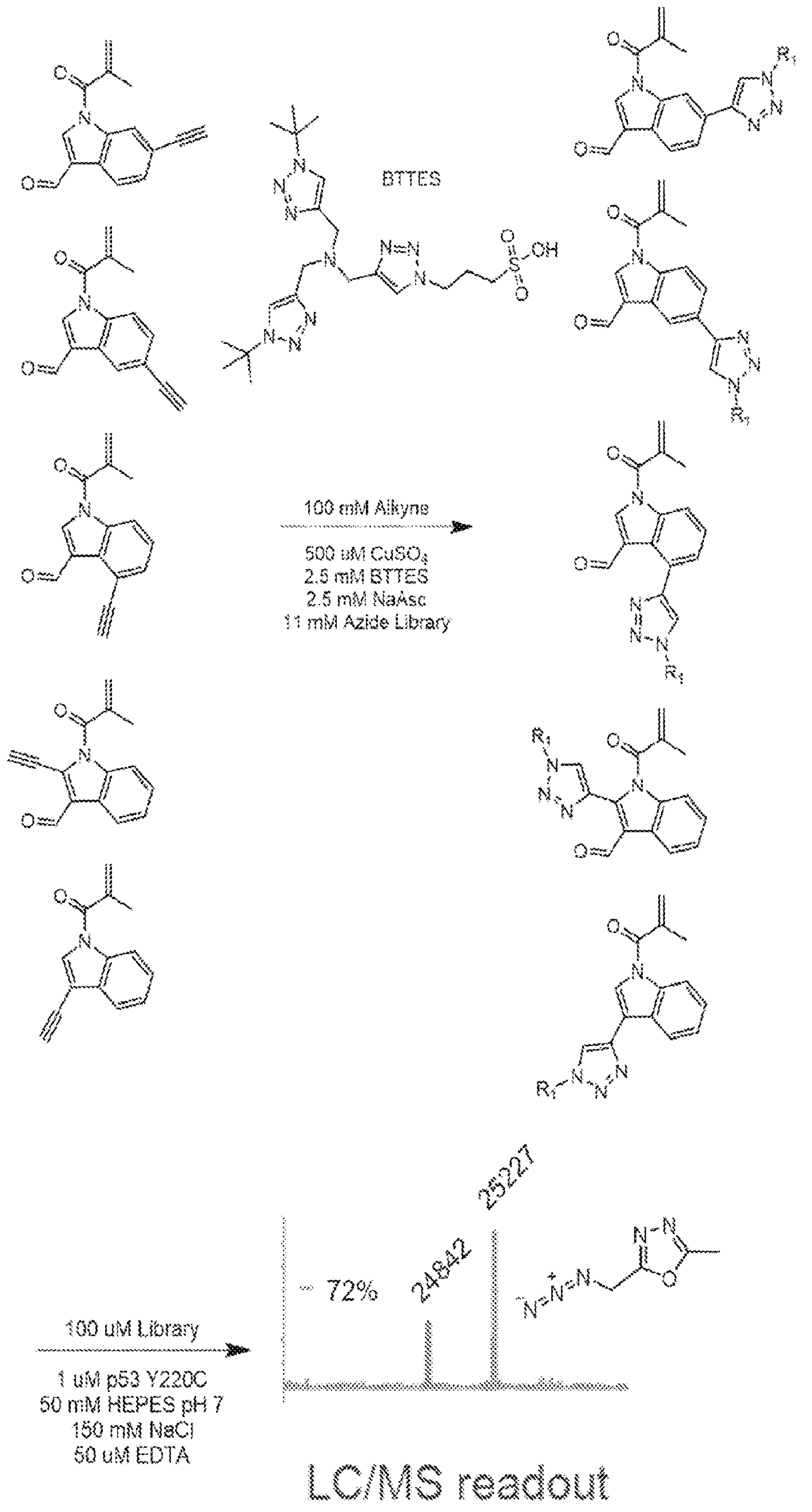

FIG. 36. High-throughput 96-well copper click chemistry library synthesis.

Figure 37:
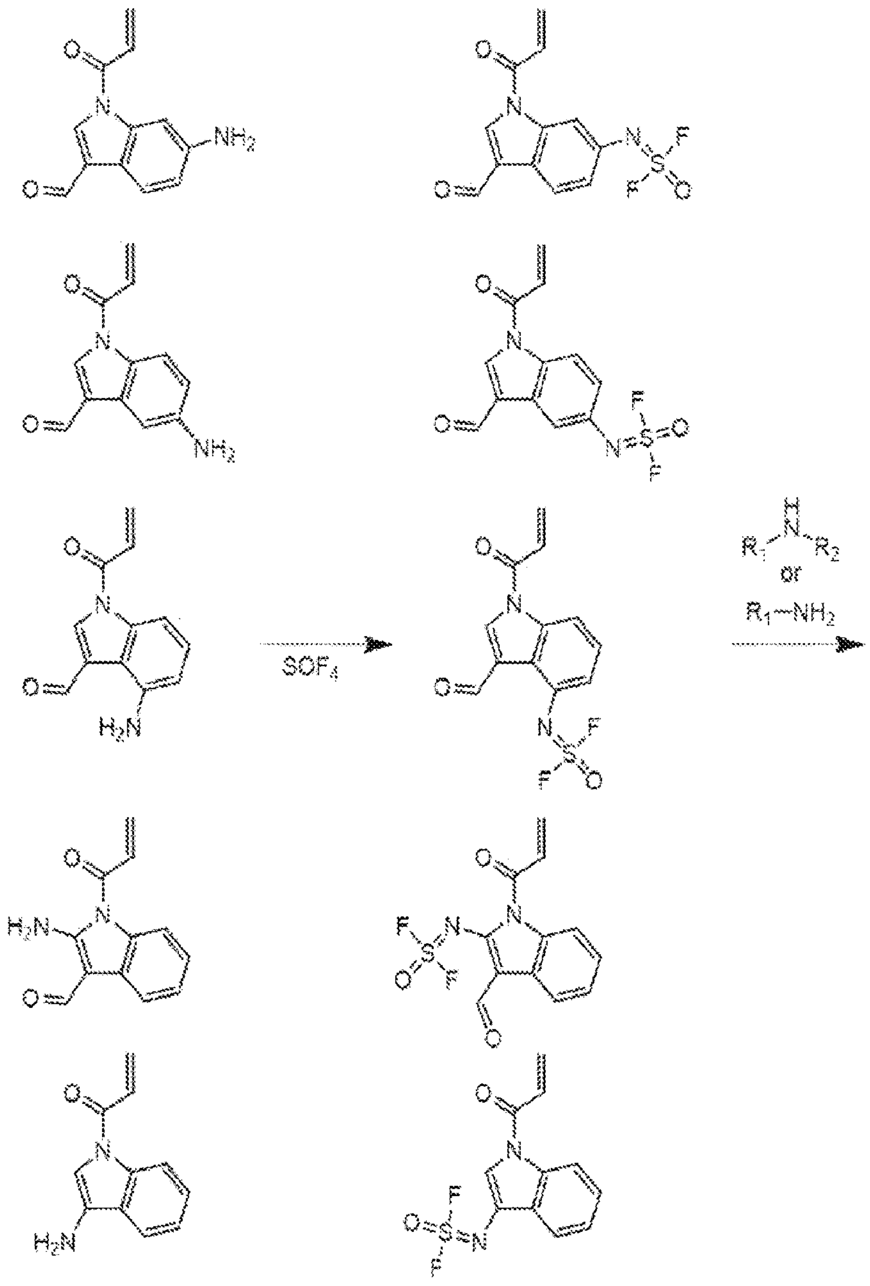
Figure 37:
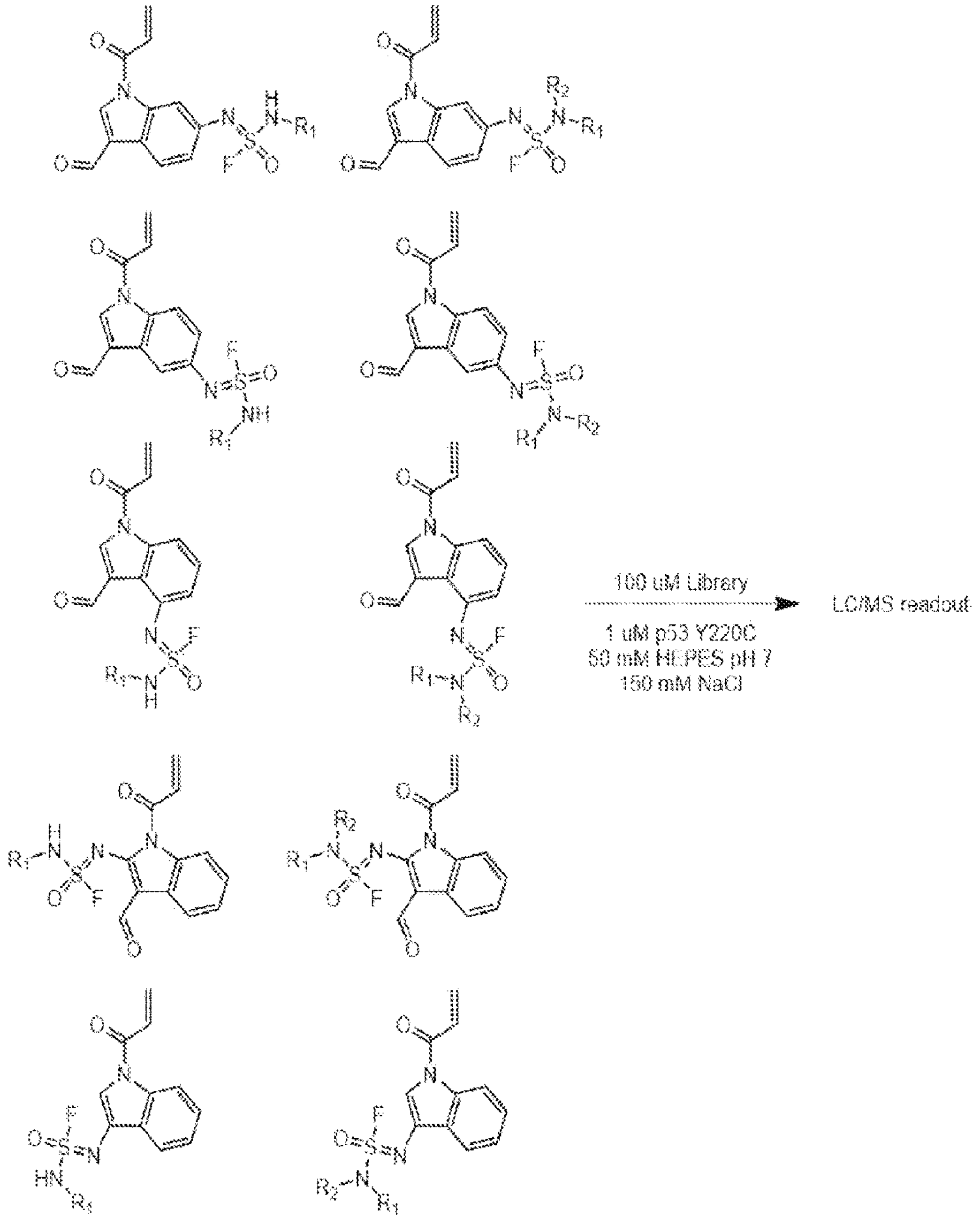

FIG. 37. High-throughput SuFEx click chemistry library synthesis.

Figure 38:
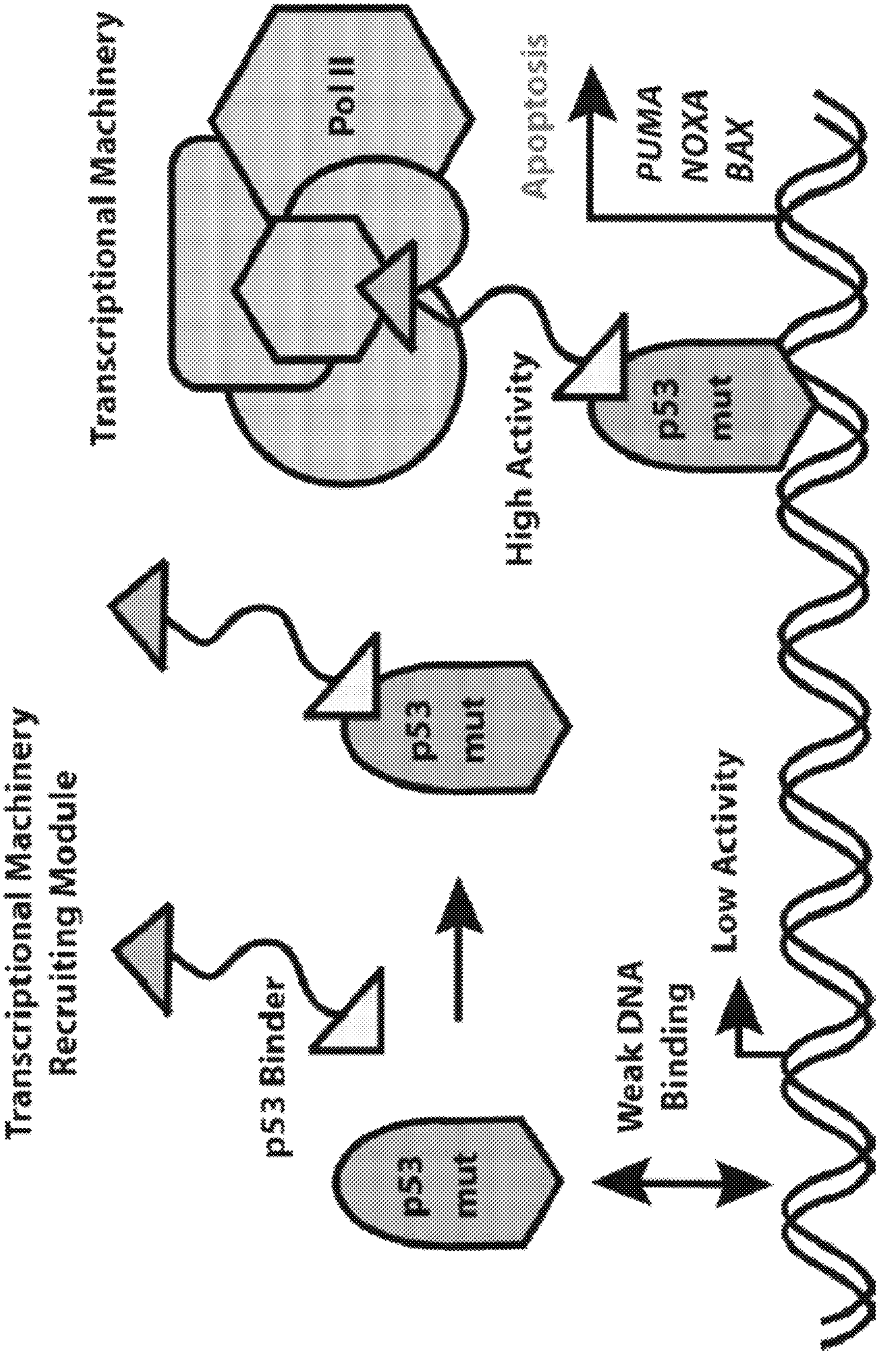

FIG. 38. Strategy of developing a bivalent bromodomain recruiter to enhance transcription of p53 target genes.

Figure 39:
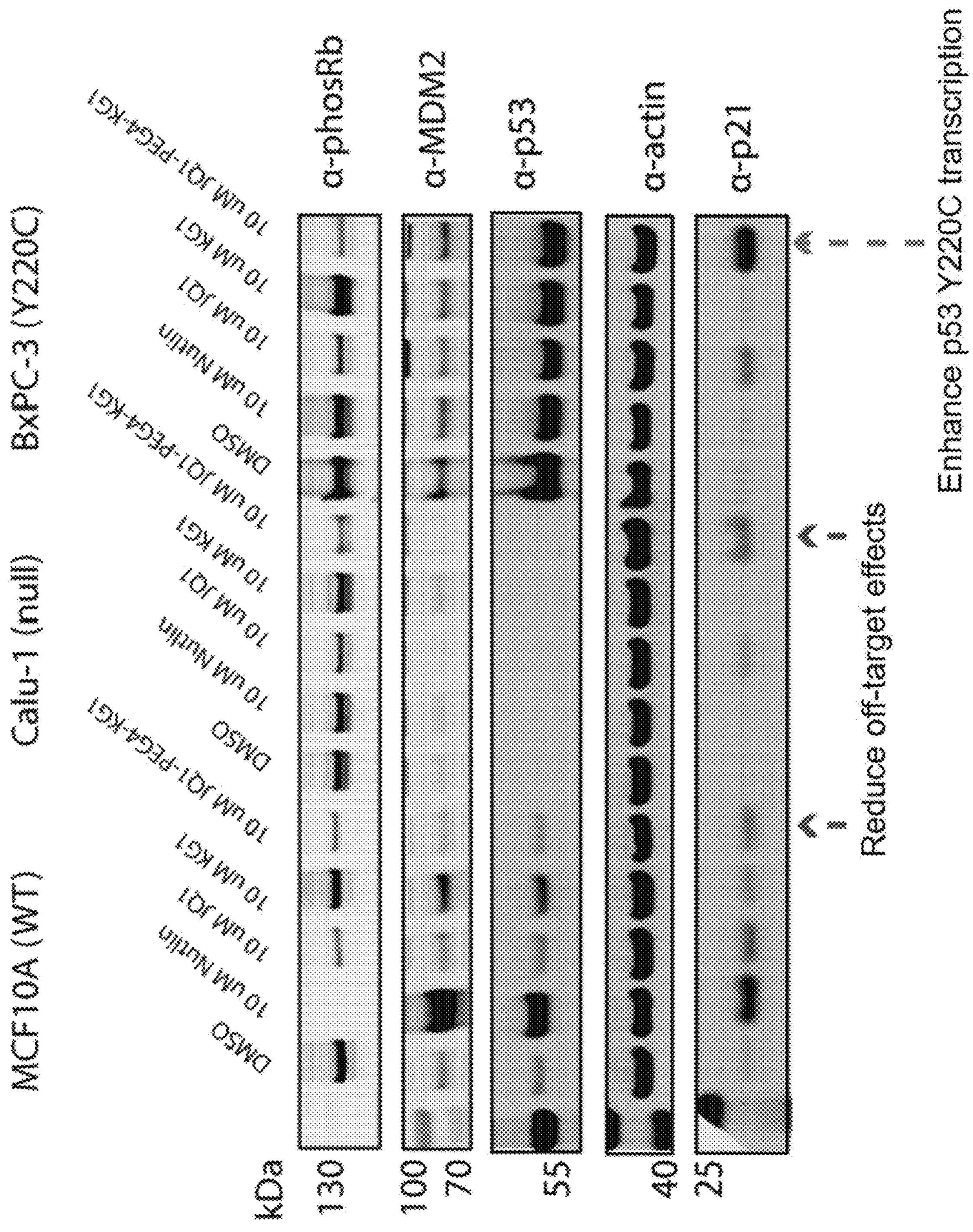

FIG. 39. Strategy of developing a bivalent bromodomain recruiter includes enhancing p53 Y220C transcription and reducing off-target effects.

Figure 40:
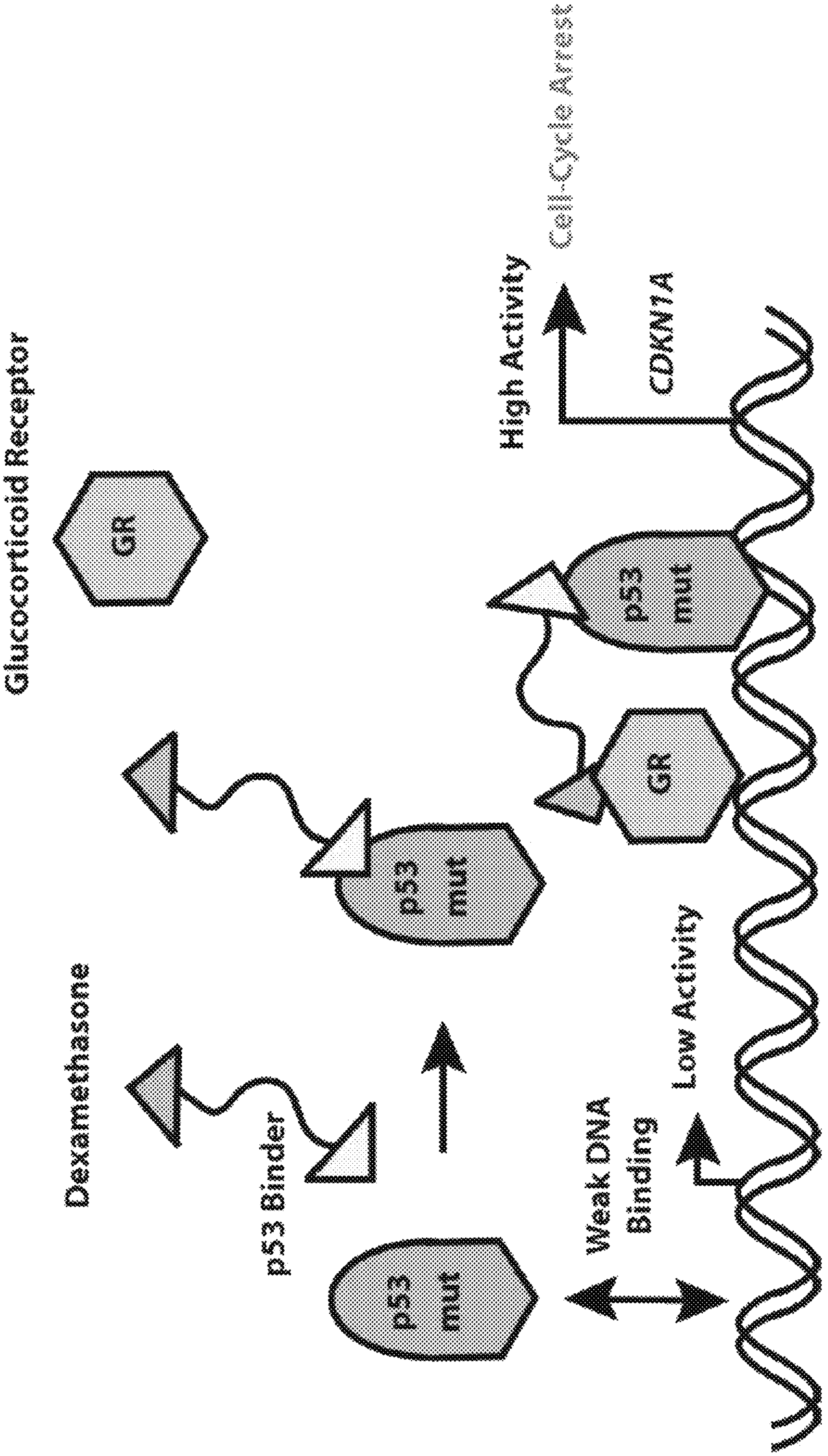

FIG. 40. Strategy of bridging a p53 mutant protein to another p21 promoter transcription factor. For example, a glucocorticoid receptor bivalent molecule may increase levels of mutant p53 protein at the p21 promoter.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S—$CH_2$—$CH_2$, —S(O)—$CH_3$, —$CH_2$—$CH_2$—S(O)$_2$—$CH_3$, —CH═CHO—$CH_3$, —Si($CH_3$)$_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from an heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, $-C(O)R$ where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom (s) are optionally quaternized. Thus, the term “heteroaryl” includes fused ring heteroaryl groups (i.e., multiple rings fused together wherein at least one of the fused rings is a heteroaromatic ring). In embodiments, the multiple rings are attached to the parent molecular moiety through any atom contained within a heteroaromatic ring of the multiple rings. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “∿” denotes the point of attachment of a chemical moiety to the remainder of a molecule or chemical formula.

The term “oxo,” as used herein, means an oxygen that is double bonded to a carbon atom.

The term “alkylarylene” as an arylene moiety covalently bonded to an alkylene moiety (also referred to herein as an alkylene linker). In embodiments, the alkylarylene group has the formula:

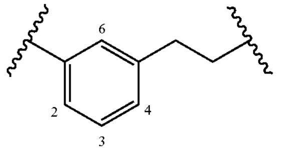

or

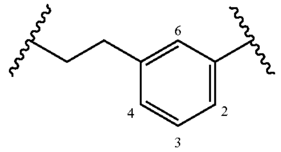

.

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R" " groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms “heteroatom” or “ring heteroatom” are meant to include oxygen (O), nitrogen (N), sulfur (S), phosphorus (P), and silicon (Si).

A “substituent group,” as used herein, means a group selected from the following moieties:

(A) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$—$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g., $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

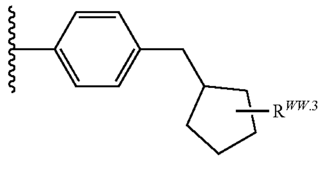

-continued

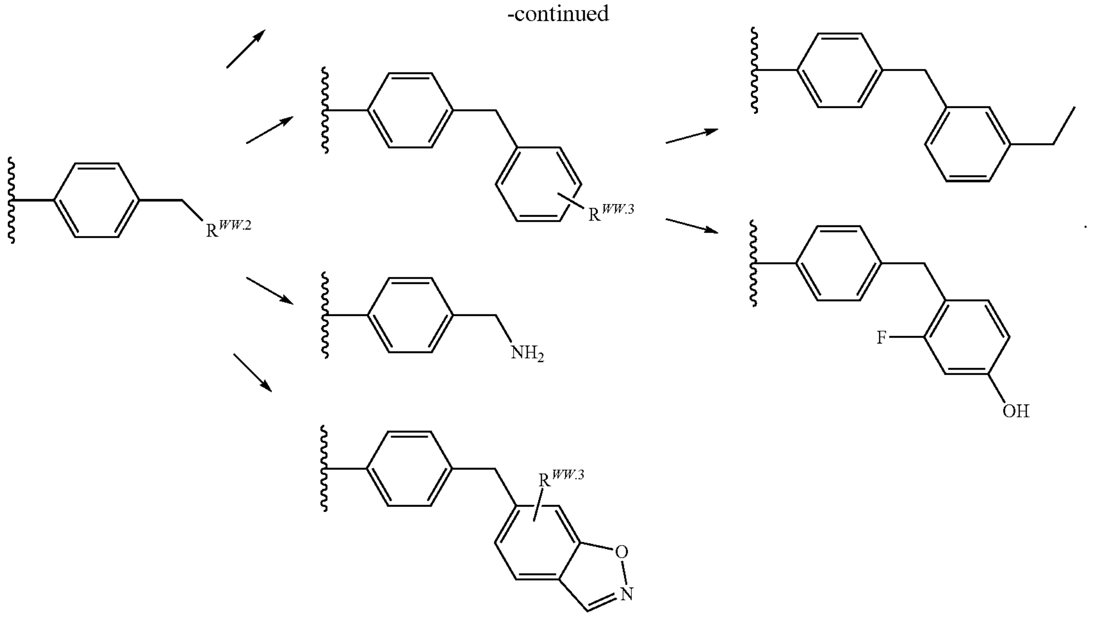

$R^{WW.1}$ is independently oxo, halogen, $—CX^{WW.1}_3$, $—CHX^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $—CX^{WW.1}_3$, $—CHX^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, $—CX^{WW.2}_3$, $—CHX^{WW.2}_2$, $—CH_2X^{WW.2}$, $—OCX^{WW.2}_3$, $—OCH_2X^{WW.2}$, $—OCHX^{WW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $—CX^{WW.2}_3$, $—CHX^{WW.2}_2$, $—CH_2X^{WW.2}$, $—OCX^{WW.2}_3$, $—OCH_2X^{WW.2}$, $—OCHX^{WW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, $—CX^{WW.3}_3$, $—CHX^{WW.3}_2$, $—CH_2X^{WW.3}$, $—OCX^{WW.3}_3$, $—OCH_2X^{WW.3}$, $—OCHX^{WW.3}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g. substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, $—CX^{LWW.3}_3$, $—CHX^{LWW.3}_2$, $—CH_2X^{LWW.3}$, $—OCX^{LWW.3}_3$, $—OCH_2X^{LWW.3}$, $—OCHX^{LWW.3}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, $—CX^{WW}_3$, $—CHX^{WW}_2$, $—CH_2X^{WW}$, $—OCX^{WW}_3$, $—OCH_2X^{WW}$, $—OCHX^{WW}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $—N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW}$-substituted or unsubstituted heterocycloalkyl (e.g., 3 to 8 membered, 3 to 6 membered, 4 to 6 membered, 4 to 5 membered, or 5 to 6 membered), R"-1-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, —$SO_2$—, —$SO_2$NH—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g., phosphines) to form, for example, phosphate diester bonds;

(n) azides coupled to alkynes using copper catalyzed cycloaddition click chemistry; and (o) biotin conjugate can react with avidin or streptavidin to form an avidin-biotin complex or streptavidin-biotin complex.

Another example of useful bioconjugate reactive moieties used for bioconjugate chemistries herein include, for example, sulfur(VI) fluoride moieties coupled to amines using SuFEx click chemistry.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

In this disclosure, "comprises," "comprising," "containing" and "having" and the like can have the meaning ascribed to them in U.S. patent law and can mean "includes," "including," and the like. "Consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and/or appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), an additional number may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$ $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb, and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent moiety or fluorescent dye moiety. In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, McOH moiety, Sapphire moiety, BODIPY FL conjugate moiety, MitoTracker Green moiety, MitoTracker Green FM, McOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2', 7'-dichlorofluorescein pH 9.0 moiety, DansylCadaverine, McOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 McOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, McOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G McOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-McOH moiety, Alexa 555 moiety, DyLight 549 moiety, BODIPY TMR-X, SE moiety, BODIPY TMR-X McOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange McOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, McOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, McOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, McOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(μ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bexl, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, Crypt®Light CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHerS, CypHerS pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, *Diversa* Cyan-FP, *Diversa* Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQS, DsRed, DsRed, DsRed, DsRed-Express, DsRed-Express2, DsRed-Express Ti, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EgFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu2O3 nanoparticles, Eu (Soini), Eu(tta) 3DEADIT, EvaGreen, EVOblue-30, EYFP, FAD, FITC, FITC, FlAsH (Adams), Flash Red EX, F1AsH-CCPGCC, F1AsH—CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™ Ge1Red™, H9-40, HcRedl, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO—Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye®700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye®800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazinl, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH—CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien 1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien 1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1. In embodiments, $R^{23}$ is independently a monovalent moiety of a compound described within this paragraph.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A “cell” as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms “treating” or “treatment” refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient’s physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term “treating” and conjugations thereof, include prevention of an injury, pathology, condition, or disease. In embodiments, treating is preventing. In embodiments, treating does not include preventing. In embodiments, the treating or treatment is not prophylactic treatment.

An “effective amount” is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition. An example of an “effective amount” is an amount sufficient to contribute to the treatment, prevention, or reduction of a symptom or symptoms of a disease, which could also be referred to as a “therapeutically effective amount” when referred to in this context. A “reduction” of a symptom or symptoms (and grammatical equivalents of this phrase) means decreasing of the severity or frequency of the symptom(s), or elimination of the symptom(s). A “prophylactically effective amount” of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An “activity decreasing amount,” as used herein, refers to an amount of antagonist required to decrease the activity of an enzyme relative to the absence of the antagonist. A “function disrupting amount,” as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

“Control” or “control experiment” is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

“Contacting” is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term “contacting” may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, small molecule, protein complex, protein aggregate, or macromolecule) that is involved in a signaling pathway.

As defined herein, the term “activation”, “activate”, “activating”, “activator” and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

Figure 3A:
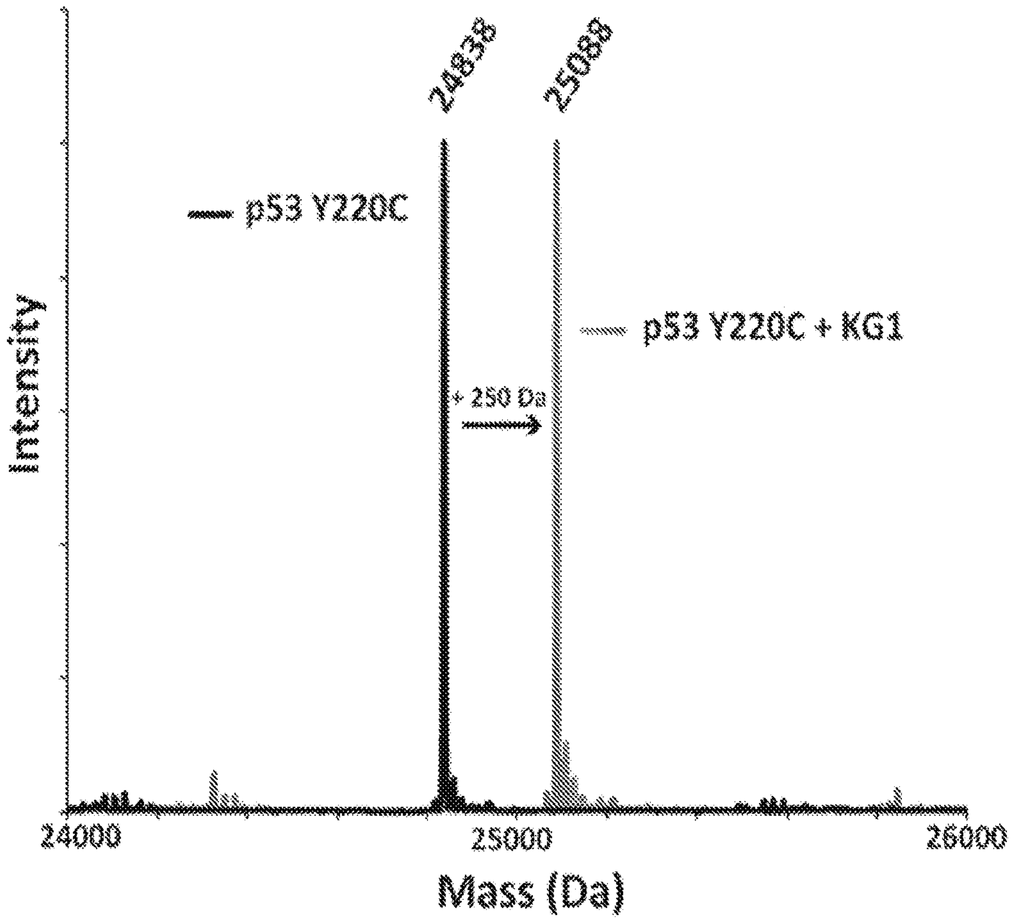
FIGS. 3A-3D. The covalent probe KG1 labels and stabilizes p53 Y220C.
Figure 3B:
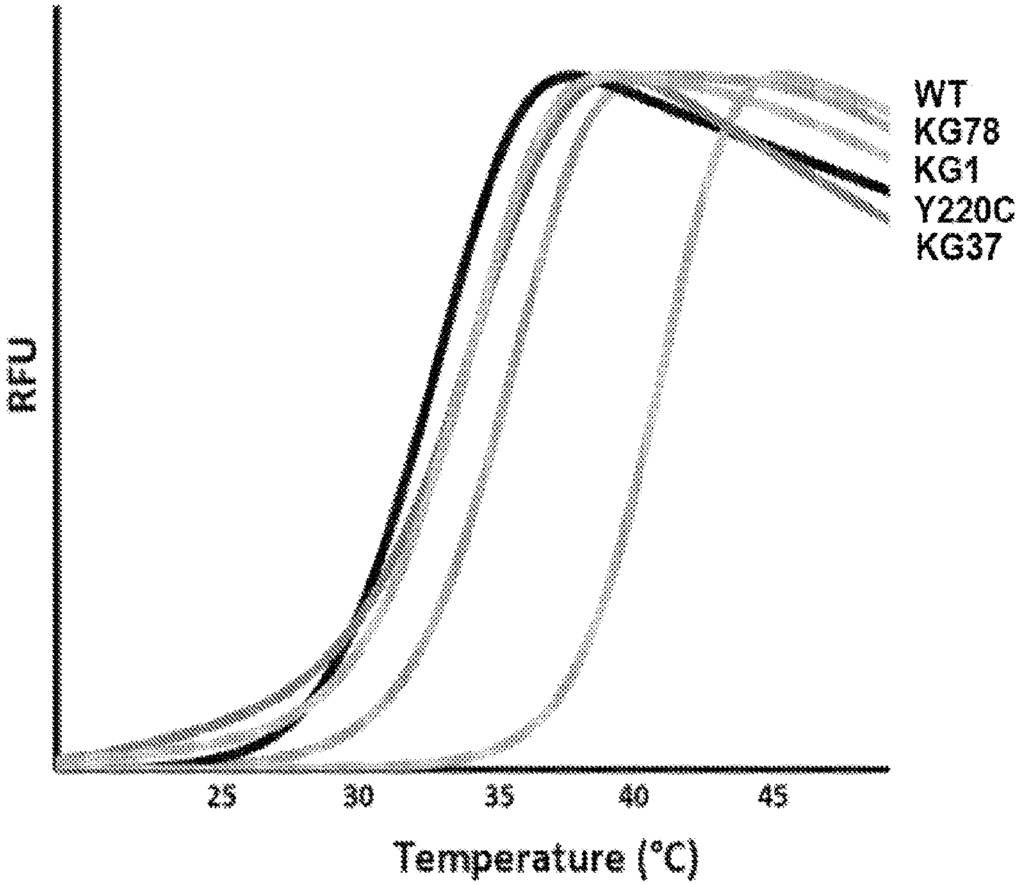

A "p53 mutant agonist" as used herein refers to a substance (e.g., compound described herein) capable of increasing the expression or activity of a mutant p53 protein (e.g., Y220C p53 protein) relative to the absence of the p53 mutant agonist. In embodiments, the p53 mutant agonist stabilizes a mutant p53 protein (e.g., Y220C p53 protein). In embodiments, the p53 mutant agonist stabilizes an active p53 protein conformation. In embodiments, the active p53 protein conformation allows p53 DNA binding. In embodiments, the active p53 protein conformation allows p53 DNA binding and transcriptional activity. In embodiments, the p53 DNA binding and/or transcriptional activity is increased relative to a non-active p53 protein conformation. In embodiments, the extent of stabilization of the active p53 protein conformation is determined by differential scanning fluorimetry (e.g., as shown in FIG. 3B). In embodiments, the p53 mutant agonist increases the transcriptional activity of a p53 protein relative to the absence of the p53 mutant agonist. In embodiments, the p53 mutant agonist increases the tumor suppressing ability of a p53 protein relative to the absence of the p53 mutant agonist. In embodiments, the p53 mutant agonist increases the activity of a p53 protein relative to the absence of the p53 mutant agonist. In embodiments, the activity of the p53 protein is arrest of cell growth. In embodiments, the activity of the p53 protein is arrest of cell growth by holding the cell cycle at the G1/S regulation point. In embodiments, the p53 mutant agonist inhibits the cell cycle transition from the G1 phase to the S phase. In embodiments, the p53 mutant agonist decreases the cell cycle transition from the G1 phase to the S phase relative to the absence of the mutant p53 agonist. In embodiments, the activity of the p53 protein is activation of DNA repair proteins. In embodiments, the p53 mutant agonist activates DNA repair proteins. In embodiments, the p53 mutant agonist increases the level of activity of DNA repair proteins relative to the absence of the p53 mutant agonist. In embodiments, the activity of the p53 protein is initiation of apoptosis. In embodiments, the p53 mutant agonist increases the level of activity of proteins involved in apoptosis relative to the absence of the p53 mutant agonist.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, small molecule, protein complex, protein aggregate, or macromolecule)), relative to the activity or function of the cellular component in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, small molecule, protein complex, protein aggregate, or macromolecule)) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "small molecule" is used in accordance with its well understood meaning and refers to a low molecular weight organic compound that may regulate a biological process. In embodiments, the small molecule is a compound that weighs less than 1000 daltons. In embodiments, the small molecule is a compound that weighs less than 900 daltons. In embodiments, the small molecule weighs less than 800 daltons. In embodiments, the small molecule weighs less than 700 daltons. In embodiments, the small molecule weighs less than 600 daltons. In embodiments, the small molecule weighs less than 500 daltons. In embodiments, the small molecule weighs less than 450 daltons. In embodiments, the small molecule weighs less than 400 daltons.

The term "PhiKan compound" as used herein refers to a small molecule capable of noncovalently binding to a p53 Y220C protein. In embodiments, the PhiKan compound reversibly binds to a p53 Y220C protein.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, small molecule, protein complex, protein aggregate, or macromolecule).

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head and neck, liver, kidney, lung, non-small cell lung, melanoma, mesothelioma, ovary, sarcoma, stomach, uterus, medulloblastoma, colorectal cancer, or pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "hematologic cancer" is used in accordance with its plain ordinary meaning and refers to a cancer that begins in blood-forming tissue (e.g., bone marrow) or in cells of the immune system. Examples of hematologic cancers include leukemia, lymphoma, and multiple myeloma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "p53 mutant cancer" as used herein refers to a cancer expressing a mutant p53 protein. p53 mutant cancers include, but are not limited to, cancers wherein the cancer cells have a $p53^{+/mut}$ genotype or a $p53^{mut/-}$ genotype. The term "$p53^{+/mut}$" is used in accordance with its plain ordinary meaning and refers to a heterozygous genotype having a p53 wildtype allele and a p53 mutant allele. The term "$p53^{mut/-}$" is used in accordance with its plain ordinary meaning and refers to a heterozygous genotype with a p53 mutant allele and a p53 null allele, wherein the p53 null allele is a p53 mutation that decreases or eliminates the translation (or production) of the p53 protein. In embodiments, the p53 mutant allele is a p53 mutant cancer allele, wherein the p53 mutant cancer allele produces a mutant p53 protein. In embodiments, the mutant p53 protein includes a Y220C mutation. In embodiments, the mutant p53 protein includes a R175H mutation. In embodiments, the mutant p53 protein includes a R273C mutation. In embodiments, the mutant p53 protein includes a R248Q mutation. In embodiments, the mutant p53 protein includes a R273H mutation. In embodiments, the mutant p53 protein includes a R248W mutation. In embodiments, the mutant p53 protein includes a R282W mutation. In embodiments, the mutant p53 protein includes a G275S mutation. In embodiments, the mutant p53 protein includes a V157F mutation. In embodiments, the mutant p53 protein includes a H193R mutation. In embodiments, the mutant p53 protein includes a Y163C mutation. In embodiments, the mutant p53 protein includes a R273L mutation. In embodiments, the mutant p53 protein includes a C176F mutation. In embodiments, the mutant p53 protein includes an E285K mutation. In embodiments, the mutant p53 protein includes a S241F mutation. In embodiments, the mutant p53 protein includes a R158L mutation. In embodiments, the mutant p53 protein includes a R249S mutation. In embodiments, the mutant p53 protein includes an I195T mutation. In embodiments, the mutant p53 protein includes a Y234C mutation. In embodiments, the mutant p53 protein includes a V272M mutation.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compounds described herein can be used in combination with one another, with other active agents known to be useful in treating a disease associated with cells expressing a disease associated cellular component, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with anti-cancer agents or conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of a disease, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer, or with adjunctive agents that may not be effective alone, but may contribute to the efficacy of the active agent.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "associated" or "associated with" in the context of a substance or substance activity or function associated with a disease (e.g., a protein associated disease, disease associated with a cellular component) means that the disease (e.g., cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). As used herein, what is described as being associated with a disease, if a causative agent, could be a target for treatment of the disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti cancer agent is an agent identified herein having utility in methods of treating cancer. In some embodiments, an anticancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. In embodiments, an anti-cancer agent is an inhibitor of K-Ras, RAF, MEK, Erk, PI3K, Akt, RTK, or mTOR. In embodiments, an anti-cancer agent is an MDM2 inhibitor or a genotoxic anti-cancer agent. In embodiments, an anti-cancer agent is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232. In embodiments, an anti-cancer agent is an alkylating agent, intercalating agent, or DNA replication inhibitor. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY- 300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e., R 55104), Dolastatin 10 (i.e., DLS-10 and NSC-376128), Mivobulin isethionate (i.e., as CI-980), Vincristine, NSC-639829, Discodermolide (i.e., as NVP-XX-A-296), ABT-751 (Abbott, i.e., E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e., LU-103793 and NSC-D-669356), Epothilones (e.g., Epothilone A, Epothilone B, Epothilone C (i.e., desoxyepothilone A or dEpoA), Epothilone D (i.e., KOS-862, dEpoB, and desoxyepothilone B), Epothilone E, Epothilone F, Epothilone B N-oxide, Epothilone A N-oxide, 16-aza-epothilone B, 21-aminoepothilone B (i.e., BMS-310705), 21-hydroxyepothilone D (i.e., Desoxyepothilone F and dEpoF), 26-fluoroepothilone, Auristatin PE (i.e., NSC-654663), Soblidotin (i.e., TZT-1027), LS-4559-P (Pharmacia, i.e., LS-4577), LS-4578 (Pharmacia, i.e., LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e., ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e., LY-355703), AC-7739 (Ajinomoto, i.e., AVE-8063A and CS-39.HCl), AC-7700 (Ajinomoto, i.e., AVE-8062, AVE-8062A, CS-39-L-Ser-.HCl, and RPR-258062A), Vitilevuamide, Tubulysin A, Canadensol, Centaureidin (i.e., NSC-106969), T-138067 (Tularik, i.e., T-67, TL-138067 and TI-138067), COBRA-1 (Parker Hughes Institute, i.e., DDE-261 and WHI-261), H10 (Kansas State University), H16 (Kansas State University), Oncocidin Al (i.e., BTO-956 and DIME), DDE-313 (Parker Hughes Institute), Fijianolide B, Laulimalide, SPA-2 (Parker Hughes Institute), SPA-1 (Parker Hughes Institute, i.e., SPIKET-P), 3-IAABU (Cytoskeleton/Mt. Sinai School of Medicine, i.e., MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e., MF-191), TMPN (Arizona State University), Vanadocene acetylacetonate, T 138026 (Tularik), Monsatrol, lnanocine (i.e., NSC-698666), 3-IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e., NSCL-96F037), D-68838 (Asta Medica), D-68836 (Asta Medica), Myoseverin B, D-43411 (Zentaris, i.e., D-81862), A-289099 (Abbott), A-318315 (Abbott), HTI-286 (i.e., SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™) erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. A moiety of an anti-cancer agent is a monovalent anti-cancer agent (e.g., a monovalent form of an agent listed above).

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent," "electrophilic chemical moiety," or "electrophilic moiety" refers to an electron-poor chemical group, substituent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue and may be referred to as a "covalent cysteine modifier moiety" or "covalent cysteine modifier substituent." The covalent bond formed between the electrophilic substituent and the sulfhydryl group of the cysteine may be a reversible or irreversible bond.

"Nucleophilic" as used herein refers to a chemical group that is capable of donating electron density.

The term "click chemistry" refers to a class of chemical reactions to form compositions by joining small modular units (i.e., a first reactive moiety and a second reactive moiety) using conjugate chemistry. Click chemistry is well known in the art and is described, for example, in H. C. Kolb, M. G. Finn, K. B. Sharpless (2001). Angew. Chem. Int. Ed., 40(11): 2004-2021; R. A. Evans (2007). Australian Journal of Chemistry 60(6): 384-395; R. S. Bohacek, C. McMartin, W. C. Guida (1996). Med. Res. Rev., 16(1): 3-50; C. Spiteri, J. E. Moses (2010). Angew. Chem. Int. Ed., 49(1): 31-33; C. E. Hoyle, C. N. Bowman (2010). Angew. Chem. Int. Ed., 49(9): 1540-1573; M. L. Blackman, M. Royzen, J. M. Fox (2008). J. Am. Chem. Soc., 130(41): 13518-13519; N. K. Devaraj, R. Weissleder, S. A. Hilderbrand (2008). Bioconj. Chem. 19(12): 2297-2299; H. Stockmann, A. A. Neves, S. Stairs, K. M. Brindle, F. J. Leeper (2011). Org. Biomol. Chem., 9, 7303-7305; all of which are hereby incorporated by reference in their entirety and for all purposes. In embodiments, the chemical reaction includes a first reactive moiety and a second reactive moiety, wherein the first reactive moiety and the second reactive moiety are a complementary reactive pair. In embodiments, the click chemistry reaction is an azide-alkyne cycloaddition, wherein the first reactive moiety is a substituted or unsubstituted alkynyl moiety and the second reactive moiety is an azidyl moiety.

The term "SuFEx" refers to sulfur(VI) fluoride exchange and is an example of a click chemistry reaction. The term "SuFEx click chemistry complementary reactive pair" as used herein refers to a first reactive moiety and a second reactive moiety that react in a SuFEx click chemistry reaction. In embodiments, SuFEx chemistry is as described in J. Dong, L. Krasnova, M. G. Finn, K. B. Sharpless (2014). Angew. Chem. Int. Ed., 53(36): 9430-9448, which is hereby incorporated by reference in its entirety and for all purposes. In embodiments, the first reactive moiety is —$SO_2F$. In embodiments, the first reactive moiety is —$NS(O)F_2$. In embodiments, the second reactive moiety is a nucleophile.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human protein and the overall structures compared. In this case, an amino acid that occupies the same essential position as a specified amino acid in the structural model is said to correspond to the specified residue. For example, a selected residue in a selected protein corresponds to C220 of a mutant p53 protein including a Y220C mutation (e.g., a Y220C p53 protein, or a human Y220C p53 protein) when the selected residue occupies the same essential spatial or other structural relationship as C220 in a mutant p53 protein including a Y220C mutation (e.g., a Y220C p53 protein, or a human Y220C p53 protein). In some embodiments, where a selected protein is aligned for maximum homology with the p53 protein (e.g., mutant p53 protein), the position in the aligned selected protein aligning with C220 is said to correspond to C220 of the mutant p53 protein including a Y220C mutation (e.g., a Y220C p53 protein, or a human Y220C p53 protein). Instead of a primary sequence alignment, a three dimensional structural alignment can also be used, e.g., where the structure of the selected protein is aligned for maximum correspondence with the p53 protein (e.g., of SEQ ID NO:6 or a mutant p53 protein including a Y220C mutation) and the overall structures compared. In this case, an amino acid that occupies the same essential position as C220 of a mutant p53 protein including a Y220C mutation (e.g., a Y220C p53 protein, or a human Y220C p53 protein) in the structural model is said to correspond to the C220 residue. Another example is wherein a selected residue in a selected protein corresponds to C220 in a mutant p53 protein including a Y220C mutation (e.g., a Y220C p53 protein, or a human Y220C p53 protein) when the selected residue (e.g., cysteine residue) occupies essential the same sequence, spatial, or other structural position within the protein as C220 in the mutant p53 protein including a Y220C mutation (e.g., a Y220C p53 protein, or a human Y220C p53 protein).

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "protein complex" is used in accordance with its plain ordinary meaning and refers to a protein which is associated with an additional substance (e.g., another protein, protein subunit, or a compound). Protein complexes typically have defined quaternary structure. The association between the protein and the additional substance may be a covalent bond. In embodiments, the association between the protein and the additional substance (e.g., compound) is via non-covalent interactions. In embodiments, a protein complex refers to a group of two or more polypeptide chains. Proteins in a protein complex are linked by non-covalent protein-protein interactions. A non-limiting example of a protein complex is the proteasome.

The term "tumor protein p53" or "p53" refers to a protein that functions as a tumor suppressor and plays a key role in preventing cancer formation. In embodiments, the p53 protein is the human p53 protein. In embodiments, the p53 protein encoded by the TP53 gene has the amino acid sequence set forth in or corresponding to Entrez 7157, UniProt P04637, RefSeq (protein) NP_000537.3, RefSeq (protein) NP_001119584.1, RefSeq (protein) NP_001119585.1, RefSeq (protein) NP_001119586.1, RefSeq (protein) NP_001119587.1, RefSeq (protein) NP_001119588.1, RefSeq (protein) NP_001119589.1, RefSeq (protein) NP_001119590.1, RefSeq (protein) NP_001263624.1, RefSeq (protein) NP_001263625.1, RefSeq (protein) NP_001263626.1, RefSeq (protein) NP_001263627.1, RefSeq (protein) NP_001263628.1, RefSeq (protein) NP_001263689.1, or RefSeq (protein) NP_001263690.1. In embodiments, the amino acid sequence or nucleic acid sequence is the sequence known at the time of filing of the present application. In embodiments, p53 has the sequence:

(SEQ ID NO: 6)

```
MEEPQSDPSVEPPLSQETFSDLWKLLPENNVLSPLPSQAMDDLMLSPD

DIEQWFTEDPGPDEAPRMPEAAPPVAPAPAAPTPAAPAPAPSWPLSSS

VPSQKTYQGSYGFRLGFLHSGTAKSVTCTYSPALNKMFCQLAKTCPVQ

LWVDSTPPPGTRVRAMAIYKQSQHMTEVVRRCPHHERCSDSDGLAPPQ
```

-continued

HLIRVEGNLRVEYLDDRNTFRHSVVVPYEPPEVGSDCTTIHYNYMCNS

SCMGGMNRRPILTIITLEDSSGNLLGRNSFEVRVCACPGRDRRTEEEN

LRKKGEPHHELPPGSTKRALPNNTSSSPQPKKKPLDGEYFTLQIRGRE

RFEMFRELNEALELKDAQAGKEPGGSRAHSSHLKSKKGQSTSRHKKLM

FKTEGPDSD.

The term “transcriptional coactivator binding moiety” refers to a chemical group or moiety capable of binding to a transcriptional coactivator (e.g., BRD4 or p300), transcription factor, or protein involved in transcription or included in a transcription protein complex. In embodiments, the transcriptional coactivator binding moiety is capable of binding to a transcriptional coactivator, and is hereinafter referred to as a “direct transcriptional coactivator binding moiety.” In embodiments, the transcriptional coactivator binding moiety is capable of binding to a transcriptional factor, and is hereinafter referred to as a “transcriptional factor binding moiety.” In embodiments, the transcriptional coactivator binding moiety is capable of binding to a protein involved in transcription (e.g., a glucocorticoid protein), and is hereinafter referred to as “transcriptional protein binding moiety.” In embodiments, the transcriptional coactivator binding moiety is capable of binding to a protein included in a transcription protein complex, and is hereinafter referred to as a “transcriptional complex protein binding moiety.”

The term “transcriptional coactivator” refers to a protein that binds to a transcription factor (e.g., transcription activator) to increase the rate of transcription of a gene or a set of genes.

The terms “BRD” and “bromodomain” refer to a protein domain that recognizes acetylated lysine residues (e.g., on the N-terminal tails of histones). In embodiments, the BRD protein is a BRD1 protein. In embodiments, the BRD protein is a BRD2 protein. In embodiments, the BRD protein is a BRD4 protein. In embodiments, the BRD protein is a BRDT protein. The “BRD binding moiety” refers to a chemical group or moiety capable of binding to BRD.

The terms “BRD1”, “bromodomain-containing protein 1”, “BRPF2”, and “bromodomain and plant homeodomain (PHD) finger containing protein 2” refer to a protein subunit of various histone acetyltransferase complexes and plays a role in regulating transcription. In embodiments, the BRD1 protein encoded by the BRD1 gene has the amino acid sequence set forth in or corresponding to UniProt 095696, RefSeq (protein) NP_001291737.1, or RefSeq (protein) NP_001291738.1, or homolog thereof. In embodiments, the amino acid sequence or nucleic acid sequence is the sequence known at the time of filing of the present application. The “BRD1 binding moiety” refers to a chemical group or moiety capable of binding to BRD1.

The terms “BRD2” and “bromodomain-containing protein 2” refer to a protein that associates with hyperacetylated chromatin and plays a role in the regulation of transcription. In embodiments, the BRD2 protein encoded by the BRD2 gene has the amino acid sequence set forth in or corresponding to Entrez 6046, UniProt P25440, RefSeq (protein) NP_001106653.1, RefSeq (protein) NP_001186384.1, RefSeq (protein) NP_001186385.1, RefSeq (protein) NP_001278915.1, or RefSeq (protein) NP_005095.1, or homolog thereof. In embodiments, the amino acid sequence or nucleic acid sequence is the sequence known at the time of filing of the present application. The “BRD2 binding moiety” refers to a chemical group or moiety capable of binding to BRD2.

The terms “BRD4” and “bromodomain-containing protein 4” refer to a protein that associates with chromosomes during mitosis and plays a key role in transmission of epigenetic memory across cell divisions and transcription regulation. In embodiments, the BRD4 protein encoded by the BRD4 gene has the amino acid sequence set forth in or corresponding to Entrez 23476, UniProt 060885, RefSeq (protein) NP_001317313.1, RefSeq (protein) NP_055114.1, or RefSeq (protein) NP_490597.1. In embodiments, the amino acid sequence or nucleic acid sequence is the sequence known at the time of filing of the present application. In embodiments, BRD4 has the sequence:

(SEQ ID NO: 7)

MSAESGPGTRLRNLPVMGDGLETSQMSTTQAQAQPQPANAASTNPPPPETSNPNKPKRQT

NQLQYLLRVVLKTLWKHQFAWPFQQPVDAVKLNLPDYYKIIKTPMDMGTIKKRLENNYYW

NAQECIQDFNTMFTNCYIYNKPGDDIVLMAEALEKLFLQKINELPTEETEIMIVQAKGRG

RGRKETGTAKPGVSTVPNTTQASTPPQTQTPQPNPPPVQATPHPFPAVTPDLIVQTPVMT

VVPPQPLQTPPPVPPQPQPPPAPAPQPVQSHPPIIAATPQPVKTKKGVKRKADTTTPTTI

DPIHEPPSLPPEPKTTKLGQRRESSRPVKPPKKDVPDSQQHPAPEKSSKVSEQLKCCSGI

LKEMFAKKHAAYAWPFYKPVDVEALGLHDYCDIIKHPMDMSTIKSKLEAREYRDAQEFGA

DVRLMFSNCYKYNPPDHEVVAMARKLQDVFEMRFAKMPDEPEEPVVAVSSPAVPPPTKVV

APPSSSDSSSDSSSDSDSSTDDSEEERAQRLAELQEQLKAVHEQLAALSQPQQNKPKKKE

KDKKEKKKEKHKRKEEVEENKKSKAKEPPPKKTKKNNSSNSNVSKKEPAPMKSKPPPTYE

SEEEDKCKPMSYEEKRQLSLDINKLPGEKLGRVVHIIQSREPSLKNSNPDEIEIDFETLK

PSTLRELERYVTSCLRKKRKPQAEKVDVIAGSSKMKGFSSSESESSSESSSSDSEDSETE

MAPKSKKKGHPGREQKKHHHHHHQQMQQAPAPVPQQPPPPPQQPPPPPPPQQQQQPPPPP

PPPSMPQQAAPAMKSSPPPFIATQVPVLEPQLPGSVFDPIGHFTQPILHLPQPELPPHLP

-continued

QPPEHSTPPHLNQHAVVSPPALHNALPQQPSRPSNRAAALPPKPARPPAVSPALTQTPLL

PQPPMAQPPQVLLEDEEPPAPPLTSMQMQLYLQQLQKVQPPTPLLPSVKVQSQPPPPLPP

PPHPSVQQQLQQQPPPPPPPQPQPPPQQQHQPPPRPVHLQPMQFSTHIQQPPPPQGQQPP

HPPPGQQPPPPQPAKPQQVIQHHHSPRHHKSDPYSTGHLREAPSPLMIHSPQMSQFQSLT

HQSPPQQNVQPKKQELRAASVVQPQPLVVVKEEKIHSPIIRSEPFSPSLRPEPPKHPESI

KAPVHLPQRPEMKPVDVGRPVIRPPEQNAPPPGAPDKDKQKQEPKTPVAPKKDLKIKNMG

SWASLVQKHPTTPSSTAKSSSDSFEQFRRAAREKEEREKALKAQAEHAEKEKERLRQERM

RSREDEDALEQARRAHEEARRRQEQQQQRQEQQQQQQQQAAAVAAAATPQAQSSQPQS

MLDQQRELARKREQERRRREAMAATIDMNFQSDLLSIFEENLF.

The "BRD4 binding moiety" refers to a chemical group or moiety capable of binding to BRD4.

The terms "BRD7" and "bromodomain-containing protein 7" refer to a protein that plays a role in p53-mediated cell cycle arrest in response to oncogene progression from G1 to S phase. In embodiments, the BRD7 protein encoded by the BRD7 gene has the amino acid sequence set forth in or corresponding to Entrez 29117, UniProt Q9NPI1, RefSeq (protein) NP_001167455.1, or RefSeq (protein) NP_037395.2, or homolog thereof. In embodiments, the amino acid sequence or nucleic acid sequence is the sequence known at the time of filing of the present application. The "BRD7 binding moiety" refers to a chemical group or moiety capable of binding to BRD7.

The terms "BRD9" and "bromodomain-containing protein 9" refer to a protein that plays a role in chromatin remodeling and regulation of transcription. In embodiments, the BRD9 protein encoded by the BRD9 gene has the amino acid sequence set forth in or corresponding to UniProt Q9H8M2, RefSeq (protein) NP_001009877.2, RefSeq (protein) NP_001304880.1, or RefSeq (protein) NP_076413.3, or homolog thereof. In embodiments, the amino acid sequence or nucleic acid sequence is the sequence known at the time of filing of the present application. The "BRD9 binding moiety" refers to a chemical group or moiety capable of binding to BRD9.

The terms "BRDT" and "bromodomain testis-specific protein" refer to a testis-specific chromatin protein that plays a key role in spermatogenesis. In embodiments, the BRDT protein encoded by the BRDT gene has the amino acid sequence set forth in or corresponding to Entrez 676, UniProt Q58F21, RefSeq (protein) NP_001229734.2, RefSeq (protein) NP_001229735.2, RefSeq (protein) NP_001229736.2, RefSeq (protein) NP_001229737.2, RefSeq (protein) NP_001229739.2, RefSeq (protein) NP_001717.3, or RefSeq (protein) NP_997072.2, or homolog thereof. In embodiments, the amino acid sequence or nucleic acid sequence is the sequence known at the time of filing of the present application. The "BRDT binding moiety" refers to a chemical group or moiety capable of binding to BRDT.

The term "p300-CBP" refers to a coactivator family composed of p300 and CREBBP. Both p300 and CBP interact with numerous transcription factors and increase the expression of their target genes. The "p300-CBP binding moiety" refers to a chemical group or moiety capable of binding to p300-CBP.

The term "histone acetyltransferase p300" or "p300" refers to a protein that regulates transcription of genes via chromatin remodeling. p300 plays an essential role in regulating cell growth and division, and prevents the growth of cancerous tumors. In embodiments, the p300 protein encoded by the EP300 gene has the amino acid sequence set forth in or corresponding to Entrez 2033, UniProt Q09472, or RefSeq (protein) NP_001420.2. In embodiments, the amino acid sequence or nucleic acid sequence is the sequence known at the time of filing of the present application. In embodiments, p300 has the sequence:

(SEQ ID NO: 8)

MAENVVEPGPPSAKRPKLSSPALSASASDGTDFGSLFDLEHDLPDELINSTELGLTNGGD

INQLQTSLGMVQDAASKHKQLSELLRSGSSPNLNMGVGGPGQVMASQAQQSSPGLGLINS

MVKSPMTQAGLTSPNMGMGTSGPNQGPTQSTGMMNSPVNQPAMGMNTGMNAGMNPGML

AAGNGQGIMPNQVMNGSIGAGRGRQNMQYPNPGMGSAGNLLTEPLQQGSPQMGGQTGLR

GPQPLKMGMMNNPNPYGSPYTQNPGQQIGASGLGLQIQTKTVLSNNLSPFAMDKKAVPGGG

MPNMGQQPAPQVQQPGLVTPVAQGMGSGAHTADPEKRKLIQQQLVLLLHAHKCQRREQAN

GEVRQCNLPHCRTMKNVLNHMTHCQSGKSCQVAHCASSRQIISHWKNCTRHDCPVCLPLKN

AGDKRNQQPILTGAPVGLGNPSSLGVGQQSAPNLSTVSQIDPSSIERAYAALGLPYQVNQM

PTQPQVQAKNQQNQQPGQSPQGMRPMSNMSASPMGVNGGVGVQTPSLLSDSMLHSAINSQ

NPMMSENASVPSLGPMPTAAQPSTTGIRKQWHEDITQDLRNHLVHKLVQAIFPTPDPAAL

KDRRMENLVAYARKVEGDMYESANNRAEYYHLLAEKIYKIQKELEEKRRTRLQKQNMLPN

AAGMVPVSMNPGPNMGQPQPGMTSNGPLPDPSMIRGSVPNQMMPRITPQSGLNQFGQMSM

-continued

```
AQPPIVPRQTPPLQHHGQLAQPGALNPPMGYGPRMQQPSNQGQFLPQTQFPSQGMNVTNI
PLAPSSGQAPVSQAQMSSSSCPVNSPIMPPGSQGSHIHCPQLPQPALHQNSPSPVPSRTP
TPHHTPPSIGAQQPPATTIPAPVPTPPAMPPGPQSQALHPPPRQTPTPPTTQLPQQVQPS
LPAAPSADQPQQQPRSQQSTAASVPTPTAPLLPPQPATPLSQPAVSIEGQVSNPPSTSST
EVNSQAIAEKQPSQEVKMEAKMEVDQPEPADTQPEDISESKVEDCKMESTETEERSTELK
TEIKEEEDQPSTSATQSSPAPGQSKKKIFKPEELRQALMPTLEALYRQDPESLPFRQPVD
PQLLGIPDYFDIVKSPMDLSTIKRKLDTGQYQEPWQYVDDIWLMFNNAWLYNRKTSRVYK
YCSKLSEVFEQEIDPVMQSLGYCCGRKLEFSPQTLCCYGKQLCTIPRDATYYSYQNRYHF
CEKCFNEIQGESVSLGDDPSQPQTTINKEQFSKRKNDTLDPELFVECTECGRKMHQICVL
HHEIIWPAGFVCDGCLKKSARTRKENKFSAKRLPSTRLGTFLENRVNDFLRRQNHPESGE
VTVRVVHASDKTVEVKPGMKARFVDSGEMAESFPYRTKALFAFEEIDGVDLCFFGMHVQE
YGSDCPPPNQRRVYISYLDSVHFFRPKCLRTAVYHEILIGYLEYVKKLGYTTGHIWACPP
SEGDDYIFHCHPPDQKIPKPKRLQEWYKKMLDKAVSERIVHDYKDIFKQATEDRLTSAKE
LPYFEGDFWPNVLEESIKELEQEEEERKREENTSNESTDVTKGDSKNAKKKNNKKTSKNK
SSLSRGNKKKPGMPNVSNDLSQKLYATMEKHKEVFFVIRLIAGPAANSLPPIVDPDPLIP
CDLMDGRDAFLTLARDKHLEFSSLRRAQWSTMCMLVELHTQSQDRFVYTCNECKHHVETR
WHCTVCEDYDLCITCYNTKNHDHKMEKLGLGLDDESNNQQAAATQSPGDSRRLSIQRCIQ
SLVHACQCRNANCSLPSCQKMKRVVQHTKGCKRKTNGGCPICKQLIALCCYHAKHCQENK
CPVPFCLNIKQKLRQQQLQHRLQQAQMLRRRMASMQRTGVVGQQQGLPSPTPATPTTPTG
QQPTTPQTPQPTSQPQPTPPNSMPPYLPRTQAAGPVSQGKAAGQVTPPTPPQTAQPPLPG
PPPAAVEMAMQIQRAAETQRQMAHVQIFQRPIQHQMPPMTPMAPMGMNPPPMTRGPSGHL
EPGMGPTGMQQQPPWSQGGLPQPQQLQSGMPRPAMMSVAQHGQPLNMAPQPGLGQVGISP
LKPGTVSQQALQNLLRTLRSPSSPLQQQQVLSILHANPQLLAAFIKQRAAKYANSNPQPI
PGQPGMPQGQPGLQPPTMPGQQGVHSNPAMQNMNPMQAGVQRAGLPQQQPQQQLQPPMG
GMSPQAQQMNMNHNTMPSQFRDILRRQQMMQQQQQGAGPGIGPGMANHNQFQQPQGV
GYPPQQQQRMQHHMQQMQQGNMGQIGQLPQALGAEAGASLQAYQQRLLQQQMGSPVQP
NPMSPQQHMLPNQAQSPHLQGQQIPNSLSNQVRSPQPVPSPRPQSQPPHSSPSPRMQPQPSPH
HVSPQTSSPHPGLVAAQANPMEQGHFASPDQNSMLSQLASNPGMANLHGASATDLGLSTDN
SDLNSNLSQSTLDIH.
```

The "p300 binding moiety" refers to a chemical group or moiety capable of binding to p300.

The terms "CREBBP", "CBP", and "CREB-binding protein" refer to a protein that activates transcription. In embodiments, the CREBBP protein encoded by the CREBBP gene has the amino acid sequence set forth in or corresponding to Entrez 1387, UniProt Q92793, RefSeq (protein) NP_001073315.1, or RefSeq (protein) NP_004371.2, or homolog thereof. In embodiments, the amino acid sequence or nucleic acid sequence is the sequence known at the time of filing of the present application. The "CREBBP binding moiety" refers to a chemical group or moiety capable of binding to CREBBP.

The terms "glucocorticoid receptor" or "GR" refer to the receptor to which cortisol and other glucocorticoids bind. The GR regulates genes controlling development, metabolism, and immune response. In embodiments, the GR protein encoded by the NR3C1 gene has the amino acid sequence set forth in or corresponding to Entrez 2908, UniProt P04150, UniProt Q3MSN4, RefSeq (protein) NP_000167.1, RefSeq (protein) NP_001018084.1, RefSeq (protein) NP_001018085.1, RefSeq (protein) NP_001018086.1, RefSeq (protein) NP_001018087.1, RefSeq (protein) NP_001018661.1, RefSeq (protein) NP_001019265.1, RefSeq (protein) NP_001191187.1, RefSeq (protein) NP_001191188.1, RefSeq (protein) NP_001191189.1, RefSeq (protein) NP_001191190.1, RefSeq (protein) NP_001191191.1, RefSeq (protein) NP_001191192.1, or RefSeq (protein) NP_001191193.1, or homolog thereof. In embodiments, the amino acid sequence or nucleic acid sequence is the sequence known at the time of filing of the present application. In embodiments, GR has the sequence:

(SEQ ID NO: 9)

```
MDSKESLTPGREENPSSVLAQERGDVMDFYKTLRGGATVKVSASSPSLA
VASQSDSKQRRLLVDFPKGSVSNAQQPDLSKAVSLSMGLYMGETETKVM
GNDLGFPQQGQISLSSGETDLKLLEESIANLNRSTSVPENPKSSASTAV
SAAPTEKEFPKTHSDVSSEQQHLKGQTGTNGGNVKLYTTDQSTFDILQD
LEFSSGSPGKETNESPWRSDLLIDENCLLSPLAGEDDSFLLEGNSNEDC
KPLILPDTKPKIKDNGDLVLSSPSNVTLPQVKTEKEDFIELCTPGVIKQ
EKLGTVYCQASFPGANIIGNKMSAISVHGVSTSGGQMYHYDMNTASLSQ
QQDQKPIFNVIPPIPVGSENWNRCQGSGDDNLTSLGTLNFPGRTVFSNG
YSSPSMRPDVSSPPSSSSTATTGPPPKLCLVCSDEASGCHYGVLTCGSC
KVFFKRAVEGQHNYLCAGRNDCIIDKIRRKNCPACRYRKCLQAGMNLEA
RKTKKKIKGIQQATTGVSQETSENPGNKTIVPATLPQLTPTLVSLLEVI
EPEVLYAGYDSSVPDSTWRIMTTLNMLGGRQVIAAVKWAKAIPGFRNLH
LDDQMTLLQYSWMFLMAFALGWRSYRQSSANLLCFAPDLIINEQRMTLP
CMYDQCKHMLYVSSELHRLQVSYEEYLCMKTLLLLSSVPKDGLKSQELF
DEIRMTYIKELGKAIVKREGNSSQNWQRFYQLTKLLDSMHEVVENLLNY
CFQTFLDKTMSIEFPEMLAEIITNQIPKYSNGNIKKLLFHQK.
```

The "glucocorticoid receptor binding moiety" refers to a chemical group or moiety capable of binding to glucocorticoid receptor.

The terms "PCAF" and "p300/CBP-associated factor" refer to a protein that plays a role in transcriptional activation. In embodiments, the PCAF protein has the amino acid sequence set forth in or corresponding to Entrez 8850, UniProt Q92831, or RefSeq (protein) NP_003875.3, or homolog thereof. In embodiments, the amino acid sequence or nucleic acid sequence is the sequence known at the time of filing of the present application. The "PCAF binding moiety" refers to a chemical group or moiety capable of binding to PCAF.

The terms "GCN5L2", "KAT2A", and "histone acetyltransferase KAT2A" refer to a protein that activates transcription. In embodiments, the GCN5L2 protein encoded by the KAT2A gene has the amino acid sequence set forth in or corresponding to Entrez 2648, UniProt Q92830, or RefSeq (protein) NP_066564.2, or homolog thereof. In embodiments, the amino acid sequence or nucleic acid sequence is the sequence known at the time of filing of the present application. The "GCN5L2 binding moiety" refers to a chemical group or moiety capable of binding to GCN5L2.

The terms "CECR2" and "cat eye syndrome critical region protein 2" refer to a protein that is part of histone-modifying complexes and plays a role in development (e.g., embryogenesis or spermatogenesis). In embodiments, the CECR2 protein has the amino acid sequence set forth in or corresponding to UniProt Q9BXF3, RefSeq (protein) NP_001276975.1, or RefSeq (protein) NP_001276976.1, or homolog thereof. In embodiments, the amino acid sequence or nucleic acid sequence is the sequence known at the time of filing of the present application. The "CECR2 binding moiety" refers to a chemical group or moiety capable of binding to CECR2.

The terms "BRPF" and "bromodomain and plant homeodomain (PHD) finger containing protein" refer to a family of proteins involved in the recruitment of histone acetyltransferases to chromatin. In embodiments, the BRPF protein is a BRPF1 protein. In embodiments, the BRPF protein is a BRPF3 protein. In embodiments, the BRPF protein is a ATAD2 protein. The "BRPF binding moiety" refers to a chemical group or moiety capable of binding to BRPF.

The terms "BRPF1" and "bromodomain and plant homeodomain (PHD) finger containing protein 1" refer to a protein subunit of various histone acetyltransferase complexes and plays a role in regulating transcription. In embodiments, the BRPF1 protein encoded by the BRPF1 gene has the amino acid sequence set forth in or corresponding to UniProt P55201, RefSeq (protein) NP_001003694.1, RefSeq (protein) NP_001305978.1, RefSeq (protein) NP_001305979.1, or RefSeq (protein) NP_004625.2, or homolog thereof. In embodiments, the amino acid sequence or nucleic acid sequence is the sequence known at the time of filing of the present application. The "BRPF1 binding moiety" refers to a chemical group or moiety capable of binding to BRPF1.

The terms "BRPF3" and "bromodomain and plant homeodomain (PHD) finger containing protein 3" refer to a protein subunit of various histone acetyltransferase complexes and plays a role in DNA replication initiation. In embodiments, the BRPF3 protein encoded by the BRPF3 gene has the amino acid sequence set forth in or corresponding to UniProt Q9ULD4, or RefSeq (protein) NP_056510.2, or homolog thereof. In embodiments, the amino acid sequence or nucleic acid sequence is the sequence known at the time of filing of the present application. The "BRPF3 binding moiety" refers to a chemical group or moiety capable of binding to BRPF3.

The terms "ATAD2" and "ATPase family AAA domain-containing protein 2" refer to a transcriptional coactivator and plays a role in the expression of target genes (e.g., estradiol genes). In embodiments, the ATAD2 protein encoded by the ATAD2 gene has the amino acid sequence set forth in or corresponding to UniProt Q6PL18, or RefSeq (protein) NP_054828.2, or homolog thereof. In embodiments, the amino acid sequence or nucleic acid sequence is the sequence known at the time of filing of the present application. The "ATAD2 binding moiety" refers to a chemical group or moiety capable of binding to ATAD2.

The terms "BAZ" and "bromodomain adjacent to zinc finger domain protein" refer to a family of bromodomain containing proteins. In embodiments, the BAZ protein is a BAZ2 protein. In embodiments, the BAZ protein is a BAZ2A protein. In embodiments, the BAZ protein is a BAZ2B protein. In embodiments, the BAZ protein is a TIF1α protein. The "BAZ binding moiety" refers to a chemical group or moiety capable of binding to BAZ.

The terms "BAZ2" and "bromodomain adjacent to zinc finger domain protein 2" refer to a family of bromodomain containing proteins. In embodiments, the BAZ2 protein is a BAZ2A protein. In embodiments, the BAZ2 protein is a BAZ2B protein. The "BAZ2 binding moiety" refers to a chemical group or moiety capable of binding to BAZ2.

The terms "BAZ2A" and "bromodomain adjacent to zinc finger domain protein 2A" refer to a protein subunit of the nucleolar remodeling complex and plays a role in regulation of transcription. In embodiments, the BAZ2A protein encoded by the BAZ2A gene has the amino acid sequence set forth in or corresponding to Entrez 11176, UniProt Q9UIF9, or RefSeq (protein) NP_038477.2, or homolog thereof. In embodiments, the amino acid sequence or nucleic acid sequence is the sequence known at the time of filing of the present application. The "BAZ2A binding moiety" refers to a chemical group or moiety capable of binding to BAZ2A.

The terms "BAZ2B" and "bromodomain adjacent to zinc finger domain protein 2B" refer to a protein involved in regulation of transcription. In embodiments, the BAZ2B protein encoded by the BAZ2B gene has the amino acid sequence set forth in or corresponding to UniProt Q9UIF8, RefSeq (protein) NP_001276904.1, or RefSeq (protein) NP_038478.2, or homolog thereof. In embodiments, the amino acid sequence or nucleic acid sequence is the sequence known at the time of filing of the present application. The "BAZ2B binding moiety" refers to a chemical group or moiety capable of binding to BAZ2B.

The terms "TIF1α" and "transcriptional intermediary factor 1α" refer to a protein involved in regulation of transcription. In embodiments, the TIF1α protein encoded by the TRIM24 gene has the amino acid sequence set forth in or corresponding to Entrez 8805, UniProt 015164, RefSeq (protein) NP_003843.3, or RefSeq (protein) NP_056989.2, or homolog thereof. In embodiments, the amino acid sequence or nucleic acid sequence is the sequence known at the time of filing of the present application. The "TIF1α binding moiety" refers to a chemical group or moiety capable of binding to TIF1α.

The terms "TAF" and "TBP-associated factor" refer to a family of proteins that associate with the TATA-binding protein in transcription initiation. In embodiments, the TAF protein is a TAF1 protein. In embodiments, the TAF protein is a TAF1L protein. The "TAF binding moiety" refers to a chemical group or moiety capable of binding to TAF.

The terms "TAF1", "TBP-associated factor 250 kDa", and "transcription initiation factor TFIID subunit 1" refer to a protein involved in initiation of transcription by RNA polymerase II. In embodiments, the TAF1 protein encoded by the TAF1 gene has the amino acid sequence set forth in or corresponding to Entrez 6872, UniProt P21675, RefSeq (protein) NP_001273003.1, RefSeq (protein) NP_004597.2, or RefSeq (protein) NP_620278.1, or homolog thereof. In embodiments, the amino acid sequence or nucleic acid sequence is the sequence known at the time of filing of the present application. The "TAF1 binding moiety" refers to a chemical group or moiety capable of binding to TAF1.

The terms "TAF1L" and "transcription initiation factor TFIID subunit 1-like" refer to a protein that may act as a functional substitute for TAF1/TAFII250 during male meiosis. In embodiments, the TAF1L protein encoded by the TAF1L gene has the amino acid sequence set forth in or corresponding to UniProt Q8IZX4 or RefSeq (protein) NP_722516.1, or homolog thereof. In embodiments, the amino acid sequence or nucleic acid sequence is the sequence known at the time of filing of the present application. The "TAF1L binding moiety" refers to a chemical group or moiety capable of binding to TAF1L.

The terms "SMARC" and "SWI/SNF related, matrix associated, actin dependent regulator of chromatin" refer to a family of proteins involved in regulation of transcription. In embodiments, the SMARC protein is a PB1 protein. In embodiments, the SMARC protein is a SMARCA2 protein. In embodiments, the SMARC protein is a SMARCA2A protein. In embodiments, the SMARC protein is a SMARCA2B protein. In embodiments, the SMARC protein is a SMARCA4 protein. The "SMARC binding moiety" refers to a chemical group or moiety capable of binding to SMARC.

The terms "PB1" and "RNA-directed RNA polymerase catalytic subunit" refer to an RNA-dependent RNA polymerase responsible for replication and transcription of virus RNA segments. In embodiments, the PB1 protein encoded by the PB1 gene has the amino acid sequence set forth in or corresponding to UniProt Q0A461, or homolog thereof. In embodiments, the amino acid sequence or nucleic acid sequence is the sequence known at the time of filing of the present application. The "PB1 binding moiety" refers to a chemical group or moiety capable of binding to PB1.

The terms "SMARCA2" and "probable global transcription activator SNF2L2" refer to a protein involved in regulation of transcription. In embodiments, the SMARCA2 protein encoded by the SMARCA2 gene has the amino acid sequence set forth in or corresponding to Entrez 6595, UniProt P51531, RefSeq (protein) NP_001276325.1, RefSeq (protein) NP_001276326.1, RefSeq (protein) NP_003061.3, or RefSeq (protein) NP_620614.2, or homolog thereof. In embodiments, the amino acid sequence or nucleic acid sequence is the sequence known at the time of filing of the present application. The "SMARCA2 binding moiety" refers to a chemical group or moiety capable of binding to SMARCA2.

The terms "SMARCA4", "transcription activator BRG1", and "ATP-dependent chromatin remodeler" refer to a protein involved in regulation of transcription. In embodiments, the SMARCA4 protein encoded by the SMARCA4 gene has the amino acid sequence set forth in or corresponding to Entrez 6597, UniProt P51532, UniProt Q9HBD4, RefSeq (protein) NP_001122316.1, RefSeq (protein) NP_001122317.1, RefSeq (protein) NP_001122318.1, RefSeq (protein) NP_001122319.1, RefSeq (protein) NP_001122320.1, RefSeq (protein) NP_003063.2, or RefSeq (protein) NP_001122321.1, or homolog thereof. In embodiments, the amino acid sequence or nucleic acid sequence is the sequence known at the time of filing of the present application. The "SMARCA4 binding moiety" refers to a chemical group or moiety capable of binding to SMARCA4.

II. Compounds

In an aspect is provided a compound, or a pharmaceutically acceptable salt thereof, having the formula:

(I)

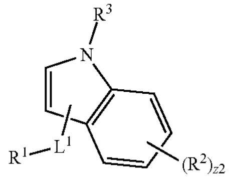

or (II)

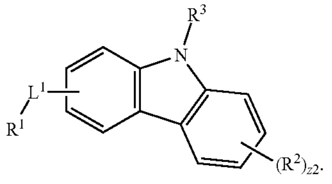

$L^1$ is a bond or covalent linker. $R^1$ is a transcriptional coactivator binding moiety. $R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, $—NS(O)F_2$, $—NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $-L^2-R^{23}$; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl. $X^2$ is independently $-F$, $-Cl$, $-Br$, or $-I$. The symbol n2 is independently an integer from 0 to 4. The symbols m2 and v2 are independently 1 or 2. The symbol z2 is an integer from 0 to 7. $L^2$ is independently a bond or covalent linker. $R^{23}$ is independently a detectable moiety. $R^3$ is a covalent cysteine modifier moiety.

In embodiments, $L^1$ is a bond or covalent linker. In embodiments, $R^1$ is a transcriptional coactivator binding moiety. In embodiments, $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl. $X^2$ is independently $-F$, $-Cl$, $-Br$, or $-I$. The symbol n2 is independently an integer from 0 to 4. The symbols m2 and v2 are independently 1 or 2. The symbol z2 is an integer from 0 to 7. $R^3$ is a covalent cysteine modifier moiety.

In embodiments, $L^1$ is a bond or covalent linker. In embodiments, $R^1$ is a transcriptional coactivator binding moiety. In embodiments, $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl. $X^2$ is independently $-F$, $-Cl$, $-Br$, or $-I$. The symbol n2 is independently an integer from 0 to 4. The symbols m2 and v2 are independently 1 or 2. The symbol z2 is an integer from 0 to 7. $R^3$ is a covalent cysteine modifier moiety.

In embodiments, the compound has the formula:

(Ia)

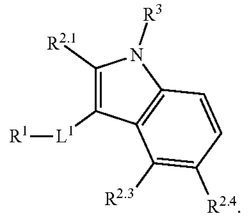

$L^1$, $R^1$, $R^{2.1}$, $R^{2.3}$, $R^{2.4}$, and $R^3$ are as described herein, including in embodiments.

In embodiments, the compound has the formula:

(Ib)

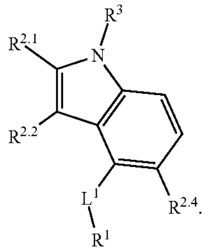

$L^1$, $R^1$, $R^{2.1}$, $R^{2.2}$, $R^{2.4}$, and $R^3$ are as described herein, including in embodiments.

In embodiments, the compound has the formula:

(Ic)

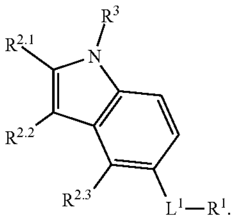

$L^1$, $R^1$, $R^{2.1}$, $R^{2.2}$, $R^{2.3}$, and $R^3$ are as described herein, including in embodiments.

In embodiments, the compound has the formula:

(Id)

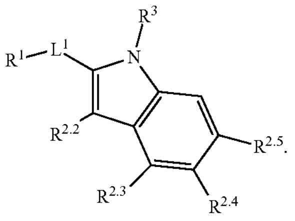

$L^1$, $R^1$, $R^{2.2}$, $R^{2.3}$, $R^{2.4}$, $R^{2.5}$, and $R^3$ are as described herein, including in embodiments.

In embodiments, the compound has the formula:

(Ie)

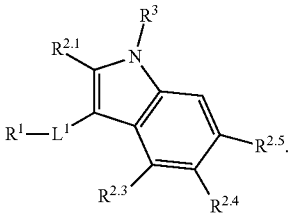

$L^1$, $R^1$, $R^{2.1}$, $R^{2.3}$, $R^{2.4}$, $R^{2.5}$, and $R^3$ are as described herein, including in embodiments.

In embodiments, the compound has the formula:

(If)

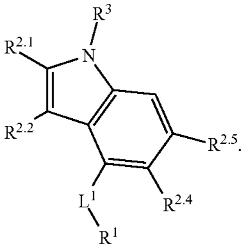

$L^1$, $R^1$, $R^{2.1}$, $R^{2.2}$, $R^{2.4}$, $R^{2.5}$, and $R^3$ are as described herein, including in embodiments.

In embodiments, the compound has the formula:

(Ig)

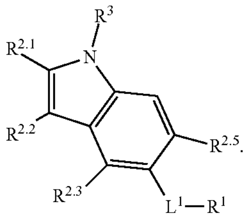

$L^1$, $R^1$, $R^{2.1}$, $R^{2.2}$, $R^{2.3}$, $R^{2.5}$, and $R^3$ are as described herein, including in embodiments.

In embodiments, the compound has the formula:

(Ih)

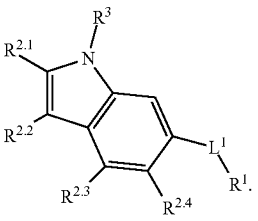

$L^1$, $R^1$, $R^{2.1}$, $R^{2.2}$, $R^{2.3}$, $R^{2.4}$, and $R^3$ are as described herein, including in embodiments.

In embodiments, the compound has the formula:

(IIa)

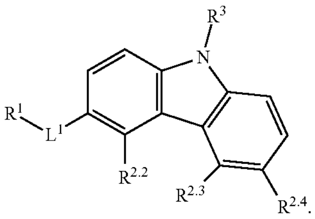

$L^1$, $R^1$, $R^{2.2}$, $R^{2.3}$, $R^{2.4}$, and $R^3$ are as described herein, including in embodiments.

In embodiments, the compound has the formula:

(IIb)

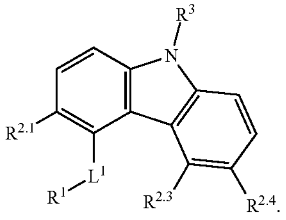

$L^1$, $R^1$, $R^{2.1}$, $R^{2.3}$, $R^{2.4}$, and $R^3$ are as described herein, including in embodiments.

In embodiments, the compound has the formula:

(IIc)

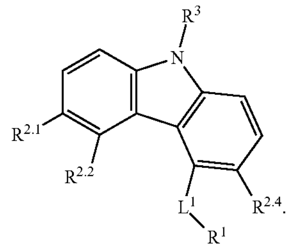

$L^1$, $R^1$, $R^{2.1}$, $R^{2.2}$, $R^{2.4}$, and $R^3$ are as described herein, including in embodiments.

In embodiments, the compound has the formula:

(IId)

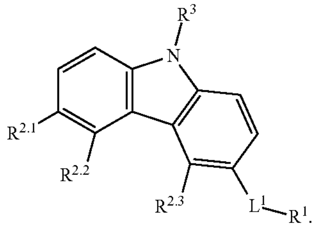

$L^1$, $R^1$, $R^{2.1}$, $R^{2.2}$, $R^{2.3}$, and $R^3$ are as described herein, including in embodiments.

In embodiments, the compound has the formula:

(IIe)

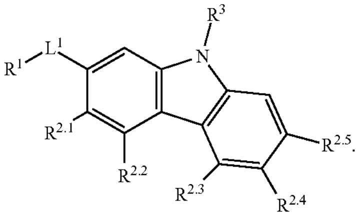

$L^1$, $R^1$, $R^{2.1}$, $R^{2.2}$, $R^{2.3}$, $R^{2.4}$, $R^{2.5}$, and $R^3$ are as described herein, including in embodiments.

In embodiments, the compound has the formula:

(IIf)

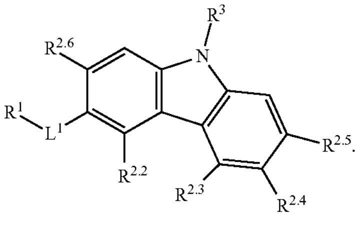

$L^1$, $R^1$, $R^{2.2}$, $R^{2.3}$, $R^{2.4}$, $R^{2.5}$, $R^{2.6}$, and $R^3$ are as described herein, including in embodiments.

In embodiments, the compound has the formula:

(IIg)

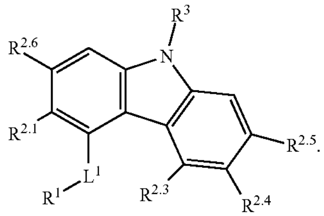

$L^1$, $R^1$, $R^{2.1}$, $R^{2.3}$, $R^{2.4}$, $R^{2.5}$, $R^{2.6}$, and $R^3$ are as described herein, including in embodiments.

In embodiments, the compound has the formula:

(IIh)

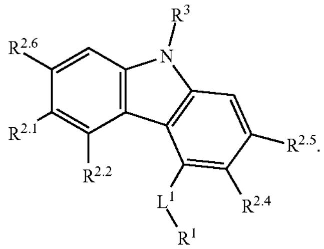

$L^1$, $R^1$, $R^{2.1}$, $R^{2.2}$, $R^{2.4}$, $R^{2.5}$, $R^{2.6}$, and $R^3$ are as described herein, including in embodiments.

In embodiments, the compound has the formula:

(IIj)

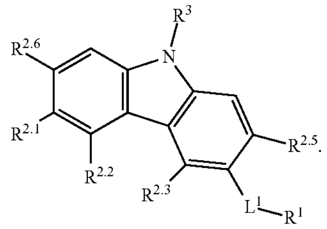

$L^1$, $R^1$, $R^{2.1}$, $R^{2.2}$, $R^{2.3}$, $R^{2.5}$, $R^{2.6}$, and $R^3$ are as described herein, including in embodiments.

In embodiments, the compound has the formula:

(IIk)

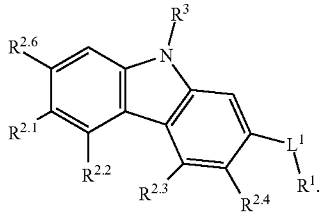

$L^1$, $R^1$, $R^{2.1}$, $R^{2.2}$, $R^{2.3}$, $R^{2.4}$, $R^{2.6}$, and $R^3$ are as described herein, including in embodiments.

$R^{2.1}$, $R^{2.2}$, $R^{2.3}$, $R^{2.4}$, $R^{2.5}$, and $R^{2.6}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC$ (O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, —NS(O)$F_2$, —NS(O)$FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^2$-$R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.1}$, $R^{2.2}$, $R^{2.3}$, $R^{2.4}$, $R^{2.5}$, and $R^{2.6}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, —NS(O)$F_2$, —NS(O)$FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.1}$, $R^{2.2}$, $R^{2.3}$, and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, —NS(O)$F_2$, —NS(O)$FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^2$-$R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.1}$, $R^{2.2}$, $R^{2.3}$, and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or -$L^2$-$R^{23}$; two adjacent $R^2$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $L^2$, $R^{2A}$, $R^{2B}$, $R^{2C}$, $R^{2D}$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^2$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^2$ is independently halogen, $—CX^2_3$, $—CHX^2_2$, $—CH_2X^2$, $—OCX^2_3$, $—OCH_2X^2$, $—OCHX^2_2$, —CN, $—SO_2R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^2$ is independently halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^2$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^2$ is independently halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NS(O)F_2$, $—NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or $-L^2-R^{23}$; two adjacent $R^2$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). $L^2$ and $R^{23}$ are as described herein, including in embodiments.

In embodiments, $R^2$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered); two adjacent $R^2$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

$R^{20}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —NS(O)$F_2$, —NS(O)$FNH_2$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), $R^{21}$-substituted or unsubstituted heteroaryl (e.g., 5 to 10 membered, 5 to 9 membered, or 5 to 6 membered), or -$L^2$-$R^{23}$. $L^2$ and $R^{23}$ are as described herein, including in embodiments.

In embodiments, $R^{20}$ is independently —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered).

$R^{21}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —NS(O)$F_2$, —NS(O)$FNH_2$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), $R^{22}$-substituted or unsubstituted heteroaryl (e.g., 5 to 10 membered, 5 to 9 membered, or 5 to 6 membered), or -$L^2$-$R^{23}$. $L^2$ and $R^{23}$ are as described herein, including in embodiments.

In embodiments, $R^{21}$ is independently —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered).

$R^{22}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —NS(O)$F_2$, —NS(O)$FNH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), unsubstituted heteroaryl (e.g., 5 to 10 membered, 5 to 9 membered, or 5 to 6 membered), or $-L^2$-$R^{23}$. $L^2$ and $R^{23}$ are as described herein, including in embodiments.

In embodiments, $R^{22}$ is independently —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^2$ is independently substituted or unsubstituted $C_1$-$C_4$ alkyl, or substituted or unsubstituted 2 to 6 membered heteroalkyl. In embodiments, $R^2$ is independently substituted or unsubstituted $C_1$-$C_4$ alkyl. In embodiments, $R^2$ is independently oxo-substituted $C_1$-$C_4$ alkyl. In embodiments, $R^2$ is independently substituted or unsubstituted 2 to 6 membered heteroalkyl. In embodiments, $R^2$ is independently oxo-substituted 2 to 6 membered heteroalkyl. In embodiments, $R^2$ is independently —C(O)H, —$CH_2C$(O)H, —$CH_2C$(O)OH, —C(O)OH, —$CH_2NHCH_3$, —$CH_2NH_2$, or —$CH_2N(CH_3)_2$. In embodiments, $R^2$ is independently —C(O)H. In embodiments, $R^2$ is independently —$CH_2C$(O)H. In embodiments, $R^2$ is independently —$CH_2C$(O)OH. In embodiments, $R^2$ is independently —C(O)OH. In embodiments, $R^2$ is independently —$CH_2NHCH_3$. In embodiments, $R^2$ is independently —$CH_2NH_2$. In embodiments, $R^2$ is independently —$CH_2N(CH_3)_2$.

In embodiments, $R^2$ is independently —$NH_2$, substituted or unsubstituted 3 to 6 membered heteroalkyl, substituted or unsubstituted 4 to 7 membered heterocycloalkyl,

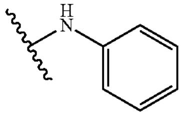, or 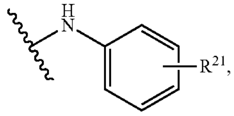, wherein $R^{21}$ is as described herein, including in embodiments. In embodiments, $R^{2.1}$ is independently

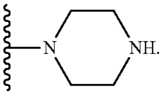

In embodiments, $R^2$ is independently

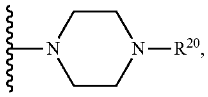, wherein $R^{20}$ is as described herein, including in embodiments.

In embodiments, $R^2$ is independently —$NH_2$, —$NHCH_3$, —$N(CH_3)_3$,

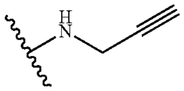, 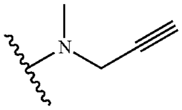,

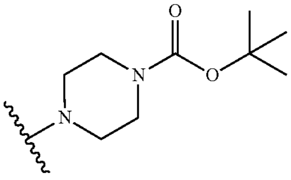, 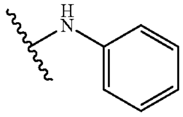,

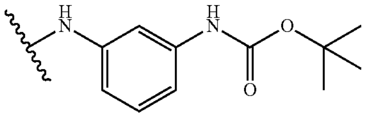,

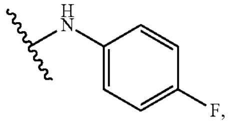, or 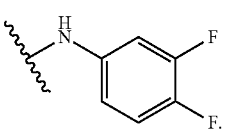

In embodiments, $R^2$ is independently —$NH_2$. In embodiments, $R^2$ is independently —$NHCH_3$. In embodiments, $R^2$ is independently —$N(CH_3)_3$. In embodiments, $R^2$ is independently

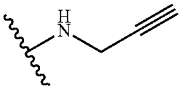.

In embodiments, $R^2$ is independently

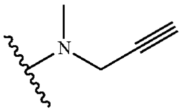.

In embodiments, $R^2$ is independently

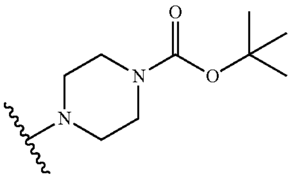.

In embodiments, $R^2$ is independently

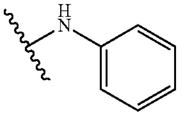.

In embodiments, $R^2$ is independently

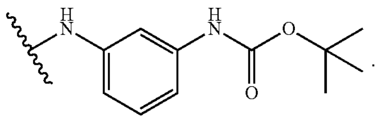 [SMILES: *Nc1cccc(NC(=O)OC(C)(C)C)c1]

In embodiments, $R^2$ is independently

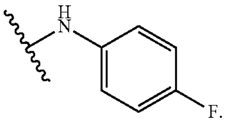 [SMILES: *Nc1ccc(F)cc1]

In embodiments, $R^2$ is independently

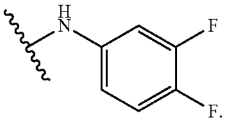

In embodiments, $R^2$ is independently —C(O)NR$^{2A}$R$^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^2$ is independently

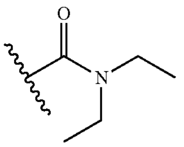,

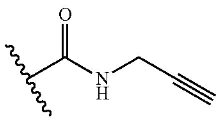, or

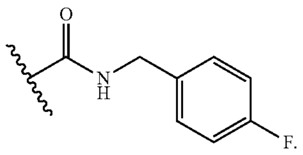

In embodiments, $R^2$ is independently

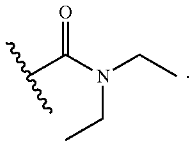 [SMILES: *C(=O)N(CC)CC]

In embodiments, $R^2$ is independently

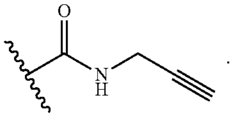 [SMILES: *C(=O)NCC#C]

In embodiments, $R^2$ is independently

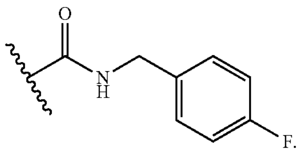 [SMILES: *C(=O)NCc1ccc(F)cc1]

In embodiments, $R^2$ is independently halogen. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently $R^{20}$-substituted or unsubstituted 5 or 6 membered heteroaryl, wherein $R^{20}$ is as described herein, including in embodiments. In embodiments, $R^2$ is independently $R^{20}$-substituted or unsubstituted thienyl, wherein $R^{20}$ is as described herein, including in embodiments. In embodiments, $R^2$ is independently

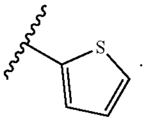 [SMILES: *c1cccs1]

In embodiments, $R^2$ is independently

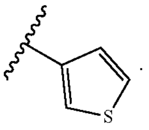 [SMILES: *c1ccsc1]

In embodiments, $R^2$ is independently

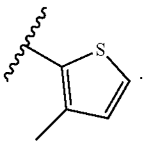 [SMILES: *c1sccc1C]

In embodiments, $R^2$ is independently

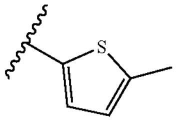
.

In embodiments, $R^2$ is independently

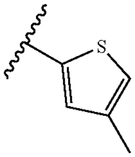
.

In embodiments, $R^2$ is independently

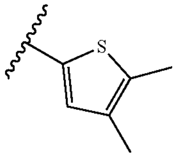
.

In embodiments, $R^2$ is independently

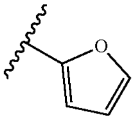
.

In embodiments, $R^2$ is independently

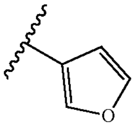
.

In embodiments, $R^2$ is independently

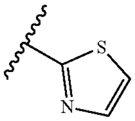
.

In embodiments, $R^2$ is independently

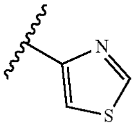
.

In embodiments, $R^2$ is independently

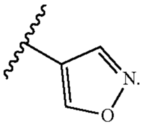 [SMILES: *c1cnoc1]
.

In embodiments, $R^2$ is independently

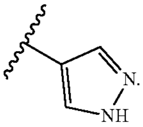
.

In embodiments, $R^2$ is independently

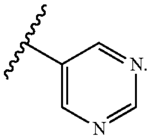 [SMILES: *c1cncnc1]
.

In embodiments, $R^2$ is independently —O-(substituted or unsubstituted alkyl). In embodiments, $R^2$ is independently —O-(unsubstituted alkyl). In embodiments, $R^2$ is independently —O-(substituted or unsubstituted $C_1$-$C_4$ alkyl). In embodiments, $R^2$ is independently —O-(unsubstituted $C_1$-$C_4$ alkyl). In embodiments, $R^2$ is independently —O-(unsubstituted methyl). In embodiments, $R^2$ is independently —O-(unsubstituted ethyl). In embodiments, $R^2$ is independently —O-(unsubstituted propyl). In embodiments, $R^2$ is independently —O-(unsubstituted n-propyl). In embodiments, $R^2$ is independently —O-(unsubstituted isopropyl). In embodiments, $R^2$ is independently —O-(unsubstituted n-butyl). In embodiments, $R^2$ is independently —O-(unsubstituted tert-butyl). In embodiments, $R^2$ is independently —O-(substituted or unsubstituted heteroalkyl). In embodiments, $R^2$ is independently —O-(unsubstituted heteroalkyl). In embodiments, $R^2$ is independently —O-(substituted or unsubstituted 2 to 6 membered heteroalkyl). In embodiments, $R^2$ is independently —O-(unsubstituted 2 to 6 membered heteroalkyl). In embodiments, $R^2$ is independently —O-(substituted or unsubstituted cycloalkyl). In embodiments, $R^2$ is independently —O-(unsubstituted cycloalkyl). In embodiments, $R^2$ is independently —O-(substituted or unsubstituted $C_3$-$C_6$ cycloalkyl). In embodiments, $R^2$ is independently —O-(unsubstituted $C_3$-$C_6$ cycloalkyl). In embodiments, $R^2$ is independently —O-(substituted or unsubstituted heterocycloalkyl). In embodiments, $R^2$ is independently —O-(unsubstituted heterocycloalkyl). In embodiments, $R^2$ is independently —O-(substituted or unsubstituted 3 to 6 membered heterocycloalkyl). In embodiments, $R^2$ is independently —O-(unsubstituted 3 to 6 membered heterocycloalkyl). In embodiments, $R^2$ is independently —O-(substituted or unsubstituted aryl). In embodiments, $R^2$ is independently —O-(unsubstituted aryl). In embodiments, $R^2$ is independently —O-(substituted or unsubstituted phenyl). In embodiments, $R^2$ is independently —O-(unsubstituted phenyl). In embodiments, $R^2$ is independently —O-(substituted or unsubstituted heteroaryl). In embodiments, $R^2$ is independently —O-(unsubstituted heteroaryl). In embodiments, $R^2$ is independently —O-(substituted or unsubstituted 5 to 6 membered heteroaryl). In embodiments, $R^2$ is independently —O-(unsubstituted 5 to 6 membered heteroaryl). In embodiments, $R^2$ is independently —O-(unsubstituted pyridyl). In embodiments, $R^2$ is independently

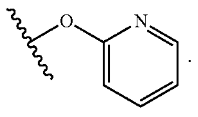 [SMILES: *Oc1ccccn1]

In embodiments, $R^2$ is independently

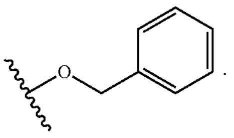

In embodiments, $R^2$ is independently

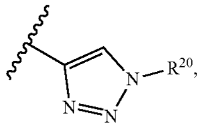

wherein $R^{20}$ is as described herein, including in embodiments.

In embodiments, $R^2$ is independently —NS(O)$F_2$. In embodiments, $R^2$ is independently —NS(O)FN$R^{2A}R^{2B}$, wherein $R^{2A}$ and $R^{2B}$ are as described herein, including in embodiments. In embodiments, $R^2$ is independently —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiments, $R^2$ is independently -$L^2$-$R^{23}$.

In embodiments, $L^2$ is independently -$L^{201}$-$L^{202}$-$L^{203}$-$L^{204}$-$L^{205}$-. $L^{201}$, $L^{202}$, $L^{203}$, $L^{204}$, and $L^{205}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker.

In embodiments, $L^{201}$, $L^{202}$, $L^{203}$, $L^{204}$, and $L^{205}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered), or a bioconjugate linker.

In embodiments, a substituted $L^{201}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{201}$ is substituted with a plurality of groups selected from substituent groups, size-limited substituent groups, and lower substituent groups; each substituent group, size-limited substituent group, and/or lower substituent group may optionally be different. In embodiments, when $L^{201}$ is substituted, it is substituted with at least one substituent group. In embodiments, when $L^{201}$ is substituted, it is substituted with at least one size-limited substituent group. In embodiments, when $L^{201}$ is substituted, it is substituted with at least one lower substituent group.

In embodiments, a substituted $L^{202}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{202}$ is substituted with a plurality of groups selected from substituent groups, size-limited substituent groups, and lower substituent groups; each substituent group, size-limited substituent group, and/or lower substituent group may optionally be different. In embodiments, when $L^{202}$ is substituted, it is substituted with at least one substituent group. In embodiments, when $L^{202}$ is substituted, it is substituted with at least one size-limited substituent group. In embodiments, when $L^{202}$ is substituted, it is substituted with at least one lower substituent group.

In embodiments, a substituted $L^{203}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{203}$ is substituted with a plurality of groups selected from substituent groups, size-limited substituent groups, and lower substituent groups; each substituent group, size-limited substituent group, and/or lower substituent group may optionally be different. In embodiments, when $L^{203}$ is substituted, it is substituted with at least one substituent group. In embodiments, when $L^{203}$ is substituted, it is substituted with at least one size-limited substituent group. In embodiments, when $L^{203}$ is substituted, it is substituted with at least one lower substituent group.

In embodiments, a substituted $L^{204}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{204}$ is substituted with a plurality of groups selected from substituent groups, size-limited substituent groups, and lower substituent groups; each substituent group, size-limited substituent group, and/or lower substituent group may optionally be different. In embodiments, when $L^{204}$ is substituted, it is substituted with at least one substituent group. In embodiments, when $L^{204}$ is substituted, it is substituted with at least one size-limited substituent group. In embodiments, when $L^{204}$ is substituted, it is substituted with at least one lower substituent group.

In embodiments, a substituted $L^{205}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{205}$ is substituted with a plurality of groups selected from substituent groups, size-limited substituent groups, and lower substituent groups; each substituent group, size-limited substituent group, and/or lower substituent group may optionally be different. In embodiments, when $L^{205}$ is substituted, it is substituted with at least one substituent group. In embodiments, when $L^{205}$ is substituted, it is substituted with at least one size-limited substituent group. In embodiments, when $L^{205}$ is substituted, it is substituted with at least one lower substituent group.

In embodiments, $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{2A}$ and $R^{2B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, a substituted $R^{2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, a substituted ring formed when $R^{2A}$ and $R^{2B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{2A}$ and $R^{2B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the ring formed when $R^{2A}$ and $R^{2B}$ substituents bonded to the same nitrogen atom are joined is substituted, it is substituted with at least one substituent group. In embodiments, when the ring formed when $R^{2A}$ and $R^{2B}$ substituents bonded to the same nitrogen atom are joined is substituted, it is substituted with at least one size-limited substituent group. In embodiments, when the ring formed when $R^{2A}$ and $R^{2B}$ substituents bonded to the same nitrogen atom are joined is substituted, it is substituted with at least one lower substituent group.

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, $R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{20}$-substituted or unsubstituted alkyl (e.g., $C_1$-$C_8$, $C_1$—$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered); $R^{2A}$ and $R^{2B}$ substituents bonded to the same nitrogen atom may optionally be joined to form a $R^{20}$-substituted or unsubstituted heterocycloalkyl (e.g., 3 to 8 membered, 3 to 6 membered, 4 to 6 membered, 4 to 5 membered, or 5 to 6 membered) or $R^{20}$-substituted or unsubstituted heteroaryl (e.g., 5 to 10 membered, 5 to 9 membered, or 5 to 6 membered).

In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7.

In embodiments, $R^{2.1}$ is hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or $-L^2-R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.1}$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.1}$(e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group;

wherein if the substituted $R^{2.1}$ is substituted with a plurality of groups selected from substituent groups, size-limited substituent groups, and lower substituent groups; each substituent group, size-limited substituent group, and/or lower substituent group may optionally be different. In embodiments, when $R^{2.1}$ is substituted, it is substituted with at least one substituent group. In embodiments, when $R^{2.1}$ is substituted, it is substituted with at least one size-limited substituent group. In embodiments, when $R^{2.1}$ is substituted, it is substituted with at least one lower substituent group.

In embodiments, $R^{2.1}$ is independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.1}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{21}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NS(O)F_2$, —$NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or -$L^2$-$R^{23}$. $L^2$ and $R^{23}$ are as described herein, including in embodiments.

In embodiments, $R^{2.1}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.1}$ is independently hydrogen, substituted or unsubstituted $C_1$-$C_4$ alkyl, or substituted or unsubstituted 2 to 6 membered heteroalkyl. In embodiments, $R^{2.1}$ is independently hydrogen. In embodiments, $R^{2.1}$ is independently substituted or unsubstituted $C_1$-$C_4$ alkyl. In embodiments, $R^{2.1}$ is independently oxo-substituted $C_1$-$C_4$ alkyl. In embodiments, $R^{2.1}$ is independently substituted or unsubstituted 2 to 6 membered heteroalkyl. In embodiments, $R^{2.1}$ is independently oxo-substituted 2 to 6 membered heteroalkyl. In embodiments, $R^{2.1}$ independently is —C(O)H, —$CH_2C(O)H$, —$CH_2C(O)OH$, —C(O)OH, —$CH_2NHCH_3$, —$CH_2NH_2$, or —$CH_2N(CH_3)_2$. In embodiments, $R^{2.1}$ is independently —C(O)H. In embodiments, $R^{2.1}$ is independently —$CH_2C(O)H$. In embodiments, $R^{2.1}$ is independently —$CH_2C(O)OH$. In embodiments, $R^{2.1}$ is independently —C(O)OH. In embodiments, $R^{2.1}$ is independently —$CH_2NHCH_3$. In embodiments, $R^{2.1}$ is independently —$CH_2NH_2$. In embodiments, $R^{2.1}$ is independently —$CH_2N(CH_3)_2$.

In embodiments, $R^{2.1}$ is independently hydrogen, —$NH_2$, substituted or unsubstituted 3 to 6 membered heteroalkyl, substituted or unsubstituted 4 to 7 membered heterocycloalkyl,

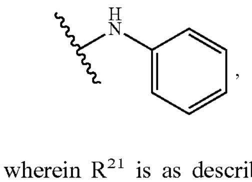
, or
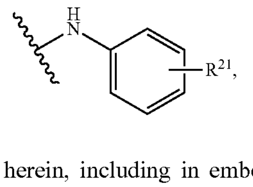

wherein $R^{21}$ is as described herein, including in embodiments. In embodiments, $R^{2.1}$ is independently

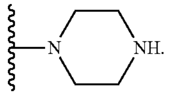 [SMILES: *N1CCNCC1]

In embodiments, $R^{2.1}$ is independently

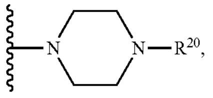

wherein $R^{20}$ is as described herein, including in embodiments.

In embodiments, $R^{2.1}$ is independently hydrogen, —$NH_2$, —$NHCH_3$, —$N(CH_3)_3$,

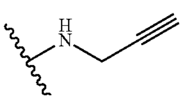,
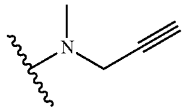,
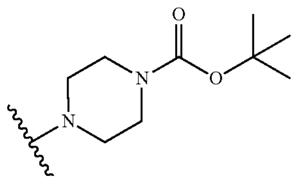,
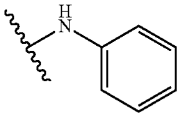,
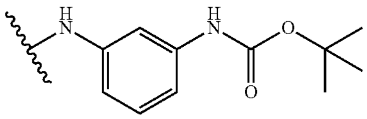,
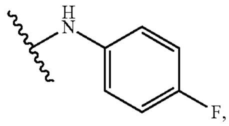 or
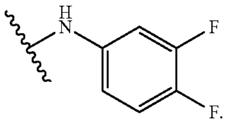

In embodiments, $R^{2.1}$ is independently hydrogen. In embodiments, $R^{2.1}$ is independently —$NH_2$. In embodiments, $R^{2.1}$ is independently —$NHCH_3$. In embodiments, $R^{2.1}$ is independently —$N(CH_3)_3$. In embodiments, $R^{2.1}$ is independently

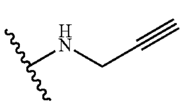

In embodiments, $R^{2.1}$ is independently

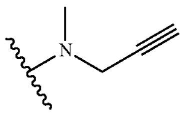

In embodiments, $R^{2.1}$ is independently

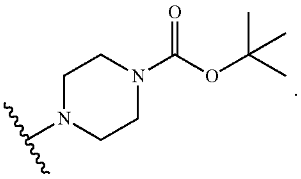 [SMILES: *N1CCN(C(=O)OC(C)(C)C)CC1]

In embodiments, $R^{2.1}$ is independently

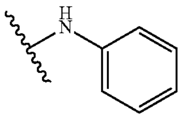

In embodiments, $R^{2.1}$ is independently

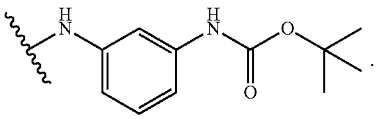 [SMILES: *Nc1cccc(NC(=O)OC(C)(C)C)c1]

In embodiments, $R^{2.1}$ is independently

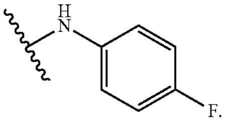 [SMILES: *Nc1ccc(F)cc1]

In embodiments, $R^{2.1}$ is independently

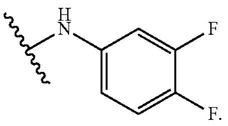 [SMILES: *Nc1ccc(F)c(F)c1]

In embodiments, $R^{2.1}$ is independently —$C(O)NR^{2A}R^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^{2.1}$ is independently

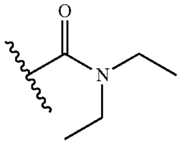 , 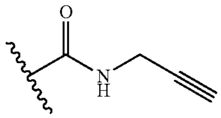 , or

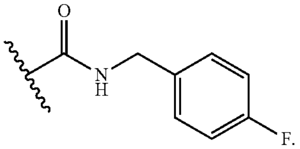

In embodiments, $R^{2.1}$ is independently

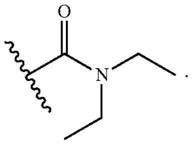 [SMILES: *C(=O)N(CC)CC]

In embodiments, $R^{2.1}$ is independently

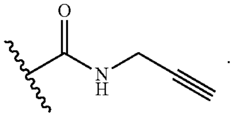 [SMILES: *C(=O)NCC#C]

In embodiments, $R^{2.1}$ is independently

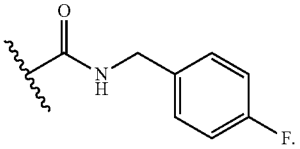 [SMILES: *C(=O)NCc1ccc(F)cc1]

In embodiments, $R^{2.1}$ is halogen. In embodiments, $R^{2.1}$ is —F. In embodiments, $R^{2.1}$ is —Cl. In embodiments, $R^{2.1}$ is —Br. In embodiments, $R^{2.1}$ is —I. In embodiments, $R^{2.1}$ is $R^{20}$-substituted or unsubstituted 5 or 6 membered heteroaryl, wherein $R^{20}$ is as described herein, including in embodiments. In embodiments, $R^{2.1}$ is $R^{20}$-substituted or unsubstituted thienyl, wherein $R^{20}$ is as described herein, including in embodiments. In embodiments, $R^{2.1}$ is

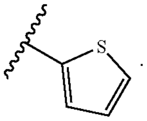

In embodiments, $R^{2.1}$ is

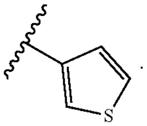 [SMILES: *c1ccsc1]

In embodiments, $R^{2.1}$ is

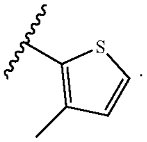 [SMILES: *c1sccc1C]

In embodiments, $R^{2.1}$ is

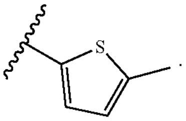 [SMILES: *c1ccc(C)s1]

In embodiments, $R^{2.1}$ is

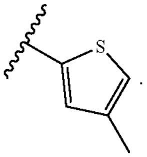 [SMILES: *c1cc(C)cs1]

In embodiments, $R^{2.1}$ is

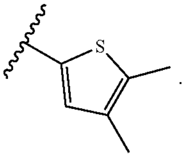 [SMILES: *c1cc(C)c(C)s1]

In embodiments, $R^{2.1}$ is

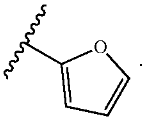

In embodiments, $R^{2.1}$ is

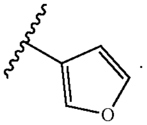 [SMILES: *c1ccoc1]

In embodiments, $R^{2.1}$ is

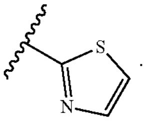 [SMILES: *c1nccs1]

In embodiments, $R^{2.1}$ is

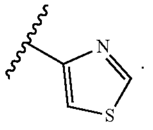 [SMILES: *c1cscn1]

In embodiments, $R^{2.1}$ is

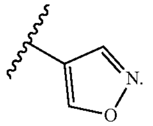 [SMILES: *c1cnoc1]

In embodiments, $R^{2.1}$ is

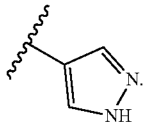 [SMILES: *c1cn[nH]c1]

In embodiments, $R^{2.1}$ is

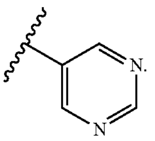 [SMILES: *c1cncnc1]

In embodiments, $R^{2.1}$ is —O-(substituted or unsubstituted alkyl). In embodiments, $R^{2.1}$ is —O-(unsubstituted alkyl). In embodiments, $R^{2.1}$ is —O-(substituted or unsubstituted $C_1$-$C_4$ alkyl). In embodiments, $R^{2.1}$ is —O-(unsubstituted $C_1$-$C_4$ alkyl). In embodiments, $R^{2.1}$ is —O-(unsubstituted methyl). In embodiments, $R^{2.1}$ is —O-(unsubstituted ethyl). In embodiments, $R^{2.1}$ is —O-(unsubstituted propyl). In embodiments, $R^{2.1}$ is —O-(unsubstituted n-propyl). In embodiments, $R^{2.1}$ is —O-(unsubstituted isopropyl). In embodiments, $R^{2.1}$ is —O-(unsubstituted n-butyl). In embodiments, $R^{2.1}$ is —O-(unsubstituted tert-butyl). In embodiments, $R^{2.1}$ is —O-(substituted or unsubstituted heteroalkyl). In embodiments, $R^{2.1}$ is —O-(unsubstituted heteroalkyl). In embodiments, $R^{2.1}$ is —O-(substituted or unsubstituted 2 to 6 membered heteroalkyl). In embodiments, $R^{2.1}$ is —O-(unsubstituted 2 to 6 membered heteroalkyl). In embodiments, $R^{2.1}$ is —O-(substituted or unsubstituted cycloalkyl). In embodiments, $R^{2.1}$ is —O-(unsubstituted cycloalkyl). In embodiments, $R^{2.1}$ is —O-(substituted or unsubstituted $C_3$-$C_6$ cycloalkyl). In embodiments, $R^{2.1}$ is —O-(unsubstituted $C_3$-$C_6$ cycloalkyl). In embodiments, $R^{2.1}$ is —O-(substituted or unsubstituted heterocycloalkyl). In embodiments, $R^{2.1}$ is —O-(unsubstituted heterocycloalkyl). In embodiments, $R^{2.1}$ is —O-(substituted or unsubstituted 3 to 6 membered heterocycloalkyl). In embodiments, $R^{2.1}$ is —O-(unsubstituted 3 to 6 membered heterocycloalkyl). In embodiments, $R^{2.1}$ is —O-(substituted or unsubstituted aryl). In embodiments, $R^{2.1}$ is —O-(unsubstituted aryl). In embodiments, $R^{2.1}$ is —O-(substituted or unsubstituted phenyl). In embodiments, $R^{2.1}$ is —O-(unsubstituted phenyl). In embodiments, $R^{2.1}$ is —O-(substituted or unsubstituted heteroaryl). In embodiments, $R^{2.1}$ is —O-(unsubstituted heteroaryl). In embodiments, $R^{2.1}$ is —O-(substituted or unsubstituted 5 to 6 membered heteroaryl). In embodiments, $R^{2.1}$ is —O-(unsubstituted 5 to 6 membered heteroaryl). In embodiments, $R^{2.1}$ is —O-(unsubstituted pyridyl). In embodiments, $R^{2.1}$ is

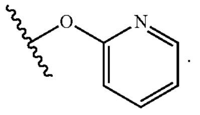

In embodiments, $R^{2.1}$ is

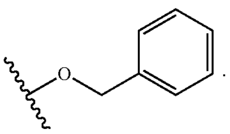 [SMILES: *OCc1ccccc1]

In embodiments, $R^{2.1}$ is

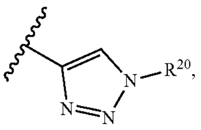

wherein $R^{20}$ is as described herein, including in embodiments.

In embodiments, $R^{2.1}$ is —NS(O)$F_2$. In embodiments, $R^{2.1}$ is —NS(O)FN$R^{2A}R^{2B}$, wherein $R^{2A}$ and $R^{2B}$ are as described herein, including in embodiments. In embodiments, $R^{2.1}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiment, $R^{2.1}$ is -$L^2$-$R^{23}$. $L^2$ and $R^{23}$ are as described herein, including in embodiments.

In embodiments, $R^{2.2}$ is hydrogen, halogen, —$CX^2_3$, —$CHX^2_2$, —$CH_2X^2$, —$OCX^2_3$, —$OCH_2X^2$, —$OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, $—NS(O)F_2$, $—NS(O)FNR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or $-L^2-R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.2}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.2}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.2}$ is substituted with a plurality of groups selected from substituent groups, size-limited substituent groups, and lower substituent groups; each substituent group, size-limited substituent group, and/or lower substituent group may optionally be different. In embodiments, when $R^{2.2}$ is substituted, it is substituted with at least one substituent group. In embodiments, when $R^{2.2}$ is substituted, it is substituted with at least one size-limited substituent group. In embodiments, when $R^{2.2}$ is substituted, it is substituted with at least one lower substituent group.

In embodiments, $R^{2.2}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.2}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.2}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NS(O)F_2$, —$NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or -$L^2$-$R^{23}$. $L^2$ and $R^{23}$ are as described herein, including in embodiments.

In embodiments, $R^{2.2}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.1}$ and $R^{2.2}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.1}$ and $R^{2.2}$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.2}$ is independently hydrogen, substituted or unsubstituted $C_1$-$C_4$ alkyl, or substituted or unsubstituted 2 to 6 membered heteroalkyl. In embodiments, $R^{2.2}$ is independently hydrogen. In embodiments, $R^{2.2}$ is independently substituted or unsubstituted $C_1$-$C_4$ alkyl. In embodiments, $R^{2.2}$ is independently oxo-substituted $C_1$-$C_4$ alkyl. In embodiments, $R^{2.2}$ is independently substituted or unsubstituted 2 to 6 membered heteroalkyl. In embodiments, $R^{2.2}$ is independently oxo-substituted 2 to 6 membered heteroalkyl. In embodiments, $R^{2.2}$ independently is —C(O)H, —$CH_2C(O)H$, —$CH_2C(O)OH$, —C(O)OH, —$CH_2NHCH_3$, —$CH_2NH_2$, or —$CH_2N(CH_3)_2$. In embodiments, $R^{2.2}$ is independently —C(O)H. In embodiments, $R^{2.2}$ is independently —$CH_2C(O)H$. In embodiments, $R^{2.2}$ is independently —$CH_2C(O)OH$. In embodiments, $R^{2.2}$ is independently —C(O)OH. In embodiments, $R^{2.2}$ is independently —$CH_2NHCH_3$. In embodiments, $R^{2.2}$ is independently —$CH_2NH_2$. In embodiments, $R^{2.2}$ is independently —$CH_2N(CH_3)_2$.

In embodiments, $R^{2.2}$ is independently hydrogen, —$NH_2$, substituted or unsubstituted 3 to 6 membered heteroalkyl, substituted or unsubstituted 4 to 7 membered heterocycloalkyl,

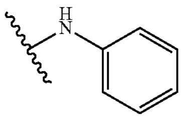, or 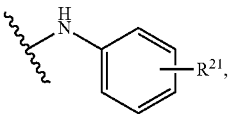, wherein $R^{21}$ is as described herein, including in embodiments. In embodiments, $R^{2.2}$ is independently

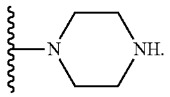 [SMILES: *N1CCNCC1].

In embodiments, $R^{2.2}$ is independently

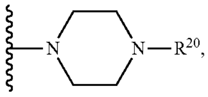, wherein $R^{20}$ is as described herein, including in embodiments.

In embodiments, $R^{2.2}$ is independently hydrogen, —$NH_2$, —$NHCH_3$, —$N(CH_3)_3$,

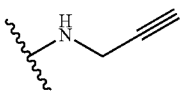, 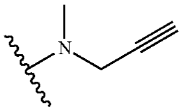,

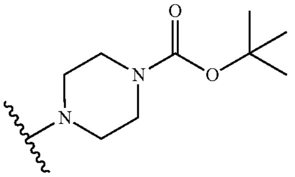, 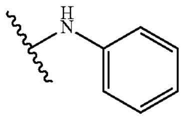,

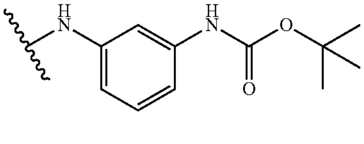,

-continued

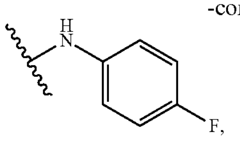

or

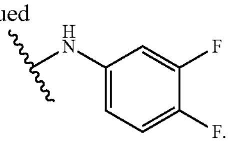

In embodiments, $R^{2.2}$ is independently hydrogen. In embodiments, $R^{2.2}$ is independently —$NH_2$. In embodiments, $R^{2.2}$ is independently —$NHCH_3$. In embodiments, $R^{2.2}$ is independently —$N(CH_3)_3$. In embodiments, $R^{2.2}$ is independently

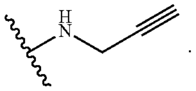 [SMILES: *NCC#C]

In embodiments, $R^{2.2}$ is independently

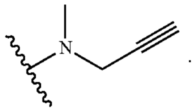 [SMILES: *N(C)CC#C]

In embodiments, $R^{2.2}$ is independently

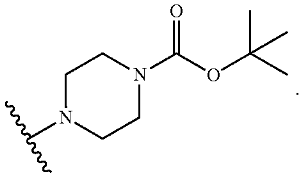 [SMILES: *N1CCN(C(=O)OC(C)(C)C)CC1]

In embodiments, $R^{2.2}$ is independently

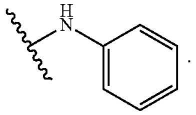 [SMILES: *Nc1ccccc1]

In embodiments, $R^{2.2}$ is independently

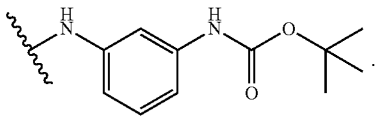 [SMILES: *Nc1cccc(NC(=O)OC(C)(C)C)c1]

In embodiments, $R^{2.2}$ is independently

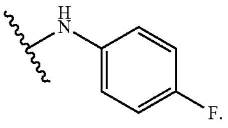

In embodiments, $R^{2.2}$ is independently

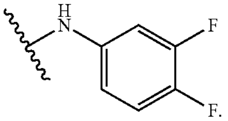 [SMILES: *Nc1ccc(F)c(F)c1]

In embodiments, $R^{2.2}$ is independently —$C(O)NR^{2A}R^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ IS independently unsubstituted isopropyl. In embodiments, $R^{2B}$ is independently n-butyl. In embodiments, $R^{2B}$ is independently tert-butyl. In embodiments, $R^{2.2}$ is independently

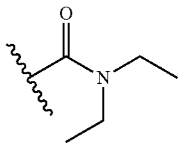

,

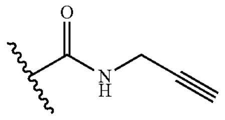

, or

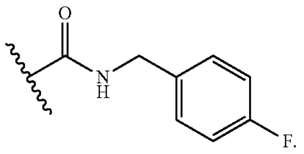

In embodiments, $R^{2.2}$ is independently

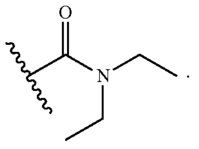 [SMILES: *C(=O)N(CC)CC]

In embodiments, $R^{2.2}$ is independently

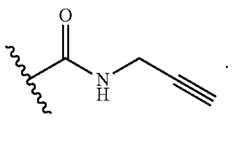 [SMILES: *C(=O)NCC#C]

In embodiments, $R^{2.2}$ is independently

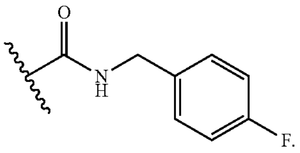 [SMILES: *C(=O)NCc1ccc(F)cc1]

In embodiments, $R^{2.2}$ is halogen. In embodiments, $R^{2.2}$ is —F. In embodiments, $R^{2.2}$ is —Cl. In embodiments, $R^{2.2}$ is —Br. In embodiments, $R^{2.2}$ is —I. In embodiments, $R^{2.2}$ is $R^{20}$-substituted or unsubstituted 5 or 6 membered heteroaryl, wherein $R^{20}$ is as described herein, including in embodiments. In embodiments, $R^{2.2}$ is $R^{20}$-substituted or unsubstituted thienyl, wherein $R^{20}$ is as described herein, including in embodiments. In embodiments, $R^{2.2}$ is

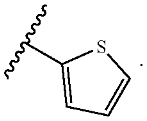 [SMILES: *c1cccs1]

In embodiments, $R^{2.2}$ is

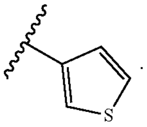 [SMILES: *c1ccsc1]

In embodiments, $R^{22}$ is

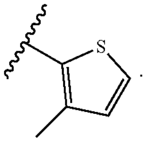 [SMILES: *c1sccc1C]

In embodiments, $R^{2.2}$ is

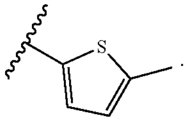 [SMILES: *c1ccc(C)s1]

In embodiments, $R^{2.2}$ is

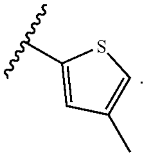 [SMILES: *c1cc(C)cs1]

In embodiments, $R^{2.2}$ is

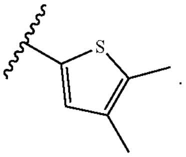 [SMILES: *c1cc(C)c(C)s1]

In embodiments, $R^{2.2}$ is

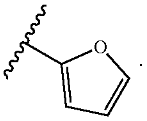

In embodiments, $R^{2.2}$ is

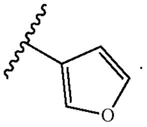 [SMILES: *c1ccoc1]

In embodiments, $R^{2.2}$ is

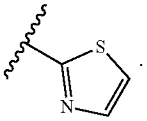 [SMILES: *c1nccs1]

In embodiments, $R^{2.2}$ is

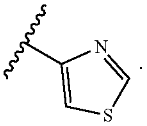 [SMILES: *c1cscn1]

In embodiments, $R^{2.2}$ is

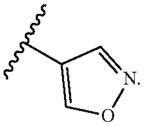 [SMILES: *c1cnoc1]

In embodiments, $R^{2.2}$ is

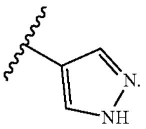 [SMILES: *c1cn[nH]c1]

In embodiments, $R^{2.2}$ is

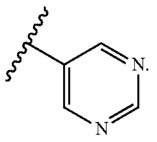 [SMILES: *c1cncnc1]

In embodiments, $R^{2.2}$ is —O-(substituted or unsubstituted alkyl). In embodiments, $R^{2.2}$ is —O-(unsubstituted alkyl). In embodiments, $R^{2.2}$ is —O-(substituted or unsubstituted $C_1$-$C_4$ alkyl). In embodiments, $R^{2.2}$ is —O-(unsubstituted $C_1$-$C_4$ alkyl). In embodiments, $R^{2.2}$ is —O-(unsubstituted methyl). In embodiments, $R^{2.2}$ is —O-(unsubstituted ethyl). In embodiments, $R^{2.2}$ is —O-(unsubstituted propyl). In embodiments, $R^{2.2}$ is —O-(unsubstituted n-propyl). In embodiments, $R^{2.2}$ is —O-(unsubstituted isopropyl). In embodiments, $R^{2.2}$ is —O-(unsubstituted n-butyl). In embodiments, $R^{2.2}$ is —O-(unsubstituted tert-butyl). In embodiments, $R^{2.2}$ is —O-(substituted or unsubstituted heteroalkyl). In embodiments, $R^{2.2}$ is —O-(unsubstituted heteroalkyl). In embodiments, $R^{2.2}$ is —O-(substituted or unsubstituted 2 to 6 membered heteroalkyl). In embodiments, $R^{2.2}$ is —O-(unsubstituted 2 to 6 membered heteroalkyl). In embodiments, $R^{2.2}$ is —O-(substituted or unsubstituted cycloalkyl). In embodiments, $R^{2.2}$ is —O-(unsubstituted cycloalkyl). In embodiments, $R^{2.2}$ is —O-(substituted or unsubstituted $C_3$-$C_6$ cycloalkyl). In embodiments, $R^{2.2}$ is —O-(unsubstituted $C_3$-$C_6$ cycloalkyl). In embodiments, $R^{2.2}$ is —O-(substituted or unsubstituted heterocycloalkyl). In embodiments, $R^{2.2}$ is —O-(unsubstituted heterocycloalkyl). In embodiments, $R^{2.2}$ is —O-(substituted or unsubstituted 3 to 6 membered heterocycloalkyl). In embodiments, $R^{2.2}$ is —O-(unsubstituted 3 to 6 membered heterocycloalkyl). In embodiments, $R^{2.2}$ is —O-(substituted or unsubstituted aryl). In embodiments, $R^{2.2}$ is —O-(unsubstituted aryl). In embodiments, $R^{2.2}$ is —O-(substituted or unsubstituted phenyl). In embodiments, $R^{2.2}$ is —O-(unsubstituted phenyl). In embodiments, $R^{2.2}$ is —O-(substituted or unsubstituted heteroaryl). In embodiments, $R^{2.2}$ is —O-(unsubstituted heteroaryl). In embodiments, $R^{2.2}$ is —O-(substituted or unsubstituted 5 to 6 membered heteroaryl). In embodiments, $R^{2.2}$ is —O-(unsubstituted 5 to 6 membered heteroaryl). In embodiments, $R^{2.2}$ is —O-(unsubstituted pyridyl). In embodiments, $R^{2.2}$ is

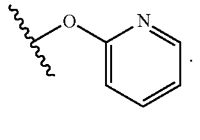 [SMILES: *Oc1ccccn1]

In embodiments, $R^{2.2}$ is

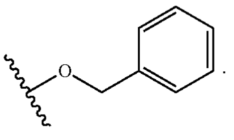 [SMILES: *OCc1ccccc1]

In embodiments, $R^{2.2}$ is

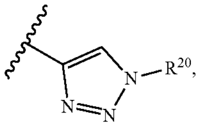

wherein $R^{20}$ is as described herein, including in embodiments.

In embodiments, $R^{2.2}$ is —NS(O)$F_2$. In embodiments, $R^{2.2}$ is —NS(O)FN$R^{2A}R^{2B}$, wherein $R^{2A}$ and $R^{2B}$ are as described herein, including in embodiments. In embodiments, $R^{2.2}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiments, $R^{2.2}$ is -$L^2$-$R^{23}$. $L^2$ and $R^{23}$ are as described herein, including in embodiments.

In embodiments, $R^{2.3}$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)O$R^{2C}$, —$NR^{2A}OR^{2C}$, —$SF_5$, —$N_3$, —NS(O)$F_2$, —NS(O)F$NR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or $-L^2-R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.3}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.3}$ is substituted with a plurality of groups selected from substituent groups, size-limited substituent groups, and lower substituent groups; each substituent group, size-limited substituent group, and/or lower substituent group may optionally be different. In embodiments, when $R^{2.3}$ is substituted, it is substituted with at least one substituent group. In embodiments, when $R^{2.3}$ is substituted, it is substituted with at least one size-limited substituent group. In embodiments, when $R^{2.3}$ is substituted, it is substituted with at least one lower substituent group.

In embodiments, $R^{2.3}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.3}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.3}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NS(O)F_2$, $—NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or $-L^2-R^{23}$. $L^2$ and $R^{23}$ are as described herein, including in embodiments.

In embodiments, $R^{2.3}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.3}$ is independently hydrogen, substituted or unsubstituted $C_1$-$C_4$ alkyl, or substituted or unsubstituted 2 to 6 membered heteroalkyl. In embodiments, $R^{2.3}$ is independently hydrogen. In embodiments, $R^{2.3}$ is independently substituted or unsubstituted $C_1$-$C_4$ alkyl. In embodiments, $R^{2.3}$ is independently oxo-substituted $C_1$-$C_4$ alkyl. In embodiments, $R^{2.3}$ is independently substituted or unsubstituted 2 to 6 membered heteroalkyl. In embodiments, $R^{2.3}$ is independently oxo-substituted 2 to 6 membered heteroalkyl. In embodiments, $R^{2.3}$ independently is —C(O)H, —$CH_2$C(O)H, —$CH_2$C(O)OH, —C(O)OH, —$CH_2NHCH_3$, —$CH_2NH_2$, or —$CH_2N(CH_3)_2$. In embodiments, $R^{2.3}$ is independently —C(O)H. In embodiments, $R^{2.3}$ is independently —$CH_2$C(O)H. In embodiments, $R^{2.3}$ is independently —$CH_2$C(O)OH. In embodiments, $R^{2.3}$ is independently —C(O)OH. In embodiments, $R^{2.3}$ is independently —$CH_2NHCH_3$. In embodiments, $R^{2.3}$ is independently —$CH_2NH_2$. In embodiments, $R^{2.3}$ is independently —$CH_2N(CH_3)_2$.

In embodiments, $R^{2.3}$ is independently hydrogen, —$NH_2$, substituted or unsubstituted 3 to 6 membered heteroalkyl, substituted or unsubstituted 4 to 7 membered heterocycloalkyl,

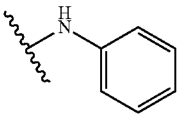
, or
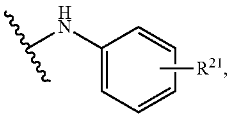
, wherein $R^{21}$ is as described herein, including in embodiments. In embodiments, $R^{2.3}$ is independently

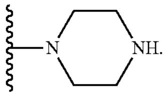

In embodiments, $R^{2.3}$ is independently

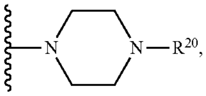
, wherein $R^{20}$ is as described herein, including in embodiments.

In embodiments, $R^{2.3}$ is independently hydrogen, —$NH_2$, —$NHCH_3$, —$N(CH_3)_3$,

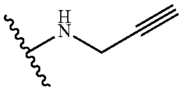
,
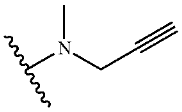
,
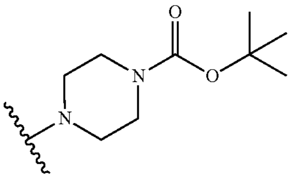
,
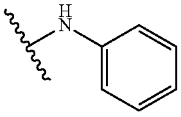
,
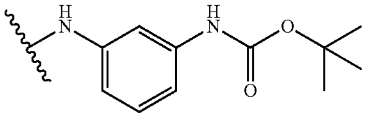
,
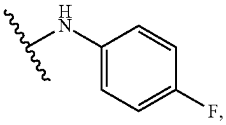
, or
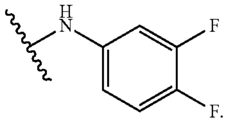

In embodiments, $R^{2.3}$ is independently hydrogen. In embodiments, $R^{2.3}$ is independently —$NH_2$. In embodiments, $R^{2.3}$ is independently —$NHCH_3$. In embodiments, $R^{2.3}$ is independently —$N(CH_3)_3$. In embodiments, $R^{2.3}$ is independently

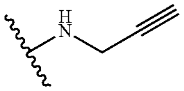
.

In embodiments, $R^{2.3}$ is independently

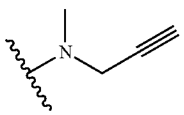
.

in embodiments, $R^{2.3}$ is independently

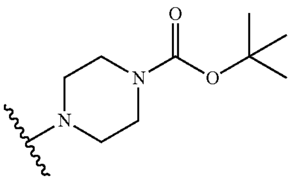
.

In embodiments, $R^{2.3}$ is independently

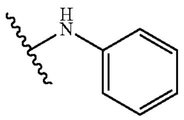
.

In embodiments, $R^{2.3}$ is independently

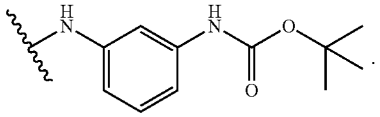 [SMILES: *Nc1cccc(NC(=O)OC(C)(C)C)c1]

In embodiments, $R^{2.3}$ is independently

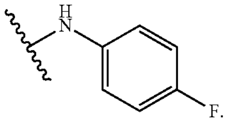

In embodiments, $R^{2.3}$ is independently

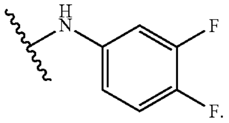

In embodiments, $R^{2.3}$ is independently —C(O)NR$^{2A}$R$^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^{2.3}$ is independently

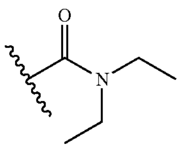, 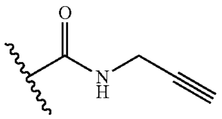, or

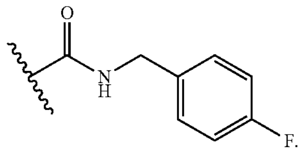

In embodiments, $R^{2.3}$ is independently

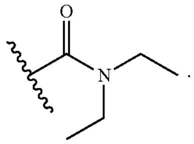 [SMILES: *C(=O)N(CC)CC]

In embodiments, $R^{2.3}$ is independently

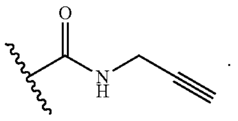 [SMILES: *C(=O)NCC#C]

In embodiments, $R^{2.3}$ is independently

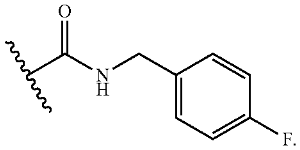 [SMILES: *C(=O)NCc1ccc(F)cc1]

In embodiments, $R^{2.3}$ is halogen. In embodiments, $R^{2.3}$ is —F. In embodiments, $R^{2.3}$ is —Cl. In embodiments, $R^{2.3}$ is —Br. In embodiments, $R^{2.3}$ is —I. In embodiments, $R^{2.3}$ is $R^{20}$-substituted or unsubstituted 5 or 6 membered heteroaryl, wherein $R^{20}$ is as described herein, including in embodiments. In embodiments, $R^{2.3}$ is $R^{20}$-substituted or unsubstituted thienyl, wherein $R^{20}$ is as described herein, including in embodiments. In embodiments, $R^{2.3}$ is

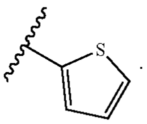 [SMILES: *c1cccs1]

In embodiments, $R^{2.3}$ is

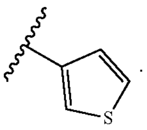 [SMILES: *c1ccsc1]

In embodiments, $R^{2.3}$ is

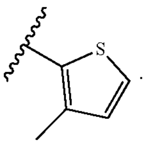 [SMILES: *c1sccc1C]

In embodiments, $R^{2.3}$ is

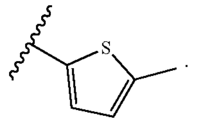 [SMILES: *c1ccc(C)s1]

In embodiments, $R^{2.3}$ is

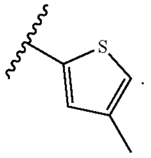 [SMILES: *c1cc(C)cs1]

In embodiments, $R^{2.3}$ is

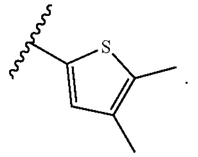 [SMILES: *c1cc(C)c(C)s1]

In embodiments, $R^{2.3}$ is

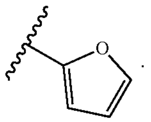 [SMILES: *c1ccco1]

In embodiments, $R^{2.3}$ is

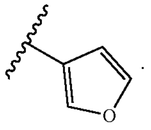 [SMILES: *c1ccoc1]

In embodiments, $R^{2.3}$ is

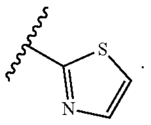 [SMILES: *c1nccs1]

In embodiments, $R^{2.3}$ is

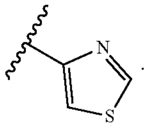 [SMILES: *c1cscn1]

In embodiments, $R^{2.3}$ is

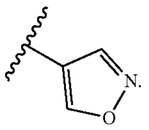 [SMILES: *c1cnoc1]

In embodiments, $R^{2.3}$ is

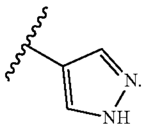 [SMILES: *c1cn[nH]c1]

In embodiments, $R^{2.3}$ is

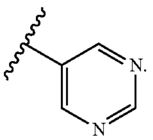 [SMILES: *c1cncnc1]

In embodiments, $R^{2.3}$ is —O-(substituted or unsubstituted alkyl). In embodiments, $R^{2.3}$ is —O-(unsubstituted alkyl). In embodiments, $R^{2.3}$ is —O-(substituted or unsubstituted $C_1$-$C_4$alkyl). In embodiments, $R^{2.3}$ is —O-(unsubstituted $C_1$-$C_4$ alkyl). In embodiments, $R^{2.3}$ is —O-(unsubstituted methyl). In embodiments, $R^{2.3}$ is —O-(unsubstituted ethyl). In embodiments, $R^{2.3}$ is —O-(unsubstituted propyl). In embodiments, $R^{2.3}$ is —O-(unsubstituted n-propyl). In embodiments, $R^{2.3}$ is —O-(unsubstituted isopropyl). In embodiments, $R^{2.3}$ is —O-(unsubstituted n-butyl). In embodiments, $R^{2.3}$ is —O-(unsubstituted tert-butyl). In embodiments, $R^{2.3}$ is —O-(substituted or unsubstituted heteroalkyl). In embodiments, $R^{2.3}$ is —O-(unsubstituted heteroalkyl). In embodiments, $R^{2.3}$ is —O-(substituted or unsubstituted 2 to 6 membered heteroalkyl). In embodiments, $R^{2.3}$ is —O-(unsubstituted 2 to 6 membered heteroalkyl). In embodiments, $R^{2.3}$ is —O-(substituted or unsubstituted cycloalkyl). In embodiments, $R^{2.3}$ is —O-(unsubstituted cycloalkyl). In embodiments, $R^{2.3}$ is —O-(substituted or unsubstituted $C_3$-$C_6$ cycloalkyl). In embodiments, $R^{2.3}$ is —O-(unsubstituted $C_3$-$C_6$ cycloalkyl). In embodiments, $R^{2.3}$ is —O-(substituted or unsubstituted heterocycloalkyl). In embodiments, $R^{2.3}$ is —O-(unsubstituted heterocycloalkyl). In embodiments, $R^{2.3}$ is —O-(substituted or unsubstituted 3 to 6 membered heterocycloalkyl). In embodiments, $R^{2.3}$ is —O-(unsubstituted 3 to 6 membered heterocycloalkyl). In embodiments, $R^{2.3}$ is —O-(substituted or unsubstituted aryl). In embodiments, $R^{2.3}$ is —O-(unsubstituted aryl). In embodiments, $R^{2.3}$ is —O-(substituted or unsubstituted phenyl). In embodiments, $R^{2.3}$ is —O-(unsubstituted phenyl). In embodiments, $R^{2.3}$ is —O-(substituted or unsubstituted heteroaryl). In embodiments, $R^{2.3}$ is —O-(unsubstituted heteroaryl). In embodiments, $R^{2.3}$ is —O-(substituted or unsubstituted 5 to 6 membered heteroaryl). In embodiments, $R^{2.3}$ is —O-(unsubstituted 5 to 6 membered heteroaryl). In embodiments, $R^{2.3}$ is —O-(unsubstituted pyridyl). In embodiments, $R^{2.3}$ is

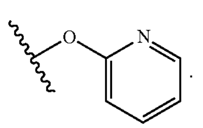 [SMILES: *Oc1ccccn1]

In embodiments, $R^{2.3}$ is

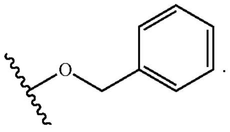 [SMILES: *OCc1ccccc1]

In embodiments, $R^{2.3}$ is

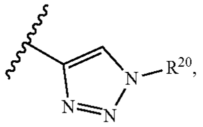

wherein $R^{20}$ is as described herein, including in embodiments.

In embodiments, $R^{2.3}$ is —NS(O)$F_2$. In embodiments, $R^{2.3}$ is —NS(O)FN$R^{2A}R^{2B}$, wherein $R^{2A}$ and $R^{2B}$ are as described herein, including in embodiments. In embodiments, $R^{2.3}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiments, $R^{2.3}$ is -$L^2$-$R^{23}$. $L^2$ and $R^{23}$ are as described herein, including in embodiments.

In embodiments, $R^{2.4}$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)O$R^{2C}$, —$NR^{2A}OR^{2C}$, —$SF_5$, —$N_3$, —NS(O)$F_2$, —NS(O)F$NR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or -$L^2$-$R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.4}$ is independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)O$R^{2C}$, —$NR^{2A}OR^{2C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$—$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.4}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.4}$ is substituted with a plurality of groups selected from substituent groups, size-limited substituent groups, and lower substituent groups; each substituent group, size-limited substituent group, and/or lower substituent group may optionally be different. In embodiments, when $R^{2.4}$ is substituted, it is substituted with at least one substituent group. In embodiments, when $R^{2.4}$ is substituted, it is substituted with at least one size-limited substituent group. In embodiments, when $R^{2.4}$ is substituted, it is substituted with at least one lower substituent group.

In embodiments, $R^{2.4}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.4}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.4}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NS(O)F_2$, $—NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or $-L^2-R^{23}$. In embodiments, $L^2$ and $R^{23}$ are as described herein, including in embodiments.

In embodiments, $R^{2.4}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.3}$ and $R^{2.4}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.3}$ and $R^{2.4}$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.4}$ is independently hydrogen, substituted or unsubstituted $C_1$-$C_4$ alkyl, or substituted or unsubstituted 2 to 6 membered heteroalkyl. In embodiments, $R^{2.4}$ is independently hydrogen. In embodiments, $R^{2.4}$ is independently substituted or unsubstituted $C_1$-$C_4$ alkyl. In embodiments, $R^{2.4}$ is independently oxo-substituted $C_1$-$C_4$ alkyl. In embodiments, $R^{2.4}$ is independently substituted or unsubstituted 2 to 6 membered heteroalkyl. In embodiments, $R^{2.4}$ is independently oxo-substituted 2 to 6 membered heteroalkyl. In embodiments, $R^{2.4}$ independently is —C(O)

H, $-CH_2C(O)H$, $-CH_2C(O)OH$, $-C(O)OH$, $-CH_2NHCH_3$, $-CH_2NH_2$, or $-CH_2N(CH_3)_2$. In embodiments, $R^{2.4}$ is independently $-C(O)H$. In embodiments, $R^{2.4}$ is independently $-CH_2C(O)H$. In embodiments, $R^{2.4}$ is independently $-CH_2C(O)OH$. In embodiments, $R^{2.4}$ is independently $-C(O)OH$. In embodiments, $R^{2.4}$ is independently $-CH_2NHCH_3$. In embodiments, $R^{2.4}$ is independently $-CH_2NH_2$. In embodiments, $R^{2.4}$ is independently $-CH_2N(CH_3)_2$.

In embodiments, $R^{2.4}$ is independently hydrogen, $-NH_2$, substituted or unsubstituted 3 to 6 membered heteroalkyl, substituted or unsubstituted 4 to 7 membered heterocycloalkyl,

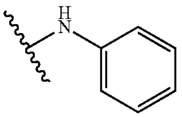, or 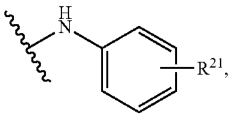

wherein $R^{21}$ is as described herein, including in embodiments. In embodiments, $R^{2.4}$ is independently

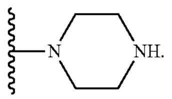 [SMILES: *N1CCNCC1]

In embodiments, $R^{2.4}$ is independently

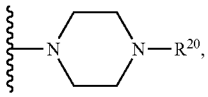

wherein $R^{20}$ is as described herein, including in embodiments.

In embodiments, $R^{2.4}$ is independently hydrogen, $-NH_2$, $-NHCH_3$, $-N(CH_3)_3$,

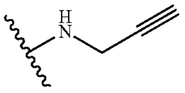, 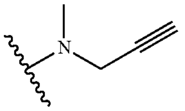, 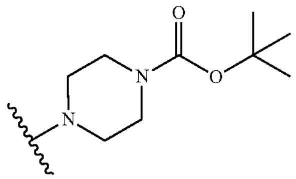, 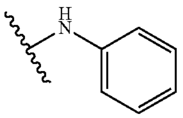, 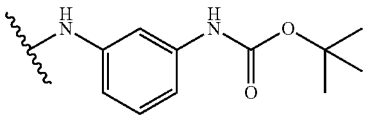, 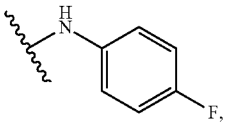 or 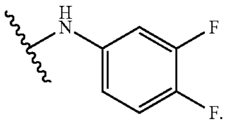

In embodiments, $R^{2.4}$ is independently hydrogen. In embodiments, $R^{2.4}$ is independently $-NH_2$. In embodiments, $R^{2.4}$ is independently $-NHCH_3$. In embodiments, $R^{2.4}$ is independently $-N(CH_3)_3$. In embodiments, $R^{2.4}$ is independently

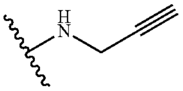.

In embodiments, $R^{2.4}$ is independently

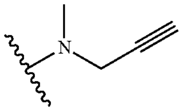.

In embodiments, $R^{2.4}$ is independently

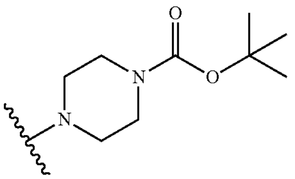.

In embodiments, $R^{2.4}$ is independently

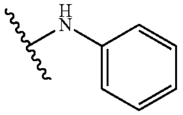.

In embodiments, $R^{2.4}$ is independently

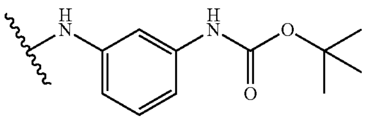.

In embodiments, $R^{2.4}$ is independently

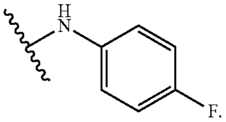 [SMILES: *Nc1ccc(F)cc1]

In embodiments, $R^{2.4}$ is independently

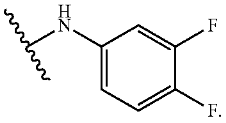 [SMILES: *Nc1ccc(F)c(F)c1]

In embodiments, $R^{2.4}$ is independently $-C(O)NR^{2A}R^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^{2.4}$ is independently

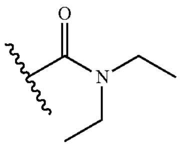
,
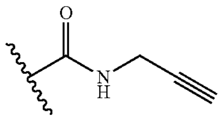
, or
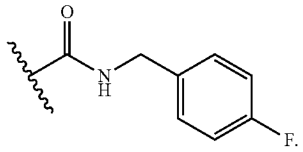

In embodiments, $R^{2.4}$ is independently

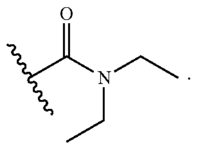 [SMILES: *C(=O)N(CC)CC]

In embodiments, $R^{2.4}$ is independently

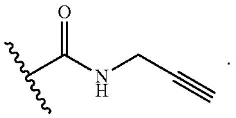 [SMILES: *C(=O)NCC#C]

In embodiments, $R^{2.4}$ is independently

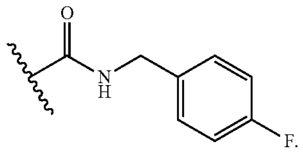 [SMILES: *C(=O)NCc1ccc(F)cc1]

In embodiments, $R^{2.4}$ is halogen. In embodiments, $R^{2.4}$ is —F. In embodiments, $R^{2.4}$ is —Cl. In embodiments, $R^{2.4}$ is —Br. In embodiments, $R^{2.4}$ is —I. In embodiments, $R^{2.4}$ is $R^{20}$-substituted or unsubstituted 5 or 6 membered heteroaryl, wherein $R^{20}$ is as described herein, including in embodiments. In embodiments, $R^{2.4}$ is $R^{20}$-substituted or unsubstituted thienyl, wherein $R^{20}$ is as described herein, including in embodiments. In embodiments, $R^{2.4}$ is

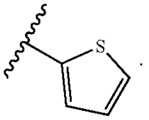

In embodiments, $R^{2.4}$ is

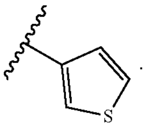 [SMILES: *c1ccsc1]

In embodiments, $R^{2.4}$ is

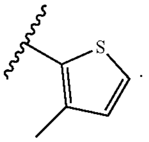 [SMILES: *c1sccc1C]

In embodiments, $R^{2.4}$ is

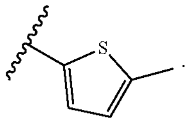 [SMILES: *c1ccc(C)s1]

In embodiments, $R^{2.4}$ is

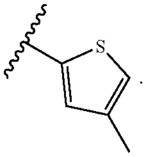 [SMILES: *c1cc(C)cs1]

In embodiments, $R^{2.4}$ is

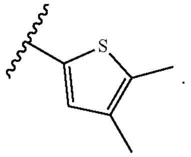 [SMILES: *c1cc(C)c(C)s1]

In embodiments, $R^{2.4}$ is

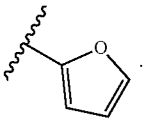

In embodiments, $R^{2.4}$ is

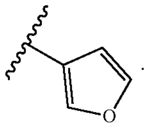 [SMILES: *c1ccoc1]

In embodiments, $R^{2.4}$ is

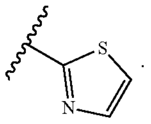 [SMILES: *c1nccs1]

In embodiments, $R^{2.4}$ is

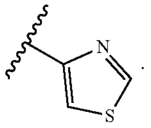 [SMILES: *c1cscn1]

In embodiments, $R^{2.4}$ is

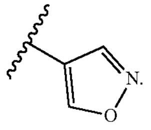 [SMILES: *c1cnoc1]

In embodiments, $R^{2.4}$ is

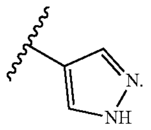 [SMILES: *c1cn[nH]c1]

In embodiments, $R^{2.4}$ is

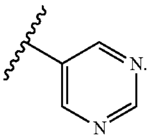 [SMILES: *c1cncnc1]

In embodiments, $R^{2.4}$ is —O-(substituted or unsubstituted alkyl). In embodiments, $R^{2.4}$ is —O-(unsubstituted alkyl). In embodiments, $R^{2.4}$ is —O-(substituted or unsubstituted $C_1$-$C_4$ alkyl). In embodiments, $R^{2.4}$ is —O-(unsubstituted $C_1$-$C_4$ alkyl). In embodiments, $R^{2.4}$ is —O-(unsubstituted methyl). In embodiments, $R^{2.4}$ is —O-(unsubstituted ethyl). In embodiments, $R^{2.4}$ is —O-(unsubstituted propyl). In embodiments, $R^{2.4}$ is —O-(unsubstituted n-propyl). In embodiments, $R^{2.4}$ is —O-(unsubstituted isopropyl). In embodiments, $R^{2.4}$ is —O-(unsubstituted n-butyl). In embodiments, $R^{2.4}$ is —O-(unsubstituted tert-butyl). In embodiments, $R^{2.4}$ is —O-(substituted or unsubstituted heteroalkyl). In embodiments, $R^{2.4}$ is —O-(unsubstituted heteroalkyl). In embodiments, $R^{2.4}$ is —O-(substituted or unsubstituted 2 to 6 membered heteroalkyl). In embodiments, $R^{2.4}$ is —O-(unsubstituted 2 to 6 membered heteroalkyl). In embodiments, $R^{2.4}$ is —O-(substituted or unsubstituted cycloalkyl). In embodiments, $R^{2.4}$ is —O-(unsubstituted cycloalkyl). In embodiments, $R^{2.4}$ is —O-(substituted or unsubstituted $C_3$-$C_6$ cycloalkyl). In embodiments, $R^{2.4}$ is —O-(unsubstituted $C_3$-$C_6$ cycloalkyl). In embodiments, $R^{2.4}$ is —O-(substituted or unsubstituted heterocycloalkyl). In embodiments, $R^{2.4}$ is —O-(unsubstituted heterocycloalkyl). In embodiments, $R^{2.4}$ is —O-(substituted or unsubstituted 3 to 6 membered heterocycloalkyl). In embodiments, $R^{2.4}$ is —O-(unsubstituted 3 to 6 membered heterocycloalkyl). In embodiments, $R^{2.4}$ is —O-(substituted or unsubstituted aryl). In embodiments, $R^{2.4}$ is —O-(unsubstituted aryl). In embodiments, $R^{2.4}$ is —O-(substituted or unsubstituted phenyl). In embodiments, $R^{2.4}$ is —O-(unsubstituted phenyl). In embodiments, $R^{2.4}$ is —O-(substituted or unsubstituted heteroaryl). In embodiments, $R^{2.4}$ is —O-(unsubstituted heteroaryl). In embodiments, $R^{2.4}$ is —O-(substituted or unsubstituted 5 to 6 membered heteroaryl). In embodiments, $R^{2.4}$ is —O-(unsubstituted 5 to 6 membered heteroaryl). In embodiments, $R^{2.4}$ is —O-(unsubstituted pyridyl). In embodiments, $R^{2.4}$ is

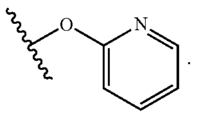

In embodiments, $R^{2.4}$ is

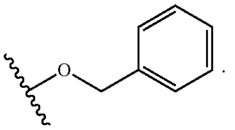

In embodiments, $R^{2.4}$ is

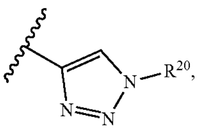

wherein $R^{20}$ is as described herein, including in embodiments.

In embodiments, $R^{2.4}$ is —NS(O)$F_2$. In embodiments, $R^{2.4}$ is —NS(O)FN$R^{2A}R^{2B}$, wherein $R^{2A}$ and $R^{2B}$ are as described herein, including in embodiments. In embodiments, $R^{2.4}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiments, $R^{2.4}$ is $-L^2-R^{23}$. $L^2$ and $R^{23}$ are as described herein, including in embodiments.

In embodiments, $R^{2.5}$ is hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or $-L^2-R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.5}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.5}$ is substituted with a plurality of groups selected from substituent groups, size-limited substituent groups, and lower substituent groups; each substituent group, size-limited substituent group, and/or lower substituent group may optionally be different. In embodiments, when $R^{2.5}$ is substituted, it is substituted with at least one substituent group. In embodiments, when $R^{2.5}$ is substituted, it is substituted with at least one size-limited substituent group. In embodiments, when $R^{2.5}$ is substituted, it is substituted with at least one lower substituent group.

In embodiments, $R^{2.5}$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.5}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.5}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, $-NS(O)F_2$, $-NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or $-L^2-R^{23}$. $L^2$ and $R^{23}$ are as described herein, including in embodiments.

In embodiments, $R^{2.5}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$—$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.4}$ and $R^{2.5}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.4}$ and $R^{2.5}$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.5}$ is independently hydrogen, substituted or unsubstituted $C_1$-$C_4$ alkyl, or substituted or unsubstituted 2 to 6 membered heteroalkyl. In embodiments, $R^{2.5}$ is independently hydrogen. In embodiments, $R^{2.5}$ is independently substituted or unsubstituted $C_1$-$C_4$ alkyl. In embodiments, $R^{2.5}$ is independently oxo-substituted $C_1$-$C_4$ alkyl. In embodiments, $R^{2.5}$ is independently substituted or unsubstituted 2 to 6 membered heteroalkyl. In embodiments, $R^{2.5}$ is independently oxo-substituted 2 to 6 membered heteroalkyl. In embodiments, $R^{2.5}$ independently is —C(O)H, $—CH_2C(O)H$, $—CH_2C(O)OH$, —C(O)OH, $—CH_2NHCH_3$, $—CH_2NH_2$, or $—CH_2N(CH_3)_2$. In embodiments, $R^{2.5}$ is independently —C(O)H. In embodiments, $R^{2.5}$ is independently $—CH_2C(O)H$. In embodiments, $R^{2.5}$ is independently $—CH_2C(O)OH$. In embodiments, $R^{2.5}$ is independently —C(O)OH. In embodiments, $R^{2.5}$ is independently $—CH_2NHCH_3$. In embodiments, $R^{2.5}$ is independently $—CH_2NH_2$. In embodiments, $R^{2.5}$ is independently $—CH_2N(CH_3)_2$.

In embodiments, $R^{2.5}$ is independently hydrogen, $—NH_2$, substituted or unsubstituted 3 to 6 membered heteroalkyl, substituted or unsubstituted 4 to 7 membered heterocycloalkyl,

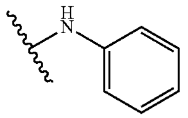

, or

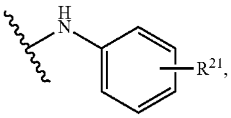

or, wherein $R^{21}$ is as described herein, including in embodiments. In embodiments, $R^{2.5}$ is independently

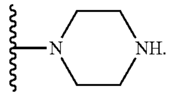

In embodiments, $R^{2.5}$ is independently

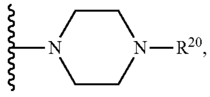

wherein $R^{20}$ is as described herein, including in embodiments.

In embodiments, $R^{2.5}$ is independently hydrogen, $—NH_2$, $—NHCH_3$, $—N(CH_3)_3$,

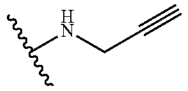

,

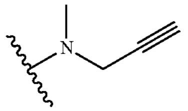

,

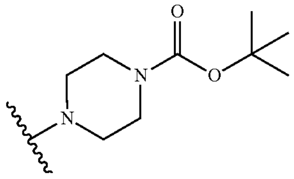

,

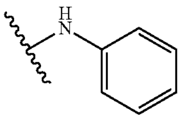

,

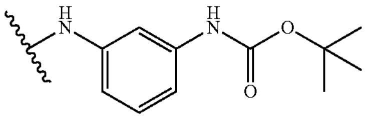

,

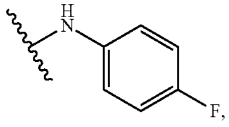

or

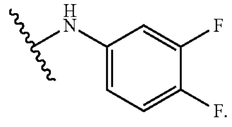

In embodiments, $R^{2.5}$ is independently hydrogen. In embodiments, $R^{2.5}$ is independently $—NH_2$. In embodiments, $R^{2.5}$ is independently $—NHCH_3$. In embodiments, $R^{2.5}$ is independently $—N(CH_3)_3$. In embodiments, $R^{2.5}$ is independently

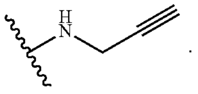 [SMILES: *NCC#C]

In embodiments, $R^{2.5}$ is independently

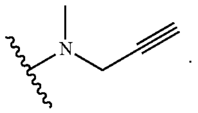 [SMILES: *N(C)CC#C]

In embodiments, $R^{2.5}$ is independently

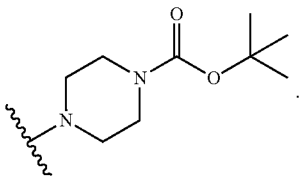 [SMILES: *N1CCN(C(=O)OC(C)(C)C)CC1]

In embodiments, $R^{2.5}$ is independently

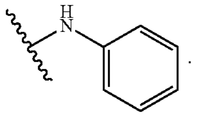 [SMILES: *Nc1ccccc1]

In embodiments, $R^{2.5}$ is independently

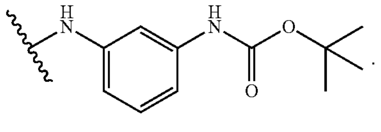 [SMILES: *Nc1cccc(NC(=O)OC(C)(C)C)c1]

In embodiments, $R^{2.5}$ is independently

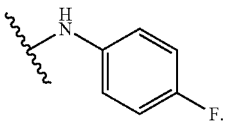

In embodiments, $R^{2.5}$ is independently

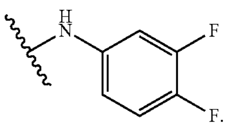

In embodiments, $R^{2.5}$ is independently —C(O)N$R^{2A}R^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^{2.5}$ is independently

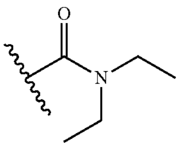
,
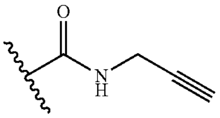
, or

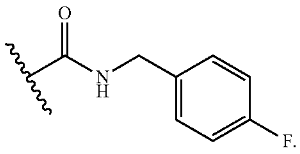

In embodiments, $R^{2.5}$ is independently

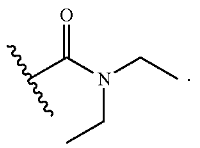 [SMILES: *C(=O)N(CC)CC]

In embodiments, $R^{2.5}$ is independently

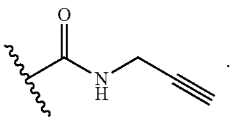 [SMILES: *C(=O)NCC#C]

In embodiments, $R^{2.5}$ is independently

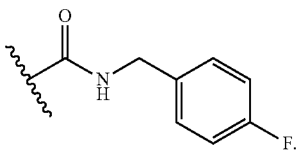 [SMILES: *C(=O)NCc1ccc(F)cc1]

In embodiments, $R^{2.5}$ is halogen. In embodiments, $R^{2.5}$ is —F. In embodiments, $R^{2.5}$ is —Cl. In embodiments, $R^{2.5}$ is —Br. In embodiments, $R^{2.5}$ is —I. In embodiments, $R^{2.5}$ is $R^{20}$-substituted or unsubstituted 5 or 6 membered heteroaryl, wherein $R^{20}$ is as described herein, including in embodiments. In embodiments, $R^{2.5}$ is $R^{20}$-substituted or unsubstituted thienyl, wherein $R^{20}$ is as described herein, including in embodiments. In embodiments, $R^{2.5}$ is

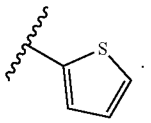 [SMILES: *c1cccs1]

In embodiments, $R^{2.5}$ is

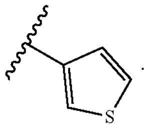 [SMILES: *c1ccsc1]

In embodiments, $R^{2.5}$ is

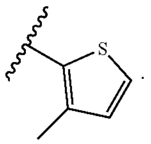 [SMILES: *c1sccc1C]

In embodiments, $R^{2.5}$ is

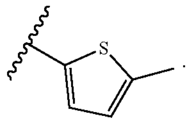 [SMILES: *c1ccc(C)s1]

In embodiments, $R^{2.5}$ is

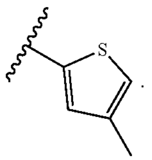 [SMILES: *c1cc(C)cs1]

In embodiments, $R^{2.5}$ is

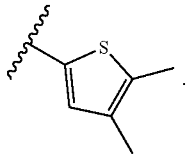 [SMILES: *c1cc(C)c(C)s1]

In embodiments, $R^{2.5}$ is

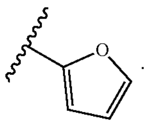 [SMILES: *c1ccco1]

In embodiments, $R^{2.5}$ is

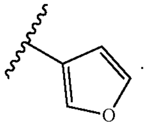 [SMILES: *c1ccoc1]

In embodiments, $R^{2.5}$ is

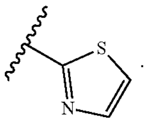 [SMILES: *c1nccs1]

In embodiments, $R^{2.5}$ is

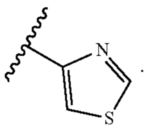 [SMILES: *c1cscn1]

In embodiments, $R^{2.5}$ is

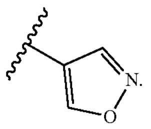 [SMILES: *c1cnoc1]

In embodiments, $R^{2.5}$ is

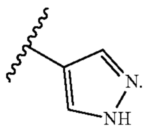 [SMILES: *c1cn[nH]c1]

In embodiments, $R^{2.5}$ is

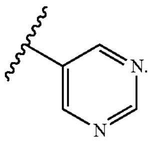 [SMILES: *c1cncnc1]

In embodiments, $R^{2.5}$ is —O-(substituted or unsubstituted alkyl). In embodiments, $R^{2.5}$ is —O-(unsubstituted alkyl). In embodiments, $R^{2.5}$ is —O-(substituted or unsubstituted $C_1$-$C_4$ alkyl). In embodiments, $R^{2.5}$ is —O-(unsubstituted $C_1$-$C_4$ alkyl). In embodiments, $R^{2.5}$ is —O-(unsubstituted methyl). In embodiments, $R^{2.5}$ is —O-(unsubstituted ethyl). In embodiments, $R^{2.5}$ is —O-(unsubstituted propyl). In embodiments, $R^{2.5}$ is —O-(unsubstituted n-propyl). In embodiments, $R^{2.5}$ is —O-(unsubstituted isopropyl). In embodiments, $R^{2.5}$ is —O-(unsubstituted n-butyl). In embodiments, $R^{2.5}$ is —O-(unsubstituted tert-butyl). In embodiments, $R^{2.5}$ is —O-(substituted or unsubstituted heteroalkyl). In embodiments, $R^{2.5}$ is —O-(unsubstituted heteroalkyl). In embodiments, $R^{2.5}$ is —O-(substituted or unsubstituted 2 to 6 membered heteroalkyl). In embodiments, $R^{2.5}$ is —O-(unsubstituted 2 to 6 membered heteroalkyl). In embodiments, $R^{2.5}$ is —O-(substituted or unsubstituted cycloalkyl). In embodiments, $R^{2.5}$ is —O-(unsubstituted cycloalkyl). In embodiments, $R^{2.5}$ is —O-(substituted or unsubstituted $C_3$-$C_8$ cycloalkyl). In embodiments, $R^{2.5}$ is —O(unsubstituted $C_3$-$C_6$ cycloalkyl). In embodiments, $R^{2.5}$ is —O-(substituted or unsubstituted heterocycloalkyl). In embodiments, $R^{2.5}$ is —O-(unsubstituted heterocycloalkyl). In embodiments, $R^{2.5}$ is —O-(substituted or unsubstituted 3 to 6 membered heterocycloalkyl). In embodiments, $R^{2.5}$ is —O-(unsubstituted 3 to 6 membered heterocycloalkyl). In embodiments, $R^{2.5}$ is —O-(substituted or unsubstituted aryl). In embodiments, $R^{2.5}$ is —O-(unsubstituted aryl). In embodiments, $R^{2.5}$ is —O-(substituted or unsubstituted phenyl). In embodiments, $R^{2.5}$ is —O-(unsubstituted phenyl). In embodiments, $R^{2.5}$ is —O-(substituted or unsubstituted heteroaryl). In embodiments, $R^{2.5}$ is —O-(unsubstituted heteroaryl). In embodiments, $R^{2.5}$ is —O-(substituted or unsubstituted 5 to 6 membered heteroaryl). In embodiments, $R^{2.5}$ is —O-(unsubstituted 5 to 6 membered heteroaryl). In embodiments, $R^{2.5}$ is —O-(unsubstituted pyridyl). In embodiments, $R^{2.5}$ is

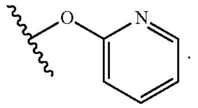 [SMILES: *Oc1ccccn1]

In embodiments, $R^{2.5}$ is

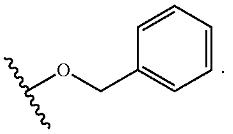 [SMILES: *OCc1ccccc1]

In embodiments, $R^{2.5}$ is

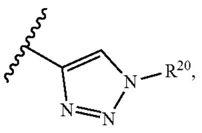

wherein $R^{20}$ is as described herein, including in embodiments.

In embodiments, $R^{2.5}$ is —NS(O)$F_2$. In embodiments, $R^{2.5}$ is —NS(O)FN$R^{2A}R^{2B}$, wherein $R^{2A}$ and $R^{2B}$ are as described herein, including in embodiments. In embodiments, $R^{2.5}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiment, $R^{2.5}$ is -$L^2$-$R^{23}$. $L^2$ and $R^{23}$ are as described herein, including in embodiments.

In embodiments, $R^{2.6}$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)O$R^{2C}$, —$NR^{2A}OR^{2C}$, —$SF_5$, —$N_3$, —NS(O)$F_2$, —NS(O)F$NR^{2A}R^{2B}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), substituted (e.g., substituted with at least one substituent group, size-limited substituent group, or lower substituent group) or unsubstituted heteroaryl (e.g., 5 to 10 membered, 5 to 9 membered, or 5 to 6 membered), or -$L^2$-$R^{23}$. $R^{2A}$, $R^{2B}$, $R^{2C}$, $R^{2D}$, $L^2$, and $R^{23}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.6}$ is independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)O$R^{2C}$, —$NR^{2A}OR^{2C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, a substituted $R^{2.6}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2.6}$ is substituted with a plurality of groups selected from substituent groups, size-limited substituent groups, and lower substituent groups; each substituent group, size-limited substituent group, and/or lower substituent group may optionally be different. In embodiments, when $R^{2.6}$ is substituted, it is substituted with at least one substituent group. In embodiments, when $R^{2.6}$ is substituted, it is substituted with at least one size-limited substituent group. In embodiments, when $R^{2.6}$ is substituted, it is substituted with at least one lower substituent group.

In embodiments, $R^{2.6}$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^{2.6}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.6}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NS(O)F_2$, $—NS(O)FNH_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), $R^{20}$-substituted or unsubstituted heteroaryl (e.g., 5 to 10 membered, 5 to 9 membered, or 5 to 6 membered), or $-L^2-R^{23}$. $L^2$ and $R^{23}$ are as described herein, including in embodiments.

In embodiments, $R^{2.6}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.1}$ and $R^{2.6}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, $R^{2.1}$ and $R^{2.6}$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{2.6}$ is independently hydrogen, substituted or unsubstituted $C_1$-$C_4$ alkyl, or substituted or unsubstituted 2 to 6 membered heteroalkyl. In embodiments, $R^{2.6}$ is independently hydrogen. In embodiments, $R^{2.6}$ is independently substituted or unsubstituted $C_1$-$C_4$ alkyl. In embodiments, $R^{2.6}$ is independently oxo-substituted $C_1$-$C_4$ alkyl. In embodiments, $R^{2.6}$ is independently substituted or unsubstituted 2 to 6 membered heteroalkyl. In embodiments, $R^{2.6}$ is independently oxo-substituted 2 to 6 membered heteroalkyl. In embodiments, $R^{2.6}$ independently is $-C(O)H$, $-CH_2C(O)H$, $-CH_2C(O)OH$, $-C(O)OH$, $-CH_2NHCH_3$, $-CH_2NH_2$, or $-CH_2N(CH_3)_2$. In embodiments, $R^{2.6}$ is independently $-C(O)H$. In embodiments, $R^{2.6}$ is independently $-CH_2C(O)H$. In embodiments, $R^{2.6}$ is independently $-CH_2C(O)OH$. In embodiments, $R^{2.6}$ is independently $-C(O)OH$. In embodiments, $R^{2.6}$ is independently $-CH_2NHCH_3$. In embodiments, $R^{2.6}$ is independently $-CH_2NH_2$. In embodiments, $R^{2.6}$ is independently $-CH_2N(CH_3)_2$.

In embodiments, $R^{2.6}$ is independently hydrogen, $-NH_2$, substituted or unsubstituted 3 to 6 membered heteroalkyl, substituted or unsubstituted 4 to 7 membered heterocycloalkyl,

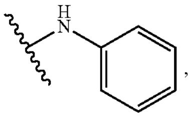
, or
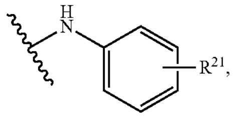

wherein $R^{21}$ is as described herein, including in embodiments. In embodiments, $R^{2.6}$ is independently

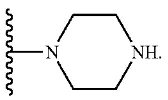 [SMILES: *N1CCNCC1]

In embodiments, $R^{2.6}$ is independently

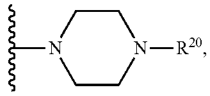

wherein $R^{20}$ is as described herein, including in embodiments.

In embodiments, $R^{2.6}$ is independently hydrogen, $-NH_2$, $-NHCH_3$, $-N(CH_3)_3$,

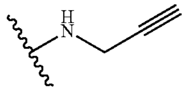
,
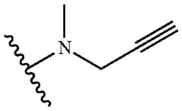
,
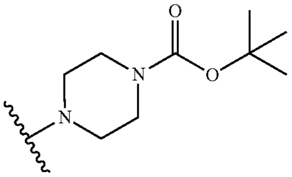
,
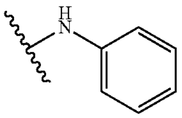
,
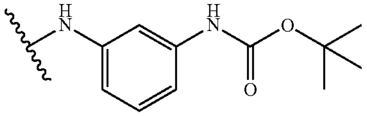
,
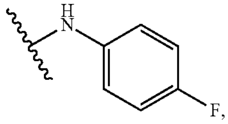
or
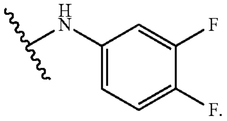

In embodiments, $R^{2.6}$ is independently hydrogen. In embodiments, $R^{2.6}$ is independently $-NH_2$. In embodiments, $R^{2.6}$ is independently $-NHCH_3$. In embodiments, $R^{2.6}$ is independently $-N(CH_3)_3$. In embodiments, $R^{2.6}$ is independently

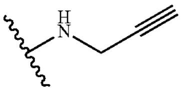

In embodiments, $R^{2.6}$ is independently

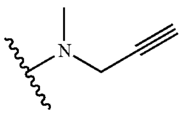

In embodiments, $R^{2.6}$ is independently

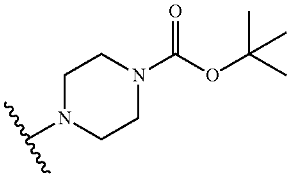

In embodiments, $R^{2.6}$ is independently

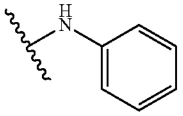

In embodiments, $R^{2.6}$ is independently

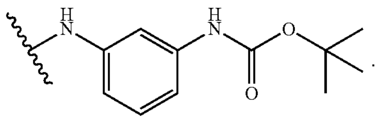 [SMILES: *Nc1cccc(NC(=O)OC(C)(C)C)c1]

In embodiments, $R^{2.6}$ is independently

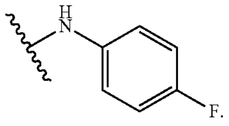 [SMILES: *Nc1ccc(F)cc1]

In embodiments, $R^{2.6}$ is independently

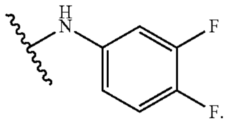 [SMILES: *Nc1ccc(F)c(F)c1]

In embodiments, $R^{2.6}$ is independently —C(O)$NR^{2A}R^{2B}$. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is substituted methyl. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently n-butyl. In embodiments, $R^{2A}$ is independently tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently n-butyl. In embodiments, $R^{2B}$ is independently tert-butyl. In embodiments, $R^{2.6}$ is independently

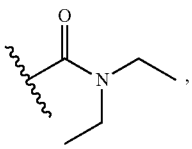,
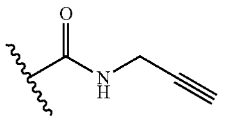, or

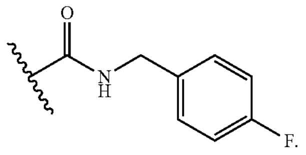

In embodiments, $R^{2.6}$ is independently

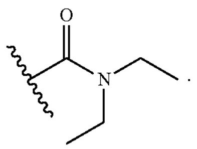 [SMILES: *C(=O)N(CC)CC]

In embodiments, $R^{2.6}$ is independently

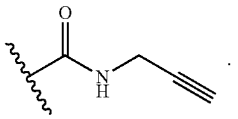 [SMILES: *C(=O)NCC#C]

In embodiments, $R^{2.6}$ is independently

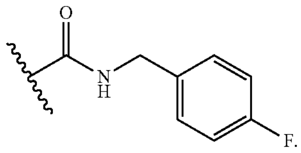 [SMILES: *C(=O)NCc1ccc(F)cc1]

In embodiments, $R^{2.6}$ is halogen. In embodiments, $R^{2.6}$ is —F. In embodiments, $R^{2.6}$ is —Cl. In embodiments, $R^{2.6}$ is —Br. In embodiments, $R^{2.6}$ is —I. In embodiments, $R^{2.6}$ is $R^{20}$-substituted or unsubstituted 5 or 6 membered heteroaryl, wherein $R^{20}$ is as described herein, including in embodiments. In embodiments, $R^{2.6}$ is $R^{20}$-substituted or unsubstituted thienyl, wherein $R^{20}$ is as described herein, including in embodiments. In embodiments, $R^{2.6}$ is

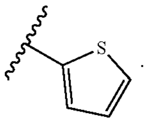 [SMILES: *c1cccs1]

In embodiments, $R^{2.6}$ is

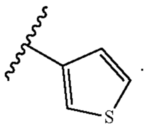 [SMILES: *c1ccsc1]

In embodiments, $R^{2.6}$ is

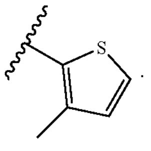 [SMILES: *c1sccc1C]

In embodiments, $R^{2.6}$ is

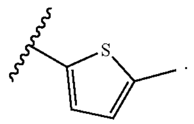 [SMILES: *c1ccc(C)s1]

In embodiments, $R^{2.6}$ is

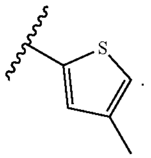 [SMILES: *c1cc(C)cs1]

In embodiments, $R^{2.6}$ is

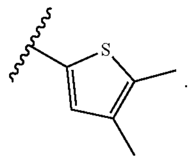 [SMILES: *c1cc(C)c(C)s1]

In embodiments, $R^{2.6}$ is

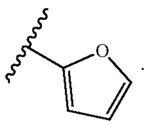 [SMILES: *c1ccco1]

In embodiments, $R^{2.6}$ is

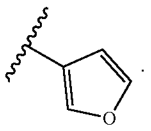 [SMILES: *c1ccoc1]

In embodiments, $R^{2.6}$ is

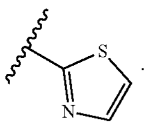 [SMILES: *c1nccs1]

In embodiments, $R^{2.6}$ is

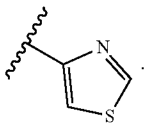 [SMILES: *c1cscn1]

In embodiments, $R^{2.6}$ is

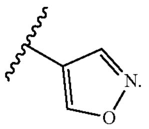 [SMILES: *c1cnoc1]

In embodiments, $R^{2.6}$ is

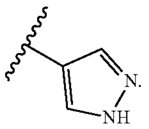 [SMILES: *c1cn[nH]c1]

In embodiments, $R^{2.6}$ is

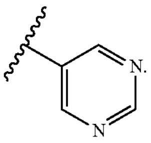 [SMILES: *c1cncnc1]

In embodiments, $R^{2.6}$ is —O-(substituted or unsubstituted alkyl). In embodiments, $R^{2.6}$ is —O-(unsubstituted alkyl). In embodiments, $R^{2.6}$ is —O-(substituted or unsubstituted $C_1$-$C_4$ alkyl). In embodiments, $R^{2.6}$ is —O-(unsubstituted $C_1$-$C_4$ alkyl). In embodiments, $R^{2.6}$ is —O-(unsubstituted methyl). In embodiments, $R^{2.6}$ is —O-(unsubstituted ethyl). In embodiments, $R^{2.6}$ is —O-(unsubstituted propyl). In embodiments, $R^{2.6}$ is —O-(unsubstituted n-propyl). In embodiments, $R^{2.6}$ is —O-(unsubstituted isopropyl). In embodiments, $R^{2.6}$ is —O-(unsubstituted n-butyl). In embodiments, $R^{2.6}$ is —O-(unsubstituted tert-butyl). In embodiments, $R^{2.6}$ is —O-(substituted or unsubstituted heteroalkyl). In embodiments, $R^{2.6}$ is —O-(unsubstituted heteroalkyl). In embodiments, $R^{2.6}$ is —O-(substituted or unsubstituted 2 to 6 membered heteroalkyl). In embodiments, $R^{2.6}$ is —O-(unsubstituted 2 to 6 membered heteroalkyl). In embodiments, $R^{2.6}$ is —O-(substituted or unsubstituted cycloalkyl). In embodiments, $R^{2.6}$ is —O-(unsubstituted cycloalkyl). In embodiments, $R^{2.6}$ is —O-(substituted or unsubstituted $C_3$-$C_6$ cycloalkyl). In embodiments, $R^{2.6}$ is —O-(unsubstituted $C_3$-$C_6$ cycloalkyl). In embodiments, $R^{2.6}$ is —O-(substituted or unsubstituted heterocycloalkyl). In embodiments, $R^{2.6}$ is —O-(unsubstituted heterocycloalkyl). In embodiments, $R^{2.6}$ is —O-(substituted or unsubstituted 3 to 6 membered heterocycloalkyl). In embodiments, $R^{2.6}$ is —O-(unsubstituted 3 to 6 membered heterocycloalkyl). In embodiments, $R^{2.6}$ is —O-(substituted or unsubstituted aryl). In embodiments, $R^{2.6}$ is —O-(unsubstituted aryl). In embodiments, $R^{2.6}$ is —O-(substituted or unsubstituted phenyl). In embodiments, $R^{2.6}$ is —O-(unsubstituted phenyl). In embodiments, $R^{2.6}$ is —O-(substituted or unsubstituted heteroaryl). In embodiments, $R^{2.6}$ is —O-(unsubstituted heteroaryl). In embodiments, $R^{2.6}$ is —O-(substituted or unsubstituted 5 to 6 membered heteroaryl). In embodiments, $R^{2.6}$ is —O-(unsubstituted 5 to 6 membered heteroaryl). In embodiments, $R^{2.6}$ is —O-(unsubstituted pyridyl). In embodiments, $R^{2.6}$ is

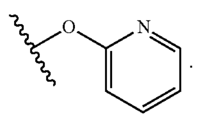 [SMILES: *Oc1ccccn1]

In embodiments, $R^{2.6}$ is

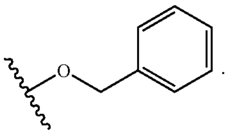 [SMILES: *OCc1ccccc1]

In embodiments, $R^{2.6}$ is

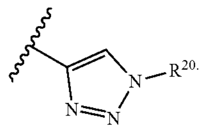

wherein $R^{20}$ is as described herein, including in embodiments.

In embodiments, $R^{2.6}$ is —NS(O)$F_2$. In embodiments, $R^{2.6}$ is —NS(O)FN$R^{2A}R^{2B}$, wherein $R^{2A}$ and $R^{2B}$ are as described herein, including in embodiments. In embodiments, $R^{2.6}$ is —NS(O)FNH$R^{2B}$, wherein $R^{2B}$ is as described herein, including in embodiments. In embodiments, $R^{2A}$ is independently hydrogen, or substituted or unsubstituted $C_1$-$C_4$ alkyl. In embodiments, $R^{2A}$ is independently hydrogen. In embodiments, $R^{2A}$ is independently unsubstituted methyl. In embodiments, $R^{2A}$ is independently unsubstituted ethyl. In embodiments, $R^{2A}$ is independently unsubstituted n-propyl. In embodiments, $R^{2A}$ is independently unsubstituted isopropyl. In embodiments, $R^{2A}$ is independently unsubstituted n-butyl. In embodiments, $R^{2A}$ is independently unsubstituted tert-butyl. In embodiments, $R^{2B}$ is independently hydrogen or unsubstituted $C_1$-$C_4$ alkyl. In embodiments, $R^{2B}$ is independently hydrogen. In embodiments, $R^{2B}$ is independently unsubstituted methyl. In embodiments, $R^{2B}$ is independently unsubstituted ethyl. In embodiments, $R^{2B}$ is independently unsubstituted n-propyl. In embodiments, $R^{2B}$ is independently unsubstituted isopropyl. In embodiments, $R^{2B}$ is independently unsubstituted n-butyl. In embodiments, $R^{2B}$ is independently unsubstituted tert-butyl. In embodiments, $R^{2A}$ and $R^{2B}$ may be joined to form a substituted or unsubstituted heterocycloalkyl. In embodiments, $R^{2A}$ and $R^{2B}$ may be joined to form a substituted heterocycloalkyl. In embodiments, $R^{2A}$ and $R^{2B}$ may be joined to form an $R^{20}$-substituted heterocycloalkyl. In embodiments, $R^{2A}$ and $R^{2B}$ may be joined to form an unsubstituted heterocycloalkyl.

In embodiment, $R^{2.6}$ is -$L^2$-$R^{23}$. $L^2$ and $R^{23}$ are as described herein, including in embodiments.

In embodiments, the compound has the formula:

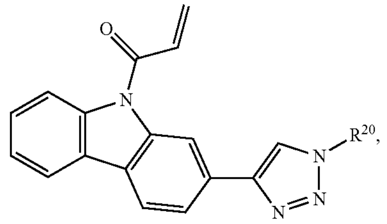

wherein $R^{20}$ is as described herein, including in embodiments. In embodiments, the compound has the formula:

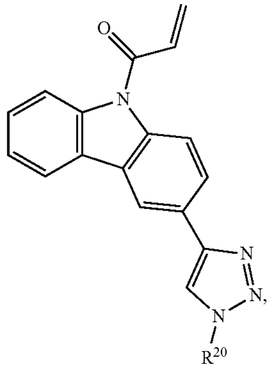

wherein $R^{20}$ is as described herein, including in embodiments. In embodiments, the compound has the formula:

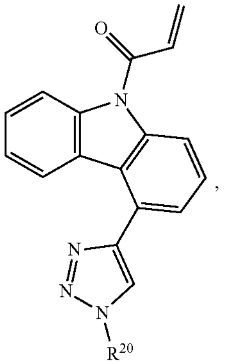

wherein $R^{20}$ is as described herein, including in embodiments.

In embodiments, the compound has the formula:

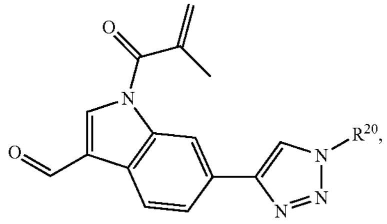

wherein $R^{20}$ is as described herein, including in embodiments. In embodiments, the compound has the formula:

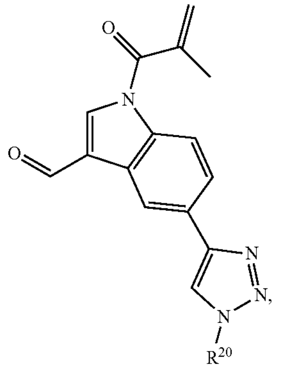

wherein $R^{20}$ is as described herein, including in embodiments. In embodiments, the compound has the formula:

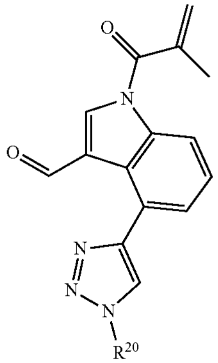
, wherein $R^{20}$ is as described herein, including in embodiments. In embodiments, the compound has the formula:

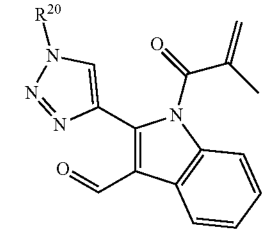
, wherein $R^{20}$ is as described herein, including in embodiments. In embodiments, the compound has the formula:

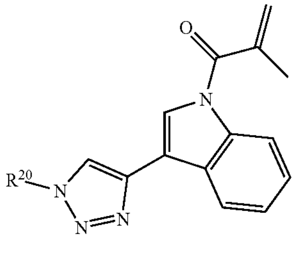
, wherein $R^{20}$ is as described herein, including in embodiments.

In embodiments, $R^{20}$ is independently $R^{21}$-substituted or unsubstituted $C_1$-$C_4$ alkyl. In embodiments, $R^{20}$ is independently $R^{21}$-substituted $C_1$-$C_4$ alkyl. In embodiments, $R^{20}$ is independently $R^{21}$-substituted methyl. In embodiments, $R^{20}$ is independently $R^{21}$-substituted ethyl. In embodiments, $R^{20}$ is independently $R^{21}$-substituted n-propyl. In embodiments, $R^{20}$ is independently $R^{21}$-substituted n-butyl. In embodiments, $R^{20}$ is independently $R^{21}$-substituted or unsubstituted $C_3$-$C_6$ cycloalkyl. In embodiments, $R^{20}$ is independently $R^{21}$-substituted $C_3$-$C_6$ cycloalkyl. In embodiments, $R^{20}$ is independently $R^{21}$-substituted cyclopropyl. In embodiments, $R^{20}$ is independently $R^{21}$-substituted cyclobutyl. In embodiments, $R^{20}$ is independently $R^{21}$-substituted cyclopentyl. In embodiments, $R^{20}$ is independently $R^{21}$-substituted cyclohexyl. In embodiments, $R^{20}$ is independently $R^{21}$-substituted or unsubstituted 3 to 6 membered heterocycloalkyl. In embodiments, $R^{20}$ is independently $R^{21}$-substituted 3 to 6 membered heterocycloalkyl. In embodiments, $R^{20}$ is independently $R^{21}$-substituted 5 membered heterocycloalkyl. In embodiments, $R^{20}$ is independently $R^{21}$-substituted 6 membered heterocycloalkyl.

In embodiments, $R^{20}$ is independently

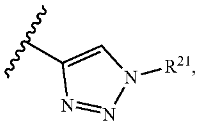

wherein $R^{21}$ is as described herein, including in embodiments. In embodiments, $R^{20}$ is independently —$NS(O)F_2$.

In embodiments, $R^{21}$ is independently —$CONH_2$. In embodiments, $R^{21}$ is independently $R^{22}$-substituted or unsubstituted 3 to 6 membered heterocycloalkyl. In embodiments, $R^{21}$ is independently $R^{22}$-substituted 3 to 6 membered heterocycloalkyl. In embodiments, $R^{21}$ is independently $R^{22}$-substituted 5 membered heterocycloalkyl. In embodiments, $R^{21}$ is independently $R^{22}$-substituted 6 membered heterocycloalkyl. In embodiments, $R^{21}$ is independently $R^{22}$-substituted or unsubstituted 5 to 10 membered heteroaryl. In embodiments, $R^{21}$ is independently $R^{22}$-substituted 5 to 10 membered heteroaryl. In embodiments, $R^{21}$ is independently $R^{22}$-substituted 5 membered heteroaryl. In embodiments, $R^{21}$ is independently $R^{22}$-substituted 6 membered heteroaryl. In embodiments, $R^{21}$ is independently unsubstituted 5 to 10 membered heteroaryl. In embodiments, $R^{21}$ is independently unsubstituted 5 membered heterocycloalkyl. In embodiments, $R^{21}$ is independently unsubstituted 6 membered heterocycloalkyl. In embodiments, $R^{21}$ is independently unsubstituted pyridyl.

In embodiments, $R^{21}$ is independently

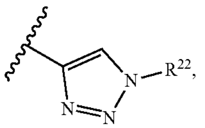

wherein $R^{22}$ is as described herein, including in embodiments. In embodiments, $R^{21}$ is independently —$NS(O)F_2$.

In embodiments, $R^{22}$ is independently oxo. In embodiments, $R^{22}$ is independently unsubstituted $C_1$-$C_4$ alkyl. In embodiments, $R^{22}$ is independently unsubstituted methyl. In embodiments, $R^{22}$ is independently unsubstituted ethyl. In embodiments, $R^{22}$ is independently unsubstituted n-propyl. In embodiments, $R^{22}$ is independently unsubstituted isopropyl. In embodiments, $R^{22}$ is independently unsubstituted n-butyl. In embodiments, $R^{22}$ is independently unsubstituted tert-butyl. In embodiments, $R^{22}$ is independently unsubstituted 2 to 6 membered heteroalkyl. In embodiments, $R^{22}$ is independently $—N(CH_3)_2$. In embodiments, $R^{22}$ is independently $—N(CH_2CH_3)_2$. In embodiments, $R^{22}$ is independently $—N(CH_2CH_2CH_3)_2$. In embodiments, $R^{22}$ is independently unsubstituted methoxy. In embodiments, $R^{22}$ is independently unsubstituted ethoxy. In embodiments, $R^{22}$ is independently unsubstituted propoxy. In embodiments, $R^{22}$ is independently $—NS(O)F_2$.

In embodiments, $R^2$ is independently

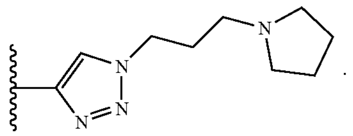 [SMILES: *c1cn(CCCN2CCCC2)nn1]

In embodiments, $R^2$ is independently

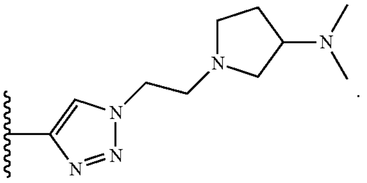 [SMILES: *c1cn(CCN2CCC(N(C)C)C2)nn1]

In embodiments, $R^2$ is independently

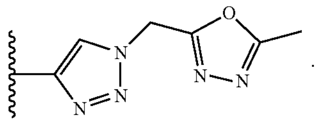 [SMILES: *c1cn(Cc2nnc(C)o2)nn1]

In embodiments, $R^2$ is independently

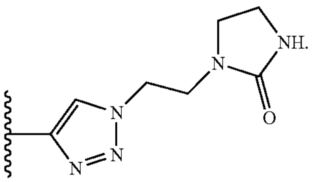 [SMILES: *c1cn(CCN2CCNC2=O)nn1]

In embodiments, R is independently

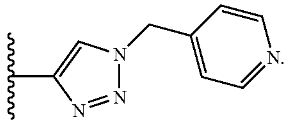 [SMILES: *c1cn(Cc2ccncc2)nn1]

In embodiments, $R^2$ is independently

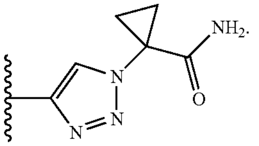 [SMILES: *c1cn(C2(C(N)=O)CC2)nn1]

In embodiments, $R^2$ is independently

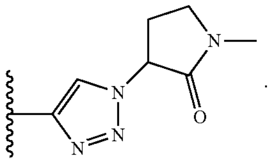 [SMILES: *c1cn(C2CCN(C)C2=O)nn1]

In embodiments, the compound has the formula:

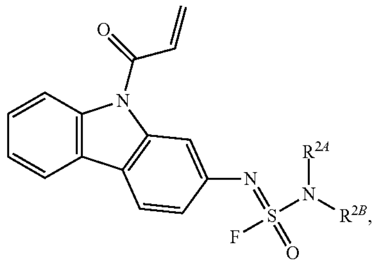

wherein $R^{2A}$ and $R^{2B}$ are as described herein, including in embodiments. In embodiments, the compound has the formula:

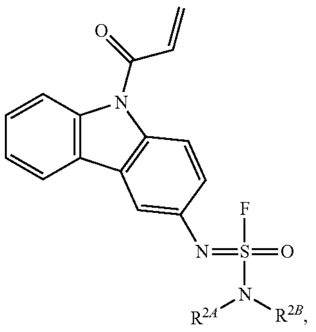

wherein $R^{2A}$ and $R^{2B}$ are as described herein, including in embodiments. In embodiments, the compound has the formula:

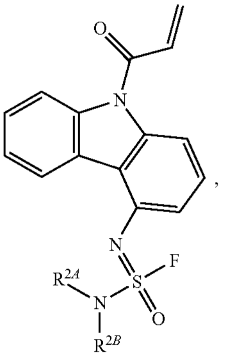

wherein $R^{2A}$ and $R^{2B}$ are as described herein, including in embodiments.

In embodiments, the compound has the formula:

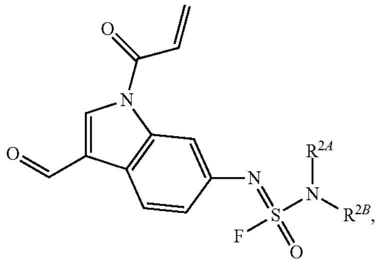

wherein $R^{2A}$ and $R^{2B}$ are as described herein, including in embodiments. In embodiments, the compound has the formula:

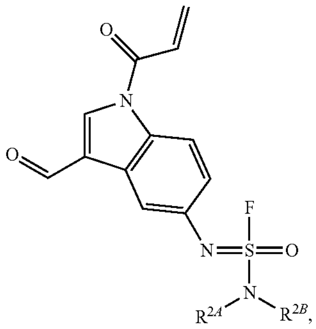

wherein $R^{2A}$ and $R^{2B}$ are as described herein, including in embodiments. In embodiments, the compound has the formula:

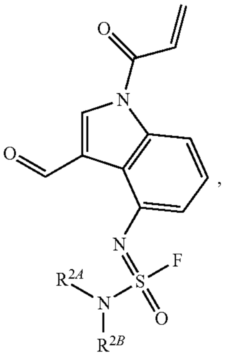

wherein $R^{2A}$ and $R^{2B}$ are as described herein, including in embodiments. In embodiments, the compound has the formula:

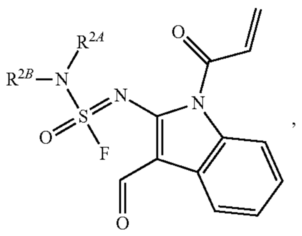

wherein $R^{2A}$ and $R^{2B}$ are as described herein, including in embodiments. In embodiments, the compound has the formula:

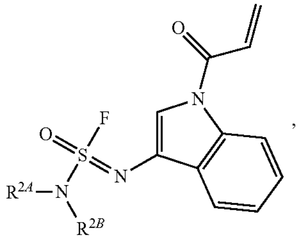

wherein $R^{2A}$ and $R^{2B}$ are as described herein, including in embodiments.

In embodiments, $R^3$ is

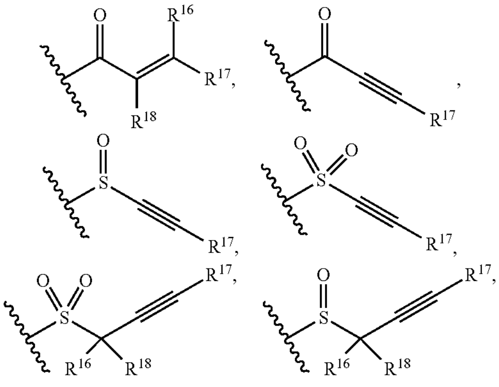

-continued

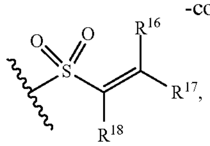

or

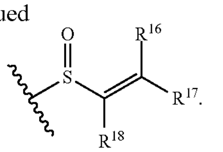

$R^{16}$, $R^{17}$, and $R^{18}$ are independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{16}$, $R^{17}$, and $R^{18}$ are independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{16}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16}$ is substituted with a plurality of groups selected from substituent groups, size-limited substituent groups, and lower substituent groups; each substituent group, size-limited substituent group, and/or lower substituent group may optionally be different. In embodiments, when $R^{16}$ is substituted, it is substituted with at least one substituent group. In embodiments, when $R^{16}$ is substituted, it is substituted with at least one size-limited substituent group. In embodiments, when $R^{16}$ is substituted, it is substituted with at least one lower substituent group.

In embodiments, a substituted $R^{17}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{17}$ is substituted with a plurality of groups selected from substituent groups, size-limited substituent groups, and lower substituent groups; each substituent group, size-limited substituent group, and/or lower substituent group may optionally be different. In embodiments, when $R^{17}$ is substituted, it is substituted with at least one substituent group. In embodiments, when $R^{17}$ is substituted, it is substituted with at least one size-limited substituent group. In embodiments, when $R^{17}$ is substituted, it is substituted with at least one lower substituent group.

In embodiments, a substituted $R^{18}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{18}$ is substituted with a plurality of groups selected from substituent groups, size-limited substituent groups, and lower substituent groups; each substituent group, size-limited substituent group, and/or lower substituent group may optionally be different. In embodiments, when $R^{18}$ is substituted, it is substituted with at least one substituent group. In embodiments, when $R^{18}$ is substituted, it is substituted with at least one size-limited substituent group. In embodiments, when $R^{18}$ is substituted, it is substituted with at least one lower substituent group.

In embodiments, $R^{16}$, $R^{17}$, and $R^{18}$ are independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{12}$ aryl, or substituted or unsubstituted 5 to 12 membered heteroaryl.

In embodiments, $R^3$ is

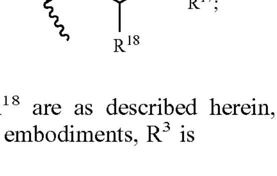

$R^{16}$, $R^{17}$, and $R^{18}$ are as described herein, including in embodiments. In embodiments, $R^3$ is

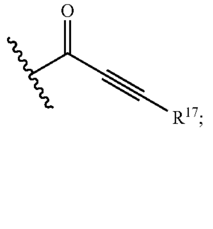

$R^{17}$ is as described herein, including in embodiments. In embodiments, $R^3$ is

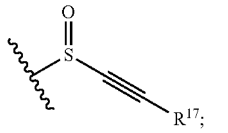

$R^{17}$ is as described herein, including in embodiments. In embodiments, $R^3$ is

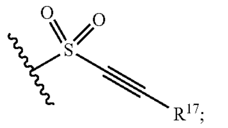

$R^{17}$ is as described herein, including in embodiments. In embodiments, $R^3$ is

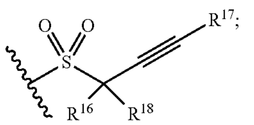

$R^{16}$, $R^{17}$, and $R^{18}$ are as described herein, including in embodiments. In embodiments, $R^3$ is

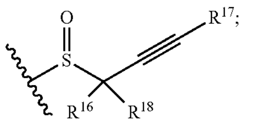

$R^{16}$, $R^{17}$, and $R^{18}$ are as described herein, including in embodiments. In embodiments, $R^3$ is

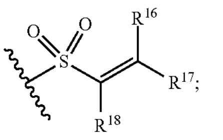

$R^{16}$, $R^{17}$, and $R^{18}$ are as described herein, including in embodiments. In embodiments, $R^3$ is

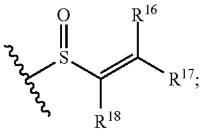

$R^{16}$, $R^{17}$, and $R^{18}$ are as described herein, including in embodiments.

In embodiments, $R^{16}$ is hydrogen, $R^{17}$ is hydrogen, and $R^{18}$ is hydrogen. In embodiments, $R^{16}$ is hydrogen, $R^{17}$ is hydrogen, and $R^{18}$ is unsubstituted methyl. In embodiments, $R^{16}$ is hydrogen, $R^{17}$ is hydrogen, and $R^{18}$ is —CN.

In embodiments, $R^3$ is

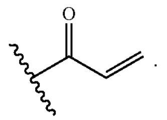 [SMILES: *C(=O)C=C]

In embodiments, $R^3$ is

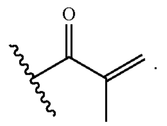 [SMILES: *C(=O)C(=C)C]

In embodiments, $R^1$ is hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, the transcriptional coactivator binding moiety is an azepine derivative such as a derivative having the formula:

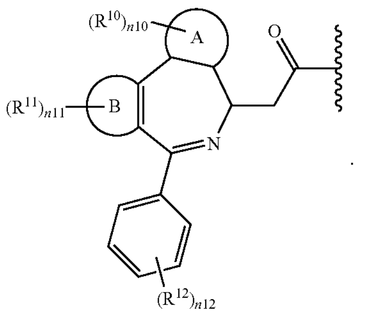

Rings A and B are each independently a $C_5$-$C_6$ cycloalkyl, 5 to 6 membered heterocycloalkyl, phenyl, or 5 to 6 membered heteroaryl. For example, rings A and B may include a ring selected from the group consisting of triazo, isoxazolo, thieno, benzo, furanyl, selenophenyl and pyridyl rings. In embodiments, ring A is triazolyl, and ring B is thienyl. In embodiments, ring A is triazolyl, and ring B is benzyl. In embodiments, ring A is isoxazolyl, and ring B is thienyl. In embodiments, ring A is isoxazolyl, and ring B is thienyl.

Each $R^{10}$ is independently unsubstituted $C_1$-$C_4$ alkyl, —O—$R^{10A}$ or —$CF_3$, wherein $R^{10A}$ is independently unsubstituted $C_1$-$C_4$ alkyl. In embodiments, $R^{10}$ is independently unsubstituted methyl. The variable n10 is 0, 1, 2 or 3. In embodiments, n10 is 0. In embodiments, n10 is 1. In embodiments, n10 is 2. In embodiments, n10 is 3.

Each $R^{11}$ is independently halogen or $C_1$-$C_4$ alkyl optionally independently substituted by halogen or hydroxyl. The variable n11 is 0, 1, 2 or 3. In embodiments, n11 is 0. In embodiments, n11 is 1. In embodiments, n11 is 2. In embodiments, n11 is 3.

Each $R^{12}$ is independently halogen or phenyl optionally independently substituted by halogen, unsubstituted $C_1$-$C_4$ alkyl, unsubstituted $C_1$-$C_4$ alkoxy, —CN, —$NR^{13}$—$(CH_2)_{v5}$—$R^{14}$ or —$NR^{13}$—C(O)—$(CH_2)_{v5}$—$R^{14}$. $R^{13}$ is hydrogen or unsubstituted $C_1$-$C_4$ alkyl. The variable v5 is an integer from 0 to 4. $R^{14}$ is phenyl optionally substituted by halogen or pyridyl optionally substituted by halogen. The variable n12 is 1 or 2. In embodiments, n12 is 1. In embodiments, n12 is 2.

In embodiments, the transcriptional coactivator binding moiety is a triazolodiazepine derivative such as a derivative having the formula:

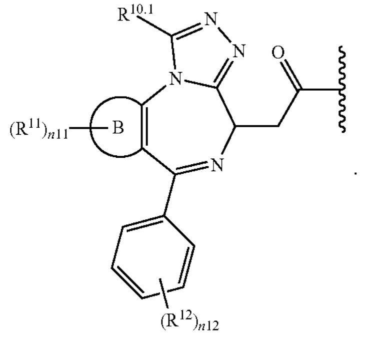

Ring B, $R^{11}$, n11, $R^{12}$, and n12 are as described herein, including in embodiments. $R^{10.1}$ is hydrogen or any value of $R^{10}$ as described herein, including in embodiments. In embodiments, $R^{10.1}$ is unsubstituted methyl.

In embodiments, the transcriptional coactivator binding moiety is a triazolodiazepine derivative such as a derivative having the formula:

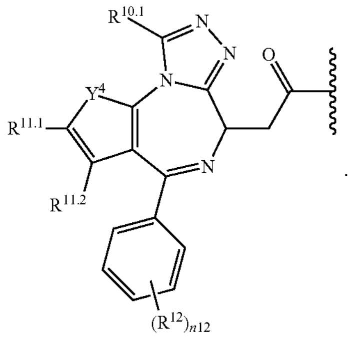

$R^{12}$ and n12 are as described herein, including in embodiments. $R^{10.1}$ is hydrogen or any value of $R^{10}$ as described herein, including in embodiments. $R^{11.1}$ and $R^{11.2}$ are independently hydrogen or any value of $R^{11}$ as described herein, including in embodiments. $Y^4$ is —S— or —CH═CH—.

In embodiments, $Y^4$ is —S—. In embodiments, $Y^4$ is —CH═CH—.

In embodiments, $R^{10.1}$ is unsubstituted methyl.

In embodiments, $R^{11.1}$ is hydrogen, halogen, or $C_1$-$C_4$ alkyl optionally substituted by halogen or hydroxyl.

In embodiments, $R^{11.2}$ is hydrogen or unsubstituted $C_1$-$C_4$ alkyl. In embodiments, $R^{11.2}$ is hydrogen. In embodiments, $R^{11.2}$ is unsubstituted $C_1$-$C_4$ alkyl.

In embodiments, the transcriptional coactivator binding moiety is a thienotriazolodiazepine derivative such as (S)-tert-butyl 2-(4-(4-chlorophenyl)-2,3,9-trimethyl-6H-thieno[3,2-f][1,2,4]triazolo[4,3-a][1,4]diazepin-6-yl)acetate (JQ1) and derivatives thereof such as those disclosed in International PCT Publication No. WO2006129623, International PCT Publication No. WO2009084693 and International PCT Publication No. WO2011143651, the contents of which are incorporated herein by reference. Other thienotriazolodiazepine derivatives are disclosed in International PCT Publication No. WO2011143669, the contents of which are incorporated herein by reference.

In embodiments, the transcriptional coactivator binding moiety has the formula:

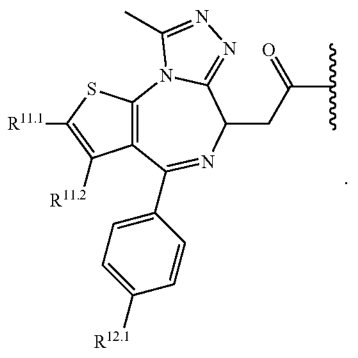

$R^{11.1}$ and $R^{11.2}$ are independently hydrogen or any value of $R^{11}$ as described herein, including in embodiments. $R^{12.1}$ is hydrogen or any value of $R^{12}$ as described herein, including in embodiments.

In embodiments, $R^{11.1}$ is unsubstituted $C_1$-$C_4$ alkyl, and $R^{11.2}$ is halogen.

In embodiments, $R^{11.1}$ and $R^{11.2}$ are each unsubstituted methyl.

In embodiments, $R^{12.1}$ is —Cl.

In embodiments, the transcriptional coactivator binding moiety is

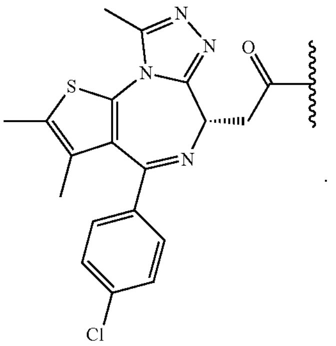 [SMILES: *C(=O)C[C@@H]1N=C(c2ccc(Cl)cc2)c2c(sc(C)c2C)-n2c(C)nnc21]

In embodiments, the transcriptional coactivator binding moiety is

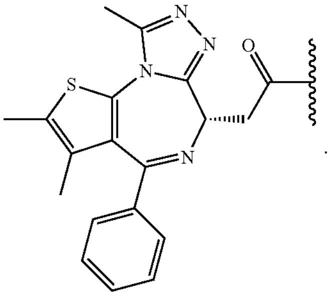 [SMILES: *C(=O)C[C@@H]1N=C(c2ccccc2)c2c(sc(C)c2C)-n2c(C)nnc21]

In embodiments, the transcriptional coactivator binding moiety a triazolodiazepine derivative such as a derivative having the formula:

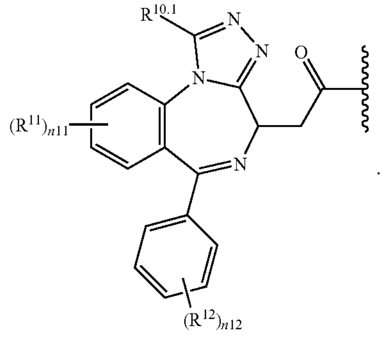

$R^{11}$, n11, $R^{12}$, and n12 are as described herein, including in embodiments. $R^{10.1}$ is hydrogen or any value of $R^{10}$ as described herein, including in embodiments. In embodiments, $R^{10.1}$ is unsubstituted methyl.

Triazolobenzodiazepine derivatives include compounds such as benzyl N-(1-methyl-6-phenyl-4H-[1,2,4]triazolo[4,3-a][1,4]benzodiazepin-4-yl)carbamate (GW841819X) and other compounds disclosed in U.S. Pat. No. 5,185,331; 2-[(4S)-6-(4-chlorophenyl)-8-methoxy-1-methyl-4H-[1,2,4]triazolo[4,3-a][1,4]benzodiazepin-4-yl]-N-ethylacetamide (molibresib) and other compounds disclosed in International PCT Publication Nos. WO2011054553, WO2011054844 and WO2011054845, the contents of which are incorporated herein by reference. Other triazolobenzodiazepines may include 8-chloro-1,4-dimethyl-6-phenyl-4h-[1,2,4]triazolo[4,3-A][1,3,4]benzotriazepine such as those compounds disclosed in U.S. Pat. No. 4,163,104 and those disclosed in International PCT Publication No. WO2011161031, the contents of which are incorporated herein by reference.

In embodiments, the transcriptional coactivator binding moiety is:

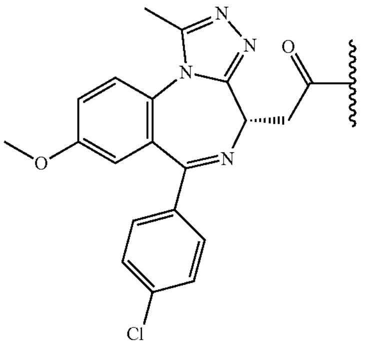

or

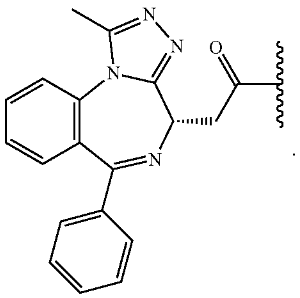

In embodiments, the transcriptional coactivator binding moiety is an isoxazoloazepine derivative such as a derivative having the formula:

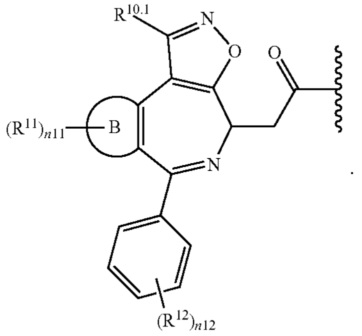

Ring B, $R^{11}$, n11, $R^{12}$, and n12 are as described herein, including in embodiments. $R^{10.1}$ is hydrogen or any value of $R^{10}$ as described herein, including in embodiments. In embodiments, $R^{10.1}$ is unsubstituted methyl.

In embodiments, the transcriptional coactivator binding moiety is a isoxazoloazepine derivative such as a derivative having the formula:

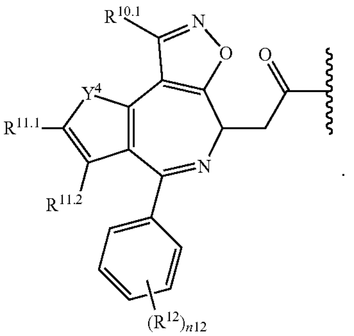

$R^{12}$ and n12 are as described herein, including in embodiments. $R^{10.1}$ is hydrogen or any value of $R^{10}$ as described herein, including in embodiments. $R^{11.1}$ and $R^{11.2}$ are independently hydrogen or any value of $R^{11}$ as described herein, including in embodiments. $Y^4$ is —S— or —CH═CH—.

In embodiments, $Y^4$ is —S—. In embodiments, $Y^4$ is —CH═CH—.

In embodiments, the transcriptional coactivator binding moiety has the formula:

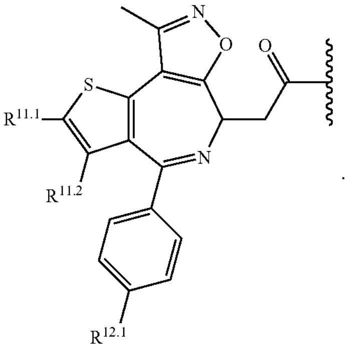

$R^{11.1}$ and $R^{11.2}$ are independently hydrogen or any value of $R^{11}$ as described herein, including in embodiments. $R^{12.1}$ is hydrogen or any value of $R^{12}$ as described herein, including in embodiments.

In embodiments, the transcriptional coactivator binding moiety is a thienoisoxazoloazepine derivative such as (S)-2-(4-(4-chlorophenyl)-2,3,9-trimethyl-6H-isoxazolo[5,4-c]thieno[2,3-e]azepin-6-yl)acetamide (CPI-3) and derivatives thereof such as those disclosed in Gehling et al., *Discovery, Design, and Optimization of Isoxazole Azepine BET Inhibitors*, ACS Med. Chem. Lett. 2013, 4, 835-840 and M. C. Hewitt et al., *Development of methyl isoxazoloazepines as inhibitors of BET*, Bioorg. Med. Chem. Lett. 25 (2015) 1842-1848, the contents of which are incorporated herein by reference.

In embodiments, the transcriptional coactivator binding moiety is

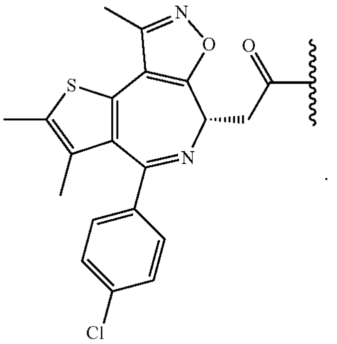 [SMILES: *C(=O)C[C@@H]1N=C(c2ccc(Cl)cc2)c2c(sc(C)c2C)-c2c(C)noc21]

In embodiments, the transcriptional coactivator binding moiety is a benzoisoxazoloazepine derivative such as a derivative having the formula:

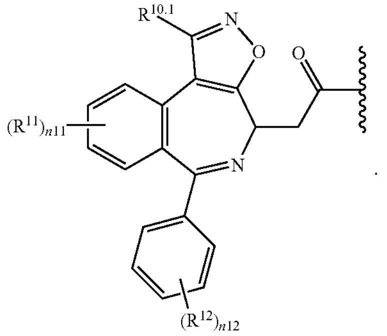

$R^{11}$, n11, $R^{12}$, and n12 are as described herein, including in embodiments. $R^{10.1}$ is hydrogen or any value of $R^{10}$ as described herein, including in embodiments. In embodiments, $R^{10.1}$ is unsubstituted methyl.

Benzoisoxazoloazepine derivatives include compounds such as 2-[(4S)-6-(4-chlorophenyl)-1-methyl-4H-[1,2]oxazolo[5,4-d][2]benzazepin-4-yl]acetamide (CPI-0610) as described in Albrecht et al., *Identification of a Benzoisoxazoloazepine Inhibitor* (*CPI*-0610) *of the Bromodomain and Extra-Terminal* (*BET*) *Family as a Candidate for Human Clinical Trials*, J. Med. Chem. 2016, 59, 1330-1339 and International PCT Publication No. WO2012075383, the contents of which are incorporated herein by reference.

In embodiments, the transcriptional coactivator binding moiety is:

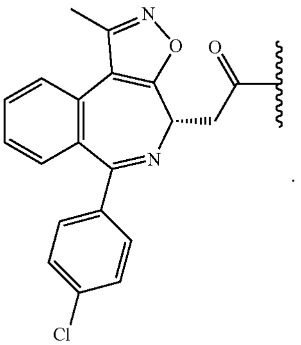 [SMILES: *C(=O)C[C@@H]1N=C(c2ccc(Cl)cc2)c2ccccc2-c2c(C)noc21]

In embodiments, the transcriptional coactivator binding moiety is a monovalent form of GSK046 disclosed in Gilan et al., Science 368, 387-394 (2020) having the formula:

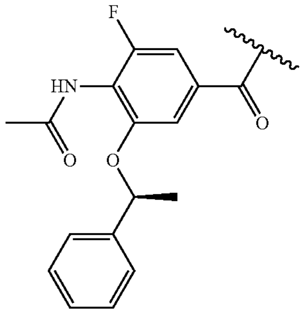

.

In embodiments, the transcriptional coactivator binding moiety is a moiety (e.g., monovalent form) of a compound selected from compounds disclosed in International PCT Publication No. WO2017/037116, the contents of which are incorporated herein by reference, such as GSK-620 having the formula:

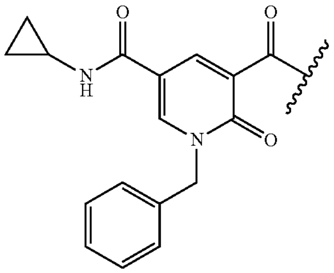

or

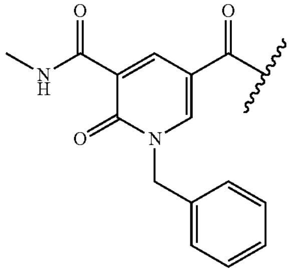

.

In embodiments, the transcriptional coactivator binding moiety is:

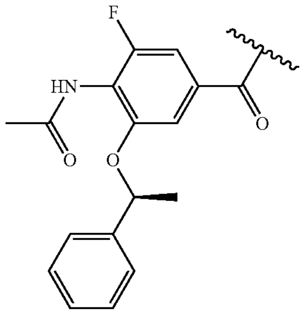

.

In embodiments, the transcriptional coactivator binding moiety is:

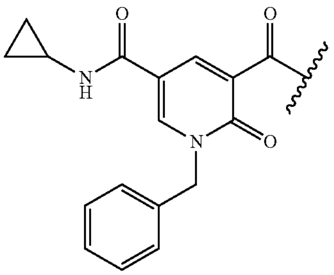

or

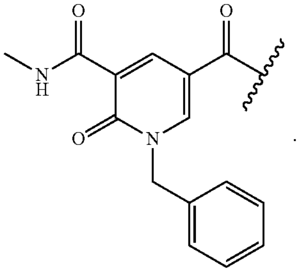

.

In embodiments, the transcriptional coactivator binding moiety is a BRD binding moiety. In embodiments, the transcriptional coactivator binding moiety is a BRD2 binding moiety. In embodiments, the transcriptional coactivator binding moiety is a BRD4 binding moiety. In embodiments, the transcriptional coactivator binding moiety is a BRDT binding moiety.

In embodiments, the BRD4 binding moiety has the formula:

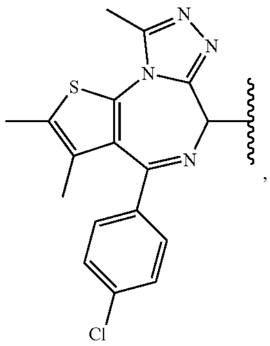

,

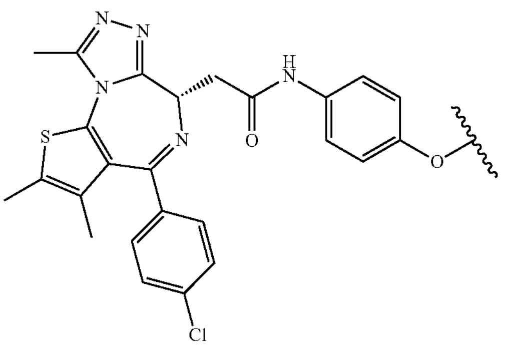

,

-continued

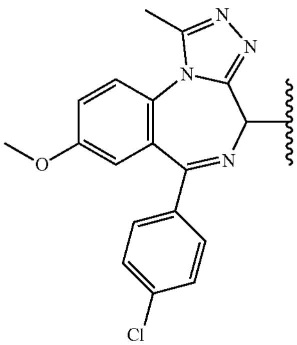

, or

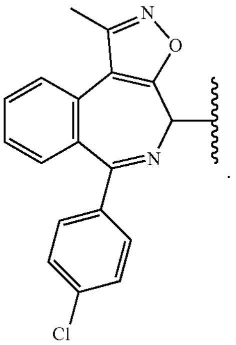

In embodiments, the BRD4 binding moiety has the formula:

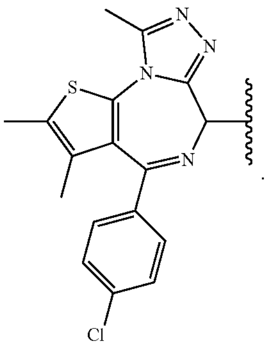 [SMILES: *C1N=C(c2ccc(Cl)cc2)c2c(sc(C)c2C)-n2c(C)nnc21]

In embodiments, the BRD4 binding moiety has the formula:

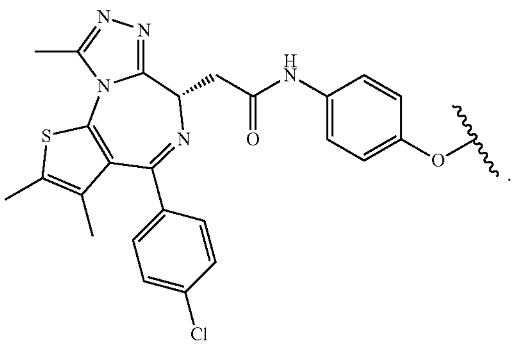 [SMILES: *Oc1ccc(NC(=O)C[C@@H]2N=C(c3ccc(Cl)cc3)c3c(sc(C)c3C)-n3c(C)nnc32)cc1]

In embodiments, the BRD4 binding moiety has the formula:

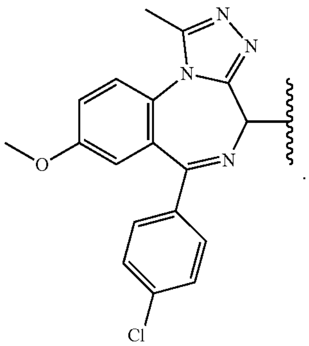 [SMILES: *C1N=C(c2ccc(Cl)cc2)c2cc(OC)ccc2-n2c(C)nnc21]

In embodiments, the BRD4 binding moiety has the formula:

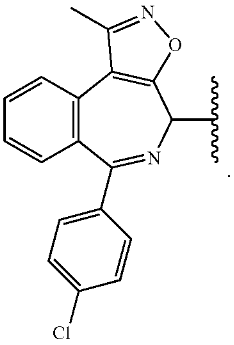 [SMILES: *C1N=C(c2ccc(Cl)cc2)c2ccccc2-c2c(C)noc21]

In embodiments, the BRD4 binding moiety has the formula:

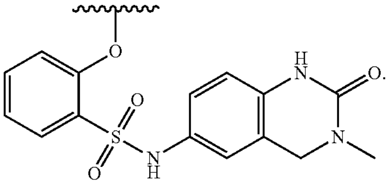 [SMILES: *Oc1ccccc1S(=O)(=O)Nc1ccc2c(c1)CN(C)C(=O)N2]

In embodiments, the BRD4 binding moiety has the formula:

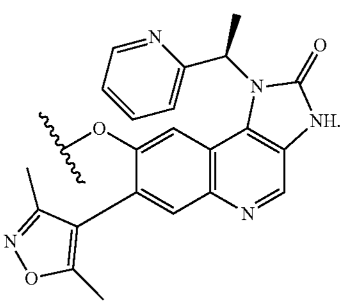 [SMILES: *Oc1cc2c(cc1-c1c(C)noc1C)ncc1[nH]c(=O)n([C@H](C)c3ccccn3)c12]

In embodiments, the BRD4 binding moiety is a monovalent form of CEM87. In embodiments, the BRD4 binding moiety has the formula:

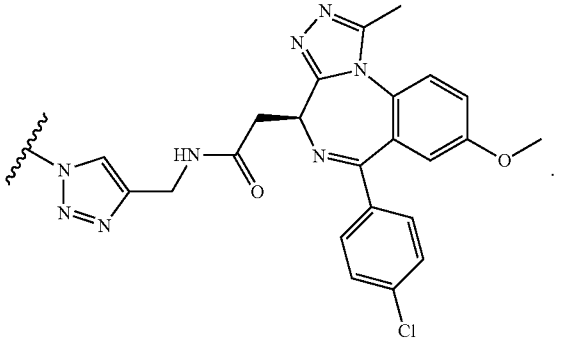 [SMILES: *n1cc(CNC(=O)C[C@@H]2N=C(c3ccc(Cl)cc3)c3cc(OC)ccc3-n3c(C)nnc32)nn1]

In embodiments, the BRD4 binding moiety is a monovalent form of (+)-JQ1, OTX 015, CPI-0610, TEN-010, PFI-1, I-BET762, or I-BET151. In embodiments, the BRD4 binding moiety is a monovalent form of a compound described in Wu, et al., A chemical toolbox for the study of bromodomains and epigenetic signaling. *Nature Communications,* 10, 1915 (2019), which is herein incorporated by reference for all purposes.

In embodiments, the transcriptional coactivator binding moiety is a p300 binding moiety.

In embodiments, the p300 binding moiety has the formula:

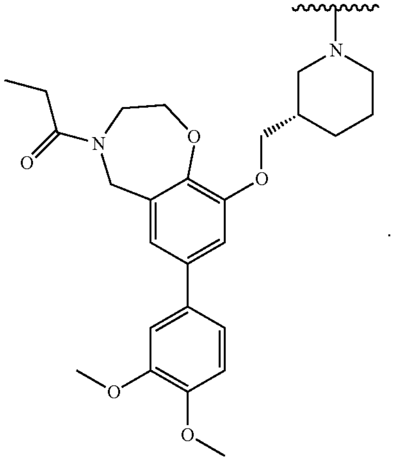 [SMILES: *N1CCC[C@H](COc2cc(-c3ccc(OC)c(OC)c3)cc3c2OCCN(C(=O)CC)C3)C1]

In embodiments, the p300 binding moiety has the formula:

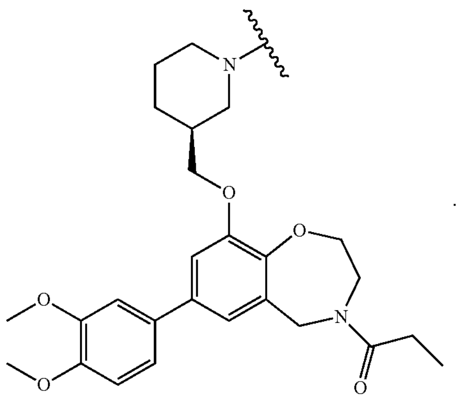 [SMILES: *N1CCC[C@H](COc2cc(-c3ccc(OC)c(OC)c3)cc3c2OCCN(C(=O)CC)C3)C1]

In embodiments, the p300 binding moiety has the formula:

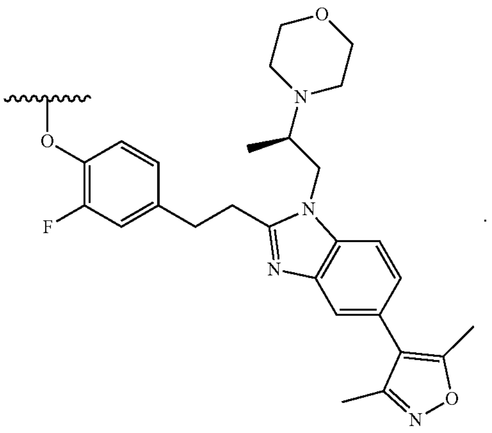 [SMILES: *Oc1ccc(CCc2nc3cc(-c4c(C)noc4C)ccc3n2C[C@@H](C)N2CCOCC2)cc1F]

In embodiments, the p300 binding moiety has the formula:

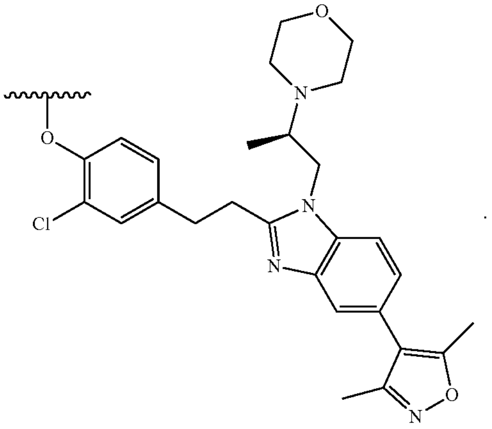 [SMILES: *Oc1ccc(CCc2nc3cc(-c4c(C)noc4C)ccc3n2C[C@@H](C)N2CCOCC2)cc1Cl]

In embodiments, the p300 binding moiety has the formula:

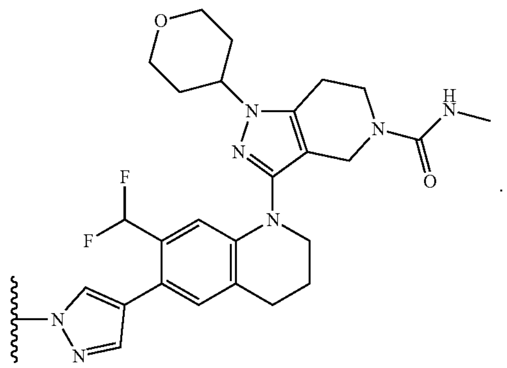 [SMILES: *n1cc(-c2cc3c(cc2C(F)F)N(c2nn(C4CCOCC4)c4c2CN(C(=O)NC)CC4)CCC3)cn1]

In embodiments, the p300 binding moiety is a monovalent form of I-CBP112, SGC-CBP30, or GNE-781. In embodiments, the p300 binding moiety is a monovalent form of a compound described in Wu, et al., A chemical toolbox for the study of bromodomains and epigenetic signaling. *Nature Communications,* 10, 1915 (2019), which is herein incorporated by reference for all purposes.

In embodiments, the transcriptional coactivator binding moiety is a p300-CBP binding moiety. In embodiments, the transcriptional coactivator binding moiety is a CREBBP binding moiety.

In embodiments, the p300-CBP binding moiety is a monovalent form of CEM114. In embodiments, the p300-CBP binding moiety has the formula:

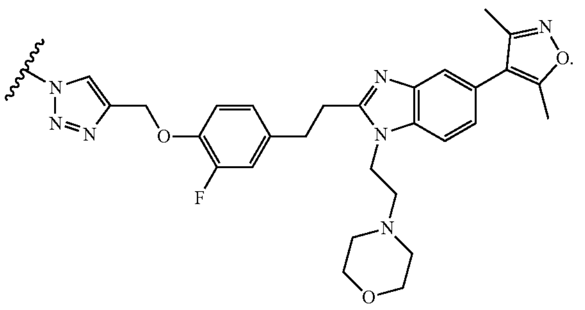 [SMILES: *n1cc(COc2ccc(CCc3nc4cc(-c5c(C)noc5C)ccc4n3CCN3CCOCC3)cc2F)nn1]

In embodiments, the transcriptional coactivator binding moiety is a glucocorticoid receptor binding moiety.

In embodiments, the glucocorticoid receptor binding moiety has the formula:

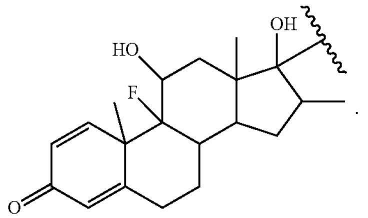 [SMILES: *C1(O)C(C)CC2C3CCC4=CC(=O)C=CC4(C)C3(F)C(O)CC21C]

In embodiments, the transcriptional coactivator binding moiety is a PCAF binding moiety. In embodiments, the transcriptional coactivator binding moiety is a GCN5L2 binding moiety. In embodiments, the transcriptional coactivator binding moiety is a CECR2 binding moiety.

In embodiments, the PCAF binding moiety is a monovalent form of GSK 4021. In embodiments, the PCAF binding moiety has the formula:

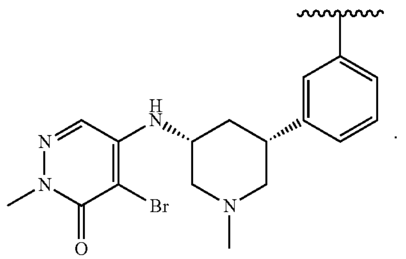 [SMILES: *c1cccc([C@H]2C[C@@H](Nc3cnn(C)c(=O)c3Br)CN(C)C2)c1]

In embodiments, the PCAF binding moiety has the formula:

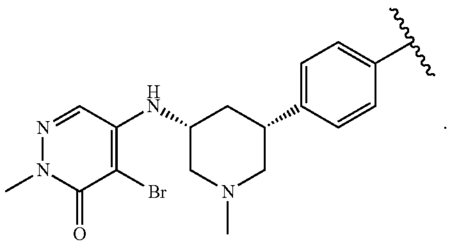 [SMILES: *c1ccc([C@H]2C[C@@H](Nc3cnn(C)c(=O)c3Br)CN(C)C2)cc1]

In embodiments, the PCAF binding moiety has the formula:

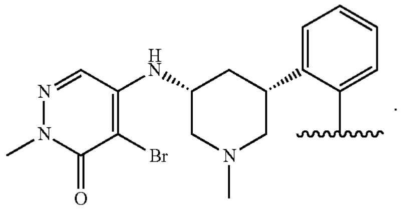 [SMILES: *c1ccccc1[C@H]1C[C@@H](Nc2cnn(C)c(=O)c2Br)CN(C)C1]

In embodiments, the PCAF binding moiety is a monovalent form of L-45. In embodiments, the PCAF binding moiety is a monovalent form of L-Moses. In embodiments, the PCAF binding moiety has the formula:

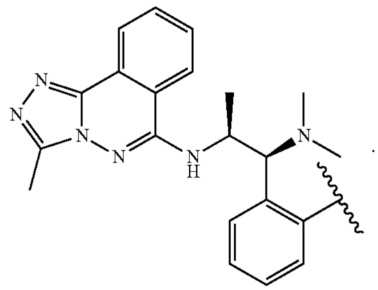 [SMILES: *c1ccccc1[C@@H]([C@H](C)Nc1nn2c(C)nnc2c2ccccc12)N(C)C]

In embodiments, the PCAF binding moiety has the formula:

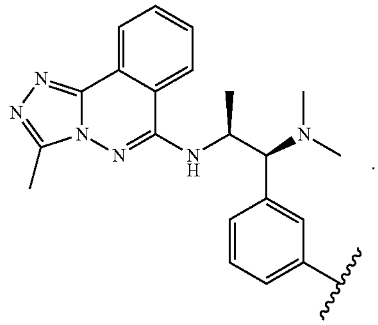 [SMILES: *c1cccc([C@@H]([C@H](C)Nc2nn3c(C)nnc3c3ccccc23)N(C)C)c1]

In embodiments, the PCAF binding moiety has the formula:

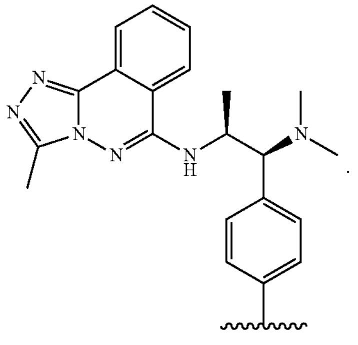 [SMILES: *c1ccc([C@@H]([C@H](C)Nc2nn3c(C)nnc3c3ccccc23)N(C)C)cc1]

In embodiments, the PCAF binding moiety is a monovalent form of NVS-CECR2-1. In embodiments, the PCAF binding moiety has the formula:

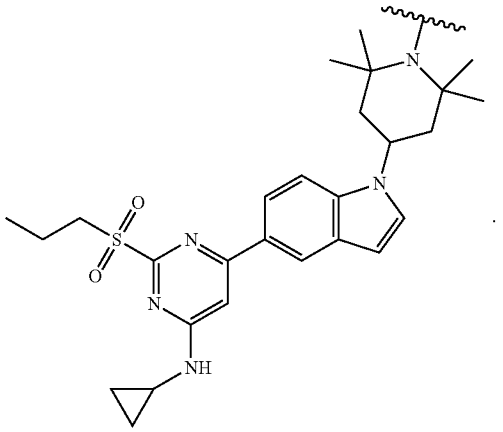 [SMILES: *N1C(C)(C)CC(n2ccc3cc(-c4cc(NC5CC5)nc(S(=O)(=O)CCC)n4)ccc32)CC1(C)C]

In embodiments, the PCAF binding moiety is a monovalent form of GNE-886. In embodiments, the PCAF binding moiety has the formula:

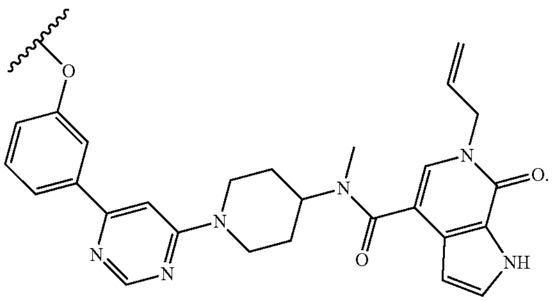 [SMILES: *Oc1cccc(-c2cc(N3CCC(N(C)C(=O)c4cn(CC=C)c(=O)c5[nH]ccc45)CC3)ncn2)c1]

In embodiments, the transcriptional coactivator binding moiety is a BRPF binding moiety. In embodiments, the transcriptional coactivator binding moiety is a BRD9 binding moiety. In embodiments, the transcriptional coactivator binding moiety is a BRD7 binding moiety. In embodiments, the transcriptional coactivator binding moiety is a BRPF3 binding moiety. In embodiments, the transcriptional coactivator binding moiety is a BRPF1 binding moiety. In embodiments, the transcriptional coactivator binding moiety is a BRPF2 binding moiety. In embodiments, the transcriptional coactivator binding moiety is an ATAD2 binding moiety.

In embodiments, the BRPF binding moiety is a monovalent form of PFI-4. In embodiments, the BRPF binding moiety has the formula:

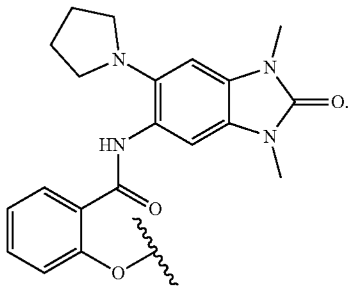 [SMILES: *Oc1ccccc1C(=O)Nc1cc2c(cc1N1CCCC1)n(C)c(=O)n2C]

In embodiments, the BRPF binding moiety has the formula:

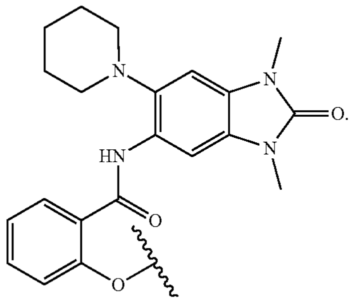 [SMILES: *Oc1ccccc1C(=O)Nc1cc2c(cc1N1CCCCC1)n(C)c(=O)n2C]

In embodiments, the BRPF binding moiety is a monovalent form of OF1. In embodiments, the BRPF binding moiety has the formula:

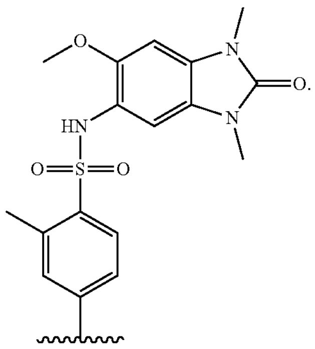 [SMILES: *c1ccc(S(=O)(=O)Nc2cc3c(cc2OC)n(C)c(=O)n3C)c(C)c1]

In embodiments, the BRPF binding moiety is a monovalent form of NI-57. In embodiments, the BRPF binding moiety has the formula:

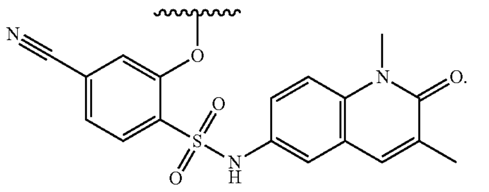 [SMILES: *Oc1cc(C#N)ccc1S(=O)(=O)Nc1ccc2c(c1)cc(C)c(=O)n2C]

In embodiments, the BRPF binding moiety is a monovalent form of GSK6853. In embodiments, the BRPF binding moiety has the formula:

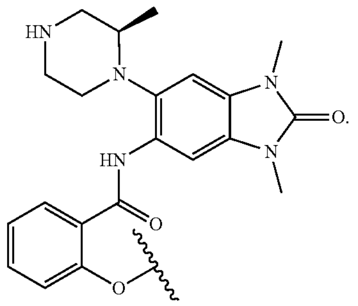 [SMILES: *Oc1ccccc1C(=O)Nc1cc2c(cc1N1CCNC[C@H]1C)n(C)c(=O)n2C]

In embodiments, the BRPF binding moiety is a monovalent form of LP99. In embodiments, the BRPF binding moiety has the formula:

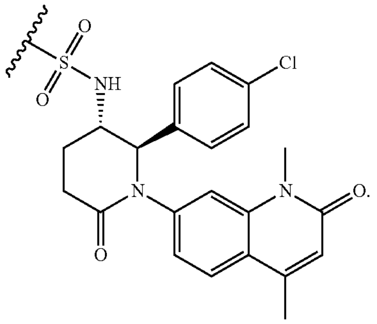 [SMILES: *S(=O)(=O)N[C@H]1CCC(=O)N(c2ccc3c(C)cc(=O)n(C)c3c2)[C@@H]1c1ccc(Cl)cc1]

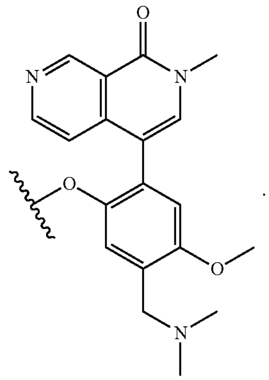 [SMILES: *Oc1cc(CN(C)C)c(OC)cc1-c1cn(C)c(=O)c2cnccc12]

In embodiments, the BRPF binding moiety is a monovalent form of I-BRD9. In embodiments, the BRPF binding moiety has the formula:

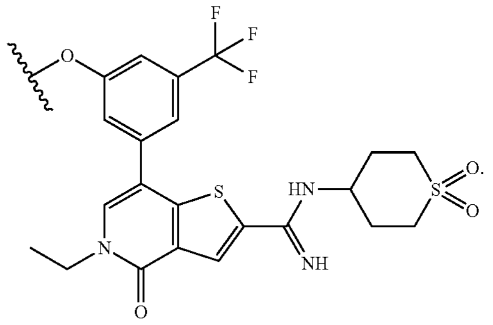 [SMILES: *Oc1cc(-c2cn(CC)c(=O)c3cc(C(=N)NC4CCS(=O)(=O)CC4)sc23)cc(C(F)(F)F)c1]

In embodiments, the BRPF binding moiety is a monovalent form of BAY-850. In embodiments the BRPF binding moiety has the formula:

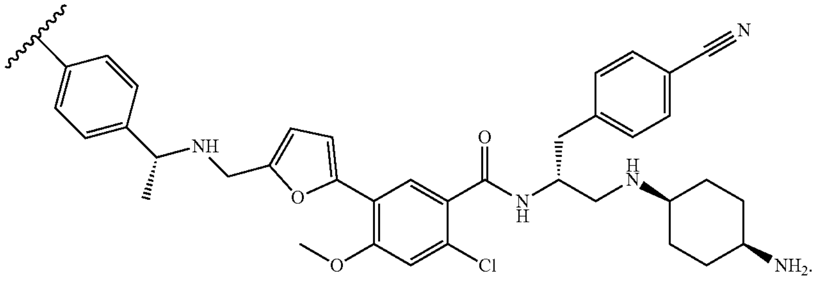 [SMILES: *c1ccc([C@@H](C)NCc2ccc(-c3cc(C(=O)N[C@@H](CN[C@H]4CC[C@@H](N)CC4)Cc4ccc(C#N)cc4)c(Cl)cc3OC)o2)cc1]

In embodiments, the BRPF binding moiety is a monovalent form of BI-9564. In embodiments, the BRPF binding moiety has the formula:

In embodiments, the BRPF binding moiety is a monovalent form of GSK8814. In embodiments, the BRPF binding moiety has the formula:

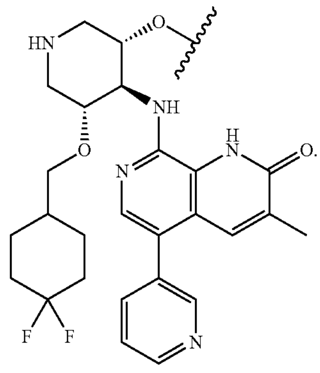 [SMILES: *O[C@H]1CNC[C@@H](OCC2CCC(F)(F)CC2)[C@@H]1Nc1ncc(-c2cccnc2)c2cc(C)c(=O)[nH]c12]

In embodiments, the BRPF binding moiety is a monovalent form of CEM88. In embodiments, the BRPF binding moiety has the formula:

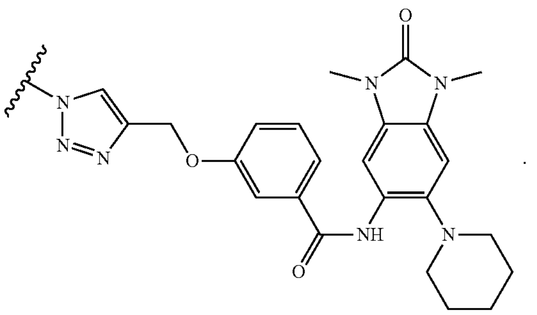 [SMILES: *n1cc(COc2cccc(C(=O)Nc3cc4c(cc3N3CCCCC3)n(C)c(=O)n4C)c2)nn1]

In embodiments, the transcriptional coactivator binding moiety is a BAZ binding moiety. In embodiments, the transcriptional coactivator binding moiety is a TIF1α binding moiety. In embodiments, the transcriptional coactivator binding moiety is a BAZ2 binding moiety. In embodiments, the transcriptional coactivator binding moiety is a BAZ2A binding moiety. In embodiments, the transcriptional coactivator binding moiety is a BAZ2B binding moiety.

In embodiments, the BAZ2 binding moiety is a monovalent form of GSK 2801. In embodiments, the BAZ2 binding moiety has the formula:

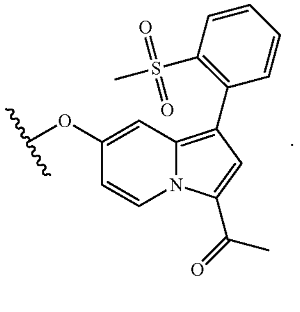 [SMILES: *Oc1ccn2c(C(C)=O)cc(-c3ccccc3S(C)(=O)=O)c2c1]

In embodiments, the BAZ2 binding moiety is a monovalent form of BAZ2-ICR. In embodiments, the BAZ2 binding moiety has the formula:

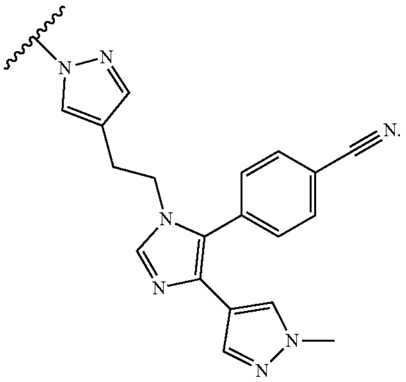 [SMILES: *n1cc(CCn2cnc(-c3cnn(C)c3)c2-c2ccc(C#N)cc2)cn1]

In embodiments, the transcriptional coactivator binding moiety is a TAF binding moiety. In embodiments, the transcriptional coactivator binding moiety is a TAF1 binding moiety. In embodiments, the transcriptional coactivator binding moiety is a TAF1L binding moiety.

In embodiments, the TAF binding moiety is a monovalent form of BAY-299. In embodiments, the TAF binding moiety has the formula:

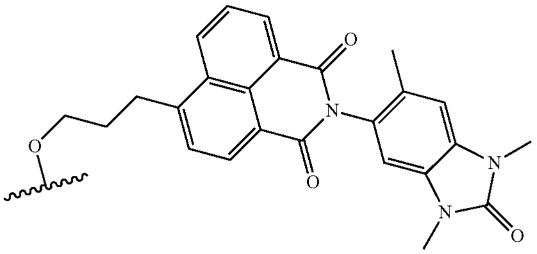

In embodiments, the TAF binding moiety has the formula:

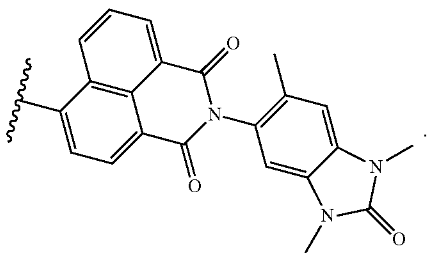 [SMILES: *c1ccc2c3c(cccc13)C(=O)N(c1cc3c(cc1C)n(C)c(=O)n3C)C2=O]

In embodiments, the transcriptional coactivator binding moiety is a SMARC binding moiety. In embodiments, the transcriptional coactivator binding moiety is a PB1 binding moiety. In embodiments, the transcriptional coactivator binding moiety is a SMARCA2 binding moiety. In embodiments, the transcriptional coactivator binding moiety is a SMARCA4 binding moiety.

In embodiments, the SMARC binding moiety is a monovalent form of PFI-3. In embodiments, the SMARC binding moiety has the formula:

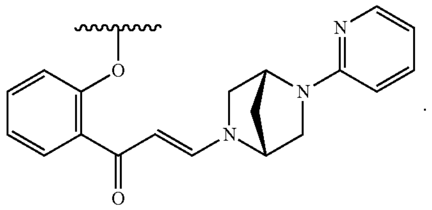 [SMILES: *Oc1ccccc1C(=O)/C=C/N1C[C@H]2C[C@@H]1CN2c1ccccn1]

In embodiments, the SMARC binding moiety has the formula:

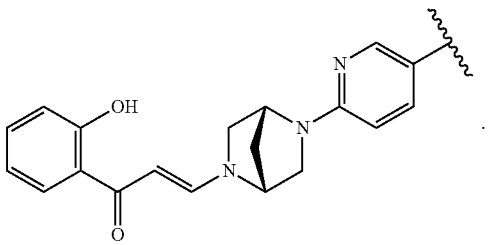 [SMILES: *c1ccc(N2C[C@H]3C[C@@H]2CN3/C=C/C(=O)c2ccccc2O)nc1]

In embodiments, the SMARC binding moiety has the formula:

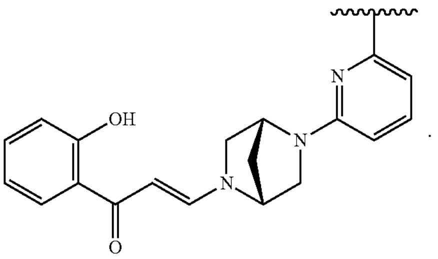 [SMILES: *c1cccc(N2C[C@H]3C[C@@H]2CN3/C=C/C(=O)c2ccccc2O)n1]

In embodiments, the transcriptional coactivator binding moiety is a monovalent form of a compound described in Wu, Q., et al., *Nature Communications,* 10, 1915 (2019); Flippakopoulos, P., et al., Nature (2010); Chiarella, A., et al., Nature Chemical Biology (2019); Picaud, S., Cancer Research (2013); Chaidos, A., et al., Blood (2014); Bouche, L., et al., J. Med. Chem. (2017); Gerstenberger, B. S., et al., J. Med. Chem. (2016); Humphreys, P. G., et al., J. Med. Chem. (2017); Moustakim, M., et al., Angew Chem. Int. Ed. Engl. (2017); Crawford, T. D., et al., ACS Med Chem Lett. (2017); Picaud, S., et al., Cancer Research (2015); Hammitzsch, A., et al., PNAS (2015); Chiarella, A., et al., Nature Chemical Biology (2019); Romero, F. A., et al., J Med Chem (2017); Demont, E. H., ACS Med Chem Lett (2014); Chiarella, A., et al., Nature Chemical Biology (2019); Igoe, N., J Med Chem (2017); Bamborough, P., ACS Med Chem Lett. (2016); Clark, P., et al., Angew Chem Int Ed Engl. (2015); Martin, L. J., et al., J. Med. Chem. (2016); Theodoulou N. H., J. Med. Chem. (2016); Fernandez-Montalvan, A. E., et al. ACS Chem. Bio. (2017); Bamborough, P., et al., J. Med. Chem. (2018); Chen, P., et al., J. Med. Chem. (2016); Drouin, L., et al., J. Med. Chem. (2015); which are herein incorporated by reference in their entirety and for all purposes.

In embodiments, $L^1$ is $-L^{101}-L^{102}-L^{103}-L^{104}-L^{105}-$. $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered), or a bioconjugate linker.

In embodiments, a substituted $L^{101}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{101}$ is substituted with a plurality of groups selected from substituent groups, size-limited substituent groups, and lower substituent groups; each substituent group, size-limited substituent group, and/or lower substituent group may optionally be different. In embodiments, when $L^{101}$ is substituted, it is substituted with at least one substituent group. In embodiments, when $L^{101}$ is substituted, it is substituted with at least one size-limited substituent group. In embodiments, when $L^{101}$ is substituted, it is substituted with at least one lower substituent group.

In embodiments, a substituted $L^{102}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{102}$ is substituted with a plurality of groups selected from substituent groups, size-limited substituent groups, and lower substituent groups; each substituent group, size-limited substituent group, and/or lower substituent group may optionally be different. In embodiments, when $L^{102}$ is substituted, it is substituted with at least one substituent group. In embodiments, when $L^{102}$ is substituted, it is substituted with at least one size-limited substituent group. In embodiments, when $L^{102}$ is substituted, it is substituted with at least one lower substituent group.

In embodiments, a substituted $L^{103}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{103}$ is substituted with a plurality of groups selected from substituent groups, size-limited substituent groups, and lower substituent groups; each substituent group, size-limited substituent group, and/or lower substituent group may optionally be different. In embodiments, when $L^{103}$ is substituted, it is substituted with at least one substituent group. In embodiments, when $L^{103}$ is substituted, it is substituted with at least one size-limited substituent group. In embodiments, when $L^{103}$ is substituted, it is substituted with at least one lower substituent group.

In embodiments, a substituted $L^{104}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{104}$ is substituted with a plurality of groups selected from substituent groups, size-limited substituent groups, and lower substituent groups; each substituent group, size-limited substituent group, and/or lower substituent group may optionally be different. In embodiments, when $L^{104}$ is substituted, it is substituted with at least one substituent group. In embodiments, when $L^{104}$ is substituted, it is substituted with at least one size-limited substituent group. In embodiments, when $L^{104}$ is substituted, it is substituted with at least one lower substituent group.

In embodiments, a substituted $L^{105}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{105}$ is substituted with a plurality of groups selected from substituent groups, size-limited substituent groups, and lower substituent groups; each substituent group, size-limited substituent group, and/or lower substituent group may optionally be different. In embodiments, when $L^{105}$ is substituted, it is substituted with at least one substituent group. In embodiments, when $L^{105}$ is substituted, it is substituted with at least one size-limited substituent group. In embodiments, when $L^{105}$ is substituted, it is substituted with at least one lower substituent group.

In embodiments, $L^{101}$ is independently a substituted 2 to 6 membered heteroalkylene. In embodiments, $L^{101}$ is independently an oxo-substituted 2 to 6 membered heteroalkylene. In embodiments, $L^{101}$ is independently an oxo-substituted 2 membered heteroalkylene. In embodiments, $L^{101}$ is independently an oxo-substituted 3 membered heteroalkylene. In embodiments, $L^{101}$ is independently an oxo-substituted 4 membered heteroalkylene. In embodiments, $L^{101}$ is independently an oxo-substituted 5 membered heteroalkylene. In embodiments, $L^{101}$ is independently an oxo-substituted 6 membered heteroalkylene. In embodiments, $L^{101}$ is independently

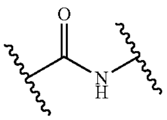
.

In embodiments, $L^{101}$ is independently

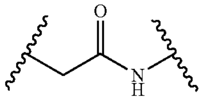
.

In embodiments, $L^{101}$ is independently

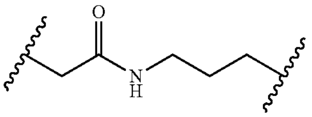
.

In embodiments, $L^{101}$ is independently

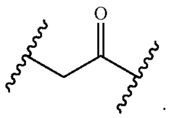 [SMILES: *CC(*)=O]
.

In embodiments, $L^{102}$ is independently an unsubstituted 3 to 24 membered heteroalkylene. In embodiments, $L^{102}$ is independently

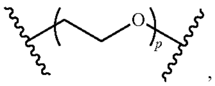
, wherein p is an integer from 1 to 8. In embodiments, $L^{102}$ is independently

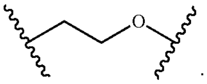 [SMILES: *CCO*]
.

In embodiments, $L^{102}$ is independently

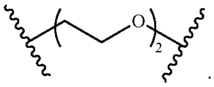
.

In embodiments $L^{102}$ is independently

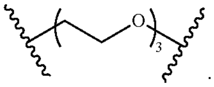
.

In embodiments, $L^{102}$ is independently

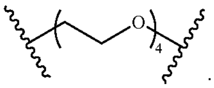
.

In embodiments, $L^{102}$ is independently

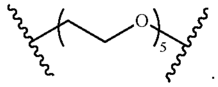

.

In embodiments, $L^{102}$ is independently

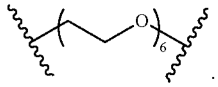

.

In embodiments, $L^{102}$ is independently

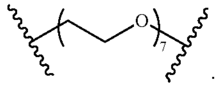

.

In embodiments, $L^{102}$ is independently

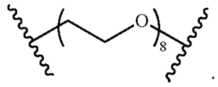

.

In embodiments, $L^{102}$ is independently an unsubstituted 4 to 7 membered heterocycloalkylene. In embodiments, $L^{102}$ is independently an unsubstituted 6 membered heterocycloalkylene. In embodiments, $L^{102}$ is independently

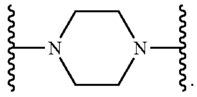

.

In embodiments, $L^{102}$ is independently an unsubstituted phenylene. In embodiments, $L^{102}$ is independently

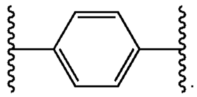 [SMILES: *c1ccc(*)cc1]

.

In embodiments, $L^{103}$ is independently a substituted 2 to 6 membered heteroalkylene. In embodiments, $L^{103}$ is independently an oxo-substituted 2 to 6 membered heteroalkylene. In embodiments, $L^{103}$ is independently an oxo-substituted 2 membered heteroalkylene. In embodiments, $L^{103}$ is independently an oxo-substituted 3 membered heteroalkylene. In embodiments, $L^{103}$ is independently an oxo-substituted 4 membered heteroalkylene. In embodiments, $L^{103}$ is independently an oxo-substituted 5 membered heteroalkylene. In embodiments, $L^{103}$ is independently an oxo-substituted 6 membered heteroalkylene. In embodiments, $L^{103}$ is independently

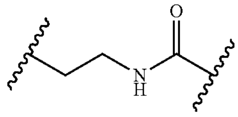

.

In embodiments, $L^{103}$ is independently

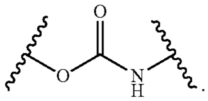 [SMILES: *NC(=O)O*]

.

In embodiments, $L^{103}$ is independently a substituted $C_1$-$C_4$ alkylene. In embodiments, $L^{103}$ is independently an oxo-substituted $C_1$-$C_4$ alkylene. In embodiments, $L^{103}$ is independently an oxo-substituted $C_1$ alkylene. In embodiments, $L^{103}$ is independently an oxo-substituted $C_2$ alkylene. In embodiments, $L^{103}$ is independently an oxo-substituted $C_3$ alkylene. In embodiments, $L^{103}$ is independently an oxo-substituted $C_4$ alkylene. In embodiments, $L^{103}$ is independently an oxo-substituted $C_1$-$C_4$ alkylene.

In embodiments, $L^{104}$ is independently a bond. In embodiments, $L^{104}$ is independently an unsubstituted 3 to 24 membered heteroalkylene. In embodiments, $L^{104}$ is independently

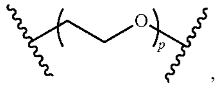

, wherein p is an integer from 1 to 8. In embodiments, $L^{104}$ is independently

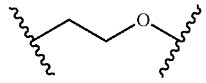

.

In embodiments, $L^{104}$ is independently

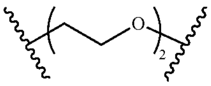

.

In embodiments, $L^{104}$ is independently

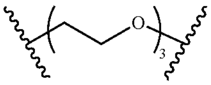

.

In embodiments $L^{104}$ is independently

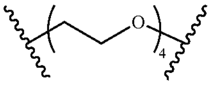

.

In embodiments, $L^{104}$ is independently

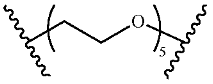

In embodiments, $L^{104}$ is independently

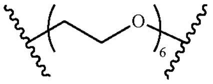

In embodiments, $L^{104}$ is independently

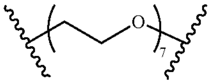

In embodiments, $L^{104}$ is independently

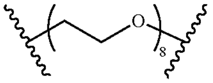

In embodiments, $L^{105}$ is independently a bond. In embodiments, $L^{105}$ is independently a substituted 2 to 6 membered heteroalkylene. In embodiments, $L^{105}$ is independently an oxo-substituted 2 to 6 membered heteroalkylene. In embodiments, $L^{105}$ is independently an oxo-substituted 2 membered heteroalkylene. In embodiments, $L^{105}$ is independently an oxo-substituted 3 membered heteroalkylene. In embodiments, $L^{105}$ is independently an oxo-substituted 4 membered heteroalkylene. In embodiments, $L^{105}$ is independently an oxo-substituted 5 membered heteroalkylene. In embodiments, $L^{105}$ is independently an oxo-substituted 6 membered heteroalkylene. In embodiments, $L^{105}$ is independently

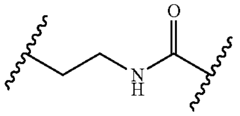

In embodiments, $L^1$ is

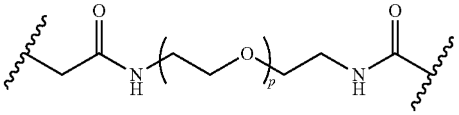

,

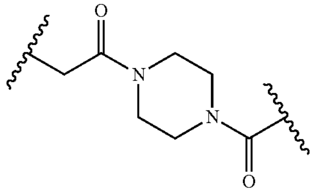

,

-continued

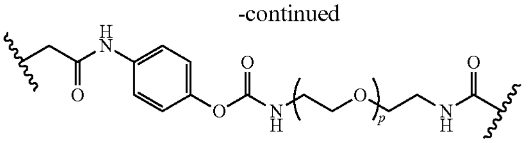

, or

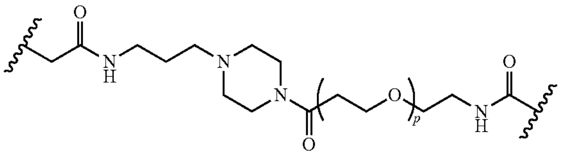

;

wherein p is an integer from 1 to 8.

In embodiments, $L^1$ is

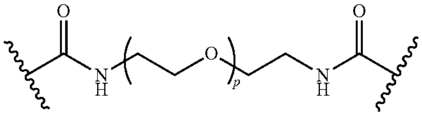

;

wherein p is an integer from 1 to 8.

In embodiments, $L^1$ is

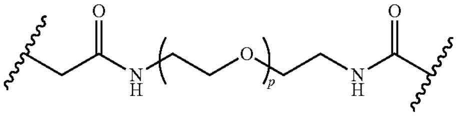

,

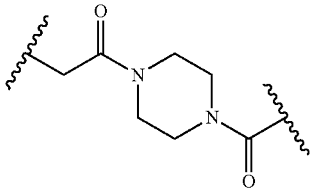

,

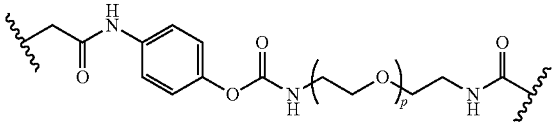

,

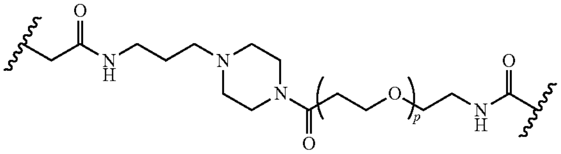

,

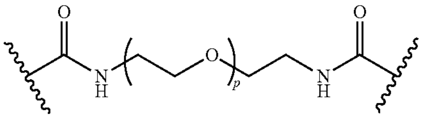

,

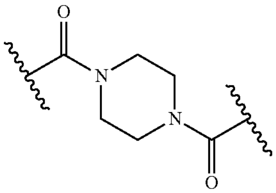

,

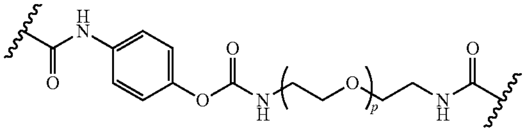

, or

-continued

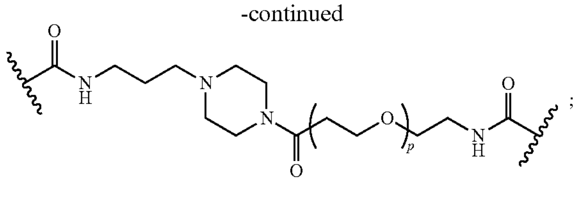

wherein p is an integer from 1 to 10.

In embodiments, $L^1$ is

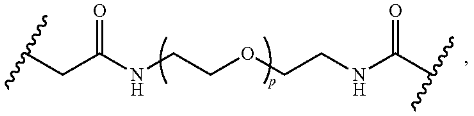

wherein p is an integer from 1 to 10. In embodiments, $L^1$ is

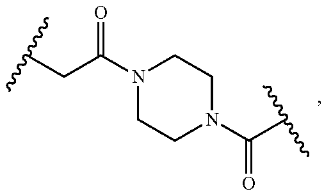

wherein p is an integer from 1 to 10. In embodiments, $L^1$ is

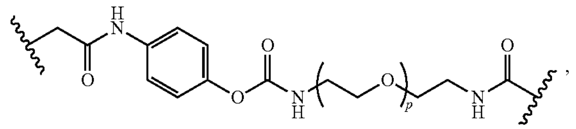

wherein p is an integer from 1 to 10. In embodiments, $L^1$ is

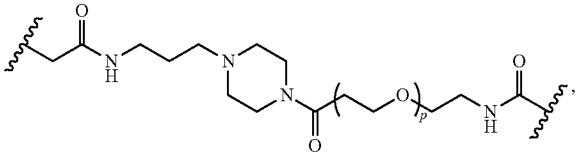

wherein p is an integer from 1 to 10.

In embodiments, $L^1$ is

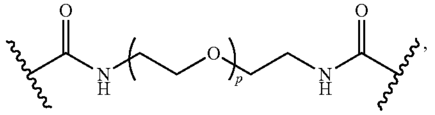

wherein p is an integer from 1 to 10. In embodiments, $L^1$ is

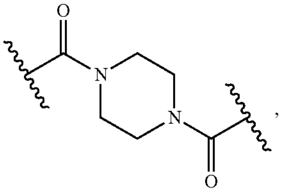

wherein p is an integer from 1 to 10. In embodiments, $L^1$ is

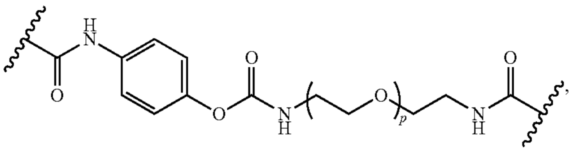

wherein p is an integer from 1 to 10. In embodiments, $L^1$ is

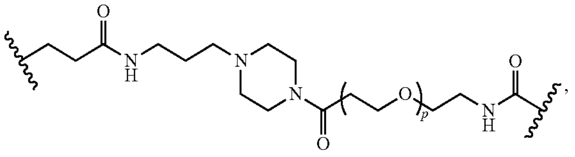

wherein p is an integer from 1 to 10.

In embodiments, the compound has the formula:

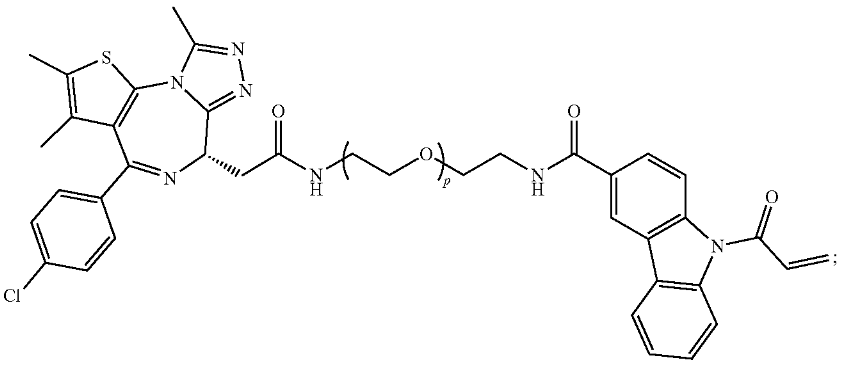

wherein p is an integer from 1 to 10. In embodiments, p is an integer from 1 to 8.
In embodiments, the compound has the formula:
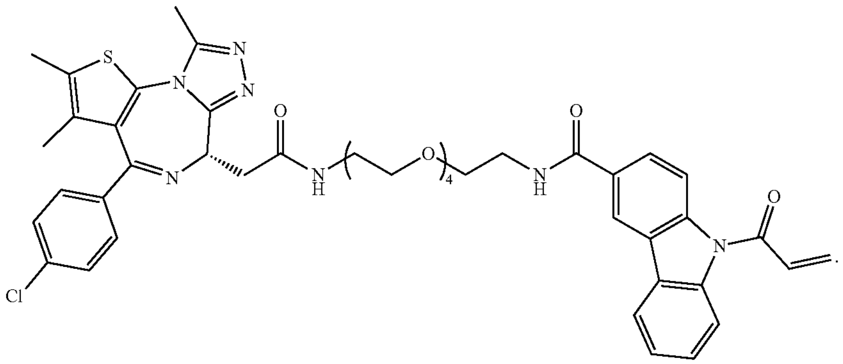
In embodiments, the compound has the formula:
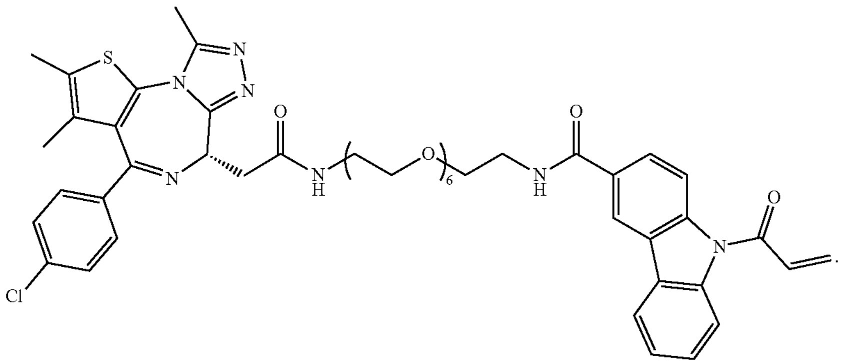
In embodiments, the compound has the formula:
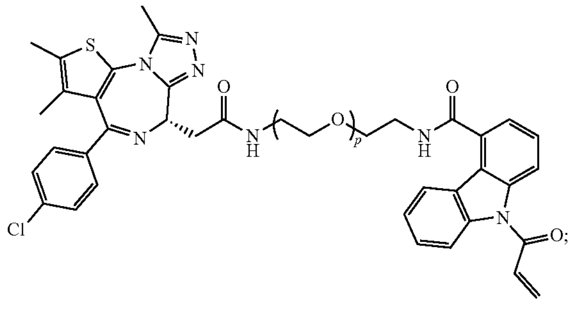
wherein p is an integer from 1 to 10. In embodiments, p is an integer from 1 to 8.

In embodiments, the compound has the formula:
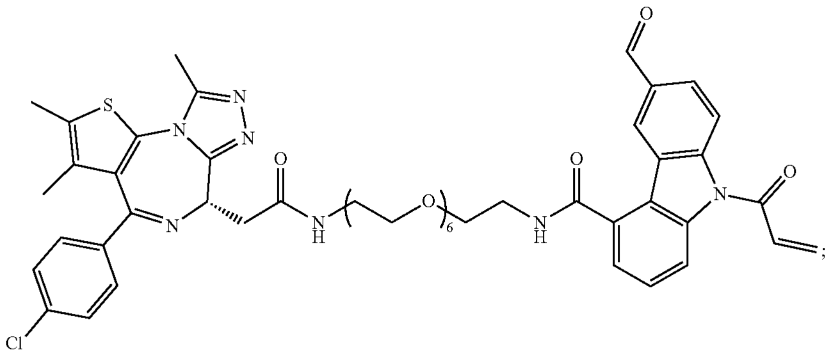
wherein p is an integer from 1 to 10. In embodiments, p is an integer from 1 to 8.
In embodiments, the compound has the formula:
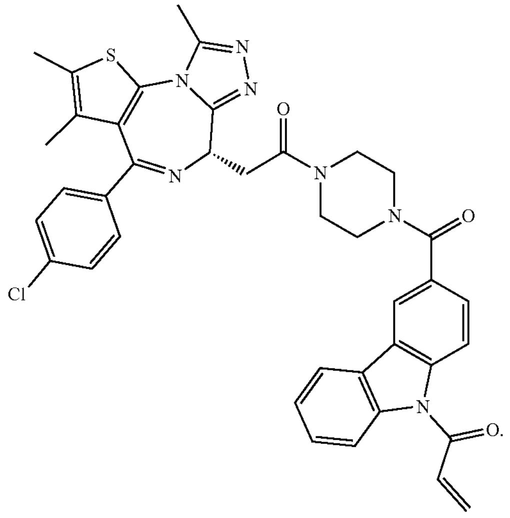 [SMILES: C=CC(=O)n1c2ccccc2c2cc(C(=O)N3CCN(C(=O)C[C@@H]4N=C(c5ccc(Cl)cc5)c5c(sc(C)c5C)-n5c(C)nnc54)CC3)ccc21]
In embodiments, the compound has the formula:
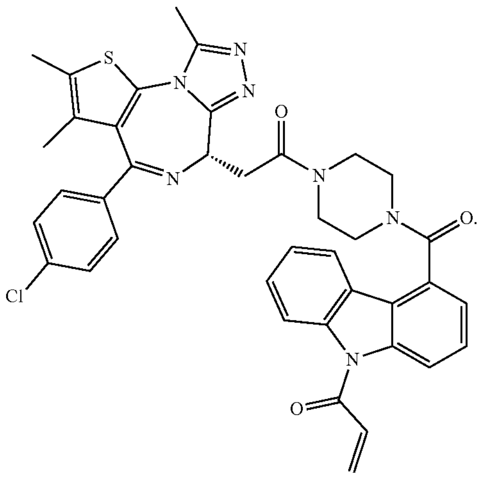 [SMILES: C=CC(=O)n1c2ccccc2c2c(C(=O)N3CCN(C(=O)C[C@@H]4N=C(c5ccc(Cl)cc5)c5c(sc(C)c5C)-n5c(C)nnc54)CC3)cccc21]
In embodiments, the compound has the formula:
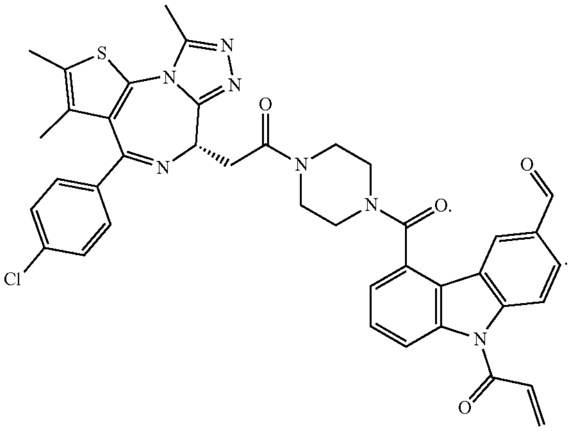 [SMILES: C=CC(=O)n1c2ccc(C=O)cc2c2c(C(=O)N3CCN(C(=O)C[C@@H]4N=C(c5ccc(Cl)cc5)c5c(sc(C)c5C)-n5c(C)nnc54)CC3)cccc21]
In embodiments, the compound has the formula:
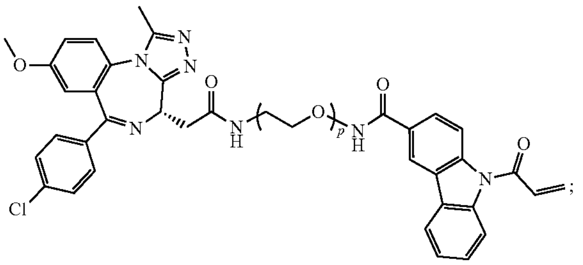
wherein p is an integer from 1 to 10. In embodiments, p is an integer from 1 to 8.

In embodiments, the compound has the formula:
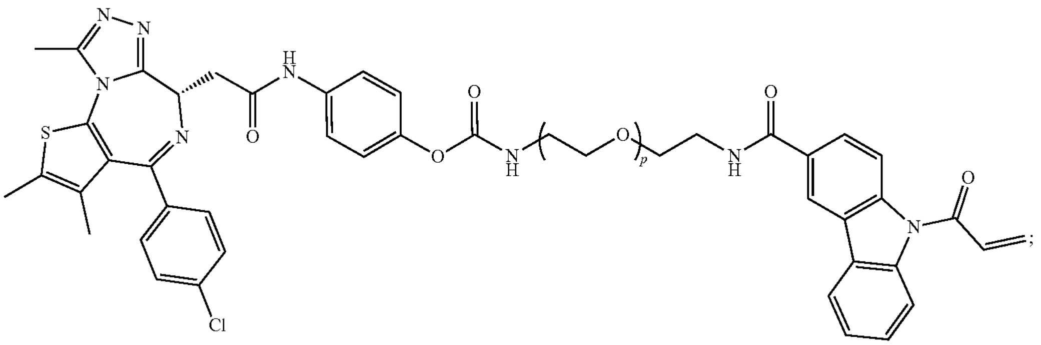
wherein p is an integer from 1 to 10. In embodiments, p is an integer from 1 to 8.
In embodiments, the compound has the formula:
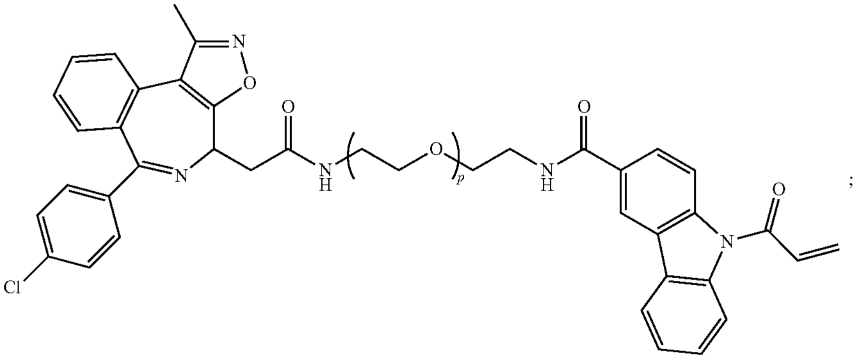
wherein p is an integer from 1 to 10. In embodiments, p is an integer from 1 to 8.
In embodiments, the compound has the formula:
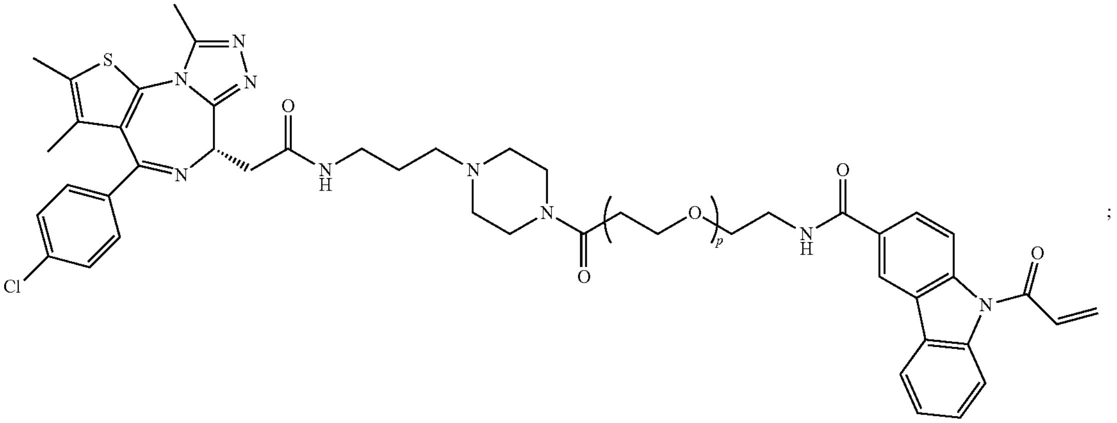
wherein p is an integer from 1 to 10. In embodiments, p is an integer from 1 to 8.

In embodiments, the compound has the formula:
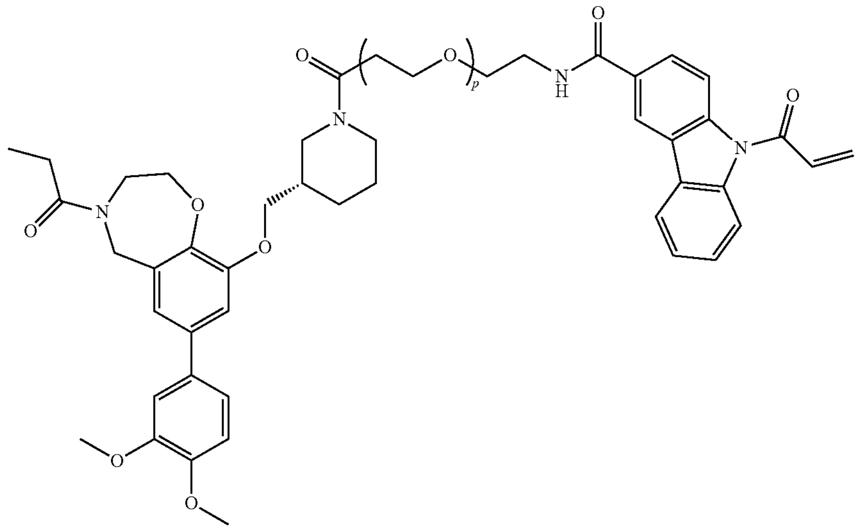
;
wherein p is an integer from 1 to 10. In embodiments, p is an integer from 1 to 8.
In embodiments, the compound has the formula:
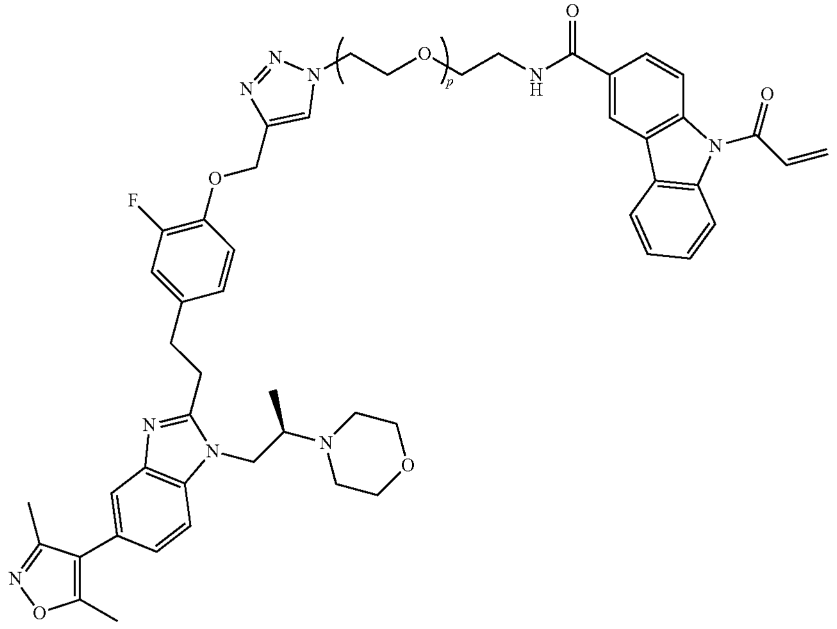
;
wherein p is an integer from 1 to 10. In embodiments, p is an integer from 1 to 8.

In embodiments, the compound has the formula:

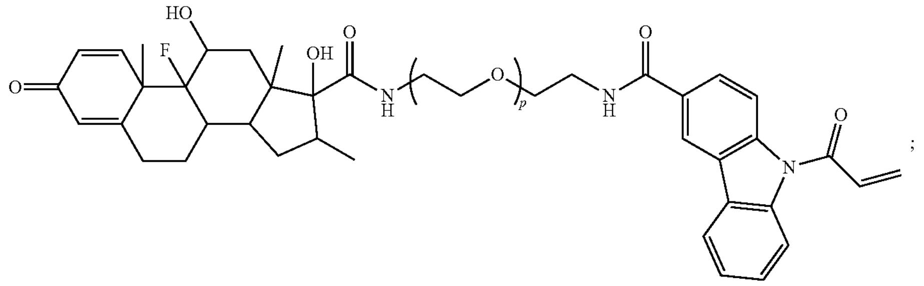

wherein p is an integer from 1 to 10. In embodiments, p is an integer from 1 to 8.

In an aspect is provided a compound having the formula:

(III)

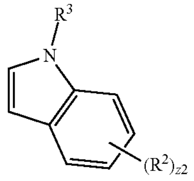

or (IV)

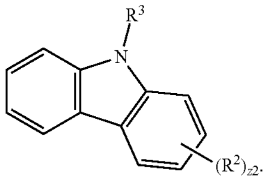

$R^2$ and $R^3$ are as described herein, including in embodiments. The symbol z2a is an integer from 0 to 8.

In embodiments, z2a is 0. In embodiments, z2a is 1. In embodiments, z2a is 2. In embodiments, z2a is 3. In embodiments, z2a is 4. In embodiments, z2a is 5. In embodiments, z2a is 6. In embodiments, z2a is 7. In embodiments, z2a is 8.

In embodiments, the compound has the formula:

(IIIa)

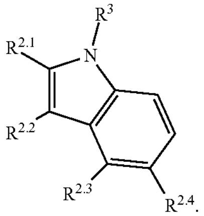

$R^{2.1}$, $R^{2.2}$, $R^{2.3}$, $R^{2.4}$, and $R^3$ are as described herein, including in embodiments.

In embodiments, the compound has the formula:

(IIIb)

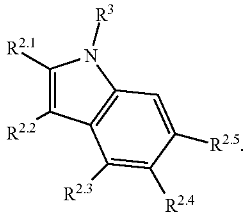

$R^{2.1}$, $R^{2.2}$, $R^{2.3}$, $R^{2.4}$, $R^{2.5}$, and $R^3$ are as described herein, including in embodiments.

In embodiments, the compound has the formula:

(IVa)

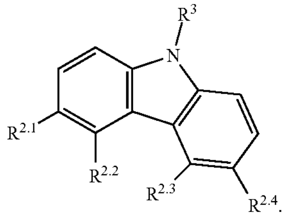

$R^{2.1}$, $R^{2.2}$, $R^{2.3}$, $R^{2.4}$, and $R^3$ are as described herein, including in embodiments.

In embodiments, the compound has the formula:

(IVb)

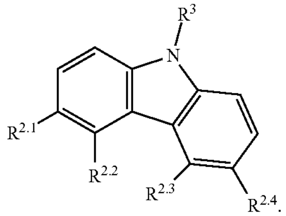

$R^{2.1}$, $R^{2.2}$, $R^{2.3}$, $R^{2.4}$, and $R^3$ are as described herein, including in embodiments.

In embodiments, the compound has the formula:
(IVc)
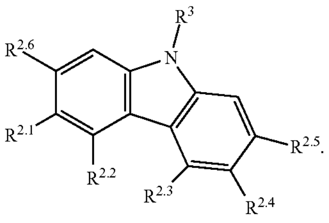
$R^{2.1}$, $R^{2.2}$, $R^{2.3}$, $R^{2.4}$, $R^{2.5}$, $R^{2.6}$, and $R^3$ are as described herein, including in embodiments.
In embodiments, the compound has the formula:
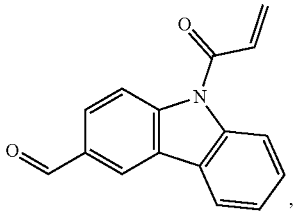
,
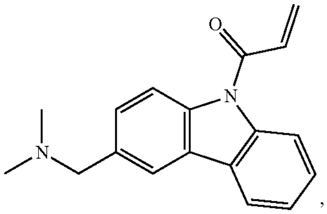
,
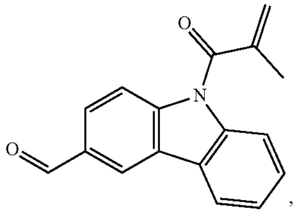
,
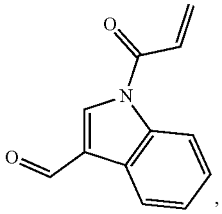
,
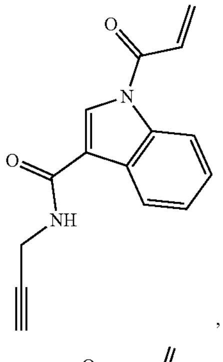
,
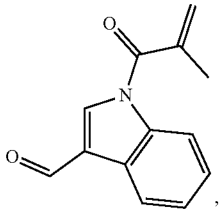
,
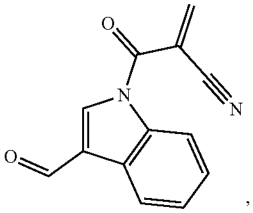
,
-continued
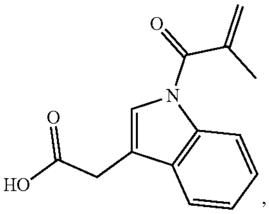
,
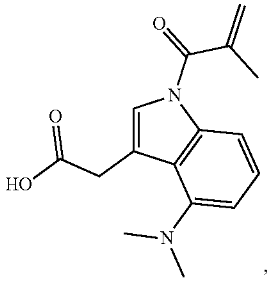
,
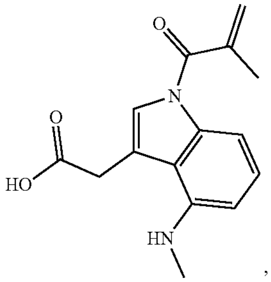
,
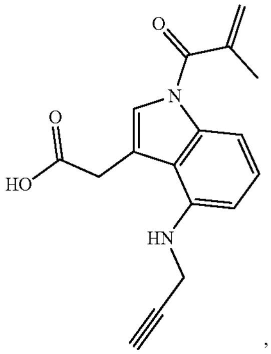
,
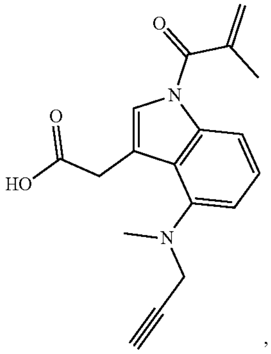
,
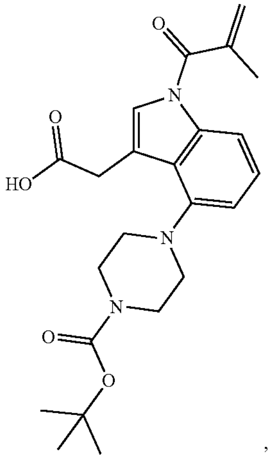
,
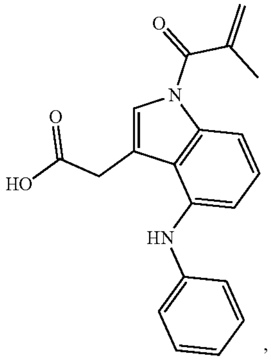
, -continued
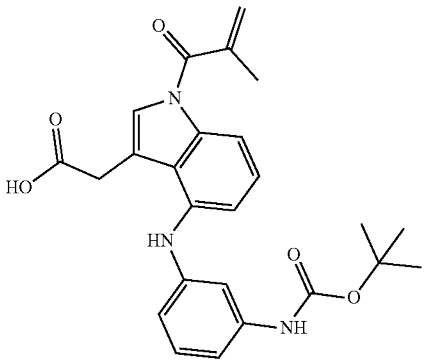
,
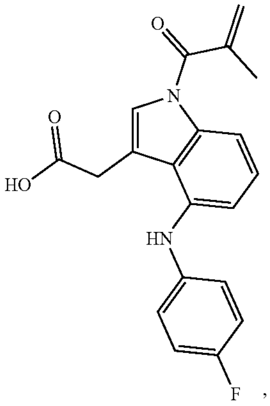
, or
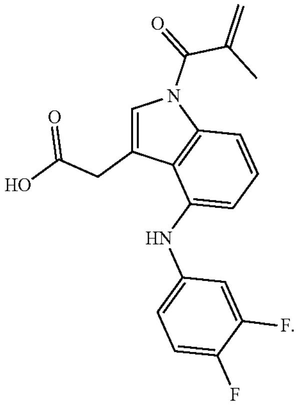
In embodiments, the compound has the formula:
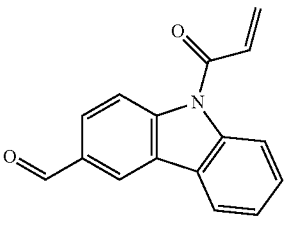
.
In embodiments, the compound has the formula:
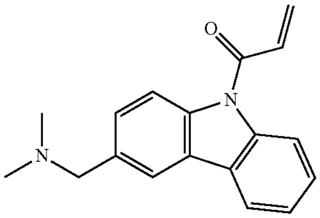
.
In embodiments, the compound has the formula:
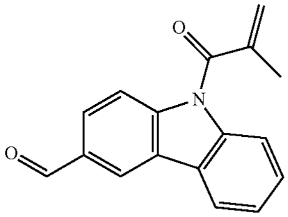
.
In embodiments, the compound has the formula:
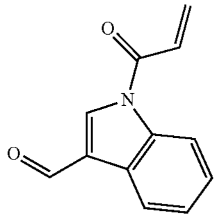
.
In embodiments, the compound has the formula:
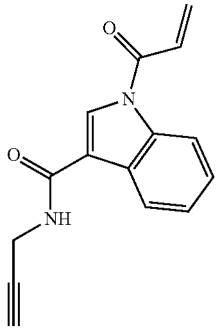
.
In embodiments, the compound has the formula:
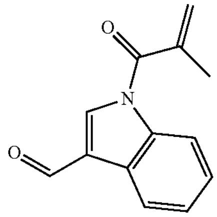
.

In embodiments, the compound has the formula:
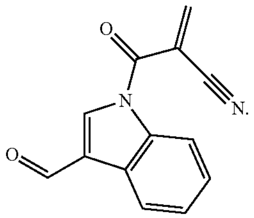 [SMILES: C=C(C#N)C(=O)n1cc(C=O)c2ccccc21]
In embodiments, the compound has the formula:
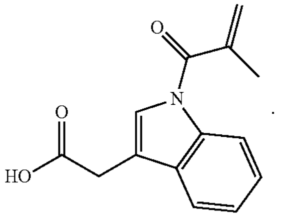 [SMILES: C=C(C)C(=O)n1cc(CC(=O)O)c2ccccc21]
In embodiments, the compound has the formula:
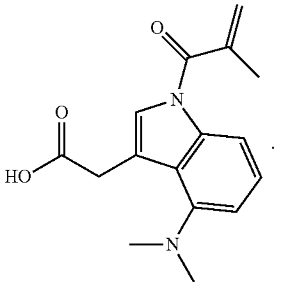 [SMILES: C=C(C)C(=O)n1cc(CC(=O)O)c2c(N(C)C)cccc21]
In embodiments, the compound has the formula:
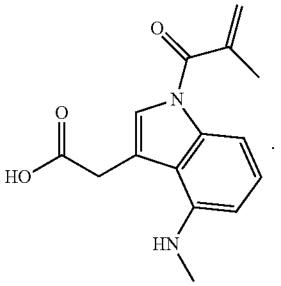 [SMILES: C=C(C)C(=O)n1cc(CC(=O)O)c2c(NC)cccc21]
In embodiments, the compound has the formula:
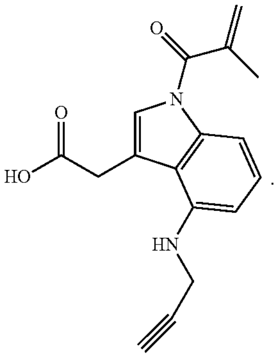 [SMILES: C#CCNc1cccc2c1c(CC(=O)O)cn2C(=O)C(=C)C]
In embodiments, the compound has the formula:
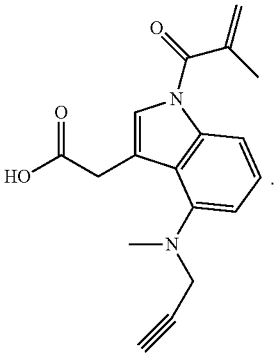 [SMILES: C#CCN(C)c1cccc2c1c(CC(=O)O)cn2C(=O)C(=C)C]
In embodiments, the compound has the formula:
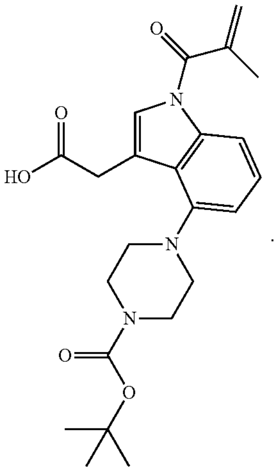 [SMILES: C=C(C)C(=O)n1cc(CC(=O)O)c2c(N3CCN(C(=O)OC(C)(C)C)CC3)cccc21]

In embodiments, the compound has the formula:
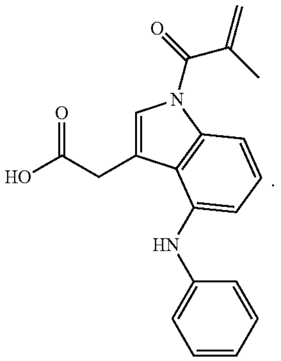 [SMILES: C=C(C)C(=O)n1cc(CC(=O)O)c2c(Nc3ccccc3)cccc21]
In embodiments, the compound has the formula:
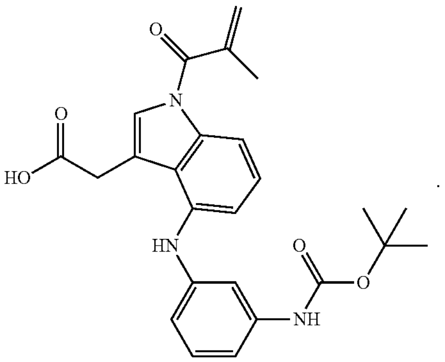 [SMILES: C=C(C)C(=O)n1cc(CC(=O)O)c2c(Nc3cccc(NC(=O)OC(C)(C)C)c3)cccc21]
In embodiments, the compound has the formula:
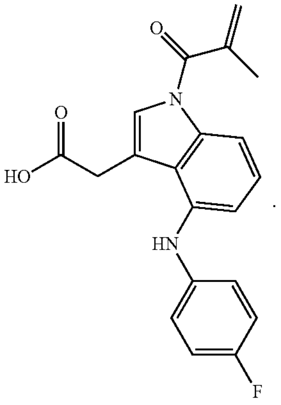 [SMILES: C=C(C)C(=O)n1cc(CC(=O)O)c2c(Nc3ccc(F)cc3)cccc21]
In embodiments, the compound has the formula:
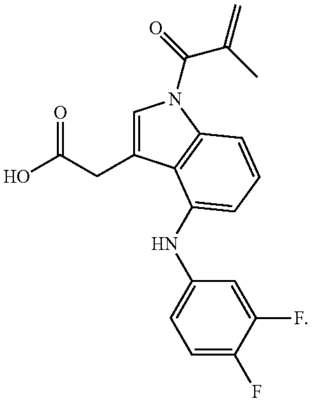 [SMILES: C=C(C)C(=O)n1cc(CC(=O)O)c2c(Nc3ccc(F)c(F)c3)cccc21]
In embodiments, the compound has the formula:
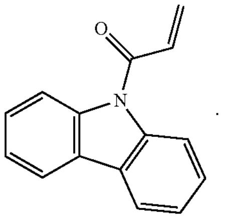 [SMILES: C=CC(=O)n1c2ccccc2c2ccccc21]
In embodiments, the compound has the formula:
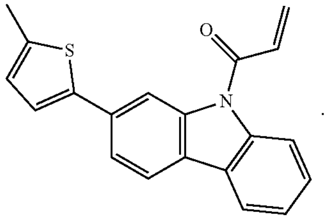 [SMILES: C=CC(=O)n1c2ccccc2c2ccc(-c3ccc(C)s3)cc21]
In embodiments, the compound has the formula:
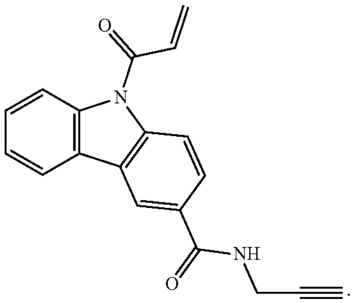 [SMILES: C#CCNC(=O)c1ccc2c(c1)c1ccccc1n2C(=O)C=C]

In embodiments, the compound has the formula:

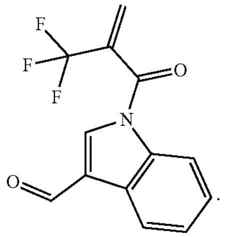 [SMILES: C=C(C(=O)n1cc(C=O)c2ccccc21)C(F)(F)F]

In embodiments, the compound has the formula:

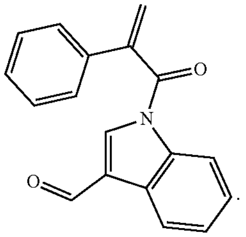 [SMILES: C=C(C(=O)n1cc(C=O)c2ccccc21)c1ccccc1]

In embodiments, the compound has the formula:

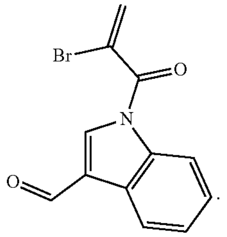 [SMILES: C=C(Br)C(=O)n1cc(C=O)c2ccccc21]

In embodiments, the compound has the formula:

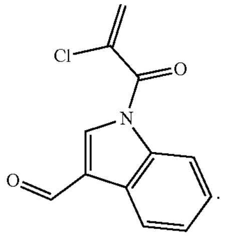 [SMILES: C=C(Cl)C(=O)n1cc(C=O)c2ccccc21]

In embodiments, the compound has the formula:

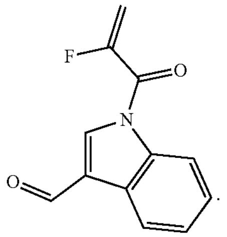 [SMILES: C=C(F)C(=O)n1cc(C=O)c2ccccc21]

In embodiments, the compound has the formula:

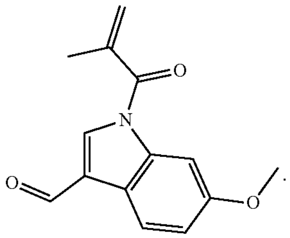 [SMILES: C=C(C)C(=O)n1cc(C=O)c2ccc(OC)cc21]

In embodiments, the compound has the formula:

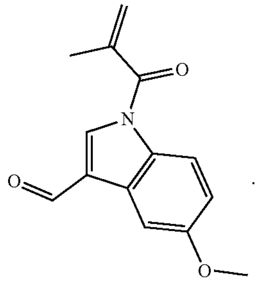 [SMILES: C=C(C)C(=O)n1cc(C=O)c2cc(OC)ccc21]

In embodiments, the compound has the formula:

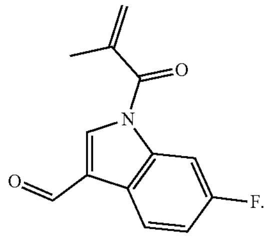 [SMILES: C=C(C)C(=O)n1cc(C=O)c2ccc(F)cc21]

In embodiments, the compound has the formula:

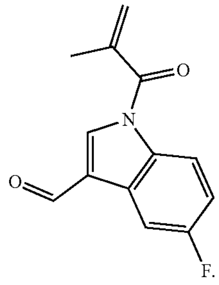 [SMILES: C=C(C)C(=O)n1cc(C=O)c2cc(F)ccc21]

In embodiments, the compound has the formula:
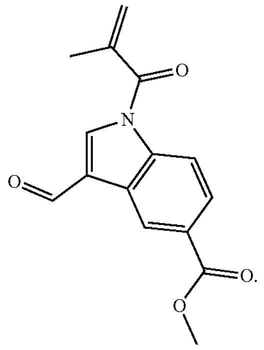 [SMILES: C=C(C)C(=O)n1cc(C=O)c2cc(C(=O)OC)ccc21]
In embodiments, the compound has the formula:
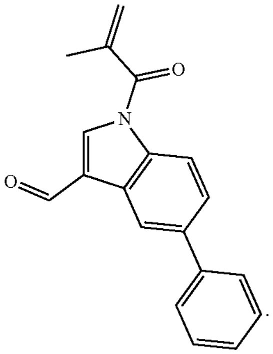 [SMILES: C=C(C)C(=O)n1cc(C=O)c2cc(-c3ccccc3)ccc21]
In embodiments, the compound has the formula:
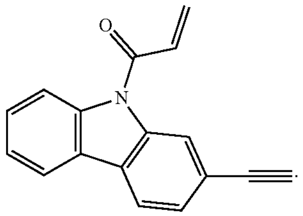 [SMILES: C#Cc1ccc2c3ccccc3n(C(=O)C=C)c2c1]
In embodiments, the compound has the formula:
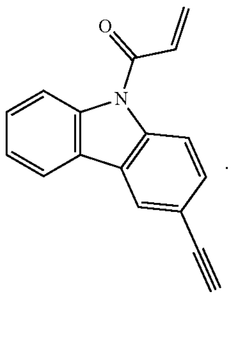 [SMILES: C#Cc1ccc2c(c1)c1ccccc1n2C(=O)C=C]
In embodiments, the compound has the formula:
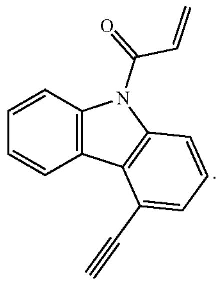 [SMILES: C#Cc1cccc2c1c1ccccc1n2C(=O)C=C]
In embodiments, the compound has the formula:
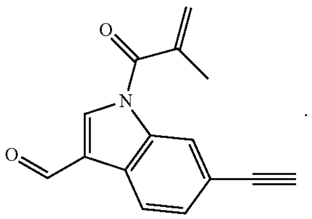 [SMILES: C#Cc1ccc2c(C=O)cn(C(=O)C(=C)C)c2c1]
In embodiments, the compound has the formula:
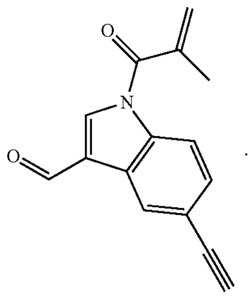 [SMILES: C#Cc1ccc2c(c1)c(C=O)cn2C(=O)C(=C)C]
In embodiments, the compound has the formula:
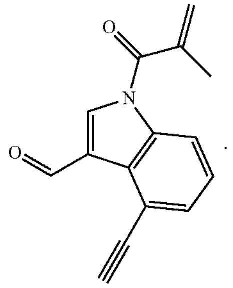 [SMILES: C#Cc1cccc2c1c(C=O)cn2C(=O)C(=C)C]

In embodiments, the compound has the formula:
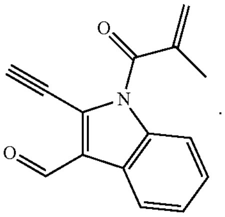 [SMILES: C#Cc1c(C=O)c2ccccc2n1C(=O)C(=C)C]
In embodiments, the compound has the formula:
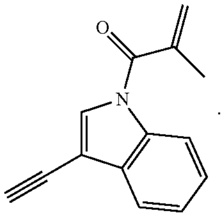 [SMILES: C#Cc1cn(C(=O)C(=C)C)c2ccccc12]
In embodiments, the compound has the formula:
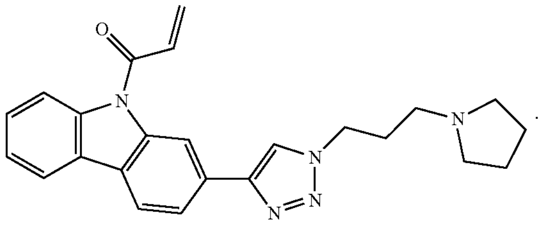 [SMILES: C=CC(=O)n1c2ccccc2c2ccc(-c3cn(CCCN4CCCC4)nn3)cc21]
In embodiments, the compound has the formula:
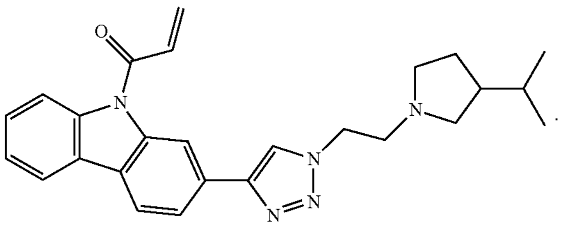 [SMILES: C=CC(=O)n1c2ccccc2c2ccc(-c3cn(CCN4CCC(C(C)C)C4)nn3)cc21]
In embodiments, the compound has the formula:
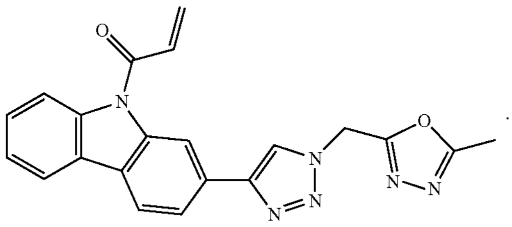 [SMILES: C=CC(=O)n1c2ccccc2c2ccc(-c3cn(Cc4nnc(C)o4)nn3)cc21]
In embodiments, the compound has the formula:
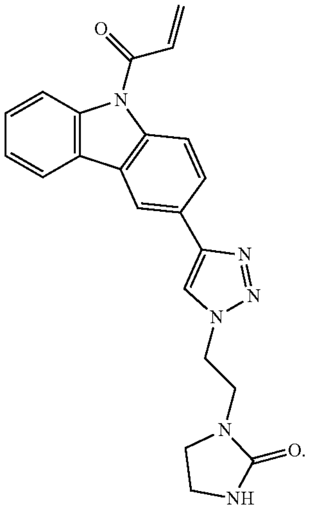 [SMILES: C=CC(=O)n1c2ccccc2c2cc(-c3cn(CCN4CCNC4=O)nn3)ccc21]
In embodiments, the compound has the formula:
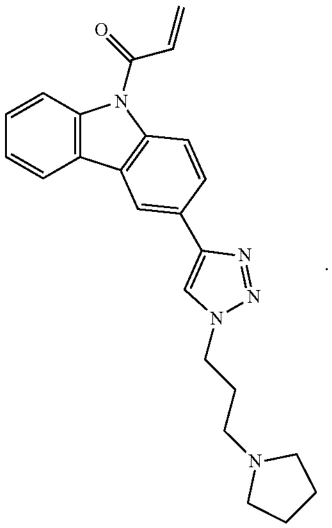 [SMILES: C=CC(=O)n1c2ccccc2c2cc(-c3cn(CCCN4CCCC4)nn3)ccc21]

In embodiments, the compound has the formula:

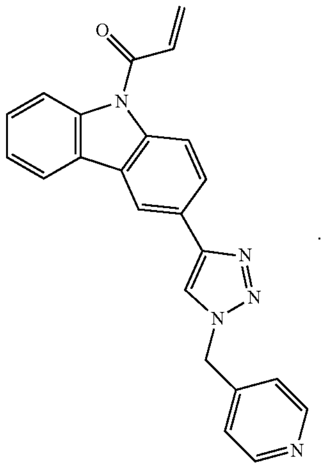 [SMILES: C=CC(=O)n1c2ccccc2c2cc(-c3cn(Cc4ccncc4)nn3)ccc21]

In embodiments, the compound has the formula:

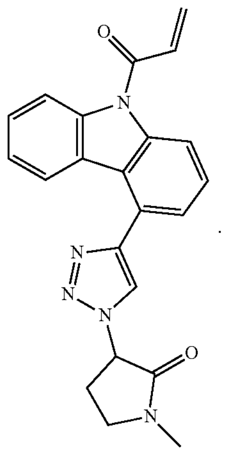

In embodiments, the compound has the formula:

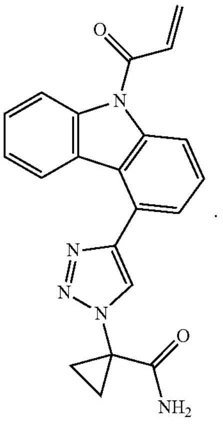 [SMILES: C=CC(=O)n1c2ccccc2c2c(-c3cn(C4(C(N)=O)CC4)nn3)cccc21]

In embodiments, the compound has the formula:

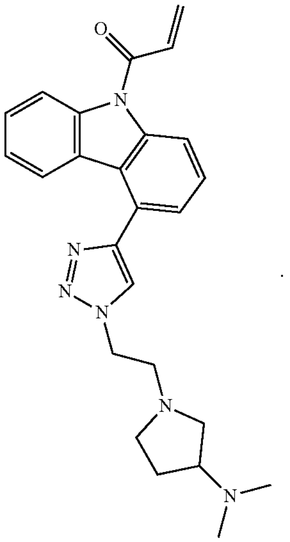 [SMILES: C=CC(=O)n1c2ccccc2c2c(-c3cn(CCN4CCC(N(C)C)C4)nn3)cccc21]

In embodiments, the compound is more selective for a mutant p53 protein (e.g., Y220C p53 protein) than a wild-type p53 protein. In embodiments, the compound is 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold more selective for a mutant p53 protein (e.g., Y220C p53 protein) than a wildtype p53 protein. In embodiments, the compound is about 1.5-fold, 2-fold, 3-fold, 4-fold, 5-fold, 10-fold, 20-fold, 30-fold, 40-fold, 50-fold, or 100-fold more selective for a mutant p53 protein (e.g., Y220C p53 protein) than a wildtype p53 protein. In embodiments, the compound is greater than 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold more selective for a mutant p53 protein (e.g., Y220C p53 protein) than a wildtype p53 protein. In embodiments, there is no measurable binding of the compound to a wildtype p53 protein.

In embodiments, the compound has a lower dissociation constant ($K_d$) for a mutant p53 protein (e.g., Y220C p53 protein) than a wildtype p53 protein. In embodiments, the compound has a dissociation constant ($K_d$) that is 1.5-fold, 2-fold, 3-fold, 4-fold, 5-fold, 10-fold, 20-fold, 30-fold, 40-fold, 50-fold, or 100-fold lower for a mutant p53 protein (e.g., Y220C p53 protein) than a wildtype p53 protein. In embodiments, the compound has a dissociation constant ($K_d$) that is about 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold lower for a mutant p53 protein (e.g., Y220C p53 protein) than a wildtype p53 protein. In embodiments, the compound has a dissociation constant ($K_d$) that is more than 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold lower for a mutant p53 protein (e.g., Y220C p53 protein) than a wildtype p53 protein. In embodiments, there is no measurable binding of the compound to a wildtype p53 protein.

In embodiments, the compound is capable of increasing the activity of a mutant p53 protein (e.g., Y220C p53 protein) relative to a wildtype p53 protein. In embodiments, the compound is capable of increasing the activity of a mutant p53 protein (e.g., Y220C p53 protein) 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold greater relative to a wildtype p53 protein. In embodiments, the compound is capable of increasing the activity of a mutant p53 protein (e.g., Y220C p53 protein) about 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold greater relative to a wildtype p53 protein. In embodiments, the compound is capable of increasing the activity of a mutant p53 protein (e.g., Y220C p53 protein) more than 1.5-fold, 2-fold, 3-fold, 4-fold, 5-fold, 10-fold, 20-fold, 30-fold, 40-fold, 50-fold, 100-fold, 200-fold, 300-fold, 400-fold, 500-fold, 1000-fold, 5000-fold, or 10,000-fold greater relative to a wildtype p53 protein. In embodiments, the activity of the mutant p53 protein is arrest of cell growth. In embodiments, the activity of the mutant p53 protein is arrest of cell growth by holding the cell cycle at the G1/S regulation point. In embodiments, the activity of the mutant p53 protein is activation of DNA repair proteins. In embodiments, the activity of the mutant p53 protein is initiation of apoptosis.

In an aspect is provided a p53 protein covalently bonded to a compound described herein. In embodiments, the p53 protein is covalently bonded to a moiety of a compound described herein following a covalent reaction of the compound with a C220 residue of p53. In embodiments, the p53 protein is a Y220C p53 protein.

In embodiments, the p53 protein is covalently bonded to a moiety of a compound described herein following a covalent reaction of the compound with a residue corresponding to C220 of a mutant p53 protein including a Y220C mutation (e.g., Y220C p53 protein). In embodiments, the mutant p53 protein is Y220C of p53 having the sequence SEQ ID NO:6. In embodiments, the cysteine (e.g., corresponding to C220 of the Y220C p53 protein (e.g., SEQ ID NO:6)) of the p53 protein reacts with $R^3$ to form a p53 conjugate. In embodiments, the p53 conjugate has a covalent linker, $L^C$, between the sulfur of the cysteine (e.g., corresponding to C220) of the Y220C p53 protein and the remainder of the compound. $L^C$ is a bond, $-S(O)_2-$, —NH—, —O—, —S—, —C(O)—, —C(O)NH—, —NHC(O)—, —NHC(O)NH—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenyl), or substituted or unsubstituted heteroarylene (e.g., 5 to 10 membered, 5 to 9 membered, or 5 to 6 membered). As a non-limiting example, the p53 protein covalently bonded to a compound may have the formula:

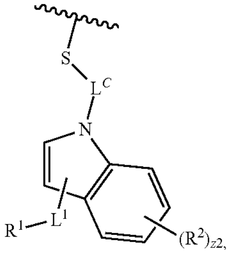

wherein S is the sulfur of a p53 protein cysteine (e.g., corresponding to C220 of a Y220C p53 protein (e.g., SEQ ID NO:6)), which is bonded to the remainder of the p53 protein and wherein $L^C$, $L^1$, $R^1$, $R^2$, and z2 are as described herein. As a non-limiting example, the p53 protein covalently bonded to a compound may have the formula:

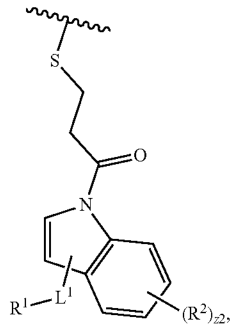

wherein S is the sulfur of a p53 protein cysteine (e.g., corresponding to C220 of a Y220C p53 protein (e.g., SEQ ID NO:6)), which is bonded to the remainder of the p53 protein and wherein $L^1$, $R^1$, $R^2$, and z2 are as described herein. As a non-limiting example, the p53 protein covalently bonded to a compound may have the formula:

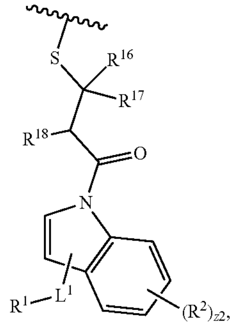

wherein S is the sulfur of a p53 protein cysteine (e.g., corresponding to C220 of a Y220C p53 protein (e.g., SEQ ID NO:6)), which is bonded to the remainder of the p53 protein and wherein $L^1$, $R^1$, $R^2$, $R^{16}$, $R^{17}$, $R^{18}$, and z2 are as described herein.

In embodiments, a substituted $L^C$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^C$ is substituted with a plurality of groups selected from substituent groups, size-limited substituent groups, and lower substituent groups; each substituent group, size-limited substituent group, and/or lower substituent group may optionally be different. In embodiments, when $L^C$ is substituted, it is substituted with at least one substituent group. In embodiments, when $L^C$ is substituted, it is substituted with at least one size-limited substituent group. In embodiments, when $L^C$ is substituted, it is substituted with at least one lower substituent group.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^{1}$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1}$, $R^{1.1}$, $R^{1.2}$, and $R^{1.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2B}$ is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A.1}$, $R^{2A.2}$, and $R^{2A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2A.1}$, $R^{2A.2}$, and $R^{2A.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B.1}$, $R^{2B.2}$, and $R^{2B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$, respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{2D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$, respectively.

In embodiments, when $R^{16}$ is substituted, $R^{16}$ is substituted with one or more first substituent groups denoted by $R^{16.1}$ as explained in the definitions section above in the description of "first substituent group(s)". In embodiments, when an $R^{16.1}$ substituent group is substituted, the $R^{16.1}$ substituent group is substituted with one or more second substituent groups denoted by $R^{16.2}$ as explained in the definitions section above in the description of "first substituent group(s)". In embodiments, when an $R^{16.2}$ substituent group is substituted, the $R^{16.2}$ substituent group is substituted with one or more third substituent groups denoted by $R^{16.3}$ as explained in the definitions section above in the description of "first substituent group(s)". In the above embodiments, $R^{16}$, $R^{16.1}$, $R^{16.2}$, and $R^{16.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16}$, $R^{16.1}$, $R^{16.2}$ and $R^{16.3}$, respectively.

In embodiments, when $R^{17}$ is substituted, $R^{17}$ is substituted with one or more first substituent groups denoted by $R^{17.1}$ as explained in the definitions section above in the description of "first substituent group(s)". In embodiments, when an $R^{17.1}$ substituent group is substituted, the $R^{17.1}$ substituent group is substituted with one or more second substituent groups denoted by $R^{17.2}$ as explained in the definitions section above in the description of "first substituent group(s)". In embodiments, when an $R^{17.2}$ substituent group is substituted, the $R^{17.2}$ substituent group is substituted with one or more third substituent groups denoted by $R^{17.3}$ as explained in the definitions section above in the description of "first substituent group(s)". In the above embodiments, $R^{17}$, $R^{17.1}$, $R^{17.2}$, and $R^{17.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17}$, $R^{17.1}$, $R^{17.2}$, and $R^{17.3}$, respectively.

In embodiments, when $R^{18}$ is substituted, $R^{18}$ is substituted with one or more first substituent groups denoted by $R^{18.1}$ as explained in the definitions section above in the description of "first substituent group(s)". In embodiments, when an $R^{18.1}$ substituent group is substituted, the $R^{18.1}$ substituent group is substituted with one or more second substituent groups denoted by $R^{18.2}$ as explained in the definitions section above in the description of "first substituent group(s)". In embodiments, when an $R^{18.2}$ substituent group is substituted, the $R^{18.2}$ substituent group is substituted with one or more third substituent groups denoted by $R^{18.3}$ as explained in the definitions section above in the description of "first substituent group(s)". In the above embodiments, $R^{18}$, $R^{18.1}$, $R^{18.2}$, and $R^{18.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$ and $R^{WW.3}$ correspond to $R^{18}$, $R^{18.1}$, $R^{18.2}$, and $R^{18.3}$, respectively.

In embodiments, when $L^{101}$ is substituted, $L^{101}$ is substituted with one or more first substituent groups denoted by $R^{L101.1}$ as explained in the definitions section above in the description of "first substituent group(s)". In embodiments, when an $R^{L101.1}$ substituent group is substituted, the $R^{L101.1}$ substituent group is substituted with one or more second substituent groups denoted by $R^{L101.2}$ as explained in the definitions section above in the description of "first substituent group(s)". In embodiments, when an $R^{L101.2}$ substituent group is substituted, the $R^{L101.2}$ substituent group is substituted with one or more third substituent groups denoted by $R^{L101.3}$ as explained in the definitions section above in the description of "first substituent group(s)". In the above embodiments, $L^{101}$, $R^{L101.1}$, $R^{L101.2}$, and $R^{L101.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{101}$, $R^{L101.1}$, $R^{L101.2}$, and $R^{L101.3}$ respectively.

In embodiments, when $L^{102}$ is substituted, $L^{102}$ is substituted with one or more first substituent groups denoted by $R^{L102.1}$ as explained in the definitions section above in the description of "first substituent group(s)". In embodiments, when an $R^{L102.1}$ substituent group is substituted, the $R^{L102.1}$ substituent group is substituted with one or more second substituent groups denoted by $R^{L102.2}$ as explained in the definitions section above in the description of "first substituent group(s)". In embodiments, when an $R^{L102.2}$ substituent group is substituted, the $R^{L102.2}$ substituent group is substituted with one or more third substituent groups denoted by $R^{L102.3}$ as explained in the definitions section above in the description of "first substituent group(s)". In the above embodiments, $L^{102}$, $R^{L102.1}$, $R^{L102.2}$, and $R^{L102.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{102}$, $R^{L102.1}$, $R^{L102.2}$, and $R^{L102.3}$, respectively.

In embodiments, when $L^{103}$ is substituted, $L^{103}$ is substituted with one or more first substituent groups denoted by $R^{L103.1}$ as explained in the definitions section above in the description of "first substituent group(s)". In embodiments, when an $R^{L103.1}$ substituent group is substituted, the $R^{L103.1}$ substituent group is substituted with one or more second substituent groups denoted by $R^{L103.2}$ as explained in the definitions section above in the description of "first substituent group(s)". In embodiments, when an $R^{L103.2}$ substituent group is substituted, the $R^{L103.2}$ substituent group is substituted with one or more third substituent groups denoted by $R^{L103.3}$ as explained in the definitions section above in the description of "first substituent group(s)". In the above embodiments, $L^{103}$, $R^{L103.1}$, $R^{L103.2}$, and $R^{L103.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{103}$, $R^{L103.1}$, $R^{L103.2}$ and $R^{L103.3}$ respectively.

In embodiments, when $L^{104}$ is substituted, $L^{104}$ is substituted with one or more first substituent groups denoted by $R^{L104.1}$ as explained in the definitions section above in the description of "first substituent group(s)". In embodiments, when an $R^{L104.1}$ substituent group is substituted, the $R^{L104.1}$ substituent group is substituted with one or more second substituent groups denoted by $R^{L104.2}$ as explained in the definitions section above in the description of "first substituent group(s)". In embodiments, when an $R^{L104.2}$ substituent group is substituted, the $R^{L104.2}$ substituent group is substituted with one or more third substituent groups denoted by $R^{L104.3}$ as explained in the definitions section above in the description of "first substituent group(s)". In the above embodiments, $L^{104}$, $R^{L104.1}$, $R^{L104.2}$, and $R^{L104.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{104}$, $R^{L104.1}$, $R^{L104.2}$ and $R^{L104.3}$ respectively.

In embodiments, when $L^{105}$ is substituted, $L^{105}$ is substituted with one or more first substituent groups denoted by $R^{L105.1}$ as explained in the definitions section above in the description of "first substituent group(s)". In embodiments, when an $R^{L105.1}$ substituent group is substituted, the $R^{L105.1}$ substituent group is substituted with one or more second substituent groups denoted by $R^{L105.2}$ as explained in the definitions section above in the description of "first substituent group(s)". In embodiments, when an $R^{L105.2}$ substituent group is substituted, the $R^{L105.2}$ substituent group is substituted with one or more third substituent groups denoted by $R^{L105.3}$ as explained in the definitions section above in the description of "first substituent group(s)". In the above embodiments, $L^{105}$, $R^{L105.1}$, $R^{L105.2}$, and $R^{L105.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{105}$, $R^{L105.1}$, $R^{L105.2}$, and $R^{L105.3}$, respectively.

In embodiments, when $L^{201}$ is substituted, $L^{201}$ is substituted with one or more first substituent groups denoted by $R^{L201.1}$ as explained in the definitions section above in the description of "first substituent group(s)". In embodiments, when an $R^{L201.1}$ substituent group is substituted, the $R^{L201.1}$ substituent group is substituted with one or more second substituent groups denoted by $R^{L201.2}$ as explained in the definitions section above in the description of "first substituent group(s)". In embodiments, when an $R^{L201.2}$ substituent group is substituted, the $R^{L201.2}$ substituent group is substituted with one or more third substituent groups denoted by $R^{L201.3}$ as explained in the definitions section above in the description of "first substituent group(s)". In the above embodiments, $L^{201}$, $R^{L201.1}$, $R^{L201.2}$ and $R^{L201.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{201}$, $R^{L201.1}$, $R^{L201.2}$, and $R^{L201.3}$, respectively.

In embodiments, when $L^{202}$ is substituted, $L^{202}$ is substituted with one or more first substituent groups denoted by $R^{L202.1}$ as explained in the definitions section above in the description of "first substituent group(s)". In embodiments, when an $R^{L202.1}$ substituent group is substituted, the $R^{L202.1}$ substituent group is substituted with one or more second substituent groups denoted by $R^{L202.2}$ as explained in the definitions section above in the description of "first substituent group(s)". In embodiments, when an $R^{L202.2}$ substituent group is substituted, the $R^{L202.2}$ substituent group is substituted with one or more third substituent groups denoted by $R^{L202.3}$ as explained in the definitions section above in the description of "first substituent group(s)". In the above embodiments, $L^{202}$, $R^{L202.1}$, $R^{L202.2}$, and $R^{L202.3}$ have values corresponding to the values of $L^{WW}$, $R^{LWW.1}$, $R^{LWW.2}$ and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{202}$, $R^{L202.1}$, $R^{L202.2}$, and $R^{L202.3}$, respectively.

In embodiments, when $L^{203}$ is substituted, $L^{203}$ is substituted with one or more first substituent groups denoted by $R^{L203.1}$ as explained in the definitions section above in the description of "first substituent group(s)". In embodiments, when an $R^{L203.1}$ substituent group is substituted, the $R^{L203.1}$ substituent group is substituted with one or more second substituent groups denoted by $R^{L203.2}$ as explained in the definitions section above in the description of "first substituent group(s)". In embodiments, when an $R^{L203.2}$ substituent group is substituted, the $R^{L203.2}$ substituent group is substituted with one or more third substituent groups denoted by $R^{L203.3}$ as explained in the definitions section above in the description of "first substituent group(s)". In the above embodiments, $L^{203}$, $R^{L203.1}$, $R^{L203.2}$, and $R^{L203.3}$ have values corresponding to the values of $L^{WW}$, $R^{LWW1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{203}$, $R^{L203.1}$, $R^{L203.2}$, and RL203.3 respectively.

In embodiments, when $L^{204}$ is substituted, $L^{204}$ is substituted with one or more first substituent groups denoted by $R^{L204.1}$ as explained in the definitions section above in the description of "first substituent group(s)". In embodiments, when an $R^{L204.1}$ substituent group is substituted, the $R^{L204.1}$ substituent group is substituted with one or more second substituent groups denoted by $R^{L204.2}$ as explained in the definitions section above in the description of "first substituent group(s)". In embodiments, when an $R^{L204.2}$ substituent group is substituted, the $R^{L204.2}$ substituent group is substituted with one or more third substituent groups denoted by $R^{L204.3}$ as explained in the definitions section above in the description of "first substituent group(s)". In the above embodiments, $L^{204}$, $R^{L204.1}$, $R^{L204.2}$, and $R^{L204.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{204}$, $R^{L204.1}$, $R^{L204.2}$ and $R^{L204.3}$ respectively.

In embodiments, when $L^{205}$ is substituted, $L^{205}$ is substituted with one or more first substituent groups denoted by $R^{L205.1}$ as explained in the definitions section above in the description of "first substituent group(s)". In embodiments, when an $R^{L205.1}$ substituent group is substituted, the $R^{L205.1}$ substituent group is substituted with one or more second substituent groups denoted by $R^{L205.2}$ as explained in the definitions section above in the description of "first substituent group(s)". In embodiments, when an $R^{L205.2}$ substituent group is substituted, the $R^{L205.2}$ substituent group is substituted with one or more third substituent groups denoted by $R^{L205.3}$ as explained in the definitions section above in the description of "first substituent group(s)". In the above embodiments, $L^{205}$, $R^{L205.1}$, $R^{L205.2}$, and $R^{L205.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{205}$, $R^{L205.1}$, $R^{L205.2}$, and $R^{L205.3}$, respectively.

In embodiments, when $L^{C}$ is substituted, $L^{C}$ is substituted with one or more first substituent groups denoted by $R^{LC.1}$ as explained in the definitions section above in the description of "first substituent group(s)". In embodiments, when an $R^{LC.1}$ substituent group is substituted, the $R^{LC.1}$ substituent group is substituted with one or more second substituent groups denoted by $R^{LC.2}$ as explained in the definitions section above in the description of "first substituent group(s)". In embodiments, when an $R^{LC.2}$ substituent group is substituted, the $R^{LC.2}$ substituent group is substituted with one or more third substituent groups denoted by $R^{LC.3}$ as explained in the definitions section above in the description of "first substituent group(s)". In the above embodiments, $L^{C}$, $R^{LC.1}$, $R^{LC.2}$, and $R^{LC.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{C}$, $R^{LC.1}$, $R^{LC.2}$, and $R^{LC.3}$, respectively.

In an aspect is provided a p53 protein covalently bonded to a p53 stabilizer (e.g., a compound described herein). In embodiments, the p53 stabilizer is a p53 mutant stabilizer. In embodiments, the p53 protein is covalently bonded to a moiety of a p53 stabilizer (e.g., a compound described herein) following a covalent reaction of the compound with a C220 residue of p53. In embodiments, the p53 protein is a Y220C p53 protein.

In embodiments, the compound (e.g., the compound as described herein) is bonded to a cysteine residue of the Y220C p53 protein. In embodiments, the compound is covalently bonded to a cysteine residue of the Y220C p53 protein. In embodiments, the compound is reversibly covalently bonded to a cysteine residue of the Y220C p53 protein. In embodiments, the compound is irreversibly covalently bonded to a cysteine residue of the Y220C p53 protein. In embodiments, the compound is covalently bonded to a cysteine corresponding to C220 of the Y220C p53 protein. In embodiments, the compound is irreversibly covalently bonded a cysteine corresponding to C220 of the Y220C p53 protein.

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein (e.g., in an aspect, embodiment, example, table, figure, or claim).

III. Pharmaceutical Compositions

In an aspect is provided a pharmaceutical composition including a compound described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent. In embodiments, the pharmaceutical composition includes a therapeutically effective amount of a second agent. In embodiments, the second agent is an anti-cancer agent. In embodiments, the anti-cancer agent is cisplatin, temozolomide, doxorubicin, gemcitabine, tamoxifen, or cetuximab. In embodiments, the second agent is an inhibitor of K-Ras, RAF, MEK, Erk, PI3K, Akt, RTK, or mTOR. In embodiments, the second agent is an MDM2 inhibitor or a genotoxic anti-cancer agent. In embodiments, the MDM2 inhibitor is a nutlin. In embodiments, the MDM2 inhibitor is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232. In embodiments, the genotoxic anti-cancer agent is an alkylating agent, intercalating agent, or DNA replication inhibitor. In embodiments, the genotoxic anti-cancer agent is a PARP inhibitor or temezolamide. In embodiments, the second agent is a compound described in Hientz, et al., The role of p53 in cancer drug resistance and targeted chemotherapy. *Oncotarget,* 8, 8921-8946 (2017), which is herein incorporated by reference for all purposes.

IV. Methods of Use

In an aspect is provided a method of treating cancer in a subject in need of such treatment, including administering to the subject an effective amount of a compound described herein.

In embodiments, the cancer is a hematologic cancer. In embodiments, the hematologic cancer is leukemia. In embodiments, the hematologic cancer is lymphoma. In embodiments, the hematologic cancer is multiple myeloma. In embodiments, the hematologic cancer is acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia. In embodiments, the hematologic cancer is non-Hodgkin lymphoma or Hodgkin's disease. In embodiments, the hematologic cancer is small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. In embodiments, the hematologic cancer is cutaneous T-cell lymphoma, peripheral T-cell lymphoma, anaplastic large cell lymphoma, mycosis fungoides, and precursor T-lymphoblastic lymphoma.

In embodiments, the cancer is thyroid cancer, endocrine system cancer, brain cancer, breast cancer, cervix cancer, colon cancer, head and neck cancer, liver cancer, kidney cancer, lung cancer, non-small cell lung cancer, melanoma, mesothelioma, ovarian cancer, sarcoma, stomach cancer, uterus cancer, medulloblastoma, colorectal cancer, pancreatic cancer. In embodiments, the cancer is neuroblastoma, glioma, glioblastoma multiforme, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, papillary thyroid cancer, hepatocellular carcinoma, or prostate cancer.

In embodiments, the method further includes co-administering a second agent to the subject in need thereof. In embodiments, the second agent is an anti-cancer agent. In embodiments, the anti-cancer agent is an inhibitor of K-Ras, RAF, MEK, Erk, PI3K, Akt, RTK, or mTOR. In embodiments, the second agent is an anti-cancer agent. In embodiments, the anti-cancer agent is cisplatin, temozolomide, doxorubicin, gemcitabine, tamoxifen, or cetuximab. In embodiments, the anti-cancer agent is an MDM2 inhibitor or a genotoxic anti-cancer agent. In embodiments, the MDM2 inhibitor is a nutlin. In embodiments, the MDM2 inhibitor is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232. In embodiments, the genotoxic anti-cancer agent is an alkylating agent, intercalating agent, or DNA replication inhibitor. In embodiments, the genotoxic anti-cancer agent is a PARP inhibitor or temezolamide. In embodiments, the second agent is a compound described in Hientz, et al., The role of p53 in cancer drug resistance and targeted chemotherapy. *Oncotarget,* 8, 8921-8946 (2017), which is herein incorporated by reference for all purposes. In embodiments, the second agent is a radiotherapeutic agent. In embodiments, the radiotherapeutic agent includes a radionuclide. In embodiments, the radionuclide is $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, or $^{212}Bi$. In embodiments, the radionuclide is conjugated to an antibody.

In embodiments, the method further comprises co-administering radiation to the subject in need thereof. In embodiments, the radiation is UV radiation. In embodiments, the radiation is IR radiation.

In an aspect is provided a method of treating a p53 mutant cancer in a subject in need thereof, the method including administering to the subject an effective amount of a compound described herein.

In embodiments, the p53 mutant cancer is a $p53^{+/mut}$ cancer or a $p53^{mut/-}$ cancer. In embodiments, the p53 mutant cancer is a $p53^{+/mut}$ cancer. In embodiments, the p53 mutant cancer is a $p53^{mut/-}$ cancer.

In embodiments, the p53 mutant cancer is a hematologic cancer. In embodiments, the hematologic cancer is leukemia. In embodiments, the hematologic cancer is lymphoma. In embodiments, the hematologic cancer is multiple myeloma. In embodiments, the hematologic cancer is acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia. In embodiments, the hematologic cancer is non-Hodgkin lymphoma or Hodgkin's disease. In embodiments, the hematologic cancer is small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. In embodiments, the hematologic cancer is cutaneous T-cell lymphoma, peripheral T-cell lymphoma, anaplastic large cell lymphoma, mycosis fungoides, and precursor T-lymphoblastic lymphoma.

In embodiments, the p53 mutant cancer is thyroid cancer, endocrine system cancer, brain cancer, breast cancer, cervix cancer, colon cancer, head and neck cancer, liver cancer, kidney cancer, lung cancer, non-small cell lung cancer, melanoma, mesothelioma, ovarian cancer, sarcoma, stomach cancer, uterus cancer, medulloblastoma, colorectal cancer, pancreatic cancer. In embodiments, the p53 mutant cancer is neuroblastoma, glioma, glioblastoma multiforme, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, papillary thyroid cancer, hepatocellular carcinoma, or prostate cancer.

In an aspect is provided a method of treating a $p53^{+/mut}$ cancer, the method including administering to a subject in need thereof an effective amount of a p53 mutant agonist to the subject. In embodiments, the p53 mutant agonist is a small molecule. In embodiments, the p53 mutant agonist is a PhiKan compound. In embodiments, the p53 mutant agonist is a compound described herein.

In embodiments, the PhiKan compound is

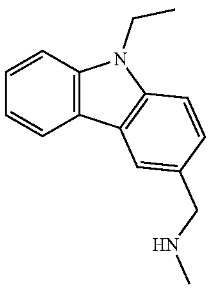

(PhiKan083).

In embodiments, the PhiKan compound is

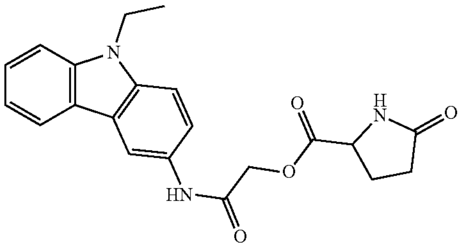

(PhiKan059).

In embodiments, the PhiKan compound is

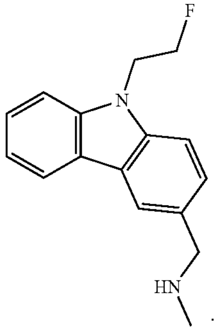 [SMILES: CNCc1ccc2c(c1)c1ccccc1n2CCF]

.

In embodiments, the PhiKan compound is
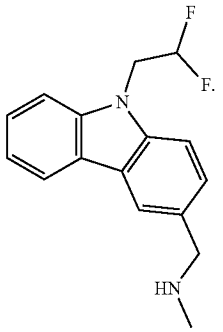 [SMILES: CNCc1ccc2c(c1)c1ccccc1n2CC(F)F]
In embodiments, the PhiKan compound is
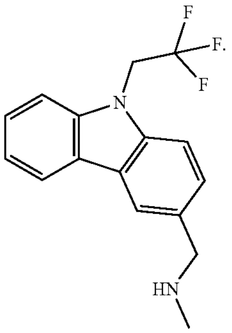 [SMILES: CNCc1ccc2c(c1)c1ccccc1n2CC(F)(F)F]
In embodiments, the PhiKan compound is
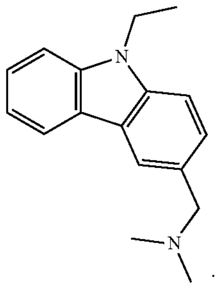 [SMILES: CCn1c2ccccc2c2cc(CN(C)C)ccc21]
In embodiments, the PhiKan compound is
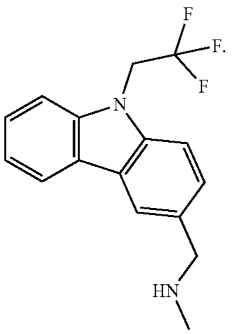 [SMILES: CNCc1ccc2c(c1)c1ccccc1n2CC(F)(F)F]
In embodiments, the PhiKan compound is
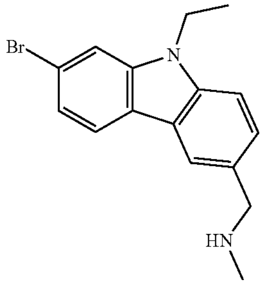
(PK9284).
In embodiments, the PhiKan compound is
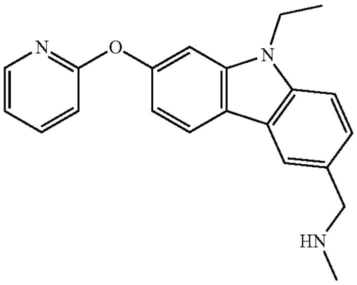
(PK9295).
In embodiments, the PhiKan compound is
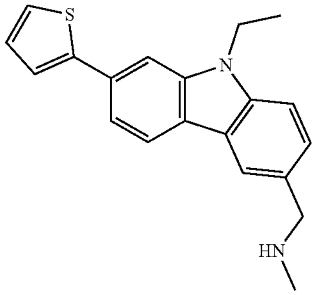
(PK9296).
In embodiments, the PhiKan compound is
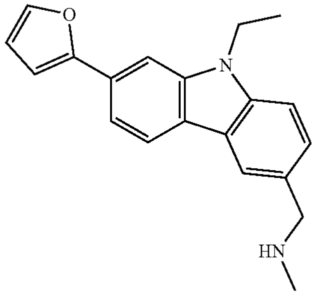
(PK9304).

In embodiments, the PhiKan compound is
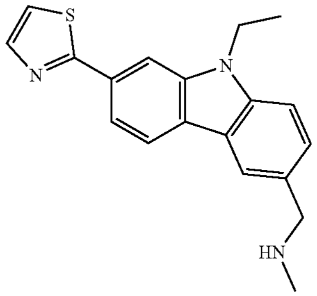
(PK9305).
In embodiments, the PhiKan compound is
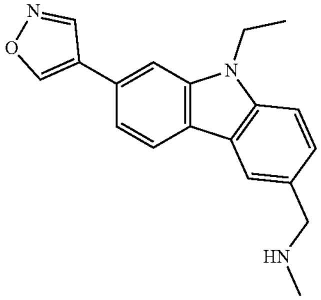
(PK9318).
In embodiments, the PhiKan compound is
(PK9319)
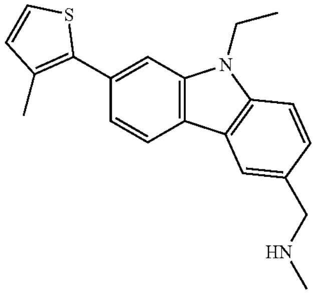
.
In embodiments, the PhiKan compound is
(PK9320)
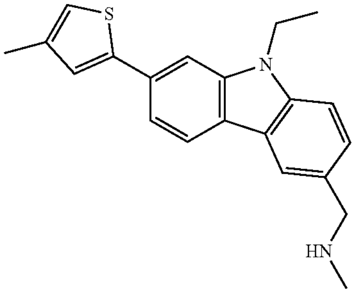
.
In embodiments, the PhiKan compound is
(PK9321)
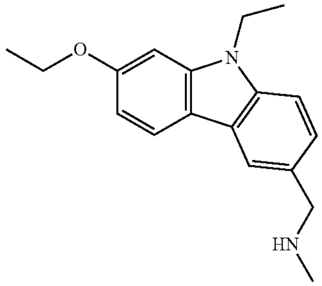
.
In embodiments, the PhiKan compound is
(PK9322)
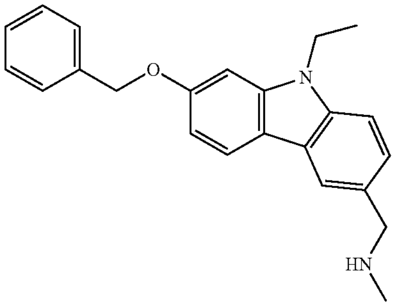
.
In embodiments, the PhiKan compound is
(PK9323)
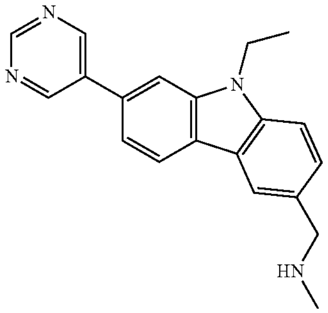
.
In embodiments, the PhiKan compound is
(PK9324)
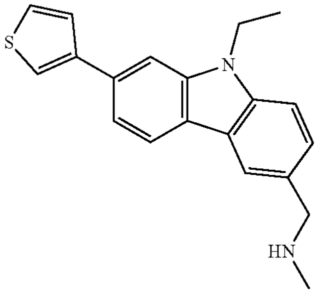
.

In embodiments, the PhiKan compound is (PK9326)

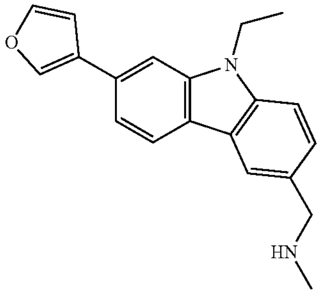

In embodiments, the PhiKan compound is (PK9327)

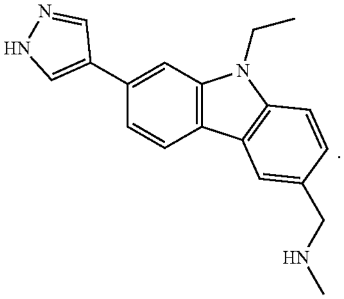

In embodiments, the PhiKan compound is (PK9328)

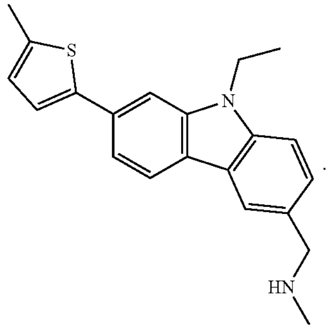

In embodiments, the PhiKan compound is (PK9329)

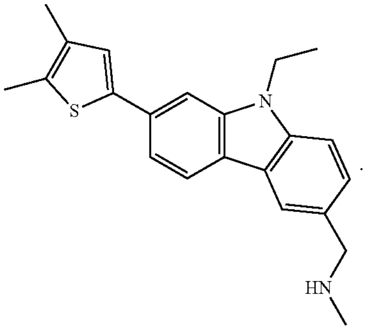

In embodiments, the PhiKan compound is (PK9331)

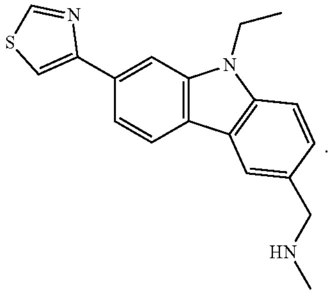

In embodiments, the PhiKan compound is (PhiKan5196)

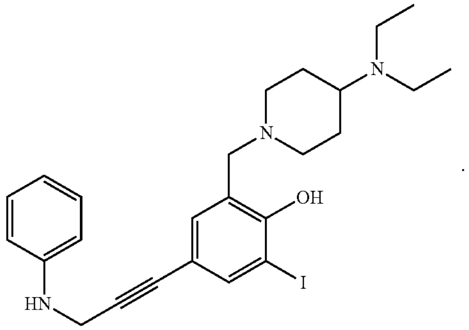

In embodiments, the PhiKan compound is (PhiKan7088)

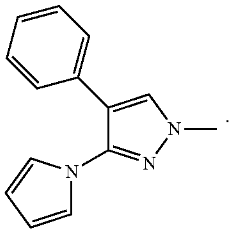

In embodiments, the nomenclature "PhiKan" is equivalent to "PK"; for example, PhiKan083 is equivalent to PK083.

In embodiments, the PhiKan compound is a compound described in Boeckler, F. M., et al. *PNAS* 2008, 105, 10360-10365, which is incorporated herein by reference in its entirety and for all purposes. In embodiments, the PhiKan compound is a compound described in Bauer, M. R., et al., *ACS Chem. Biol.* 2016, 11, 2265-2274, which is incorporated herein by reference in its entirety and for all purposes. In embodiments, the PhiKan compound is a compound described in Bauer, M. R., et al. *Future Med. Chem.* 2019, 11, 2491-2504, which is incorporated herein by reference in its entirety and for all purposes.

In an aspect is provided a method of increasing the level of a protein in a cell, wherein the level of the protein is regulated by p53, the method including contacting the cell with a compound described herein. In embodiments, the compound covalently binds C220 of a mutant human p53 protein including a Y220C mutation. In embodiments, the increasing level of the protein is an increasing level of p21 protein.

In an aspect is provided a method of increasing the level of activity of mutant p53 protein, the method including contacting the mutant p53 protein with a compound described herein. In embodiments, the mutant p53 protein is a mutant p53 protein with a $p53^{+/mut}$ genotype. In embodiments, the mutant p53 protein is a mutant p53 protein with a $p53^{mut/-}$ genotype.

In an aspect is provided a method of detecting a detectable p53 protein-compound conjugate including a p53 protein (e.g., Y220C p53 protein) conjugated to a compound described herein wherein $R^2$ independently includes a first reactive moiety, the method including:

(i) contacting the p53 protein with the compound to form a p53 protein-compound conjugate;

(ii) contacting the p53 protein-compound conjugate with a detectable agent, wherein the detectable agent includes a detectable moiety and a second reactive moiety, thereby forming the detectable p53 protein-compound conjugate; and (iii) detecting the detectable p53 protein-compound conjugate;

wherein the first reactive moiety and the second reactive moiety are a complementary reactive pair.

In embodiments, the step (iii) includes detecting the detectable p53 protein-compound conjugate by LC-MS. In embodiments, the step (iii) includes detecting the detectable p53 protein-compound conjugate by Western blot.

In embodiments, the complementary reactive pair is a click chemistry complementary reactive pair. In embodiments, the first reactive moiety is a substituted or unsubstituted alkynyl. In embodiments, the second reactive moiety is an azidyl moiety. In embodiments, the complementary reactive pair is a SuFEx click chemistry complementary reactive pair. In embodiments, the first reactive moiety is independently $—NS(O)F_2$. In embodiments, the second reactive moiety is an amine. In embodiments, the second reactive moiety is a primary amine. In embodiments, the second reactive moiety is a secondary amine. In embodiments, the method can be used in drug discovery.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A compound having the formula:

(I)

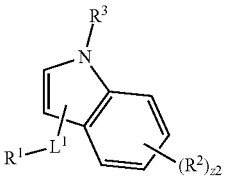

or

-continued (II)

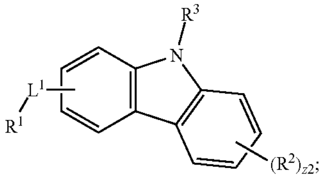

wherein $L^1$ is a bond or covalent linker;

$R^1$ is a transcriptional coactivator binding moiety;

$R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^{2A}$, $R^{2B}$, $R^{2C}$, and $R^{2D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$X^2$ is independently —F, —Cl, —Br, or —I;

n2 is independently an integer from 0 to 4;

m2 and v2 are independently 1 or 2;

z2 is an integer from 0 to 7; and $R^3$ is a covalent cysteine modifier moiety.

Embodiment P2. The compound of embodiment P1, wherein $L^1$ is $-L^{101}$-$L^{102}$-$L^{103}$-$L^{104}$-$L^{105}$-; and $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker.

Embodiment P3. The compound of one of embodiments P1 to P2, having the formula:

(Ia)

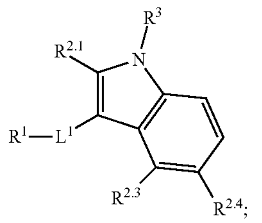

wherein $R^{2.1}$, $R^{2.3}$, and $R^{2.4}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P4. The compound of embodiment P3, wherein $R^{2.1}$ is hydrogen.

Embodiment P5. The compound of one of embodiments P3 to P4, wherein $R^{2.4}$ is hydrogen.

Embodiment P6. The compound of one of embodiments P3 to P5, wherein $R^{2.3}$ is hydrogen, $—NH_2$, $—NHCH_3$, $—N(CH_3)_3$,

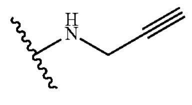
,
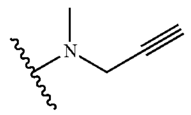
,
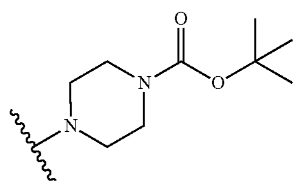
,
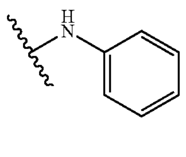
,
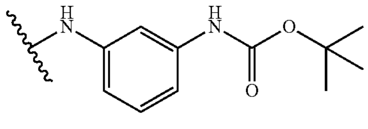
,
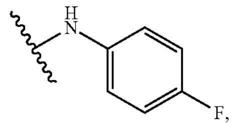
or
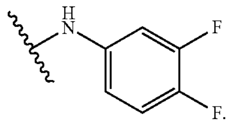

Embodiment P7. The compound of one of embodiments P1 to P2, having the formula:

(Ib)

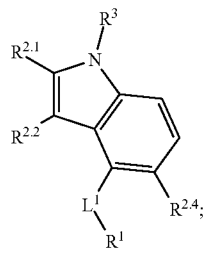

wherein $R^{2.1}$, $R^{2.2}$, and $R^{2.4}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P8. The compound of embodiment P7, wherein $R^{2.1}$ is hydrogen.

Embodiment P9. The compound of one of embodiments P7 to P8, wherein $R^{2.4}$ is hydrogen.

Embodiment P10. The compound of one of embodiments P7 to P9, wherein $R^{2.2}$ is $—C(O)H$, $—CH_2C(O)H$, $—CH_2C(O)OH$, $—C(O)OH$, $—CH_2NHCH_3$, $—CH_2NH_2$, or $—CH_2N(CH_3)_2$.

Embodiment P11. The compound of one of embodiments P1 to P2, having the formula:

(Ic)

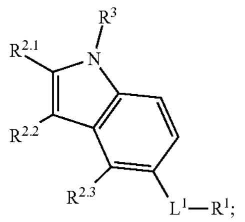

wherein $R^{2.1}$, $R^{2.2}$, and $R^{2.3}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P12. The compound of embodiment P11, wherein $R^{2.1}$ is hydrogen.

Embodiment P13. The compound of one of embodiments P11 to P12, wherein $R^{2.2}$ is hydrogen, —C(O)H, —$CH_2C$(O)H, —$CH_2C(O)OH$, —C(O)OH, —$CH_2NHCH_3$, —$CH_2NH_2$, or —$CH_2N(CH_3)_2$.

Embodiment P14. The compound of one of embodiments P11 to P13, wherein $R^{2.3}$ is hydrogen, —$NH_2$, —$NHCH_3$, —$N(CH_3)_3$,

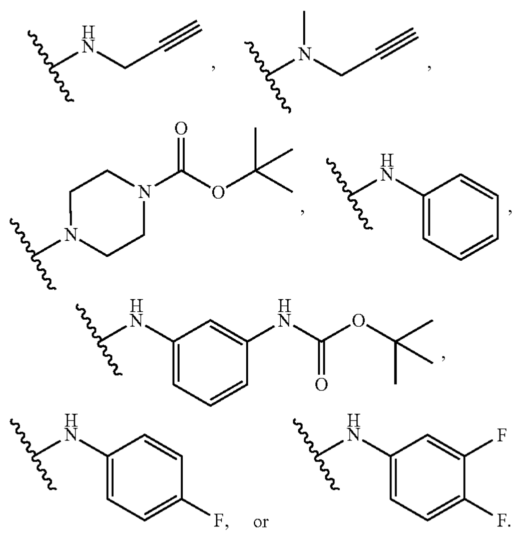

, or

Embodiment P15. The compound of one of embodiments P1 to P2, having the formula:

(IIa)

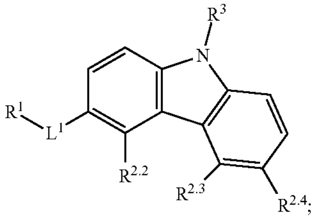

wherein $R^{2.2}$, $R^{2.3}$, and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)$OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P16. The compound of one of embodiments P1 to P2, having the formula:

(IIb)

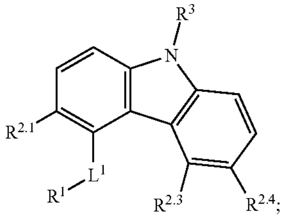

wherein $R^{2.1}$, $R^{2.3}$, and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)$OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P17. The compound of one of embodiments P1 to P2, having the formula:

(IIc)

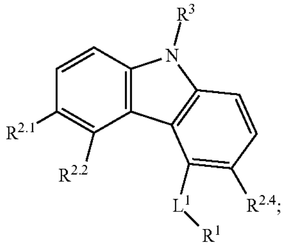

wherein $R^{2.1}$, $R^{2.2}$ and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}$C(O)$R^{2C}$, —$NR^{2A}$C(O)$OR^{2C}$, —$NR^{2A}OR^{2C}$, —$SF_5$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P18. The compound of one of embodiments P1 to P2, having the formula:

(IId)

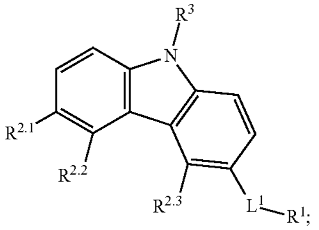

wherein $R^{2.1}$, $R^{2.2}$, and $R^{2.3}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P19. The compound of one of embodiments P16 to P18, wherein $R^{2.1}$ is —C(O)H, $—CH_2C(O)H$, $—CH_2C(O)OH$, —C(O)OH, $—CH_2NHCH_3$, $—CH_2NH_2$, or $—CH_2N(CH_3)_2$.

Embodiment P20. The compound of one of embodiments P1 to P19, wherein $R^3$ is

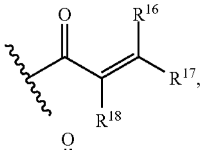

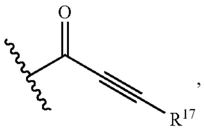

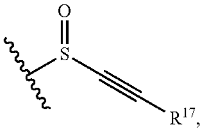

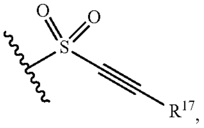

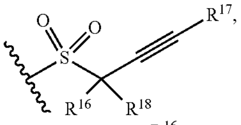

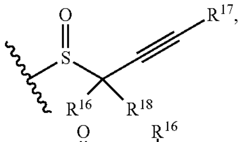

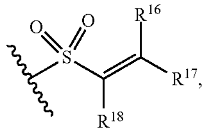

or

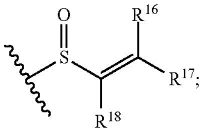

and $R^{16}$, $R^{17}$, and $R^{18}$ are independently hydrogen, oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{12}$ aryl, or substituted or unsubstituted 5 to 12 membered heteroaryl.

Embodiment P21. The compound of embodiment P20, wherein $R^3$ is

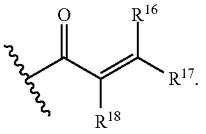

Embodiment P22. The compound of embodiment P21, wherein $R^{16}$ is hydrogen, $R^{17}$ is hydrogen, and $R^{18}$ is hydrogen.

Embodiment P23. The compound of embodiment P21, wherein $R^{16}$ is hydrogen, $R^{17}$ is hydrogen, and $R^{18}$ is unsubstituted methyl.

Embodiment P24. The compound of embodiment P21, wherein $R^{16}$ is hydrogen, $R^{17}$ is hydrogen, and $R^{18}$ is —CN.

Embodiment P25. The compound of one of embodiments P1 to P24, wherein the transcriptional coactivator binding moiety is a BRD4 binding moiety.

Embodiment P26. The compound of embodiment P25, wherein the BRD4 binding moiety has the formula:

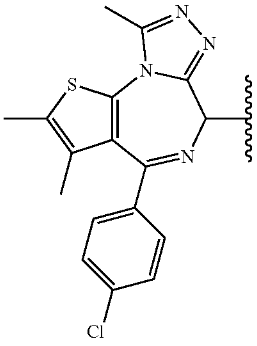

,

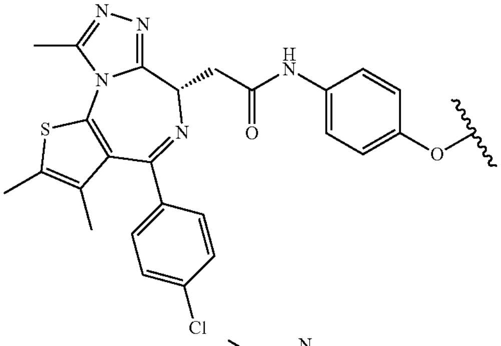

,

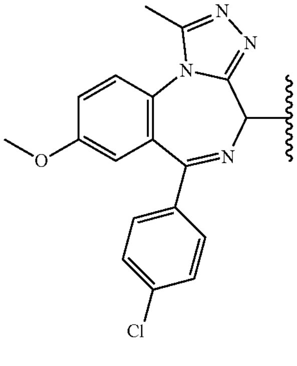

, or

-continued

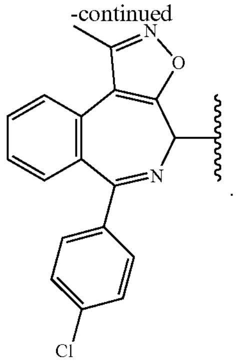

Embodiment P27. The compound of one of embodiments P1 to P24, wherein the transcriptional coactivator binding moiety is a p300 binding moiety.

Embodiment P28. The compound of embodiment P27, wherein the p300 binding moiety has the formula:

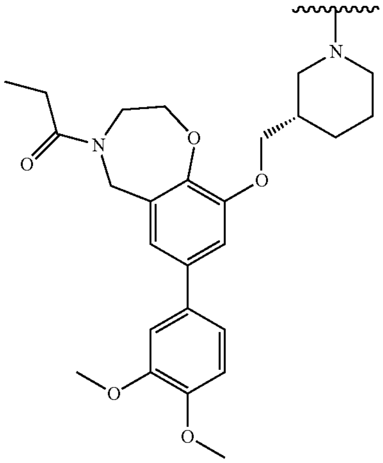

Embodiment P29. The compound of one of embodiments P1 to P28, wherein $L^1$ is

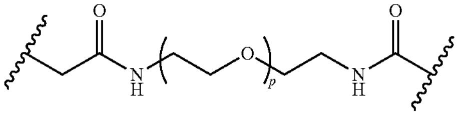

,

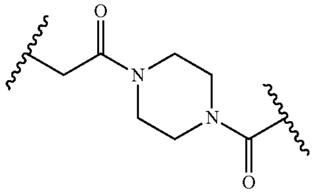

,

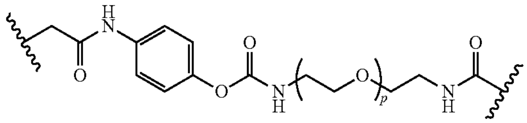

, or

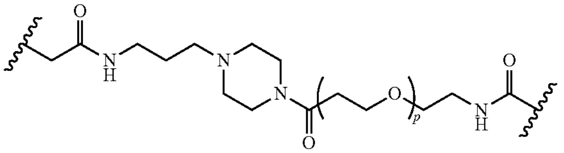

;

wherein p is an integer from 1 to 8.

Embodiment P30. The compound of embodiment P1, having the formula

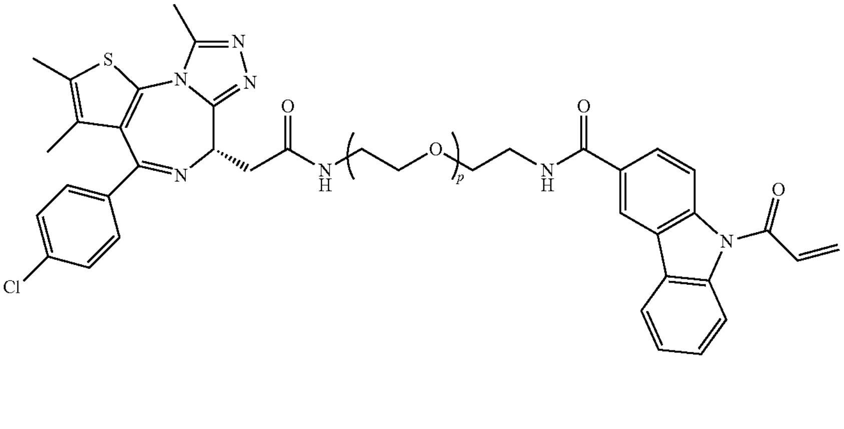

;

wherein p is an integer from 1 to 8.

Embodiment P31. A compound having the formula:

(III)

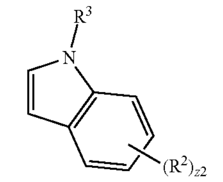

or (IV)

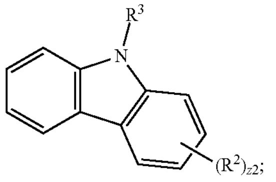

wherein $R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^{2A}$, $R^{2B}$, $R^{2C}$, and $R^{2D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$X^2$ is independently —F, —Cl, —Br, or —I;

n2 is independently an integer from 0 to 4;

m2 and v2 are independently 1 or 2;

z2a is an integer from 0 to 8; and $R^3$ is a covalent cysteine modifier moiety.

Embodiment P32. The compound of embodiment P31, having the formula:

(IIIa)

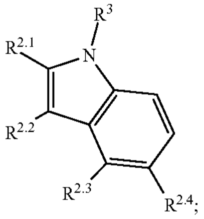

wherein $R^{2.1}$, $R^{2.2}$, $R^{2.3}$, and $R^{2.4}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P33. The compound of embodiment P32, wherein $R^{21}$ is hydrogen.

Embodiment P34. The compound of one of embodiments P32 to P33, wherein $R^{2.4}$ is hydrogen.

Embodiment P35. The compound of one of embodiments P32 to P34, wherein $R^{2.2}$ is —C(O)H, $—CH_2C(O)H$, $—CH_2C(O)OH$, —C(O)OH, $—CH_2NHCH_3$, $—CH_2NH_2$, or $—CH_2N(CH_3)_2$.

Embodiment P36. The compound of one of embodiments P32 to P35, wherein $R^{2.3}$ is hydrogen, $—NH_2$, $—NHCH_3$, $—N(CH_3)_3$,

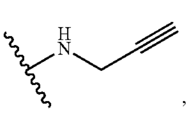

,

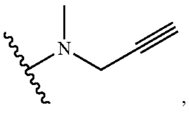

,

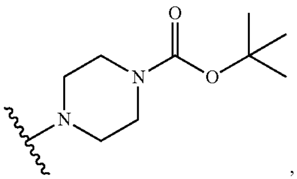

,

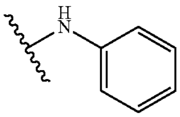

,

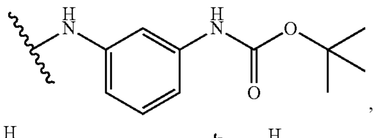

,

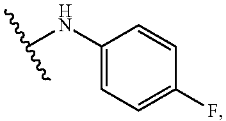

, or

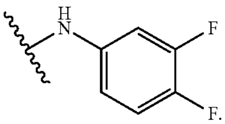

.

Embodiment P37. The compound of embodiment P31, having the formula:

(IVa)

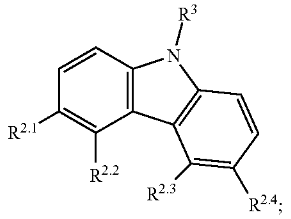

wherein $R^{2.1}$, $R^{2.2}$, $R^{2.3}$, and $R^{2.4}$ are independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl.

Embodiment P38. The compound of embodiment P37, wherein $R^{2.1}$ is —C(O)H, $—CH_2C(O)H$, $—CH_2C(O)OH$, —C(O)OH, $—CH_2NHCH_3$, $—CH_2NH_2$, or $—CH_2N(CH_3)_2$.

Embodiment P39. The compound of one of embodiments P31 to P38, wherein $R^3$ is

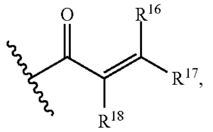

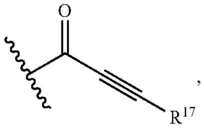

,

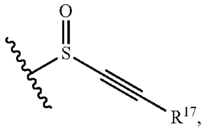

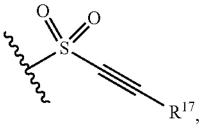

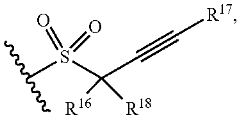

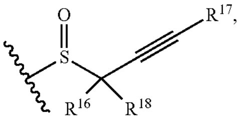

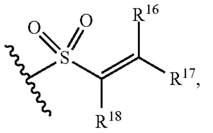

or

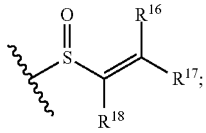

and $R^{16}$, $R^{17}$, and $R^{18}$ are independently hydrogen, oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{12}$ aryl, or substituted or unsubstituted 5 to 12 membered heteroaryl Embodiment P40. The compound of embodiment P39, wherein $R^3$ is

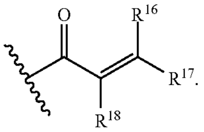

Embodiment P41. The compound of embodiment P40, wherein $R^{16}$ is hydrogen, $R^{17}$ is hydrogen, and $R^{18}$ is hydrogen.

Embodiment P42. The compound of embodiment P40, wherein $R^{16}$ is hydrogen, $R^{17}$ is hydrogen, and $R^{18}$ is unsubstituted methyl.

Embodiment P43. The compound of embodiment P40, wherein $R^{16}$ is hydrogen, $R^{17}$ is hydrogen, and $R^{18}$ is —CN.

Embodiment P44. A pharmaceutical composition comprising the compound of any one of embodiments P1 to P43 and a pharmaceutically acceptable excipient.

Embodiment P45. A method of increasing the level of a protein in a cell, wherein the level of the protein is regulated by p53, said method comprising contacting the cell with a compound of one of embodiments P1 to P43.

Embodiment P46. The method of embodiment P45, wherein the compound covalently binds C220 of a mutant human p53 protein comprising a Y220C mutation.

Embodiment P47. The method of one of embodiments P45 to P46, wherein the increasing level of the protein is an increasing level of p21 protein.

Embodiment P48. A method of treating cancer, said method comprising administering to a subject in need thereof an effective amount of a compound of one of embodiments P1 to P43.

Embodiment P49. The method of embodiment P48, wherein the cancer is a hematologic cancer.

Embodiment P50. The method of one of embodiments P48 to P49, wherein the method further comprises co-administering a second agent to the subject in need thereof.

Embodiment P51. The method of embodiment P50, wherein the second agent is an anti-cancer agent.

Embodiment P52. The method of embodiment P51, wherein the anti-cancer agent is an inhibitor of K-Ras, RAF, MEK, Erk, PI3K, Akt, RTK, or mTOR.

Embodiment P53. The method of embodiment P51, wherein the anti-cancer agent is an MDM2 inhibitor or a genotoxic anti-cancer agent.

Embodiment P54. The method of embodiment P53, wherein the MDM2 inhibitor is a nutlin.

Embodiment P55. The method of embodiment P53, wherein the MDM2 inhibitor is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232.

Embodiment P56. The method of embodiment P53, wherein the genotoxic anti-cancer agent is an alkylating agent, intercalating agent, or DNA replication inhibitor.

VI. Additional Embodiments

Embodiment 1. A compound having the formula:

(I)

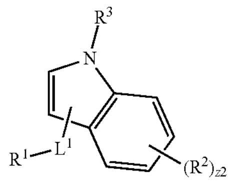

or (II)

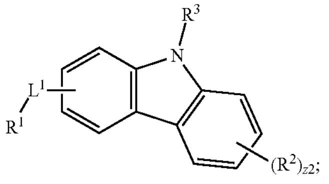

wherein $L^1$ is a bond or covalent linker;

$R^1$ is a transcriptional coactivator binding moiety;

$R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{2A}$, $R^{2B}$, $R^{2C}$, and $R^{2D}$ are independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$X^2$ is independently $-F$, $-Cl$, $-Br$, or $-I$;

n2 is independently an integer from 0 to 4;

m2 and v2 are independently 1 or 2;

z2 is an integer from 0 to 7; and $R^3$ is a covalent cysteine modifier moiety.

Embodiment 2. The compound of embodiment 1, wherein $L^1$ is $-L^{101}-L^{102}-L^{103}-L^{104}-L^{105}-$; and $L^{101}$, $L^{102}$, $L^{103}$, $L^{104}$, and $L^{105}$ are independently a bond, $-NH-$, $-S-$, $-O-$, $-C(O)-$, $-C(O)O-$, $-OC(O)-$, $-NHC(O)-$, $-C(O)NH-$, $-NHC(O)NH-$, $-NHC(NH)NH-$, $-C(S)-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker.

Embodiment 3. The compound of one of embodiments 1 to 2, having the formula:

(Ia)

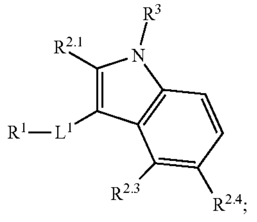

wherein $R^{2.1}$, $R^{2.3}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 4. The compound of embodiment 3, wherein $R^{21}$ is hydrogen.

Embodiment 5. The compound of one of embodiments 3 to 4, wherein $R^{2.4}$ is hydrogen.

Embodiment 6. The compound of one of embodiments 3 to 5, wherein $R^{2.3}$ is hydrogen, $-NH_2$, $-NHCH_3$, $-N(CH_3)_3$,

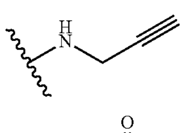

,

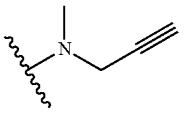

,

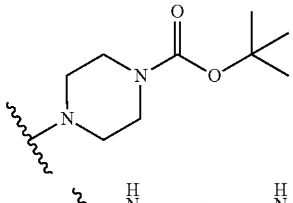

,

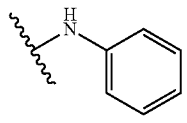

,

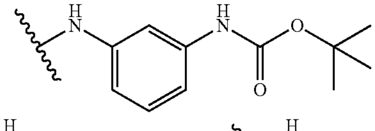

,

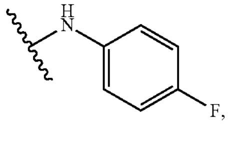

or

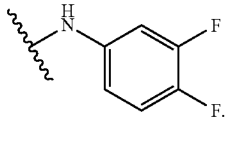

Embodiment 7. The compound of one of embodiments 1 to 2, having the formula:

(Ib)

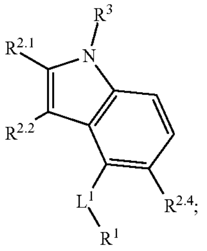

wherein $R^{2.1}$, $R^{2.2}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 8. The compound of embodiment 7, wherein $R^{2.1}$ is hydrogen.

Embodiment 9. The compound of one of embodiments 7 to 8, wherein $R^{2.4}$ is hydrogen.

Embodiment 10. The compound of one of embodiments 7 to 9, wherein $R^{2.2}$ is $-C(O)H$, $-CH_2C(O)H$, $-CH_2C(O)OH$, $-C(O)OH$, $-CH_2NHCH_3$, $-CH_2NH_2$, or $-CH_2N(CH_3)_2$.

Embodiment 11. The compound of one of embodiments 1 to 2, having the formula:

(Ic)

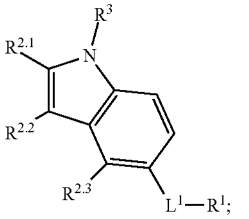

wherein $R^{2.1}$, $R^{2.2}$, and $R^{2.3}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 12. The compound of embodiment 11, wherein $R^{2.1}$ is hydrogen.

Embodiment 13. The compound of one of embodiments 11 to 12, wherein $R^{2.2}$ is hydrogen, $-C(O)H$, $-CH_2C(O)H$, $-CH_2C(O)OH$, $-C(O)OH$, $-CH_2NHCH_3$, $-CH_2NH_2$, or $-CH_2N(CH_3)_2$.

Embodiment 14. The compound of one of embodiments 11 to 13, wherein $R^{2.3}$ is hydrogen, $-NH_2$, $-NHCH_3$, $-N(CH_3)_3$,

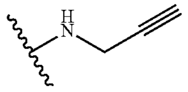
,
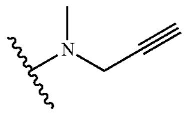
,
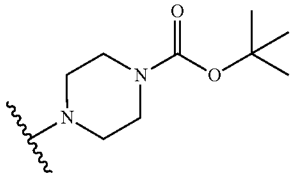
,
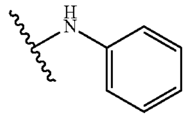
,
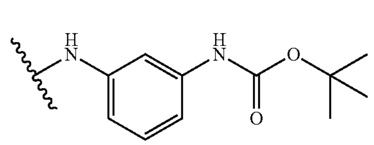
,
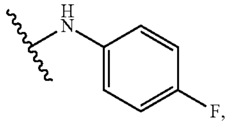
or
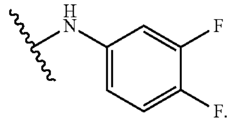

Embodiment 15. The compound of one of embodiments 1 to 2, having the formula:

(IIa)

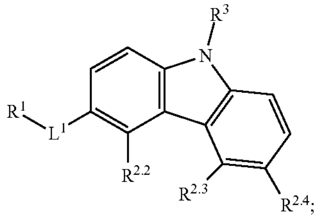

wherein $R^{2.2}$, $R^{2.3}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 16. The compound of one of embodiments 1 to 2, having the formula:

(IIb)

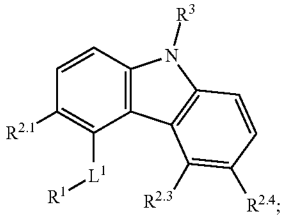

wherein $R^{2.1}$, $R^{2.3}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 17. The compound of one of embodiments 1 to 2, having the formula:

(IIc)

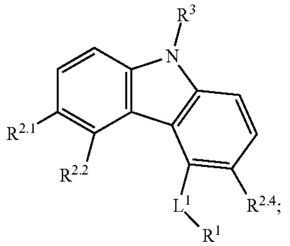

wherein $R^{2.1}$, $R^{2.2}$ and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 18. The compound of one of embodiments 1 to 2, having the formula:

(IId)

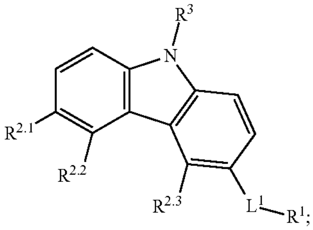

wherein $R^{2.1}$, $R^{2.2}$, and $R^{2.3}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_2R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 19. The compound of one of embodiments 16 to 18, wherein $R^{2.1}$ is $-C(O)H$, $-CH_2C(O)H$, $-CH_2C(O)OH$, $-C(O)OH$, $-CH_2NHCH_3$, $-CH_2NH_2$, or $-CH_2N(CH_3)_2$.

Embodiment 20. The compound of one of embodiments 1 to 19, wherein $R^3$ is

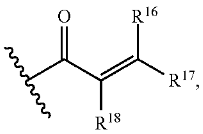
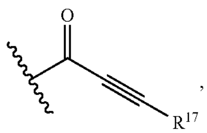
,
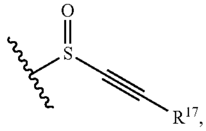
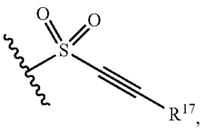
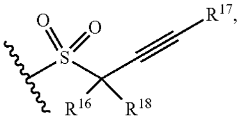
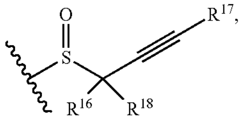
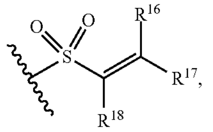
or
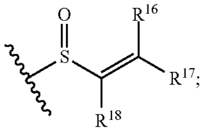

and $R^{16}$, $R^{17}$, and $R^{18}$ are independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 21. The compound of embodiment 20, wherein $R^3$ is

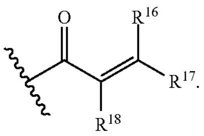

Embodiment 22. The compound of embodiment 21, wherein $R^{16}$ is hydrogen, $R^{17}$ is hydrogen, and $R^{18}$ is hydrogen.

Embodiment 23. The compound of embodiment 21, wherein $R^{16}$ is hydrogen, $R^{17}$ is hydrogen, and $R^{18}$ is unsubstituted methyl.

Embodiment 24. The compound of embodiment 21, wherein $R^{16}$ is hydrogen, $R^{17}$ is hydrogen, and $R^{18}$ is —CN.

Embodiment 25. The compound of one of embodiments 1 to 24, wherein the transcriptional coactivator binding moiety is a BRD4 binding moiety.

Embodiment 26. The compound of embodiment 25, wherein the BRD4 binding moiety has the formula:

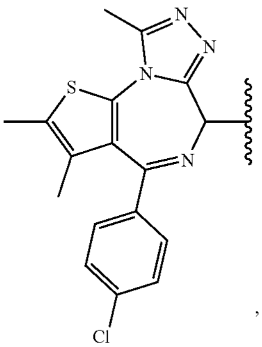

,

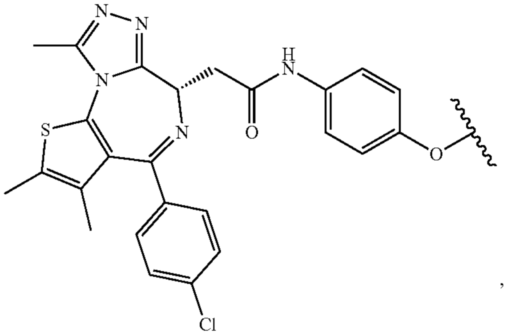

,

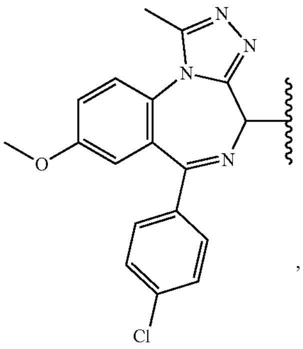

, or

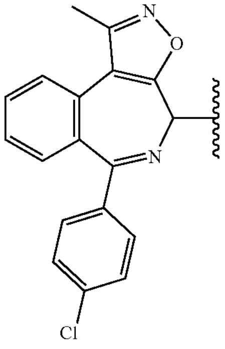

.

Embodiment 27. The compound of one of embodiments 1 to 24, wherein the transcriptional coactivator binding moiety is a p300 binding moiety.

Embodiment 28. The compound of embodiment 27, wherein the p300 binding moiety has the formula:

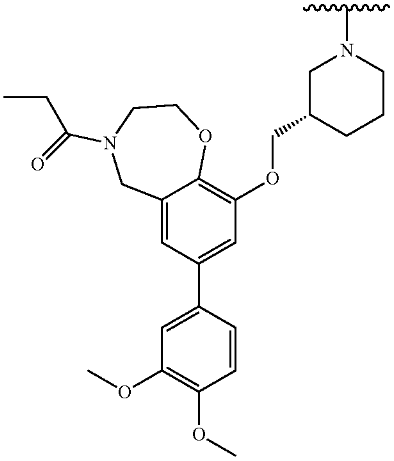

Embodiment 29. The compound of one of embodiments 1 to 24, wherein the transcriptional coactivator binding moiety is a glucocorticoid receptor binding moiety.

Embodiment 30. The compound of embodiment 27, wherein the glucocorticoid receptor binding moiety has the formula:

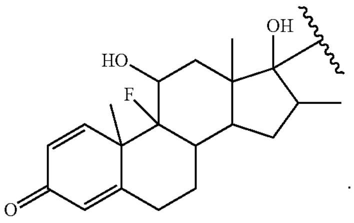 [SMILES: *C1(O)C(C)CC2C3CCC4=CC(=O)C=CC4(C)C3(F)C(O)CC21C]

.

Embodiment 31. The compound of one of embodiments 1 to 28, wherein $L^1$ is

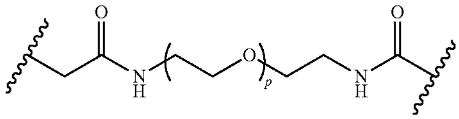

,

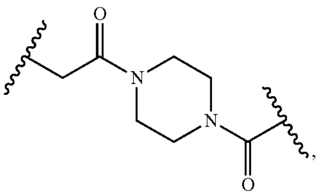

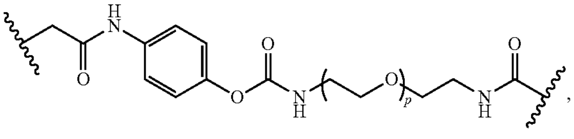

,

-continued

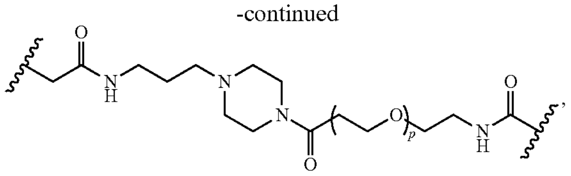

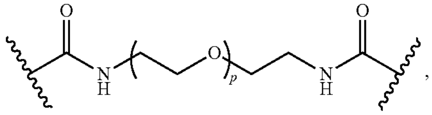
,

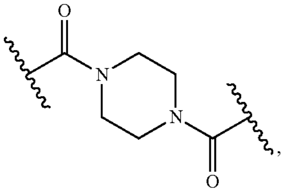
,

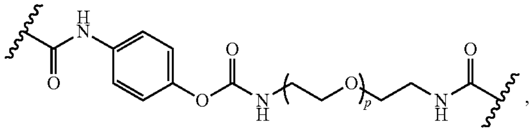
, or

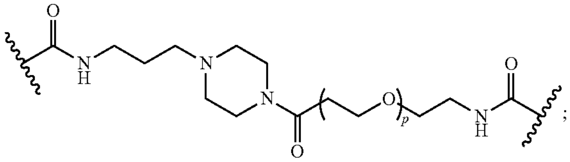
;

wherein p is an integer from 1 to 10.

Embodiment 32. The compound of embodiment 1, having the formula

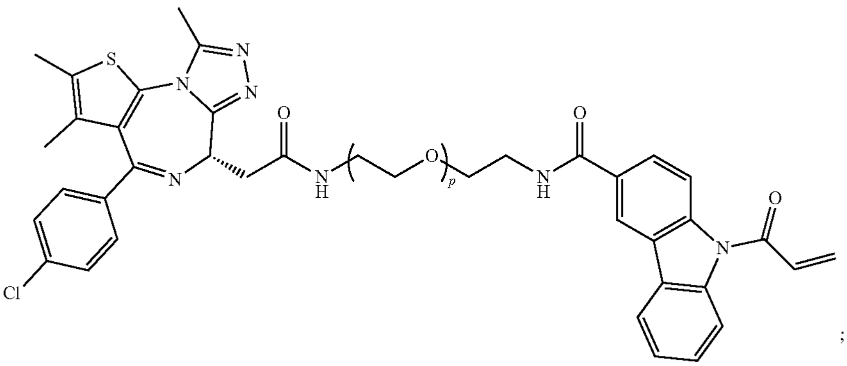
;

wherein p is an integer from 1 to 8.

Embodiment 33. A compound having the formula:

(III)

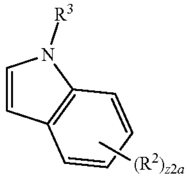
or

-continued (IV)

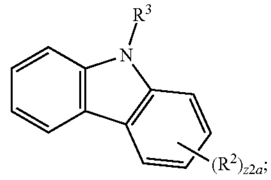

wherein $R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, $—NS(O)F_2$, $—NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{2A}$, $R^{2B}$, $R^{2C}$, and $R^{2D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$X^2$ is independently —F, —Cl, —Br, or —I;

n2 is independently an integer from 0 to 4;

m2 and v2 are independently 1 or 2;

z2a is an integer from 0 to 8; and $R^3$ is a covalent cysteine modifier moiety.

Embodiment 34. The compound of embodiment 33, having the formula:

(IIIa)

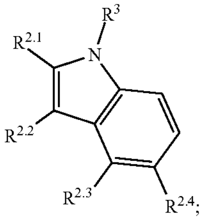

wherein $R^{2.1}$, $R^{2.2}$, $R^{2.3}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 35. The compound of embodiment 34, wherein $R^{21}$ is hydrogen.

Embodiment 36. The compound of one of embodiments 34 to 35, wherein $R^{2.4}$ is hydrogen.

Embodiment 37. The compound of one of embodiments 34 to 36, wherein $R^{2.2}$ is $-C(O)H$, $-CH_2C(O)H$, $-CH_2C(O)OH$, $-C(O)OH$, $-CH_2NHCH_3$, $-CH_2NH_2$, or $-CH_2N(CH_3)_2$.

Embodiment 38. The compound of one of embodiments 34 to 37, wherein $R^{2.3}$ is hydrogen, $-NH_2$, $-NHCH_3$, $-N(CH_3)_3$,

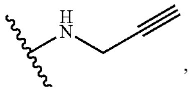 , 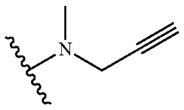 ,

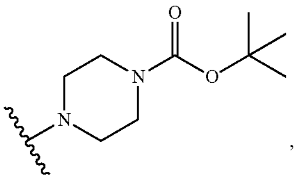 , 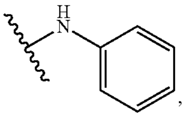 ,

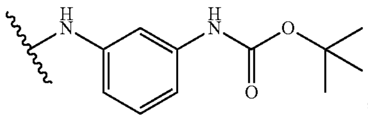 ,

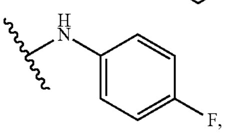 or 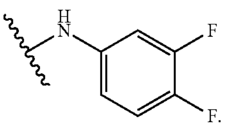

Embodiment 39. The compound of embodiment 33, having the formula:

(IVa)

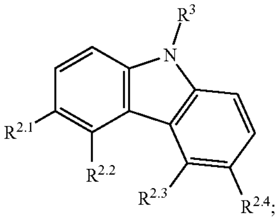

wherein $R^{2.1}$, $R^{2.2}$, $R^{2.3}$, and $R^{2.4}$ are independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, $-NS(O)F_2$, $-NS(O)FNR^{2A}R^{2B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 40. The compound of embodiment 39, wherein $R^{2.1}$ is $-C(O)H$, $-CH_2C(O)H$, $-CH_2C(O)OH$, $-C(O)OH$, $-CH_2NHCH_3$, $-CH_2NH_2$, or $-CH_2N(CH_3)_2$.

Embodiment 41. The compound of one of embodiments 33 to 40, wherein $R^3$ is

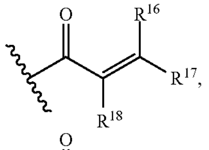 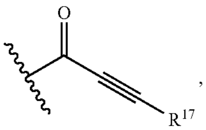 ,

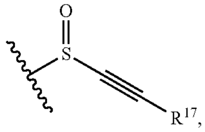 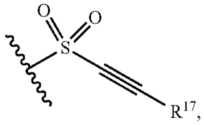

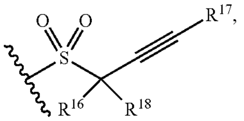 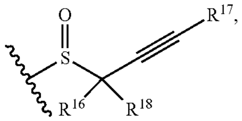

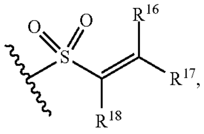 or 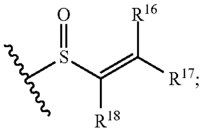

and $R^{16}$, $R^{17}$, and $R^{18}$ are independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl Embodiment 42. The compound of embodiment 41, wherein $R^3$ is

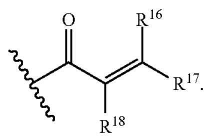

Embodiment 43. The compound of embodiment 42, wherein $R^{16}$ is hydrogen, $R^{17}$ is hydrogen, and $R^{18}$ is hydrogen.

Embodiment 44. The compound of embodiment 42, wherein $R^{16}$ is hydrogen, $R^{17}$ is hydrogen, and $R^{18}$ is unsubstituted methyl.

Embodiment 45. The compound of embodiment 42, wherein $R^{16}$ is hydrogen, $R^{17}$ is hydrogen, and $R^{18}$ is —CN.

Embodiment 46. A pharmaceutical composition comprising the compound of any one of embodiments 1 to 45 and a pharmaceutically acceptable excipient.

Embodiment 47. A method of increasing the level of a protein in a cell, wherein the level of the protein is regulated by p53, said method comprising contacting the cell with a compound of one of embodiments 1 to 45.

Embodiment 48. The method of embodiment 47, wherein the compound covalently binds C220 of a mutant human p53 protein comprising a Y220C mutation.

Embodiment 49. The method of one of embodiments 47 to 48, wherein the increasing level of the protein is an increasing level of p21 protein.

Embodiment 50. A method of treating cancer, said method comprising administering to a subject in need thereof an effective amount of a compound of one of embodiments 1 to 45.

Embodiment 51. The method of embodiment 50, wherein the cancer is a hematologic cancer.

Embodiment 52. The method of one of embodiments 50 to 51, wherein the method further comprises co-administering a second agent to the subject in need thereof.

Embodiment 53. The method of embodiment 52, wherein the second agent is an anti-cancer agent.

Embodiment 54. The method of embodiment 53, wherein the anti-cancer agent is an inhibitor of K-Ras, RAF, MEK, Erk, PI3K, Akt, RTK, or mTOR.

Embodiment 55. The method of embodiment 53, wherein the anti-cancer agent is an MDM2 inhibitor or a genotoxic anti-cancer agent.

Embodiment 56. The method of embodiment 55, wherein the MDM2 inhibitor is a nutlin.

Embodiment 57. The method of embodiment 55, wherein the MDM2 inhibitor is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232.

Embodiment 58. The method of embodiment 55, wherein the genotoxic anti-cancer agent is an alkylating agent, intercalating agent, or DNA replication inhibitor.

Embodiment 59. A method of treating a p53 mutant cancer in a subject in need thereof, said method comprising administering to the subject an effective amount of a compound of one of embodiments 1 to 45.

Embodiment 60. The method of embodiment 59, wherein the p53 mutant cancer is a $p53^{+/mut}$ cancer or a $p53^{mut/-}$ cancer.

Embodiment 61. The method of embodiment 59, wherein the p53 mutant cancer is a $p53^{+/mut}$ cancer.

Embodiment 62. The method of one of embodiments 59 to 61, wherein the p53 mutant cancer is a hematologic cancer.

Embodiment 63. The method of one of embodiments 59 to 62, wherein the method further comprises co-administering a second agent to the subject in need thereof.

Embodiment 64. The method of embodiment 63, wherein the second agent is an anti-cancer agent.

Embodiment 65. The method of embodiment 64, wherein the anti-cancer agent is an inhibitor of K-Ras, RAF, MEK, Erk, PI3K, Akt, RTK, or mTOR.

Embodiment 66. The method of embodiment 64, wherein the anti-cancer agent is an MDM2 inhibitor or a genotoxic anti-cancer agent.

Embodiment 67. The method of embodiment 66, wherein the MDM2 inhibitor is a nutlin.

Embodiment 68. The method of embodiment 66, wherein the MDM2 inhibitor is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232.

Embodiment 69. The method of embodiment 66, wherein the genotoxic anti-cancer agent is an alkylating agent, intercalating agent, or DNA replication inhibitor.

Embodiment 70. A method of treating a $p53^{+/mut}$ cancer, said method comprising administering to a subject in need thereof an effective amount of a p53 mutant agonist to said subject.

Embodiment 71. The method of embodiment 70, wherein the p53 mutant agonist is a small molecule.

Embodiment 72. The method of embodiment 70, wherein the p53 mutant agonist is a PhiKan compound.

Embodiment 73. The method of embodiment 70, wherein the p53 mutant agonist is a compound of one of embodiments 1 to 45.

EXAMPLES

Example 1: Re-Awakening the Dormant Tumor Suppressor p53 (Y220C)

The most commonly mutated gene in cancer is the transcription factor and tumor suppressor p53 (TP53) (1). p53 is most frequently found with a somatic missense mutation in one allele and a chromosome 17p deletion of the WT-allele (2). Genetic mouse models have suggested that restoration of p53 WT in p53 mutant cancers drives tumor regression and a cure (3, 4). A pharmacological approach to treat patients with one particular recurrent hotspot mutation in p53, the destabilization mutation Y220C, is described herein. The central hypothesis being tested in this application is whether mutant p53 (p53*) directed chemical probes that rescue (re-awaken) WT function by restabilization or enhancement of transcriptional activity represent a viable therapeutic modality to treat patients with the recurrent p53 (Y220C) mutation as single agents or in combination with other agents.

We designed and developed covalent small molecules which enhance stability of the p53 Y220C mutant. Our current lead molecule, KG1, increases the stabilization of the p53 Y220C mutant. We have solved a co-crystal of KG1 bound to p53 (Y220C) and have used this high resolution structural insight to design further improved covalent ligands which show enhanced stabilization. We test the hypothesis that functional groups R1 and R2 branching from the carbazole scaffold of KG1 increase the p53 (Y220C) $T_m$ above our current level of 35° C.

We stabilized p53 (Y220C) and enhanced transactivation of p53 target genes through bivalent small molecule. Our objective is to create a bivalent molecule that reactivates p53 (Y220C) through the direct recruitment of the basal transcriptional machinery. We test the hypothesis that a KG1-JQ1 bivalent molecule will simultaneously stabilize p53 (Y220C) and directly recruit BRD4 to enhance p53 transcriptional activity.

We test p53 (Y220C) monovalent and bivalent activators as single agents and in combination with other targeted agents in p53 (Y220C) mutant cancer cells and patient derived xenografts. The small molecules targeting mutant p53 may on their own induce an anti-proliferative or apoptotic program and thus have the potential to work as single agents. It is also known that other targeted agents such as RAS→Raf→Mek pathway inhibitors are less effective in the context of mutant p53. We test the monovalent and bivalent molecules in combination with K-Ras (G12C), RAF, MEK, Erk, PI3K, and mTOR inhibitors. Importantly, since p53 (Y220C) targeting compounds are tumor cell specific, we expect the combinations tested to be well tolerated.

p53 functions as a regulator of both cell proliferation and cell death. When cells encounter DNA damage or replicative stress, p53 is stabilized and binds to p53 response elements in gene promoters to transactivate gene expression through the recruitment of the p300/CBP transcriptional co-activator (5). The primary transcriptional targets of p53 are p21 (CDKN1A), which functions as a potent cell cycle inhibitor, and Bcl-2 family proteins (PUMA, BAX andNOXA), which facilitate caspase activation within the apoptotic pathway. p53 function can vary with cell type, where activation in sarcomas leads to cell cycle arrest (3), whereas activation in lymphomas leads to apoptosis (4). The levels and activity of p53 are regulated through several post-transcriptional modifications including phosphorylation, ubiquitination, and acetylation (6).

Figure 1A:
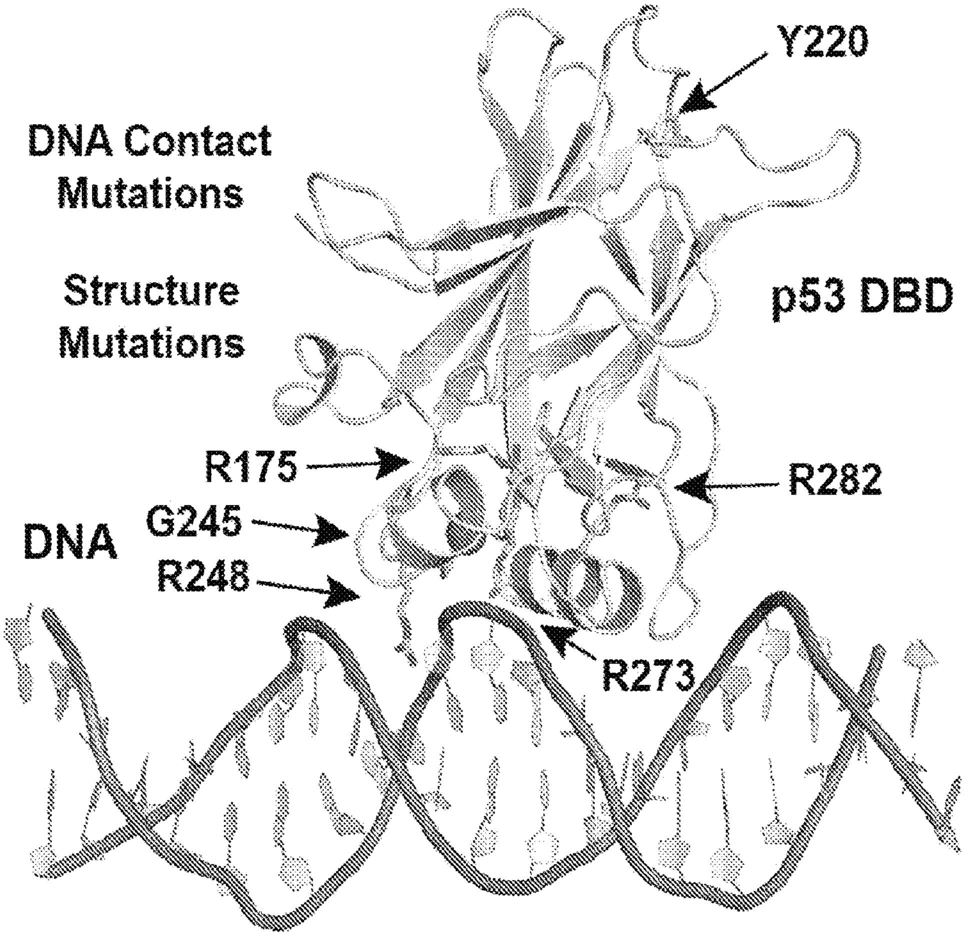
FIGS. 1A-1B. The p53 hotspot mutations are on the DNA-binding domain.
Figure 1B:
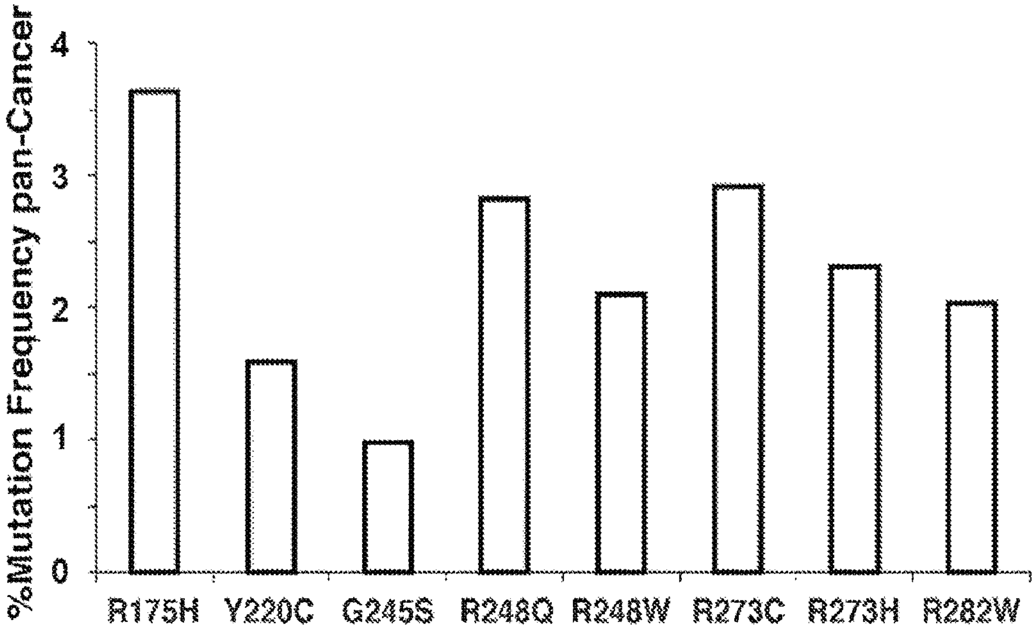

The most frequent p53 missense mutations in cancer are found within the DNA-binding domain (DBD) of p53, where the mutations can be divided into two classes (FIGS. 1A-1B). The first class of mutations are DNA-contact mutations, where the mutagenic protein is no longer able to bind DNA directly through loss of interactions with the DNA phosphate backbone or nucleotides. The most common mutations in this class are R248Q/W and R273C/H. The second class of mutations are structural, which indirectly inhibit DNA binding through the loss of stability in the protein fold. The most common mutants in this class are R175H, Y220C, G245S, and R282W (FIGS. 1A-1B). All of the hotspot p53 mutations result in lower p53 target gene expression through the loss of DNA binding affinity (7). We focus on the hotspot Y220C mutation for two reasons: 1) the somatic mutation of Tyrosine 220 to Cysteine provides a tumor cell specific covalent handle to "guide" our molecules to p53 (Y220C) which is only expressed in cancer cells; and 2) the Y220C mutation is a destabilizing mutation rather than a DNA-contact residue, so its "correction" by a small molecule does not require making precise (drug mediated) contact at the DNA binding interface of p53.

Figure 2A:
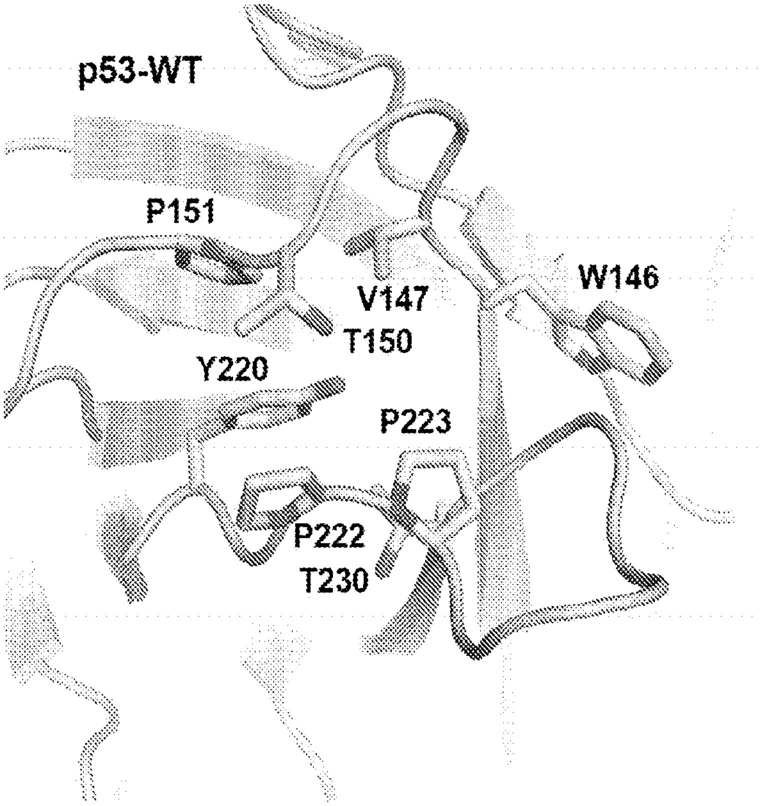
FIGS. 2A-2B. Crystal structures of WT and Y220C-KG1 p53 DBD.

There are several small molecules that have been shown to directly interact with p53 mutants with favorable response in cancer cells, however none have received FDA approval (8-10). The only series of molecules that have been successful in a structure-activity relationship campaign have targeted the structural Y220C mutant. Using a computational screen, the Y220C specific binding carbazole molecule PhiKan083 was identified (10). Crystal structures of the p53 hotspot mutations revealed a "druggable" crevice in the p53 Y220C mutant (11) (FIG. 2A). Numerous compounds with 10-300 μM affinity for the Y220C mutant have been synthesized including modifications of the carbazole, sulfonylpyrimidines, and aminobenzothiazole based scaffolds (12-14). Although these molecules demonstrate the potential of targeting p53 (Y220C), none of the compounds reach sub-μM biochemical potency and are unlikely in their current form to satisfy requirements of drug candidates.

We first set out to test whether restabilization of p53 (Y220C) can increase transcriptional activation of the canonical p53 transcriptional program. Using a small molecule to rescue a misfolded protein has been successful in the clinic as demonstrated in the treatment of the cystic fibrosis transmembrane conductance regulator (CFTR) mutation F508del. The molecule VX-809 both stabilizes the fold of CFTR F508del and reactivates its native function of shuttling chloride across epithelial cell membrane (15). We tested whether, similar to VX-809 in cystic fibrosis, a stand-alone small molecule would successfully rescue the p53 (Y220C) fold and its WT activity in cancer. We applied this restabilization strategy to develop a p53 Y220C chemical chaperone to restore p53 target gene expression, as well as enhance target gene activity through the design of a bivalent molecule.

To generate a p53 (Y220C) molecule with improved affinity and selectivity, we analyzed the known reversible binding molecules and incorporated a covalent warhead (acrylamide) to react with the somatic Cys-220 residue. This effort was successful, and has led to the identification of a preliminary covalent molecule (KG1, Table 1) that reacts with p53 (Y220C) and increases the melting temperature ($T_m$) by 1.5° C. This represents a significant advancement in biochemical potency compared to the Y220C molecules developed over the last decade. KG1 is a derivative of PhiKan083 that substitutes the ethyl on the carbazole amine with an acrylamide and the C3 methylamine with an aldehyde.

TABLE 1

| Covalent molecules | |
|---|---|
| 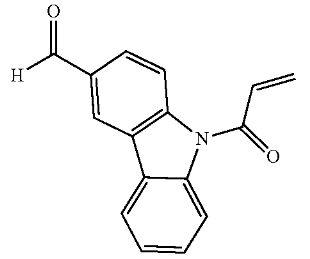<br>KG1 | KG1 |
| 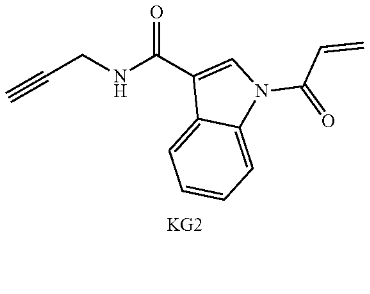 [SMILES: C#CCNC(=O)c1cn(C(=O)C=C)c2ccccc12]<br>KG2 | KG2 |

TABLE 1-continued

| Covalent molecules |
| --- |
| 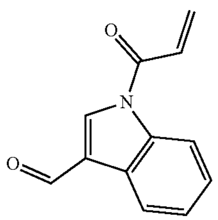 KG37 |
| 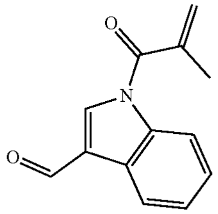 KG78 |

Figure 2B:
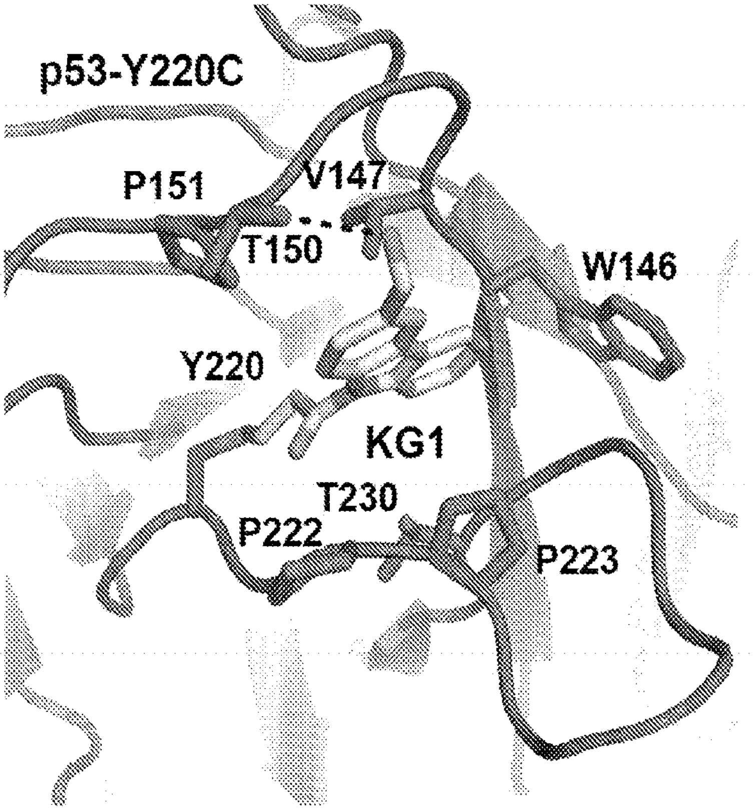

We have solved the X-ray crystal structure of this molecule bound to the Y220C mutant (FIG. 2B). The crystal structure of p53 (Y220C)-KGT reveals a different binding mode for KG1 in comparison to PhiKan083 and previous carbazole based reversible binding molecules. This alternative binding mode enables the incorporation of additional chemical groups to KG1 that have been shown to provide favorable interactions in the reversible binding compounds. Moreover, we have designed and synthesized an indole derivative (KG2, Table 1) which also labels p53 (Y220C). Our preliminary data has thus revealed the first covalent binders (FIG. 3A) and stabilizers of p53 (Y220C) (FIG. 3B) as well as a valuable co-crystal structure (FIG. 3C) to aid in future chemical optimization as evidenced by KG2.

To explore whether our current best stabilizer (KG2) is able to act specifically in p53 (Y220C) expressing cells we utilized a panel of cell lines (MCF10A are non-transformed WT p53 breast cells, BxPC-3 is a p53 (Y220C) mutant pancreatic cell line, and Calu-1 lung cells are null for p53. To assess p53 levels in cells under different treatment conditions, we used Western blotting for p53. To determine whether p53 is activating transcription and translation of downstream effectors, we monitored p21 expression levels. To activate WT p53 we used the MDM2 inhibitor (E3-ligase) Nutlin. As shown in FIG. 3D, KG2 shows activation of p21 expression in Y220C cells to the same level as nutlin in WT p53 cells. As expected the KG2 molecule does not show induction of p21 in a p53 null setting. This is exciting preliminary evidence of successful re-animation of p53 (Y220C) with our lead compound KG2. The fact that it is active at μM concentrations bodes well for the chemical tractability of the target and the mechanism of action.

Recent evidence suggests p53 (Y220C) occupies many p53 target gene promoters but does not activate transcription at these sites (16). We sought to specifically enhance transcriptional activity of p53 (Y220C) in order to restore WT-like p53 tumor suppressor function. To achieve this alternative activation mode of perturbing p53* function (in contrast to simply stabilizing the protein), we exploited new discoveries within bivalent molecule development. Bivalent molecules are the product of linking two pharmacologically active drugs to invent new function, and they are showing promising antitumor activity for targets with resistance towards traditional small molecule inhibition (16-18). Novel functions of bivalent molecules include inhibition of enzymes through immunophilin recruitment (18,19), protein degradation through proteolysis targeting chimera (PROTAC) E-3 ligase recruitment (16), and synthetic transcription factor transactivation of genes through bromodomain recruitment (the precedent for our chemical strategy) (20).

Figure 4A:
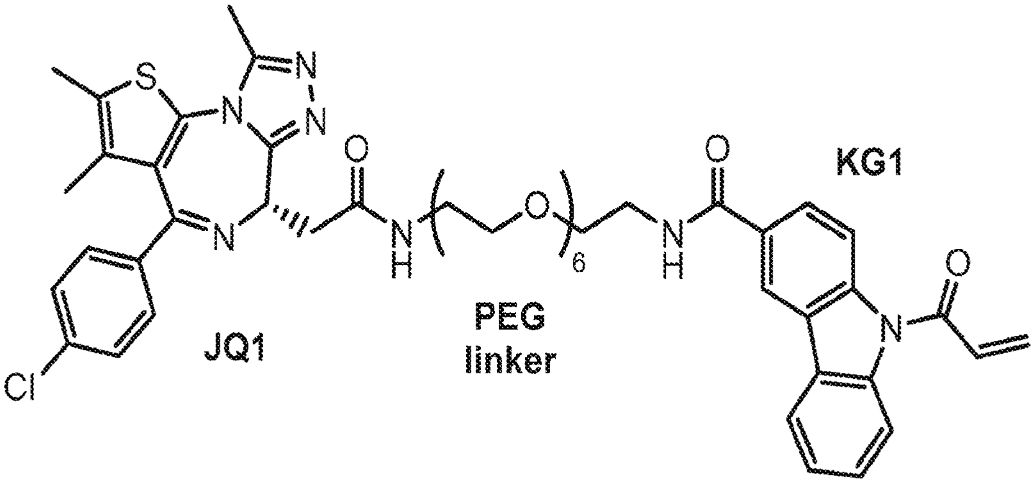
FIGS. 4A-4C. Model for bivalent JQ1-KG1 reactivation of p53 Y220C.

For p53*, the strategy was to build a molecule that will enhance transcriptional activity through the direct recruitment of bromodomain containing transcriptional activators to p53 target gene promoters. In order to achieve this goal, we designed a covalent warhead on a bivalent molecule that selectively reacts with the p53 Y220C mutagenic cysteine and links this molecule to the bromodomain binding molecule JQ1 (FIG. 4A).

Figure 4B:
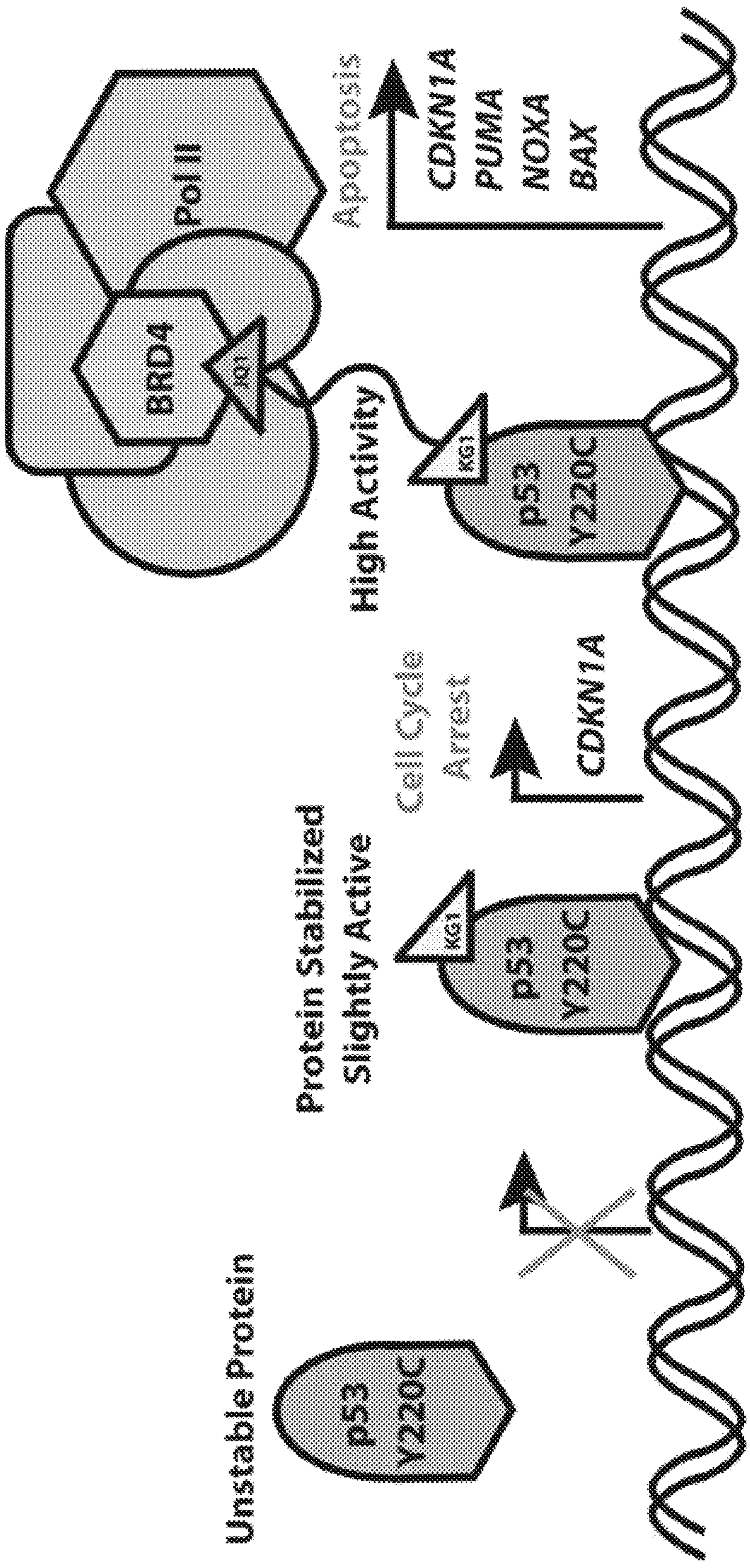

The covalent warhead on KG1 and KG2 provide enhanced residence time, robust target engagement, and the ability to measure the fraction of p53 (Y220C) engaged by the ligand. The crystal structure of Y220C-KG1 (FIG. 2B) reveals an opportunity to create a bivalent molecule given the orientation permits the addition of a polyethylene glycol (PEG) linker without steric clash (FIG. 2B and FIG. 4A). We hypothesized that linking KG1 to the bromodomain binding molecule JQ1 (JQ1PEG6KG1) will provide significant enhancement in p53 target gene expression (FIG. 4B) in p53 Y220C cells.

Figure 3D:
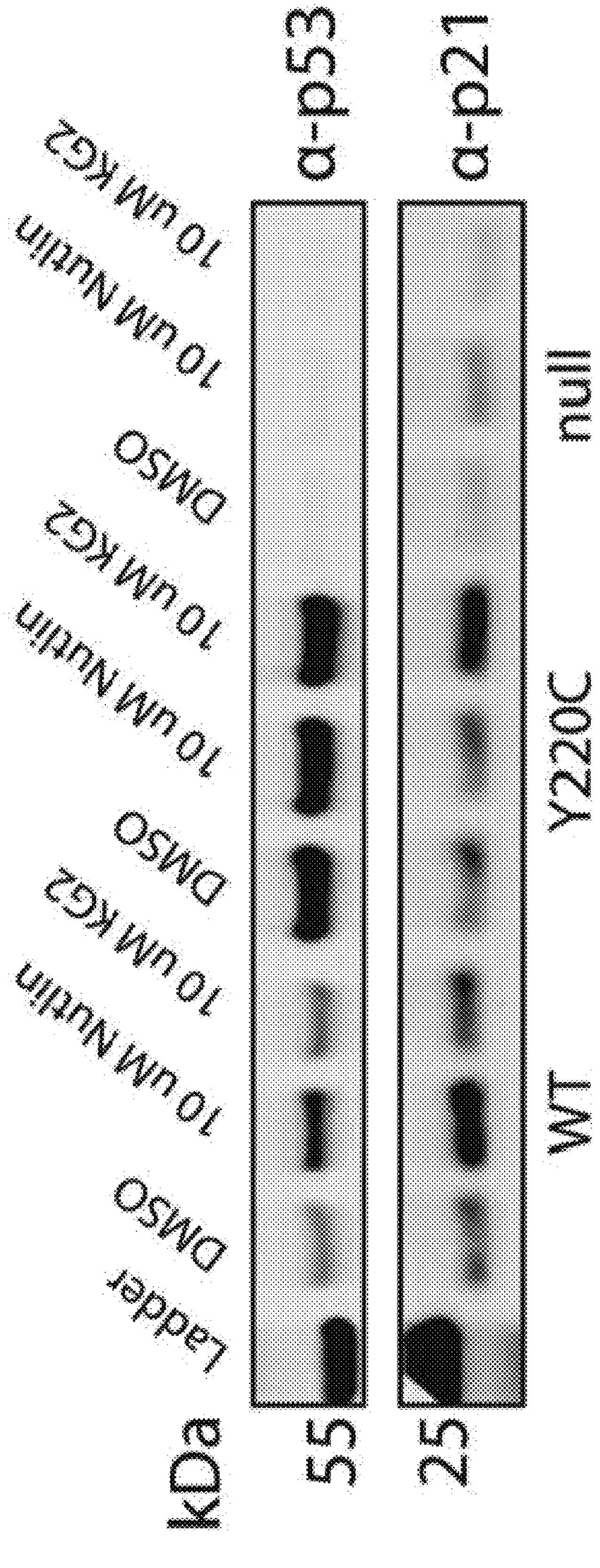
Figure 4C:
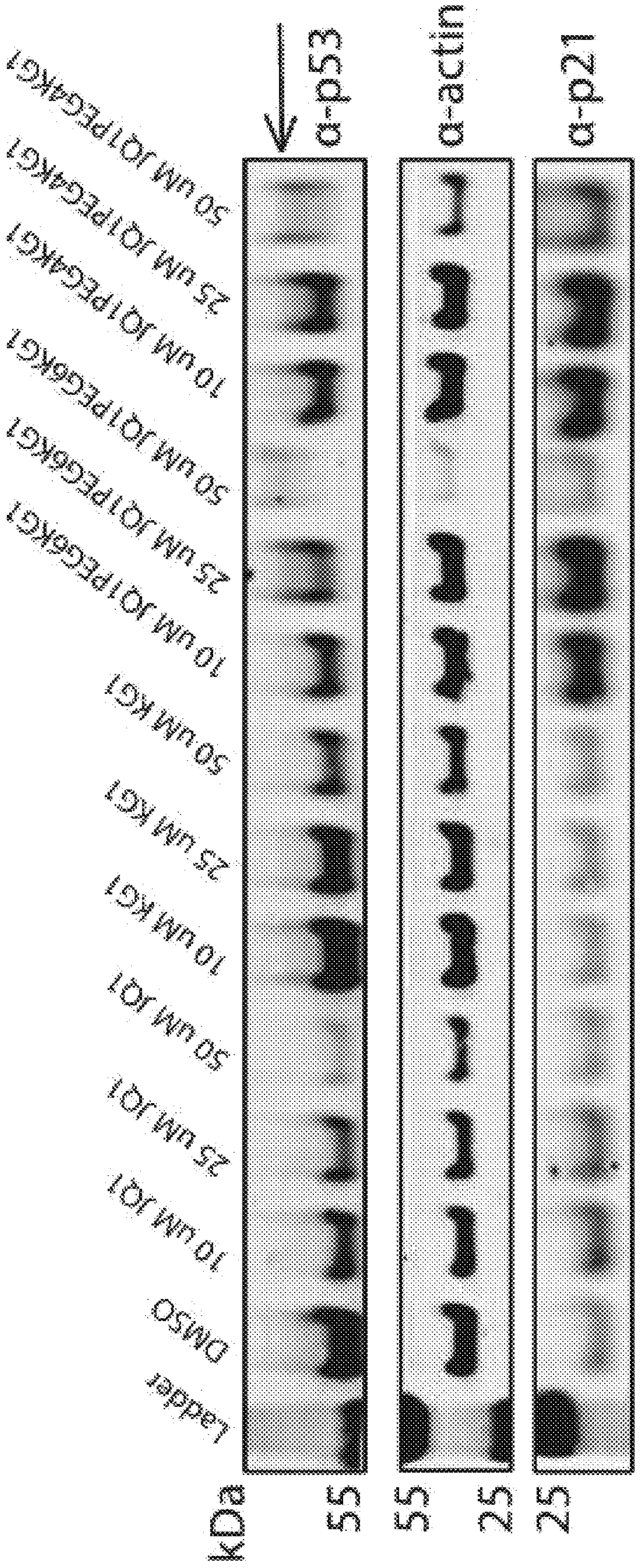
Figure 5:
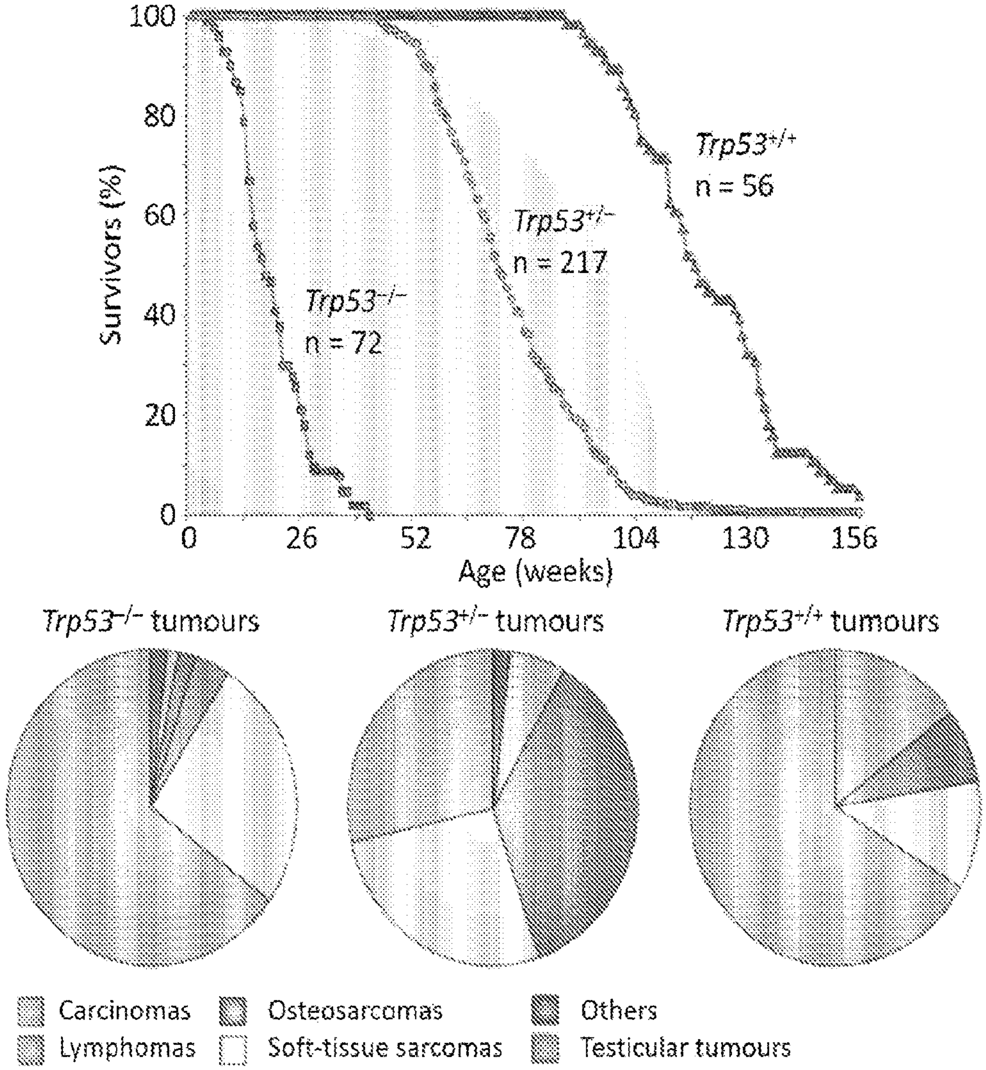
FIG. 5. TP53 is not an essential gene. Mice deficient for p53 are developmentally normal but susceptible to spontaneous tumors (Donehower, et al., *Nature Reviews,* 2009).
Figure 6:
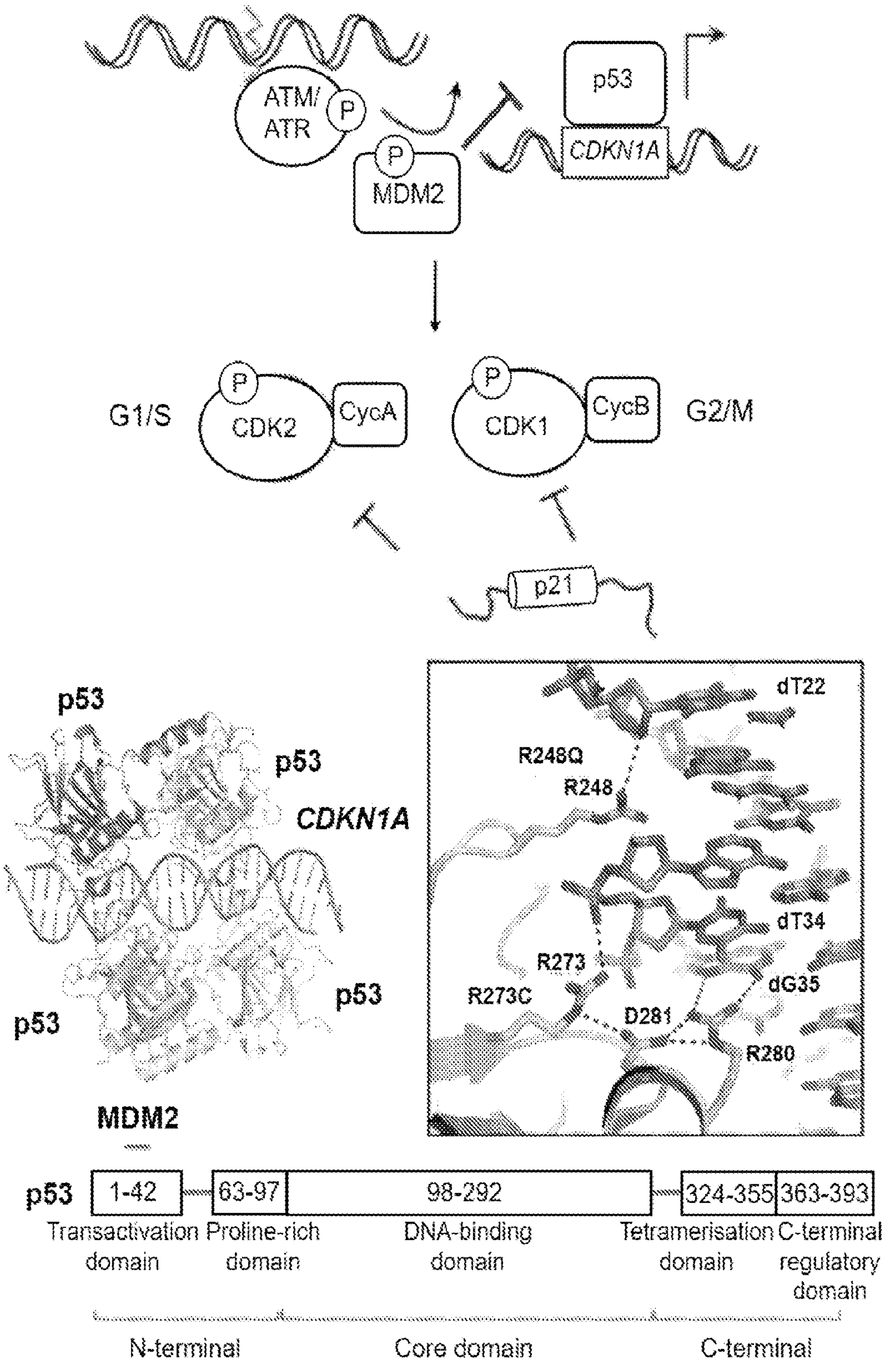
FIG. 6. Role of p53.
Figure 7:
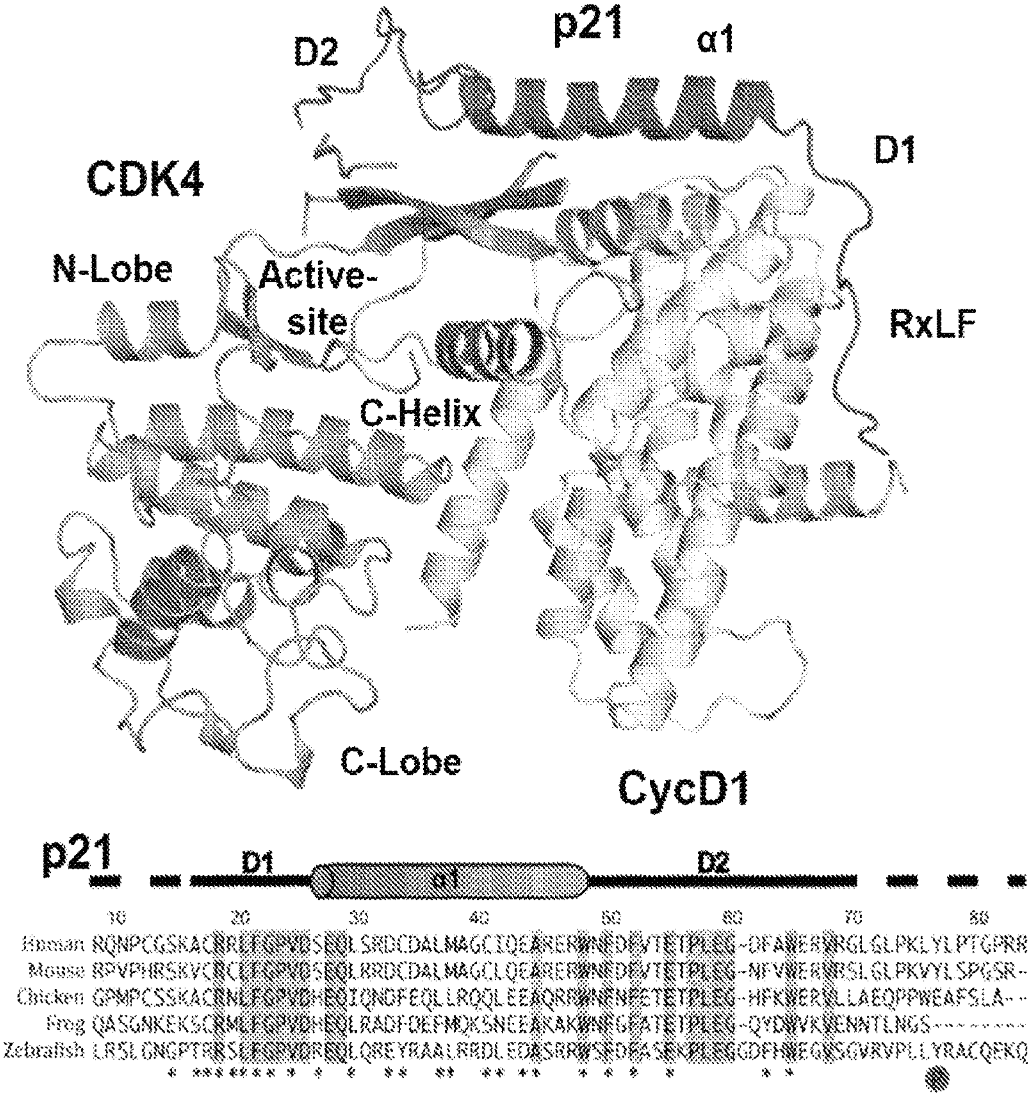
FIG. 7. p21 inhibits cycling dependent kinases (CDK). Sequences shown are as follows.
Figure 7:
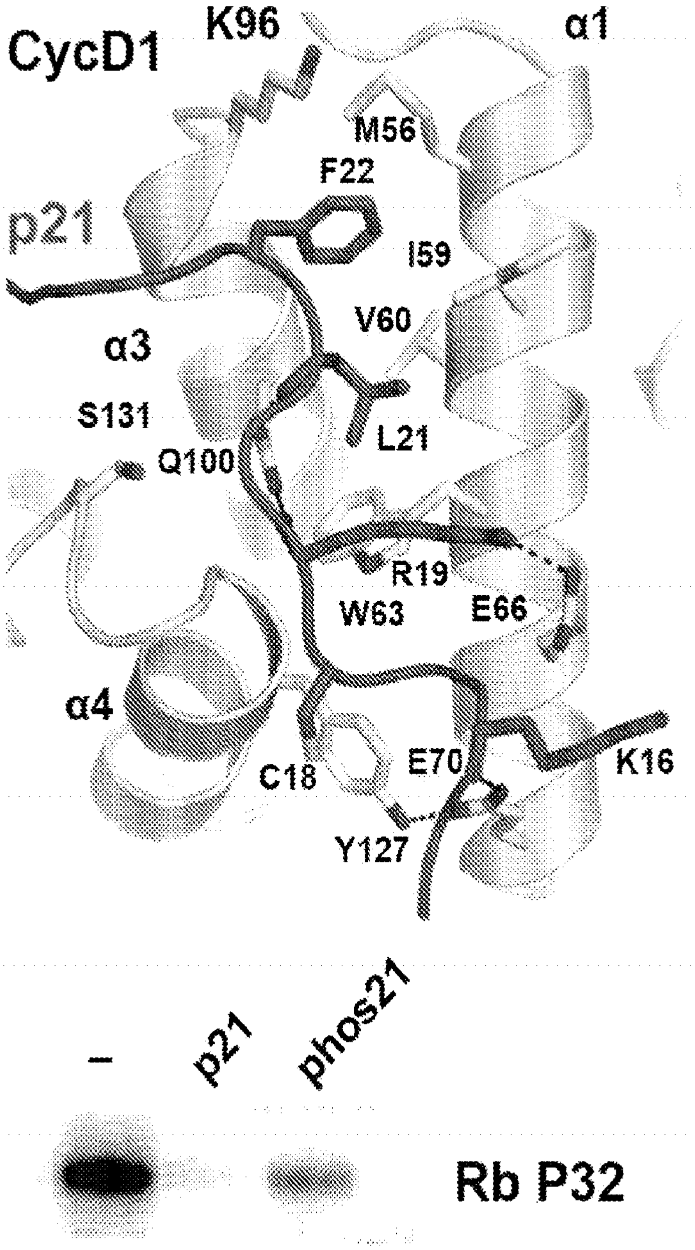

We have successfully synthesized several PEG linked versions of JQ1-KG1 bivalent molecules. We synthesized two PEG linker lengths (PEG-4 "JQ1PEG4KG1" and PEG-6 "JQ1PEG6KG1"), with JQ1PEG6KG1 shown in FIG. 4A. We tested the two bivalent molecules in the p53 (Y220C) BxPC-3 cells as shown in FIG. 3D middle lanes. We also treated BxPC-3 cells with free KG1 and JQ1 compounds as additional controls. We have performed western blots on p53, p21 and actin as a control (FIG. 4C). In the initial cellular experiments we see modest activation of p21 by the two lower doses of JQ1, and little or no effects of KG1 (first generation Y220C molecule) alone. However, consistent with our hypothesis, the bivalent linked versions of JQ1 and KG1 do indeed strongly induce p21 suggesting a p53 specific activation. At the higher concentrations at this time point there was extensive cell death (lower actin staining), which in fact we expect if we are turning on a robust p53 tumor suppressive response. We also saw evidence of target p53 (Y220C) engagement due to the higher MW shifting of the p53 band (arrow on right of FIG. 4C).

We optimized KG1 to enhance stability of the p53 (Y220C) mutant. The KG1 molecule increases the stabilization of the p53 (Y220C) mutant, however a molecule that restores WT level stability could function as a stand-alone therapeutic in the absence of JQ1. We tested the hypothesis that functional groups R1 and R2 branching from the carbazole scaffold (FIG. 3C) will increase the p53 (Y220C) $T_m$ above 35° C. achieved by the carbazole-3-aldehyde alone.

We synthesized a series of compounds, covalently labelled recombinant p53 (Y220C) with the compound, and performed differential scanning fluorimetry (DSF) assay to determine $T_m$ relative to Y220C alone. We tested our lead compounds with the largest increase in $T_m$ in homozygous p53 (Y220C) cell lines BxPC-3 and HCC1419 to determined how the covalent molecules alter p53 target gene expression. p53 WT MCF10A and p53 null Calu-1 cells were used as controls. The cell panel was treated with concentrations of compound ranging 100 nM-10 μM for 4 hr, 24 hr, and 48 hr. DMSO was used as a negative control, KG2 as a positive control, and Nutlin-3a as a positive control for p53 WT (FIG. 3D). We determined the differences in p53 target gene activation by performing qPCR on CDKN1A, MDM2, PUMA, BAX, NOXA, and used GAPDH as a negative control. We also performed a western blot on p53, p21, MDM2, and actin as a control to monitor the expected increase in protein levels of p21 and MDM2 protein. The antibody Pab240 has been shown to bind specifically to folded WT conformation of p53 (21). We immunoprecipitated p53 Y220C from the compound treated cell panel with Pab240 or IgG control, and western blot for p53 to determine the relative rescue of the native fold compared to DMSO treated cells.

Figure 3C:
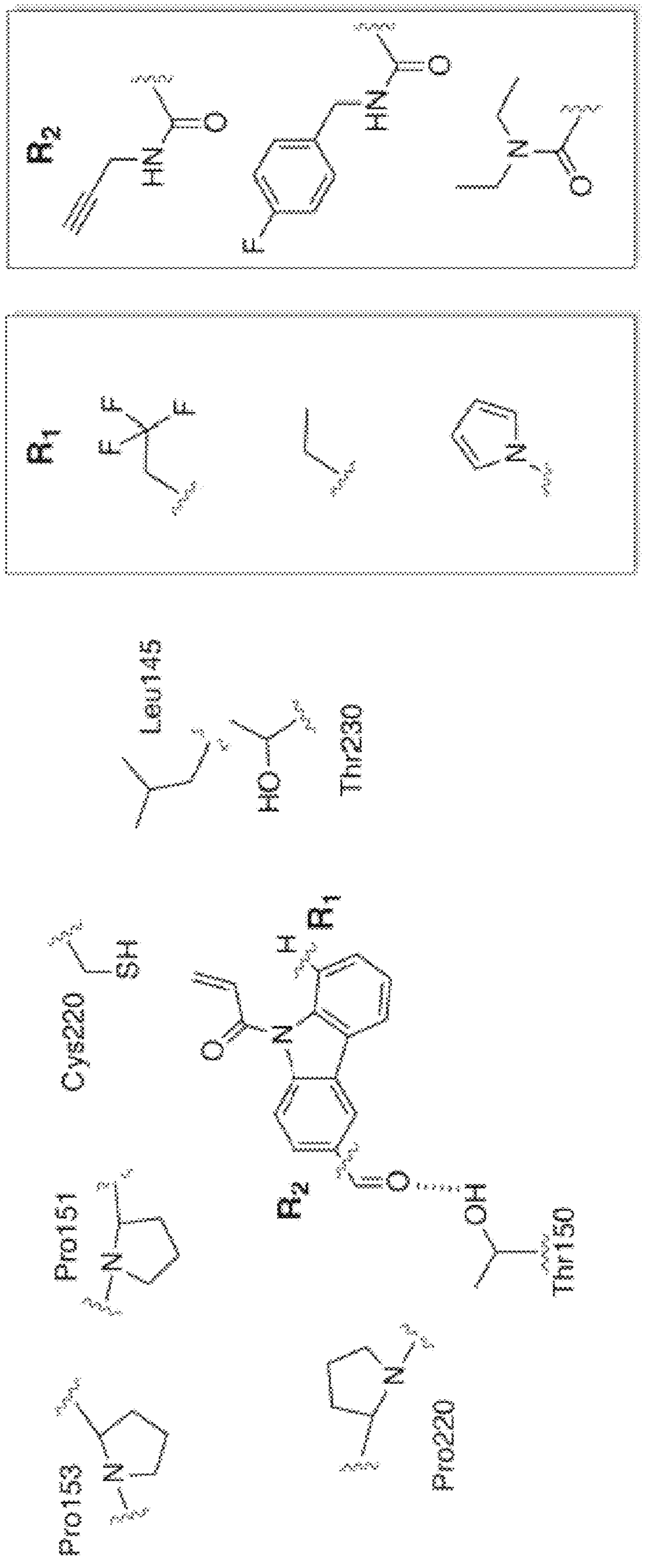

Previous studies investigating reversible Y220C compounds found a hydrophobic pocket and a proline rich groove that constitute favorable binding interactions (12) positioned around the mutagenic cysteine 220 (FIG. 2A and FIG. 3C). Trifluoromethyl, ethyl, and pyrrole functional groups have all shown to promote favorable interactions in the hydrophobic pocket in the reversible Y220C compounds, and we incorporated these groups at the R1 position (FIG. 3C). These functional groups are commercially available starting materials with a tertiary amine at the C2 position. For a two-step synthesis, we first performed a reductive amination reaction with a 4-oxocyclohexanecarboxylic to produce a joint ring system. We then attached our warhead to the C2 secondary amine through nucleophilic addition of an acryloyl chloride. To determine which functional group improves stability at the proline rich groove, we derive a clickable handle, a fluorobenzene, or a diethylamine at the R2 position (FIG. 3C). The clickable handle allows analysis of labeling efficiency of KG1 in live cells or by PAGE fluorescent scan through the addition of TAMARA-azide following a copper catalyzed click reaction. The fluorobenzene and diethyl amine were chosen because they have shown favorable interactions at the proline groove on aminobenzothiazole reversible compounds (12). To generate a two-step synthesis of the R2 series of molecules, we first perform a HATU amide coupling reaction using a carbazole-3-carboxylic acid scaffold and with the various R2 functional groups commercially available as tertiary amines. The covalent warhead is again incorporated onto the secondary amine on the carbazole through a nucleophilic addition using acryloyl chloride.

Using the alkyne clickable handle on KG1, we analyze total protein labeled by KG1-alkyne by performing a copper-catalyzed click reaction with TAMARA-azide following treatment of cells. We then view the total labeled protein by SDS-PAGE and a fluorescence scan. The structure of p53 (Y220C)-KG1 presents the opportunity to incorporate reversible covalent warheads such as cyanoacrylamides (22). If we observe significant off-target labeling by KG1-TAMARA, we incorporate the reversible covalent warhead 2-cyanoacrylamide in the position of acrylamide on our derivatizations.

We stabilize p53 (Y220C) and enhance transactivation of p53 target genes through bivalent small molecule. Our objective is to create a bivalent molecule that will reactivate p53 (Y220C) through the direct recruitment of the basal transcriptional machinery. We test the hypothesis that a KG1-JQ1 bivalent molecule partially stabilizes p53 (Y220C) and directly recruits BRD4 to enhance its transcriptional activity. JQ1 was originally designed to inhibit c-Myc directed transactivation in cancers (23). However, a recent study has found that when the molecule is tethered to a synthetic transcription factor, it promotes transcription (20). BRD4 functions as a chromatin reader that recognizes acetylated lysines as a component of the transcriptional activator complexes PTEFB and TFIID (24). BRD4 has been shown to be co-localized with p53 on gene promoters and promote CDKN1A expression in a native context (25).

The KG1 molecule has been tethered to JQ1 through a PEG4 as well as PEG6 linker using a carboxylic acid substituted in the position of the aldehyde (FIG. 4A). We use the HATU amide coupling reaction previously described in the synthesis of bivalent JQ1 molecules (26). The amide linked PEG will allow for the hydrogen bond and between Thr150 and the carbonyl of the molecule to be maintained (FIG. 2A). A PEG6 linker was used to tether the synthetic factor to JQ1, however we also derivatize linker lengths PEG(2-8) to identify the maximum transcriptional activity. We test whether recombinant p53 DBD and BRD4 bromodomain 1 will co-elute on size exclusion chromatography in the presence of KG1-JQ1 compounds (e.g., JQ1PEG6KG1). We test our KG1-JQ1 compounds in the cell panel using the concentration and duration described herein. We perform qPCR and western blot on the target genes and proteins described herein. We also treat the cell panel with free KG1 and JQ1 compounds as additional controls. To determine target engagement of the bivalent molecules, we immunoprecipitate p53 (Y220C) or IgG control, and western blot for BRD4. In addition, the covalent adduct between p53 (Y220C) and KG1-JQ1 will alter the migration of p53 (Y220C) on an SDS-PAGE gel and can be observed by western blot.

It is possible that the low nM affinity of JQ1 results in an affinity sink in which BRD4 is saturated with KG1-JQ1 and the molecule fails to engage p53 (Y220C). To overcome this challenge, we pre-treat the cells with JQ1, washout the drug, and then treat with KG1-JQ1. This allows for KG1 to covalently attach to p53 (Y220C), and the free JQ1 to act initially as a blocking agent before freely diffusing from BRD4. It is also possible that KG1-JQ1 is not sufficient to stabilize Y220C to a state that is able to bind to promoters. p53 (G245S) represents the least damaging hotspot mutation in terms of reduction in stability and DNA binding (7). To test our hypothesis that a bivalent molecule will enhance p53* activity, we synthesize a JQ1-chloroalkane molecule using HATU coupling and express p53 (G245S) fused to a HaloTag protein. This allows for linkage to occur between JQ1 and p53 (G245S)-HaloTag in the cell without the identification of a suitable p53 G245S small molecule ligand.

We test p53 (Y220C) monovalent and bivalent activators as single agents and in combination with other targeted agents in p53 (Y220C) mutant cancer cells and patient derived xenografts. We review both public and private databases for cell lines with the p53 (Y220C) mutation and annotate these for other oncogenic lesions or tumor suppressor losses. Based on those other mutations we select the agents that target the other (non-p53*) lesions (e.g., if K-Ras (G12C) we use our ARS-1620 inhibitor of this oncogene, if B-Raf (V600E) we select Vemurafenib, etc.). Our goal is to annotate the anti-proliferative vs. apoptotic effects of the single agents and the combinations. We particularly focus on pro-apoptotic combinations. We anticipate that the use of a tumor suppressor re-awakening small molecule and an inhibitor of an oncogenic driver will be particularly effective. We prioritize mutant specific agents such as KG1 for p53(Y220C) and ARS-1620 for K-Ras (G12C) as these will be most likely to be well tolerated in animal studies and the clinic.

Scientific innovation/rationale. The last 20 years has seen an explosion in the number of approved protein kinase inhibitors which target oncogenic drivers of cancer. While there has been an equal effort to understand the basic mechanisms of tumor suppressor function, there has been much less effort and almost no examples of drug strategies which directly impact the defective tumor suppressor functions in tumor cells. We take the unusual approach of developing small molecules to rescue the function of one such tumor suppressor, the Y220C hotspot mutation in p53, which would be a completely new therapeutic approach in cancer. The occurrence of hotspot mutations in tumor suppressors is unexpected, since loss of function mutations would be predicted to occur randomly. The emerging view is that these hotspot mutations occur recurrently because the mutants exhibit a dominant negative function on the WT p53. In some cases p53 mutations are thought to exhibit a gain of function effect-though this mechanism is not thought to be operative in the Y220C mutation studied here. After occurrence of the mutant tumor suppressor during tumor evolution, loss of heterozygosity leads to loss of the WT allele resulting in one mutant allele and no WT allele. We have chosen to attack the Y220C allele of p53 because it produces a somatic cysteine mutation that only occurs in the tumor cells and provides a chemical handle to develop electrophilic binders to p53 (Y220C).

Clinical significance. Cancer is a genetic disease caused broadly by mutations in two classes of genes called oncogenes and tumor suppressors. Using the car as an analogy, an oncogene is the gas pedal and a tumor suppressor is the brake of the car. Most tumor cells have an activating mutation in an oncogene to push harder on the gas pedal and an in-activating mutation in a tumor suppressor to "take the brakes off" cell growth. In the last 20 years we have seen an explosion in the numbers of drugs to block the proteins which serve as the accelerators, but we have not figured out how to re-engage our cell's own brakes on cancer after mutations have inactivated them. Described herein is strong preliminary data with evidence of re-activation of a recurrent genetic lesion in the most commonly mutated tumor suppressor (p53). The drug would work in a selected group of patients (already identified by common cancer screening panels) and the drug would not affect non-cancer cells because they do not contain the mutant the drug specifically targets. This therapeutic modality would be the first of its kind and is predicted to synergize well with current approved inhibitors of oncogenes. In 2018 an estimated 1.7 million patients in the US will be diagnosed with cancer, of these roughly 1.5% will have the p53(Y220C) mutation, or >25,000 patients per year.

We have developed a series of covalent drugs KG1, KG2, and KG3 that both label and reactivate the p53 somatic hotspot cancer mutant Y220C using recombinant protein and in patient derived cell-lines. This technology involves synthesizing small molecules that react covalently with the somatic p53 Y220C mutation and not WT p53 or other non-specific proteins. We have obtained a crystal structure of the covalent probe KG1 bound to p53 Y220C, which will guide further structure based design of novel drugs. We have further developed a "super enhancing p53" by linking the covalent drugs with a transcriptional activating molecule JQ1 to further enhance transcription of p53 target genes in p53 Y220C cells.

We have developed covalent molecules that gain selectivity and potency through the cysteine reactive covalent warhead. In addition, the linkage of JQ1 to a small molecule to engage a transcription factor and enhance its transcriptional activity is unprecedented and serves as a breakthrough in design of drugs that modulate transcription factor activity. Moreover, there are no drugs reported that directly reactivate tumor suppressors.

To the best of our knowledge, there are no p53 mutant targeted therapies. This is the first series of molecules showing potent induction of p53 target genes in p53 mutant cancer cells by directly targeting the somatic p53 Y220C mutant protein. The compounds have been synthesized and tested on recombinant protein and patient derived p53 homozygous Y220C cells line BxPC-3.

Next steps include expanding the cell panel with more patient derived p53 Y220C cell-lines (HCC1419, NCI-H2342, H748) and through the invention of stable p53 Y220C expressing cell lines using p53 null cells (Calu-1, MCF10A p53 KO). Also, the covalent molecules will be tested in transgenic p53 Y220C mice or p53 Y220C xenografts.

Example 2: Experimental Procedures and Characterization Data

Recombinant protein expression. Human p53 WT, R273C, and Y220C (residues 94-312, (C124S, M133L, C182S, C229S, N239Y, N268D, C275S, C277S) were expressed as 6×HIS fusion proteins in *E. coli* BL21(DE3). Lysates were first purified by Ni Sepharose High Performance (GE Healthcare) affinity chromatography. Proteins were then eluted from the resin and subject to Heparin (GE Healthcare) affinity chromatography. The elution fraction was then subjected to TEV protease cleavage overnight in 50 mM HEPES, 200 mM NaCl, and 1 mM DTT (pH 7.0). The protein was then passed over Heparin affinity resin again to remove free 6×HIS and TEV protease, concentrated, and stored in a buffer containing 50 mM HEPES, 200 mM NaCl, and 20% glycerol (pH 7.0).

Crystallization, data collection, structure determination, and model refinement. For crystallization, human p53 Y220C (residues 94-312, (C124S, M133L, C182S, C229S, N239Y, N268D, C275S, C277S, Y220C) was prepared for crystallization by incubation with excess KG1 compound overnight at 4 C. The p53 Y220C-KG1 adduct was then eluted from a Superdex 75 column (GE Healthcare) in a buffer containing 10 mM Tris, 100 mM NaCl, and 1 mM DTT (pH 8.0). The p53 Y220C-KG1 complex was crystallized from an 10 mg/mL solution by hanging drop vapor diffusion method at 22° C. Pyramidal crystals formed after seven days in 100 mM HEPES, 2.2M $MgSO_4$ (pH 7.0). Crystals were cryo-protected in reservoir solution supplemented with 25% ethylene glycol and cryo-cooled in liquid nitrogen.

Data were collected at the Advanced Light Source, Laurence Berkeley National Laboratory at beamline 8.2.1. Diffraction spots were integrated using MOSFLM (Leslie, 2006), and data were merged and scaled using Scala in the CCP4 software package (Bailey, 1994). The model was built with Coot (Emsley, 2004), and the model was refined with Phenix (Adams, 2010). Phenix indicated a perfect merohedral twin and the -h, -k, l twin law was applied to refinement.

X-ray crystallography data collection and refinement statistics. Values in parentheses are for highest resolution shell.

TABLE 2

| | p53 Y220C-KG1 |
|---|---|
| Data collection | |
| Space group | $P3_1$ |
| Cell dimensions | |
| a, b, c (Å) | 68.56, 68.56, 220.21 |
| a, b, γ (°) | 90, 90, 120 |
| Resolution (Å) | 73.40-2.4 (2.53-2.40) |
| $R_{merge}$ | 0.195 (0.662) |
| $R_{pim}$ | 0.103 (0.335) |
| I/σI | 5 (2) |
| CC 1/2 | 0.959 (0.533) |
| Total reflections | 209141 (32542) |
| Unique Reflections | 45347 (6668) |
| Completeness (%) | 100.0 (100.0) |
| Redundancy | 4.6 (4.9) |
| Refinement | |
| Resolution (Å) | 59.37-2.40 |
| No. reflections | 45286 (4509) |
| $R_{work}/R_{free}$ | 16.8/22.0 |
| No. atoms | 6697 |
| Protein | 6363 |
| Water | 76 |
| Zn | 4 |
| Refined B-factors ($Å^2$) | |
| Overall | 35.72 |
| P53 Y220C | 35.76 |
| water | 32.25 |
| R.m.s. deviations | |
| Bond lengths (Å) | 0.011 |
| Bond angles (°) | 1.07 |
| Ramachandran analysis | |
| Favored (%) | 98 |
| Disallowed (%) | 0 |

Western blots and antibodies. Whole-cell extracts from MCF10A (Gift from Prof. Sourav Bandyopadhyay, UCSF), BxPC-3 (ATCC, CRL-1687), Calu-1 (ATCC, HTB-54) were prepared by lysing cells with lysis buffer containing 50 mM HEPES, 150 mM NaCl, 1 mM DTT, 10% glycerol, and 1% NP-40 (pH 7.0) in the presence of 1×cOmplete EDTA-free protease inhibitor cocktail (Roche). Whole-cell extracts were combined with 2×SDS-loading buffer for western blot analysis.

Western blots were performed with 10 μg protein and were resolved by SDS-PAGE on 4-12% BT gels (Invitrogen) at 150 V for 1 hr in MES buffer and transferred to nitrocellulose membranes, which were then incubated with primary antibodies at 4° C. overnight, followed by incubation with LI-COR IRDye anti-mouse and anti-rabbit secondary antibodies at room temperature for 1 hr. Bands were imaged on a LI-COR Odyssey scanner.

Antibodies for western blot detection were as follows: p53 (DO-1, SCBT), actin (8H10D10, CST), Rb phosS807/811 (85165, CST), and p21 (SX118, SCBT).

LC-MS analysis of p53 Y220C covalent labeling. Recombinant p53 Y220C (1 μM) in buffer containing 50 mM HEPES and 150 mM NaCl (pH 7.0) was treated with covalent compounds. The extent of covalent labeling was assessed by LC-MS (Waters Xevo G2-XS QTof, ACQUITY UPLC Protein BEH C4 Column, 300 Å, 1.7 μm, 2.1 mm×50 mm). Deconvolution of multiply charged ions was performed using Waters MassLynx software (version 4.1).

TABLE 3

Covalent adducts for p53 Y220C calculated from LC-MS.

| Compound | Mass (Da) |
|---|---|
| none - | 24838 |
| KG1 | 25088 |
| difference | 250 (predicted 249) |
| KG2 | 25090 |
| difference | 252 (predicted 252) |
| KG37 | 25037 |
| difference | 199 (predicted 199) |
| KG78 | 25053 |
| difference | 215 (predicted 213) |
| KG1-PEG4-JQ1 | 25704 |
| difference | 866 (predicted 866) |
| KG1-PEG6-JQ1 | 25793 |
| difference | 955 (predicted 955) |

Chemical Synthesis. Nuclear magnetic resonance (NMR) spectra were recorded on a Varian spectrometer at 400 MHz. Chemical shifts were reported as parts per million (ppm) from solvent references. Liquid chromatography-mass spectrometry (LC-MS) was performed on a Waters Xevo G2-XS QTof (0.6 mL/min) using an ACQUITY UPLC BEH C18 column (Waters) and a water/acetonitrile gradient (0.05% formic acid) using Optima LC-MS grade solvents (Fisher Scientific). All other solvents were of ACS grade (Fisher Scientific, Millipore Sigma) and used without further purification. (+)-JQ1 was obtained Advanced ChemBlocks and t-Boc-N-amido-PEG4/6-amine was obtained from BroadPharm. Commercially available reagents were used without further purification. Analytical thin-layer chromatography was performed with silica gel 60 F254 glass plates (Millipore Sigma). Silica gel chromatography was performed with RediSep Rf normal-phase silica flash columns using a CombiFlash Rf+(Teledyne ISCO).

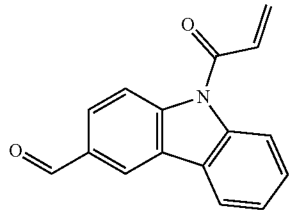 [SMILES: C=CC(=O)n1c2ccccc2c2cc(C=O)ccc21]

KG1. A reaction vessel was charged with 9H-carbazole-3-carbaldehyde (200 mg, 1.0245 mmol). DCM (2 mL), triethylamine (428.38 uL, 3.0735 mmol), and acryloyl chloride (107.63 uL, 1.3318 mmol) were added and the reaction was stirred at room temperature 1 hr. The mixture was concentrated in vacuo. The crude was purified by flash chromatography over silica gel eluting with a gradient from 0% methanol-dichloromethane to 20% methanol-dichloromethane to afford KG1 (200 mg, 0.8024 mmol, 78% yield) as a yellow semisolid. 1H NMR (400 MHz, $CDCl_3$): δ 10.13 (s, 1H), 8.56-8.52 (m, 1H), 8.32-8.28 (m, 1H), 8.1-7.98 (m, 3H) 7.56-7.38 (m, 3H), 6.78-6.7 (m, 1H), 6.8-6.73 (m, 1H), 6.18-6.13 (m, 1H). LC-MS 250 Da (MW 249 g/mol).

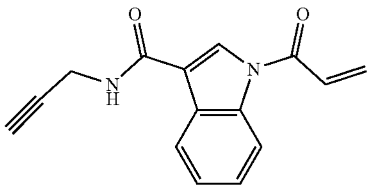 [SMILES: C#CCNC(=O)c1cn(C(=O)C=C)c2ccccc12]

KG2. A reaction vessel was charged with 3-Indolecarboxylic acid (200 mg, 1.241 mmol). DMF (2 mL), triethylamine (505.88 uL, 3.7095 mmol), HATU (378.19 mg, 1.6075 mmol), and 3-aminopropyne (95.378 uL, 1.4892 mmol) were added and the reaction was stirred at room temperature overnight. The mixture was partitioned with water, and extracted with ethyl acetate and concentrated in vacuo. The crude was purified by flash chromatography over silica gel eluting with a gradient from 0% ethyl acetate-hexanes to 100% ethyl acetate-hexanes to afford N-prop-2-ynyl-1H-indole-3-carboxamide (100 mg, 0.5045 mmol, 40% yield) as a white semisolid. A reaction vessel was charged with N-prop-2-ynyl-1H-indole-3-carboxamide (50 mg, 0.2522 mmol). DCM (2 mL), triethylamine (105.47 uL, 0.7567 mmol), and acryloyl chloride (18.293 uL, 0.3027 mmol) were added and the reaction was stirred at room temperature for 1 hr. The mixture was partitioned with water, and extracted DCM and concentrated in vacuo. The crude was purified by flash chromatography over silica gel eluting with a gradient from 0% ethyl acetate-hexanes to 100% ethyl acetate-hexanes to afford KG2 (15 mg, 0.0595 mmol, 23% yield) as a white semisolid. $^1$H NMR (400 MHz, $CDCl_3$): δ 8.54-8.47 (m, 1H), 8.07 (s, 1H), 7.97-7.9 (m, 1H), 7.47-7.37 (m, 2H) 7.0-6.93 (m, 1H), 6.76-6.63 (m, 1H), 6.19-6.08 (m, 2H), 4.32-4.25 (m, 2H), 4.14-4.06 (m, 1H). LC-MS 252 Da (MW 252 g/mol).

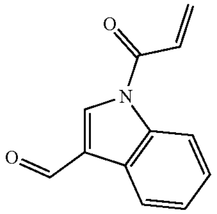

KG37. A reaction vessel was charged with 1H-indole-3-carbaldehyde (100 mg, 0.6889 mmol). DCM (2 mL), triethylamine (288.05 uL, 2.0667 mmol), and acryloyl chloride (72.373 uL, 0.8956 mmol) were added and the reaction was stirred at room temperature 1 hr. The mixture was concentrated in vacuo. The crude was purified by flash chromatography over silica gel eluting with a gradient from 0% methanol-dichloromethane to 20% methanol-dichloromethane to afford KG37 (100 mg, 0.8024 mmol, 78% yield) as a white semisolid. $^1$H NMR (400 MHz, $CDCl_3$): δ 10.13 (s, 1H), 8.46-8.42 (m, 1H), 8.3-8.26 (m, 1H), 8.15 (s, 1H) 7.49-7.39 (m, 2H), 7.04-6.96 (m, 1H), 6.8-6.73 (m, 1H), 6.2-6.15 (m, 1H). LC-MS 199 Da (MW 199 g/mol).

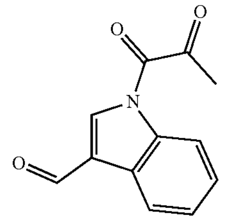 [SMILES: CC(=O)C(=O)n1cc(C=O)c2ccccc21]

KG78. A reaction vessel was charged with 1H-indole-3-carbaldehyde (100 mg, 0.6889 mmol). DCM (2 mL), triethylamine (288.05 uL, 2.0667 mmol), and methacrylic anhydride (123.27, 0.8956 mmol) were added and the reaction was stirred at room temperature 1 hr. The mixture was concentrated in vacuo. The crude was purified by flash chromatography over silica gel eluting with a gradient from 0% methanol-dichloromethane to 20% methanol-dichloromethane to afford KG78 (55 mg, 0.8024 mmol, 37% yield) as a white semisolid. $^1$H NMR (400 MHz, $CDCl_3$): δ 10.14 (s, 1H), 8.46-8.4 (m, 1H), 8.3-8.27 (m, 1H), 8.16 (s, 1H) 7.5-7.39 (m, 2H), 7.04-6.95 (m, 1H), 6.8-6.72 (m, 1H), 6.2-6.15 (m, 1H), 1.54-1.46 (m, 2H). LC-MS 215 Da (MW 213 g/mol).

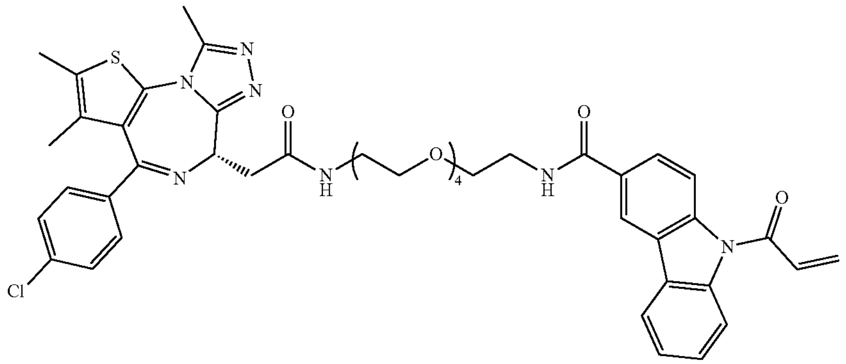

KG1-PEG4-JQ1. A reaction vessel was charged with (+)-JQ1 (102 mg, 0.2232 mmol). Formic acid (2 mL) was added and the reaction was stirred at room temperature overnight. JQ1 was mixed with water and extracted with DCM. The mixture was concentrated in vacuo to afford a yellow powder, "free acid JQ1" (89.4 mg, 0.2230 mmol, 99% yield). A reaction vessel was charged with free acid JQ1 (44 mg, 0.1098 mmol). DMF (2 mL), triethylamine (44.905 uL, 0.3293 mmol), HATU (38.734 mg, 0.1646 mmol), and $NH_2$—PEG4-Boc (55.408 mg, 0.1647 mmol) were added and the reaction was stirred at room temperature overnight. The crude, JQ1-PEG4-Boc, was mixed with water and extracted with DCM. The mixture was concentrated in vacuo, and DCM (1 mL) and TFA (1 mL) were added to the reaction for 1 hr at room temperature to remove the Boc protecting group and form the free amine. KG1 was prepared as described above except using 100 mg 9H-carbazole-3-carboxylic acid to yield 9-prop-2-enoylcarbazole-3-carboxylic acid or "free acid KG1" (40 mg, 0.1508 mmol, 31% yield). A reaction vessel was charged with free acid KG1 (14.137 mg, 0.0533 mmol). DMF (2 mL), triethylamine (29.073 uL, 0.7420 mmol), HATU (12.539 mg, 0.0533 mmol), and JQ1-PEG4-$NH_2$ (22 mg, 0.0355 mmol) were added and the reaction was stirred at room temperature overnight. The crude was purified by flash chromatography over silica gel eluting with a gradient from 0% methanol-dichloromethane to 20% methanol-dichloromethane to afford KG1-PEG4-JQ1 (7.7 mg, 0.0089 mmol, 25% yield) as a clear semisolid. LC-MS 866 Da (MW 866 g/mol).

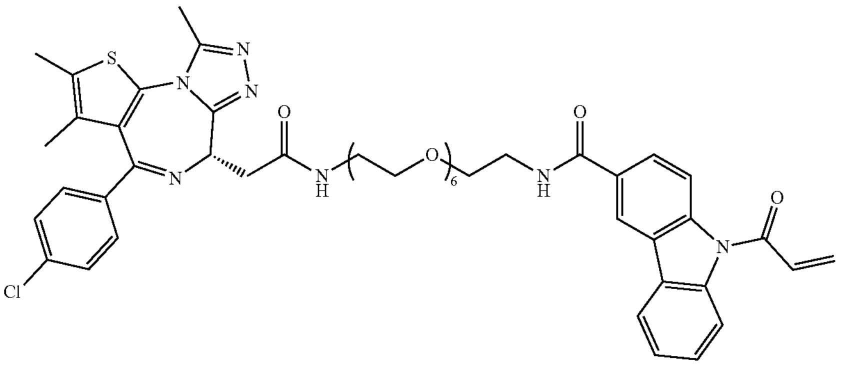

KG1-PEG6-JQ1. A reaction vessel was charged with (+)-JQ1 (102 mg, 0.2232 mmol). Formic acid (2 mL) was added and the reaction was stirred at room temperature overnight. JQ1 was mixed with water and extracted with DCM. The mixture was concentrated in vacuo to afford a yellow powder, "free acid JQ1" (89.4 mg, 0.2230 mmol, 99% yield). A reaction vessel was charged with free acid JQ1 (44 mg, 0.1098 mmol). DMF (2 mL), triethylamine (44.905 uL, 0.3293 mmol), HATU (38.734 mg, 0.1646 mmol), and $NH_2$—PEG6-Boc (69.894 mg, 0.1646 mmol) were added and the reaction was stirred at room temperature overnight. The crude, JQ1-PEG6-Boc, was mixed with water and extracted with DCM. The mixture was concentrated in vacuo, and DCM (1 mL) and TFA (1 mL) were added to the reaction for 1 hr at room temperature to remove the Boc protecting group and form the free amine. KG1 was prepared as described above except using 100 mg 9H-carbazole-3-carboxylic acid to yield 9-prop-2-enoylcarbazole-3-carboxylic acid or "free acid KG1" (40 mg, 0.1508 mmol, 31% yield). A reaction vessel was charged with free acid KG1 (19.127 mg, 0.0721 mmol). DMF (2 mL), riethylamine (39.334 uL, 0.2884 mmol), HATU (16.965 mg, 0.0721 mmol), and JQ1-PEG6-$NH_2$ (34 mg, 0.0481 mmol) were added and the reaction was stirred at room temperature overnight. The crude was purified by flash chromatography over silica gel eluting with a gradient from 0% methanol-dichloromethane to 20% methanol-dichloromethane to afford KG1-PEG6-JQ1 (7.2 mg, 0.0089 mmol, 15% yield) as a clear semisolid. LC-MS 955 Da (MW 955 g/mol).

Thermal Stability Assays. The thermal denaturation of p53 was monitored using fluorescence-based differential scanning fluorimetry assay. Purified p53 was incubated with excess covalent ligand overnight at 4° C. and purified by gel-filtration into 50 mM HEPES, 100 mM NaCl, and 15% glycerol (pH 7.0). 5 μM protein was prepared in assay buffer 50 mM HEPES and 100 mM NaCl (pH 7.0) with 2×SYPRO Orange (ThermoFisher). The plate was heated from 15° C. to 65° C. at a rate of 0.5° C./min. The fluorescence intensity was monitored at Ex/Em: 492/610 nm.

TABLE 4

Thermal Shifts Calculated for p53 and compound adducts

| Protein | Tm (° C.) |
|---|---|
| p53 WT | 41.5 |
| p53 Y220C | 33.0 |
| p53 Y220C-KG1 | 34.5 (Δ 1.5) |
| p53 Y220C-KG37 | 34.5 (Δ 1.5) |
| p53 Y220C-KG78 | 36 (Δ 3) |

Gel Shift "click" Assay. Huh-7 (p53 Y220C) and HepG2 (p53 WT) cells were treated with the indicated concentration of KG3-76 for 1 hr at 37° C. Cells were harvested, washed in PBS, and lysed with 20.75 μL lysis buffer containing 50 mM HEPES pH 7, 150 mM NaCl, 0.1% NP-40, 1×10cOmplete EDTA-free protease inhibitor cocktail. Lysates were clarified by centrifuging at 20,000 g for 10 min. 20.75 μL of lysate was treated with 4.25 μL of a master mix to give final concentrations of 1% SDS, 50 μM TAMRA-azide (in DMSO), 1 mM TCEP, 100 μM TBTA (in 1:4 DMSO:t-butyl alcohol) and 1 mM $CuSO_4$. The resulting mixture was incubated at room temperature for 1 hr before being quenched with 5 μL 6×SDS loading buffer and analyzed by western blot as described above. The TAMRA dye was used to add mass to KG3-76-labelled p53, so the KG3-76 modification is observable as a gel shift by using SDS-PAGE.

Copper "click" KG series Library. To identify novel fragments on KG1 that would improve labeling of p53 Y220C, a copper "click" library was synthesized (FIGS. 27-29). Alkyne substituted carbazoles were synthesized as described in Al-Balushi R., et al., Inorganic Chemistry, 2004, with the acrylamide attached in the final step similar to KG1 synthesis (FIG. 27). In a 96-well plate, 2 uL of 100 mM carbazole (in DMSO) was mixed with 2.2 uL 100 mM azide fragment (in DMSO, Enamine Ltd.), 3.3 uL t-butyl alcohol, 2.5 uL 20 mM sodium ascorbate (in water) and 10 uL of a mix of 3-(4-((Bis((1-(tert-butyl)-1H-1,2,3-triazol-4-yl)methyl)amino)methyl)-1H-1,2,3-triazol-1-yl)propane-1-sulfonic acid (BTTES) and $CuSO_4$ (in water) to a final concentration of 2.5 mM BTTES and 500 uM $CuSO_4$ (FIG. 28). The reaction was complete after 4 hours at room temperature with 60-90% conversion. 1 uL from each well of the 96-well click library was transferred into a mixture of 1 uM p53 Y220C recombinant protein in 50 mM HEPES pH 7, 150 mM NaCl, and 50 uM EDTA at 4° C. The reaction proceeded for 1 hour before being quenched with 0.03% formic acid and analyzed by LC/MS (FIG. 28). The percent labeling for the azide fragments (Enamine Ltd.) ranged from 5-80% in the screen, showing improvement compared to the starting alkyne derivatives (FIG. 29A). The top hits from the "click" library were scaled up from 20 uL to 2 mL and purified by HPLC. Each purified compound was tested for p53 Y220C labeling and pyrrolidine fragments were found to label >95% (FIG. 29B).

REFERENCES

1. Bailey, M. H. et al. Comprehensive Characterization of Cancer Driver Genes and Mutations. *Cell* 173, 371-385.e18 (2018). 2. Alexandrova, E. M. et al. P53 loss-of-heterozygosity is a necessary prerequisite for mutant p53 stabilization and gain-of-function in vivo. *Cell Death and Disease* 8, e2661-5 (2017). 3. Ventura, A. et al. Restoration of p53 function leads to tumour regression in vivo. *Nature* 445, 661-665 (2007). 4. Xue, W. et al. Senescence and tumour clearance is triggered by p53 restoration in murine liver carcinomas. *Nature* 445, 656-660 (2007). 5. Lill, N. L., Ginsberg, D., DeCaprio, J., Livingston, D. M. & Grossman, S. R. Binding and modulation of p53 by p300/CBP coactivators. *Nature* 387, 823-827 (2002). 6. Kruse, J. P. & Gu, W. Modes of p53 Regulation. *Cell* 137, 609-622 (2009). 7. Bullock, A. N., Henckel, J. & Fersht, A. R. Quantitative analysis of residual folding and DNA binding in mutant p53 core domain: Definition of mutant states for rescue in cancer therapy. *Oncogene* 19, 1245-1256 (2000). 8. Yu, X. et al. Small molecule restoration of wildtype structure and function of mutant p53 using a novel zinc-metallochaperone based mechanism. *Oncotarget* 5, 8879-8892 (2014). 9. Bykov, V. J. N. et al. Restoration of the tumor suppressor function to mutant p53 by a low-molecular-weight compound. *Nature Medicine* 8, 282-288 (2002). 10. Boeckler, F. M. et al. Targeted rescue of a destabilized mutant of p53 by an in silico screened drug. *Proceedings of the National Academy of Sciences* 105, 10360-10365 (2008). 11. Joerger, A. C., Ang, H. C. & Fersht, A. R. Structural basis for understanding oncogenic p53 mutations and designing rescue drugs. (2006). 12. Baud, M. G. J. et al. Aminobenzothiazole derivatives stabilize the thermolabile p53 cancer mutant Y220C and show anticancer activity in p53-Y220C cell lines. *Eur J Med Chem* 152, 101-114 (2018). 13. Bauer, M. R. et al. Harnessing Fluorine-Sulfur Contacts and Multipolar Interactions for the Design of p53 Mutant Y220C Rescue Drugs. *ACS Chem Biol* 11, 2265-2274 (2016). 14. Wilcken, R. et al. Halogen-Enriched Fragment Libraries as Leads for Drug Rescue of Mutant p53. *J. Am. Chem. Soc.* 134, 6810-6818 (2012). 15. Goor, F. V. et al. Correction of the F508del-CFTR protein processing defect in vitro by the investigational drug VX-809. *Proc. Nat. Acad. Sci.* 108, 18843-18848 (2011). 16. Crews, C. M. Targeting the Undruggable Proteome: The Small Molecules of My Dreams. *Chem Biol* 17, 551-555 (2010). 17. Fan, Q. et al. A Kinase Inhibitor Targeted to mTORCl Drives Regression in Glioblastoma. *Cancer Cell* 31, 424-435 (2017). 18. Rodrik-Outmezguine, V. S. et al. Overcoming mTOR resistance mutations with a new-generation mTOR inhibitor. *Nature* 534, 272-276 (2016). 19. Zhang, Z. & Shokat, K. M. Bifunctional Small Molecule Ligands of K-Ras Induce Its Association with Immunophilin Proteins. (2019). 20. Srivastava, A. K. et al. Synthetic transcription elongation factors license transcription across repressive chromatin. *Science* 358, 1617-1622 (2017). 21. Wang, P. L., Sait, F. & Winter, G. The 'wildtype' conformation of p53: epitope mapping using hybrid proteins. 2318-2324 (2001). 22. Serafimova, I. M. et al. Reversible targeting of noncatalytic cysteines with chemically tuned electrophiles. *Nature Chemical Biology* 8, 471-476 (2012). 23. Delmore, J. E. et al. BET bromodomain inhibition as a therapeutic strategy to target c-Myc. *Cell* 146, 904-917 (2011). 24. Fujisawa, T. & Filippakopoulos, P. Functions of bromodomain-containing proteins and their roles in homeostasis and cancer. *Nat Rev Mol Cell Biol* 18, 246-262 (2017). 25. Wu, S. Y., Lee, A. Y., Lai, H. T., Zhang, H. & Chiang, C. M. Phospho switch triggers brd4 chromatin binding and activator recruitment for gene-specific targeting. *Mol Cell* 49, 843-857 (2013). 26. Zengerle, M., Chan, K.-H. & Ciulli, A. Selective Small Molecule Induced Degradation of the BET Bromodomain Protein BRD4. *ACS Chem. Biol.* 10, 1770-1777 (2015). 27. N. Basse et al., Toward the Rational Design of p53-Stabilizing Drugs: Probing the Surface of the Oncogenic Y220C Mutant. *Chem. Biol.* 17, 46-56 (2010). 28. S. Sirimulla, J. B. Bailey, R. Vegesna, M. Narayan, Halogen interactions in protein-ligand complexes: Implications of halogen bonding for rational drug design. *J. Chem. Inf. Model.* 53, 2781-2791 (2013). 29. M. R. Bauer, A. C. Joerger, A. R. Fersht, 2-Sulfonylpyrimidines: Mild alkylating agents with anticancer activity toward p53-compromised cells. *Proc. Natl. Acad. Sci.* 113, E5271-E5280 (2016). 30. G. S. Erwin et al., Synthetic transcription elongation factors license transcription across repressive chromatin. *Science.* 358, 1617-1622 (2017). 31. Boettcher et al., A dominant-negative effect drives selection of TP53 missense mutations in myeloid malignancies. *Science* 365, 599-604 (2019).

What is claimed is:

1. A compound having the formula:

(II)

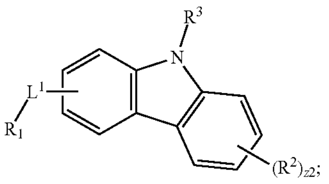

wherein $L^1$ is a bond or covalent linker;

$R^1$ is a transcriptional coactivator binding moiety, wherein the transcriptional coactivator binding moiety is a BRD4 binding moiety, wherein the BRD4 binding moiety has the formula:

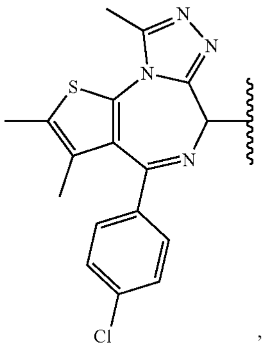

,

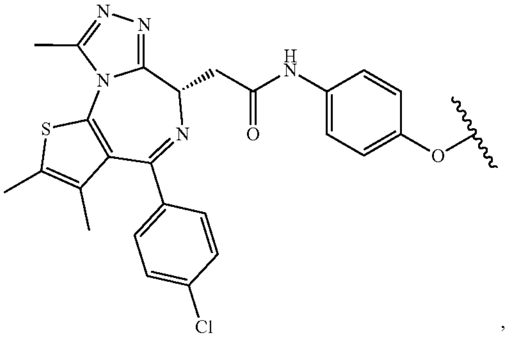

,

-continued

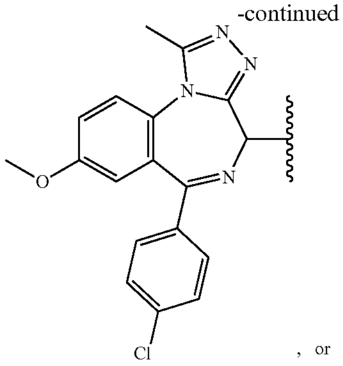

, or

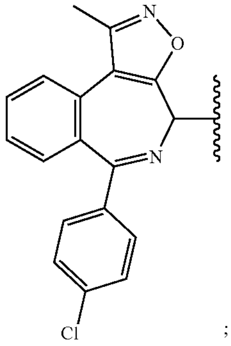

;

$R^2$ is independently halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, $—NS(O)F_2$, $—NS(O)FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{2A}$, $R^{2B}$, $R^{2C}$, and $R^{2D}$ are independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl;

$X^2$ is independently —F, —Cl, —Br, or —I;

n2 is independently an integer from 0 to 4;

m2 and v2 are independently 1 or 2;

z2 is an integer from 0 to 7; and $R^3$ is:

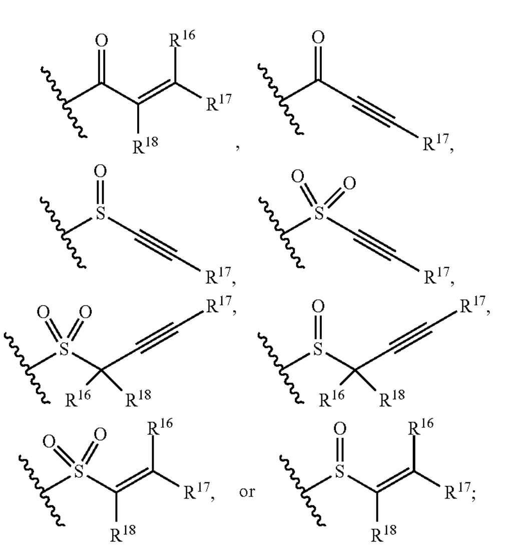

wherein $R^{16}$, $R^{17}$, and $R^{18}$ are independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OCC, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The compound of claim 1, wherein $L^1$ is $L^{101}$-$L^{102}$-$L^{103}$-$L^{104}$-$L^{105}$-; and $L^{101}$, $L^{102}$, $L^{103}$, $L^{104}$, and $L^{105}$ are independently a bond, —NH-, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker.

3. The compound of claim 1, having the formula:

(IIa)

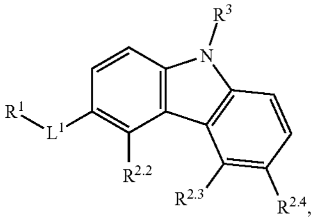

-continued (IIb)

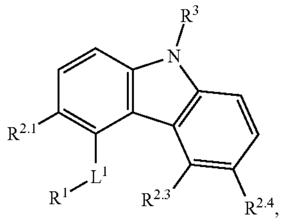

(IIc)

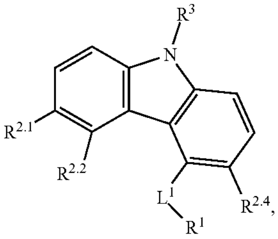

or (IId)

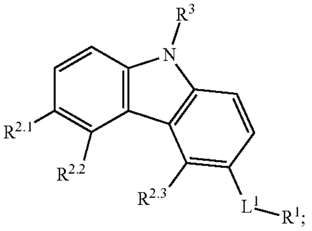

wherein $R^{2.1}$, $R^{2.2}$, $R^{2.3}$, and $R^{2.4}$ are independently hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C$(O) $R^{2C}$, —$NR^{2A}C$ (O) $OR^{2C}$, —$NR^{2A}OR^{2C}$, —$SF_5$, —$N_3$, —NS(O)$F_2$, —NS(O)$FNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

4. The compound of claim 1, wherein $R^3$ is

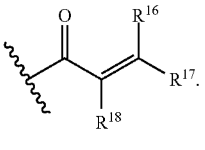

5. The compound of claim 1, wherein the BRD4 binding moiety has the formula:

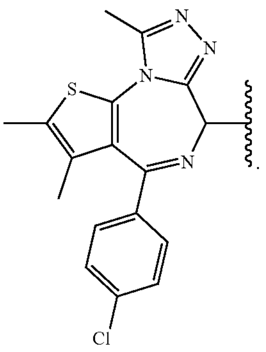 [SMILES: *C1N=C(c2ccc(Cl)cc2)c2c(sc(C)c2C)-n2c(C)nnc21]

6. The compound of claim 1, wherein $L^1$ is

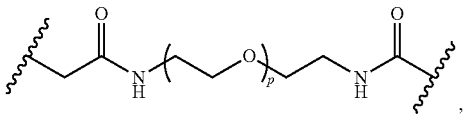

,

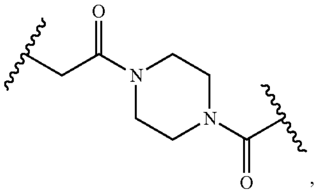

,

-continued

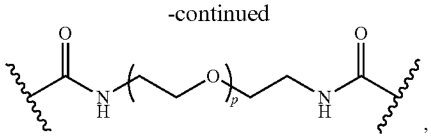

,

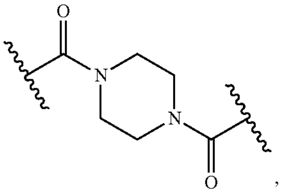

,

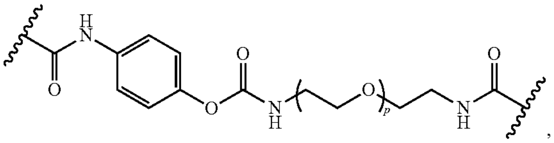

, or

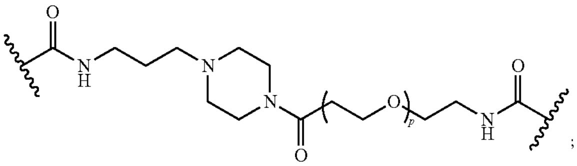

;

wherein p is an integer from 1 to 10.

7. The compound of claim 1, having the formula

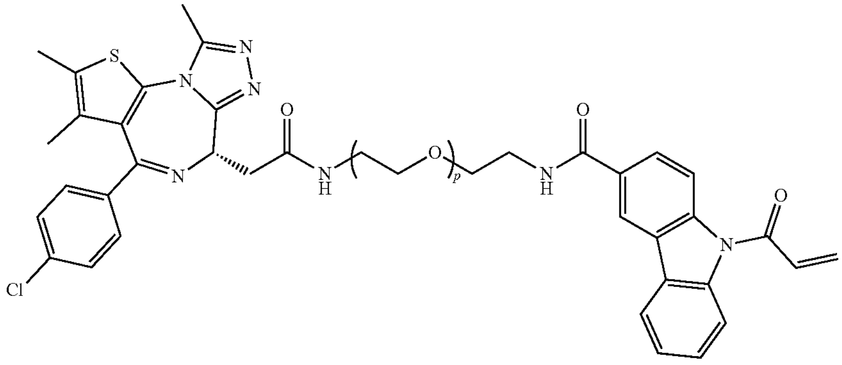

;

-continued

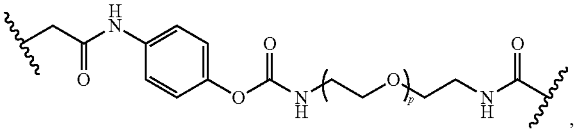

,

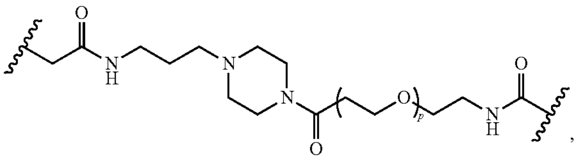

, wherein p is an integer from 1 to 8.

8. The compound of claim 4, wherein $R^{16}$ is hydrogen, $R^{17}$ is hydrogen, and $R^{18}$ is hydrogen.

9. The compound of claim 4, wherein $R^{16}$ is hydrogen, $R^{17}$ is hydrogen, and $R^{18}$ is unsubstituted methyl.

10. The compound of claim 4, wherein $R^{16}$ is hydrogen, $R^{17}$ is hydrogen, and $R^{18}$ is —CN.

11. A pharmaceutical composition comprising the compound of claim 1 and a pharmaceutically acceptable excipient.

12. A method of increasing the level of a protein in a cell, wherein the level of the protein is regulated by p53, said method comprising contacting the cell with the compound of claim 1.

13. A method of treating a p53 Y220C mutant cancer in a subject in need thereof, said method comprising administering to the subject an effective amount of the compound of claim 1.

14. A method of treating a $p53^{+/mut}$ cancer, said method comprising administering to a subject in need thereof an effective amount of the compound of claim 1 to said subject.

* * * * *

SEQUENCE LISTING

<160> NUMBER OF SEQ ID NOS: 9

<210> SEQ ID NO 1
<211> LENGTH: 76
<212> TYPE: PRT
<213> ORGANISM: Artificial Sequence
<220> FEATURE:
<223> OTHER INFORMATION: Synthetic polypeptide

<400> SEQUENCE: 1

```
Arg Gln Asn Pro Cys Gly Ser Lys Ala Cys Arg Arg Leu Phe Gly Pro
1               5                   10                  15

Val Asp Ser Glu Gln Leu Ser Arg Asp Cys Asp Ala Leu Met Ala Gly
            20                  25                  30

Cys Ile Gln Glu Ala Arg Glu Arg Trp Asn Phe Asp Phe Val Thr Glu
        35                  40                  45

Thr Pro Leu Glu Gly Asp Phe Ala Trp Glu Arg Val Arg Gly Leu Gly
    50                  55                  60

Leu Pro Lys Leu Tyr Leu Pro Thr Gly Pro Arg Arg
65                  70                  75
```

<210> SEQ ID NO 2
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 2

```
Arg Pro Val Pro His Arg Ser Lys Val Cys Arg Cys Leu Phe Gly Pro
1               5                   10                  15

Val Asp Ser Glu Gln Leu Arg Arg Asp Cys Asp Ala Leu Met Ala Gly
            20                  25                  30

Cys Leu Gln Glu Ala Arg Glu Arg Trp Asn Phe Asp Phe Val Thr Glu
        35                  40                  45

Thr Pro Leu Glu Gly Asn Phe Val Trp Glu Arg Val Arg Ser Leu Gly
    50                  55                  60

Leu Pro Lys Val Tyr Leu Ser Pro Gly Ser Arg
65                  70                  75
```

<210> SEQ ID NO 3
<211> LENGTH: 74
<212> TYPE: PRT
<213> ORGANISM: Artificial Sequence
<220> FEATURE:
<223> OTHER INFORMATION: Synthetic polypeptide

<400> SEQUENCE: 3

```
Gly Pro Met Pro Cys Ser Ser Lys Ala Cys Arg Asn Leu Phe Gly Pro
1               5                   10                  15

Val Asp His Glu Gln Ile Gln Asn Asp Phe Glu Gln Leu Leu Arg Gln
            20                  25                  30

Gln Leu Glu Glu Ala Gln Arg Arg Trp Asn Phe Asn Phe Glu Thr Glu
        35                  40                  45

Thr Pro Leu Glu Gly His Phe Lys Trp Glu Arg Val Leu Leu Ala Glu
    50                  55                  60

Gln Pro Pro Trp Glu Ala Phe Ser Leu Ala
65                  70
```

<210> SEQ ID NO 4

<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 4

Gln Ala Ser Gly Asn Lys Glu Lys Ser Cys Arg Met Leu Phe Gly Pro
1               5                   10                  15

Val Asp His Glu Gln Leu Arg Ala Asp Phe Asp Glu Phe Met Gln Lys
            20                  25                  30

Ser Asn Glu Glu Ala Lys Ala Lys Trp Asn Phe Gly Phe Ala Thr Glu
        35                  40                  45

Thr Pro Leu Glu Gly Gln Tyr Asp Trp Val Lys Val Glu Asn Asn Thr
    50                  55                  60

Leu Asn Gly Ser
65

<210> SEQ ID NO 5
<211> LENGTH: 77
<212> TYPE: PRT
<213> ORGANISM: Artificial Sequence
<220> FEATURE:
<223> OTHER INFORMATION: Synthetic polypeptide

<400> SEQUENCE: 5

Leu Arg Ser Leu Gly Asn Gly Pro Thr Arg Arg Ser Leu Phe Gly Pro
1               5                   10                  15

Val Asp Arg Glu Gln Leu Gln Arg Glu Tyr Arg Ala Ala Leu Arg Arg
            20                  25                  30

Asp Leu Glu Asp Ala Ser Arg Arg Trp Ser Phe Asp Phe Ala Ser Glu
        35                  40                  45

Lys Pro Leu Glu Gly Gly Asp Phe His Trp Glu Gly Val Ser Gly Val
    50                  55                  60

Arg Val Pro Leu Leu Tyr Arg Ala Cys Gln Glu Lys Gln
65                  70                  75

<210> SEQ ID NO 6
<211> LENGTH: 393
<212> TYPE: PRT
<213> ORGANISM: Artificial Sequence
<220> FEATURE:
<223> OTHER INFORMATION: Synthetic polypeptide

<400> SEQUENCE: 6

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

-continued

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 7
<211> LENGTH: 1362
<212> TYPE: PRT
<213> ORGANISM: Artificial Sequence
<220> FEATURE:
<223> OTHER INFORMATION: Synthetic polypeptide

<400> SEQUENCE: 7

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro Pro
        35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

-continued

```
Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
        115                 120                 125

Phe Asn Thr Met Phe Thr Asn Cys Tyr Ile Tyr Asn Lys Pro Gly Asp
    130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
        195                 200                 205

Gln Thr Pro Gln Pro Asn Pro Pro Pro Val Gln Ala Thr Pro His Pro
    210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Pro Val Pro Pro Gln
                245                 250                 255

Pro Gln Pro Pro Pro Ala Pro Ala Pro Gln Pro Val Gln Ser His Pro
            260                 265                 270

Pro Ile Ile Ala Ala Thr Pro Gln Pro Val Lys Thr Lys Lys Gly Val
        275                 280                 285

Lys Arg Lys Ala Asp Thr Thr Thr Pro Thr Thr Ile Asp Pro Ile His
    290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
        355                 360                 365

His Ala Ala Tyr Ala Trp Pro Phe Tyr Lys Pro Val Asp Val Glu Ala
    370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
        435                 440                 445

Val Phe Glu Met Arg Phe Ala Lys Met Pro Asp Glu Pro Glu Glu Pro
    450                 455                 460

Val Val Ala Val Ser Ser Pro Ala Val Pro Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
```

-continued

```
            500                 505                 510

Glu Leu Gln Glu Gln Leu Lys Ala Val His Glu Gln Leu Ala Ala Leu
        515                 520                 525

Ser Gln Pro Gln Gln Asn Lys Pro Lys Lys Lys Glu Lys Asp Lys Lys
    530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Pro Lys Lys Thr Lys Lys Asn
                565                 570                 575

Asn Ser Ser Asn Ser Asn Val Ser Lys Lys Glu Pro Ala Pro Met Lys
            580                 585                 590

Ser Lys Pro Pro Pro Thr Tyr Glu Ser Glu Glu Glu Asp Lys Cys Lys
        595                 600                 605

Pro Met Ser Tyr Glu Glu Lys Arg Gln Leu Ser Leu Asp Ile Asn Lys
    610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
            660                 665                 670

Ser Cys Leu Arg Lys Lys Arg Lys Pro Gln Ala Glu Lys Val Asp Val
        675                 680                 685

Ile Ala Gly Ser Ser Lys Met Lys Gly Phe Ser Ser Ser Glu Ser Glu
    690                 695                 700

Ser Ser Ser Glu Ser Ser Ser Ser Asp Ser Glu Asp Ser Glu Thr Glu
705                 710                 715                 720

Met Ala Pro Lys Ser Lys Lys Lys Gly His Pro Gly Arg Glu Gln Lys
                725                 730                 735

Lys His His His His His His Gln Gln Met Gln Gln Ala Pro Ala Pro
            740                 745                 750

Val Pro Gln Gln Pro Pro Pro Pro Pro Gln Gln Pro Pro Pro Pro Pro
        755                 760                 765

Pro Pro Gln Gln Gln Gln Gln Pro Pro Pro Pro Pro Pro Pro Pro Ser
    770                 775                 780

Met Pro Gln Gln Ala Ala Pro Ala Met Lys Ser Ser Pro Pro Pro Phe
785                 790                 795                 800

Ile Ala Thr Gln Val Pro Val Leu Glu Pro Gln Leu Pro Gly Ser Val
                805                 810                 815

Phe Asp Pro Ile Gly His Phe Thr Gln Pro Ile Leu His Leu Pro Gln
            820                 825                 830

Pro Glu Leu Pro Pro His Leu Pro Gln Pro Pro Glu His Ser Thr Pro
        835                 840                 845

Pro His Leu Asn Gln His Ala Val Val Ser Pro Pro Ala Leu His Asn
    850                 855                 860

Ala Leu Pro Gln Gln Pro Ser Arg Pro Ser Asn Arg Ala Ala Ala Leu
865                 870                 875                 880

Pro Pro Lys Pro Ala Arg Pro Pro Ala Val Ser Pro Ala Leu Thr Gln
                885                 890                 895

Thr Pro Leu Leu Pro Gln Pro Pro Met Ala Gln Pro Pro Gln Val Leu
            900                 905                 910

Leu Glu Asp Glu Glu Pro Pro Ala Pro Pro Leu Thr Ser Met Gln Met
        915                 920                 925
```

-continued

```
Gln Leu Tyr Leu Gln Gln Leu Gln Lys Val Gln Pro Pro Thr Pro Leu
    930                 935                 940

Leu Pro Ser Val Lys Val Gln Ser Gln Pro Pro Pro Pro Leu Pro Pro
945                 950                 955                 960

Pro Pro His Pro Ser Val Gln Gln Gln Leu Gln Gln Gln Pro Pro Pro
                965                 970                 975

Pro Pro Pro Pro Gln Pro Gln Pro Pro Pro Gln Gln Gln His Gln Pro
            980                 985                 990

Pro Pro Arg Pro Val His Leu Gln  Pro Met Gln Phe Ser  Thr His Ile
        995                 1000                 1005

Gln Gln  Pro Pro Pro Pro Gln  Gly Gln Gln Pro Pro  His Pro Pro
    1010                 1015                 1020

Pro Gly  Gln Gln Pro Pro Pro  Pro Gln Pro Ala Lys  Pro Gln Gln
    1025                 1030                 1035

Val Ile  Gln His His His Ser  Pro Arg His His Lys  Ser Asp Pro
    1040                 1045                 1050

Tyr Ser  Thr Gly His Leu Arg  Glu Ala Pro Ser Pro  Leu Met Ile
    1055                 1060                 1065

His Ser  Pro Gln Met Ser Gln  Phe Gln Ser Leu Thr  His Gln Ser
    1070                 1075                 1080

Pro Pro  Gln Gln Asn Val Gln  Pro Lys Lys Gln Glu  Leu Arg Ala
    1085                 1090                 1095

Ala Ser  Val Val Gln Pro Gln  Pro Leu Val Val Val  Lys Glu Glu
    1100                 1105                 1110

Lys Ile  His Ser Pro Ile Ile  Arg Ser Glu Pro Phe  Ser Pro Ser
    1115                 1120                 1125

Leu Arg  Pro Glu Pro Pro Lys  His Pro Glu Ser Ile  Lys Ala Pro
    1130                 1135                 1140

Val His  Leu Pro Gln Arg Pro  Glu Met Lys Pro Val  Asp Val Gly
    1145                 1150                 1155

Arg Pro  Val Ile Arg Pro Pro  Glu Gln Asn Ala Pro  Pro Pro Gly
    1160                 1165                 1170

Ala Pro  Asp Lys Asp Lys Gln  Lys Gln Glu Pro Lys  Thr Pro Val
    1175                 1180                 1185

Ala Pro  Lys Lys Asp Leu Lys  Ile Lys Asn Met Gly  Ser Trp Ala
    1190                 1195                 1200

Ser Leu  Val Gln Lys His Pro  Thr Thr Pro Ser Ser  Thr Ala Lys
    1205                 1210                 1215

Ser Ser  Ser Asp Ser Phe Glu  Gln Phe Arg Arg Ala  Ala Arg Glu
    1220                 1225                 1230

Lys Glu  Glu Arg Glu Lys Ala  Leu Lys Ala Gln Ala  Glu His Ala
    1235                 1240                 1245

Glu Lys  Glu Lys Glu Arg Leu  Arg Gln Glu Arg Met  Arg Ser Arg
    1250                 1255                 1260

Glu Asp  Glu Asp Ala Leu Glu  Gln Ala Arg Arg Ala  His Glu Glu
    1265                 1270                 1275

Ala Arg  Arg Arg Gln Glu Gln  Gln Gln Gln Gln Arg  Gln Glu Gln
    1280                 1285                 1290

Gln Gln  Gln Gln Gln Gln Gln  Ala Ala Ala Val Ala  Ala Ala Ala
    1295                 1300                 1305

Thr Pro  Gln Ala Gln Ser Ser  Gln Pro Gln Ser Met  Leu Asp Gln
    1310                 1315                 1320
```

```
Gln Arg  Glu Leu Ala Arg Lys  Arg Glu Gln Glu Arg  Arg Arg Arg
    1325                 1330                 1335

Glu Ala  Met Ala Ala Thr Ile  Asp Met Asn Phe Gln  Ser Asp Leu
    1340                 1345                 1350

Leu Ser  Ile Phe Glu Glu Asn  Leu Phe
    1355                 1360


<210> SEQ ID NO 8
<211> LENGTH: 2414
<212> TYPE: PRT
<213> ORGANISM: Artificial Sequence
<220> FEATURE:
<223> OTHER INFORMATION: Synthetic polypeptide

<400> SEQUENCE: 8

Met Ala Glu Asn Val Val Glu Pro Gly Pro Pro Ser Ala Lys Arg Pro
1               5                   10                  15

Lys Leu Ser Ser Pro Ala Leu Ser Ala Ser Ala Ser Asp Gly Thr Asp
            20                  25                  30

Phe Gly Ser Leu Phe Asp Leu Glu His Asp Leu Pro Asp Glu Leu Ile
        35                  40                  45

Asn Ser Thr Glu Leu Gly Leu Thr Asn Gly Gly Asp Ile Asn Gln Leu
    50                  55                  60

Gln Thr Ser Leu Gly Met Val Gln Asp Ala Ala Ser Lys His Lys Gln
65                  70                  75                  80

Leu Ser Glu Leu Leu Arg Ser Gly Ser Ser Pro Asn Leu Asn Met Gly
                85                  90                  95

Val Gly Gly Pro Gly Gln Val Met Ala Ser Gln Ala Gln Gln Ser Ser
            100                 105                 110

Pro Gly Leu Gly Leu Ile Asn Ser Met Val Lys Ser Pro Met Thr Gln
        115                 120                 125

Ala Gly Leu Thr Ser Pro Asn Met Gly Met Gly Thr Ser Gly Pro Asn
    130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
            180                 185                 190

Asn Gly Ser Ile Gly Ala Gly Arg Gly Arg Gln Asn Met Gln Tyr Pro
        195                 200                 205

Asn Pro Gly Met Gly Ser Ala Gly Asn Leu Leu Thr Glu Pro Leu Gln
    210                 215                 220

Gln Gly Ser Pro Gln Met Gly Gly Gln Thr Gly Leu Arg Gly Pro Gln
225                 230                 235                 240

Pro Leu Lys Met Gly Met Met Asn Asn Pro Asn Pro Tyr Gly Ser Pro
                245                 250                 255

Tyr Thr Gln Asn Pro Gly Gln Gln Ile Gly Ala Ser Gly Leu Gly Leu
            260                 265                 270

Gln Ile Gln Thr Lys Thr Val Leu Ser Asn Asn Leu Ser Pro Phe Ala
        275                 280                 285

Met Asp Lys Lys Ala Val Pro Gly Gly Gly Met Pro Asn Met Gly Gln
    290                 295                 300

Gln Pro Ala Pro Gln Val Gln Gln Pro Gly Leu Val Thr Pro Val Ala
305                 310                 315                 320
```

-continued

```
Gln Gly Met Gly Ser Gly Ala His Thr Ala Asp Pro Glu Lys Arg Lys
                325                 330                 335

Leu Ile Gln Gln Gln Leu Val Leu Leu Leu His Ala His Lys Cys Gln
            340                 345                 350

Arg Arg Glu Gln Ala Asn Gly Glu Val Arg Gln Cys Asn Leu Pro His
        355                 360                 365

Cys Arg Thr Met Lys Asn Val Leu Asn His Met Thr His Cys Gln Ser
    370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                405                 410                 415

Leu Lys Asn Ala Gly Asp Lys Arg Asn Gln Gln Pro Ile Leu Thr Gly
            420                 425                 430

Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
    450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Gln Asn Gln Gln Pro
                485                 490                 495

Gly Gln Ser Pro Gln Gly Met Arg Pro Met Ser Asn Met Ser Ala Ser
            500                 505                 510

Pro Met Gly Val Asn Gly Gly Val Gly Val Gln Thr Pro Ser Leu Leu
        515                 520                 525

Ser Asp Ser Met Leu His Ser Ala Ile Asn Ser Gln Asn Pro Met Met
    530                 535                 540

Ser Glu Asn Ala Ser Val Pro Ser Leu Gly Pro Met Pro Thr Ala Ala
545                 550                 555                 560

Gln Pro Ser Thr Thr Gly Ile Arg Lys Gln Trp His Glu Asp Ile Thr
                565                 570                 575

Gln Asp Leu Arg Asn His Leu Val His Lys Leu Val Gln Ala Ile Phe
            580                 585                 590

Pro Thr Pro Asp Pro Ala Ala Leu Lys Asp Arg Arg Met Glu Asn Leu
        595                 600                 605

Val Ala Tyr Ala Arg Lys Val Glu Gly Asp Met Tyr Glu Ser Ala Asn
    610                 615                 620

Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
                645                 650                 655

Met Leu Pro Asn Ala Ala Gly Met Val Pro Val Ser Met Asn Pro Gly
            660                 665                 670

Pro Asn Met Gly Gln Pro Gln Pro Gly Met Thr Ser Asn Gly Pro Leu
        675                 680                 685

Pro Asp Pro Ser Met Ile Arg Gly Ser Val Pro Asn Gln Met Met Pro
    690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Pro Leu Gln His His
                725                 730                 735

Gly Gln Leu Ala Gln Pro Gly Ala Leu Asn Pro Pro Met Gly Tyr Gly
```

-continued

```
            740                 745                 750

Pro Arg Met Gln Gln Pro Ser Asn Gln Gly Gln Phe Leu Pro Gln Thr
        755                 760                 765

Gln Phe Pro Ser Gln Gly Met Asn Val Thr Asn Ile Pro Leu Ala Pro
    770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
                805                 810                 815

Ile His Cys Pro Gln Leu Pro Gln Pro Ala Leu His Gln Asn Ser Pro
            820                 825                 830

Ser Pro Val Pro Ser Arg Thr Pro Thr Pro His His Thr Pro Pro Ser
        835                 840                 845

Ile Gly Ala Gln Gln Pro Pro Ala Thr Thr Ile Pro Ala Pro Val Pro
    850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
                885                 890                 895

Val Gln Pro Ser Leu Pro Ala Ala Pro Ser Ala Asp Gln Pro Gln Gln
            900                 905                 910

Gln Pro Arg Ser Gln Gln Ser Thr Ala Ala Ser Val Pro Thr Pro Thr
        915                 920                 925

Ala Pro Leu Leu Pro Pro Gln Pro Ala Thr Pro Leu Ser Gln Pro Ala
    930                 935                 940

Val Ser Ile Glu Gly Gln Val Ser Asn Pro Pro Ser Thr Ser Ser Thr
945                 950                 955                 960

Glu Val Asn Ser Gln Ala Ile Ala Glu Lys Gln Pro Ser Gln Glu Val
                965                 970                 975

Lys Met Glu Ala Lys Met Glu Val Asp Gln Pro Glu Pro Ala Asp Thr
            980                 985                 990

Gln Pro Glu Asp Ile Ser Glu Ser  Lys Val Glu Asp Cys  Lys Met Glu
        995                 1000                1005

Ser Thr  Glu Thr Glu Glu Arg  Ser Thr Glu Leu Lys  Thr Glu Ile
    1010                1015                1020

Lys Glu  Glu Glu Asp Gln Pro  Ser Thr Ser Ala Thr  Gln Ser Ser
    1025                1030                1035

Pro Ala  Pro Gly Gln Ser Lys  Lys Lys Ile Phe Lys  Pro Glu Glu
    1040                1045                1050

Leu Arg  Gln Ala Leu Met Pro  Thr Leu Glu Ala Leu  Tyr Arg Gln
    1055                1060                1065

Asp Pro  Glu Ser Leu Pro Phe  Arg Gln Pro Val Asp  Pro Gln Leu
    1070                1075                1080

Leu Gly  Ile Pro Asp Tyr Phe  Asp Ile Val Lys Ser  Pro Met Asp
    1085                1090                1095

Leu Ser  Thr Ile Lys Arg Lys  Leu Asp Thr Gly Gln  Tyr Gln Glu
    1100                1105                1110

Pro Trp  Gln Tyr Val Asp Asp  Ile Trp Leu Met Phe  Asn Asn Ala
    1115                1120                1125

Trp Leu  Tyr Asn Arg Lys Thr  Ser Arg Val Tyr Lys  Tyr Cys Ser
    1130                1135                1140

Lys Leu  Ser Glu Val Phe Glu  Gln Glu Ile Asp Pro  Val Met Gln
    1145                1150                1155
```

Ser Leu Gly Tyr Cys Cys Gly Arg Lys Leu Glu Phe Ser Pro Gln
1160 1165 1170

Thr Leu Cys Cys Tyr Gly Lys Gln Leu Cys Thr Ile Pro Arg Asp
1175 1180 1185

Ala Thr Tyr Tyr Ser Tyr Gln Asn Arg Tyr His Phe Cys Glu Lys
1190 1195 1200

Cys Phe Asn Glu Ile Gln Gly Glu Ser Val Ser Leu Gly Asp Asp
1205 1210 1215

Pro Ser Gln Pro Gln Thr Thr Ile Asn Lys Glu Gln Phe Ser Lys
1220 1225 1230

Arg Lys Asn Asp Thr Leu Asp Pro Glu Leu Phe Val Glu Cys Thr
1235 1240 1245

Glu Cys Gly Arg Lys Met His Gln Ile Cys Val Leu His His Glu
1250 1255 1260

Ile Ile Trp Pro Ala Gly Phe Val Cys Asp Gly Cys Leu Lys Lys
1265 1270 1275

Ser Ala Arg Thr Arg Lys Glu Asn Lys Phe Ser Ala Lys Arg Leu
1280 1285 1290

Pro Ser Thr Arg Leu Gly Thr Phe Leu Glu Asn Arg Val Asn Asp
1295 1300 1305

Phe Leu Arg Arg Gln Asn His Pro Glu Ser Gly Glu Val Thr Val
1310 1315 1320

Arg Val Val His Ala Ser Asp Lys Thr Val Glu Val Lys Pro Gly
1325 1330 1335

Met Lys Ala Arg Phe Val Asp Ser Gly Glu Met Ala Glu Ser Phe
1340 1345 1350

Pro Tyr Arg Thr Lys Ala Leu Phe Ala Phe Glu Glu Ile Asp Gly
1355 1360 1365

Val Asp Leu Cys Phe Phe Gly Met His Val Gln Glu Tyr Gly Ser
1370 1375 1380

Asp Cys Pro Pro Pro Asn Gln Arg Arg Val Tyr Ile Ser Tyr Leu
1385 1390 1395

Asp Ser Val His Phe Phe Arg Pro Lys Cys Leu Arg Thr Ala Val
1400 1405 1410

Tyr His Glu Ile Leu Ile Gly Tyr Leu Glu Tyr Val Lys Lys Leu
1415 1420 1425

Gly Tyr Thr Thr Gly His Ile Trp Ala Cys Pro Pro Ser Glu Gly
1430 1435 1440

Asp Asp Tyr Ile Phe His Cys His Pro Pro Asp Gln Lys Ile Pro
1445 1450 1455

Lys Pro Lys Arg Leu Gln Glu Trp Tyr Lys Lys Met Leu Asp Lys
1460 1465 1470

Ala Val Ser Glu Arg Ile Val His Asp Tyr Lys Asp Ile Phe Lys
1475 1480 1485

Gln Ala Thr Glu Asp Arg Leu Thr Ser Ala Lys Glu Leu Pro Tyr
1490 1495 1500

Phe Glu Gly Asp Phe Trp Pro Asn Val Leu Glu Glu Ser Ile Lys
1505 1510 1515

Glu Leu Glu Gln Glu Glu Glu Glu Arg Lys Arg Glu Glu Asn Thr
1520 1525 1530

Ser Asn Glu Ser Thr Asp Val Thr Lys Gly Asp Ser Lys Asn Ala
1535 1540 1545

-continued

```
Lys Lys  Lys Asn Asn Lys Lys  Thr Ser Lys Asn Lys  Ser Ser Leu
    1550                 1555                 1560

Ser Arg  Gly Asn Lys Lys Lys  Pro Gly Met Pro Asn  Val Ser Asn
    1565                 1570                 1575

Asp Leu  Ser Gln Lys Leu Tyr  Ala Thr Met Glu Lys  His Lys Glu
    1580                 1585                 1590

Val Phe  Phe Val Ile Arg Leu  Ile Ala Gly Pro Ala  Ala Asn Ser
    1595                 1600                 1605

Leu Pro  Pro Ile Val Asp Pro  Asp Pro Leu Ile Pro  Cys Asp Leu
    1610                 1615                 1620

Met Asp  Gly Arg Asp Ala Phe  Leu Thr Leu Ala Arg  Asp Lys His
    1625                 1630                 1635

Leu Glu  Phe Ser Ser Leu Arg  Arg Ala Gln Trp Ser  Thr Met Cys
    1640                 1645                 1650

Met Leu  Val Glu Leu His Thr  Gln Ser Gln Asp Arg  Phe Val Tyr
    1655                 1660                 1665

Thr Cys  Asn Glu Cys Lys His  His Val Glu Thr Arg  Trp His Cys
    1670                 1675                 1680

Thr Val  Cys Glu Asp Tyr Asp  Leu Cys Ile Thr Cys  Tyr Asn Thr
    1685                 1690                 1695

Lys Asn  His Asp His Lys Met  Glu Lys Leu Gly Leu  Gly Leu Asp
    1700                 1705                 1710

Asp Glu  Ser Asn Asn Gln Gln  Ala Ala Ala Thr Gln  Ser Pro Gly
    1715                 1720                 1725

Asp Ser  Arg Arg Leu Ser Ile  Gln Arg Cys Ile Gln  Ser Leu Val
    1730                 1735                 1740

His Ala  Cys Gln Cys Arg Asn  Ala Asn Cys Ser Leu  Pro Ser Cys
    1745                 1750                 1755

Gln Lys  Met Lys Arg Val Val  Gln His Thr Lys Gly  Cys Lys Arg
    1760                 1765                 1770

Lys Thr  Asn Gly Gly Cys Pro  Ile Cys Lys Gln Leu  Ile Ala Leu
    1775                 1780                 1785

Cys Cys  Tyr His Ala Lys His  Cys Gln Glu Asn Lys  Cys Pro Val
    1790                 1795                 1800

Pro Phe  Cys Leu Asn Ile Lys  Gln Lys Leu Arg Gln  Gln Gln Leu
    1805                 1810                 1815

Gln His  Arg Leu Gln Gln Ala  Gln Met Leu Arg Arg  Arg Met Ala
    1820                 1825                 1830

Ser Met  Gln Arg Thr Gly Val  Val Gly Gln Gln Gln  Gly Leu Pro
    1835                 1840                 1845

Ser Pro  Thr Pro Ala Thr Pro  Thr Thr Pro Thr Gly  Gln Gln Pro
    1850                 1855                 1860

Thr Thr  Pro Gln Thr Pro Gln  Pro Thr Ser Gln Pro  Gln Pro Thr
    1865                 1870                 1875

Pro Pro  Asn Ser Met Pro Pro  Tyr Leu Pro Arg Thr  Gln Ala Ala
    1880                 1885                 1890

Gly Pro  Val Ser Gln Gly Lys  Ala Ala Gly Gln Val  Thr Pro Pro
    1895                 1900                 1905

Thr Pro  Pro Gln Thr Ala Gln  Pro Pro Leu Pro Gly  Pro Pro Pro
    1910                 1915                 1920

Ala Ala  Val Glu Met Ala Met  Gln Ile Gln Arg Ala  Ala Glu Thr
    1925                 1930                 1935

Gln Arg  Gln Met Ala His Val  Gln Ile Phe Gln Arg  Pro Ile Gln
```

-continued

```
    1940                1945                1950

His Gln Met Pro Pro Met Thr Pro Met Ala Pro Met Gly Met Asn
    1955                1960                1965

Pro Pro Pro Met Thr Arg Gly Pro Ser Gly His Leu Glu Pro Gly
    1970                1975                1980

Met Gly Pro Thr Gly Met Gln Gln Gln Pro Pro Trp Ser Gln Gly
    1985                1990                1995

Gly Leu Pro Gln Pro Gln Gln Leu Gln Ser Gly Met Pro Arg Pro
    2000                2005                2010

Ala Met Met Ser Val Ala Gln His Gly Gln Pro Leu Asn Met Ala
    2015                2020                2025

Pro Gln Pro Gly Leu Gly Gln Val Gly Ile Ser Pro Leu Lys Pro
    2030                2035                2040

Gly Thr Val Ser Gln Gln Ala Leu Gln Asn Leu Leu Arg Thr Leu
    2045                2050                2055

Arg Ser Pro Ser Ser Pro Leu Gln Gln Gln Gln Val Leu Ser Ile
    2060                2065                2070

Leu His Ala Asn Pro Gln Leu Leu Ala Ala Phe Ile Lys Gln Arg
    2075                2080                2085

Ala Ala Lys Tyr Ala Asn Ser Asn Pro Gln Pro Ile Pro Gly Gln
    2090                2095                2100

Pro Gly Met Pro Gln Gly Gln Pro Gly Leu Gln Pro Pro Thr Met
    2105                2110                2115

Pro Gly Gln Gln Gly Val His Ser Asn Pro Ala Met Gln Asn Met
    2120                2125                2130

Asn Pro Met Gln Ala Gly Val Gln Arg Ala Gly Leu Pro Gln Gln
    2135                2140                2145

Gln Pro Gln Gln Gln Leu Gln Pro Pro Met Gly Gly Met Ser Pro
    2150                2155                2160

Gln Ala Gln Gln Met Asn Met Asn His Asn Thr Met Pro Ser Gln
    2165                2170                2175

Phe Arg Asp Ile Leu Arg Arg Gln Gln Met Met Gln Gln Gln Gln
    2180                2185                2190

Gln Gln Gly Ala Gly Pro Gly Ile Gly Pro Gly Met Ala Asn His
    2195                2200                2205

Asn Gln Phe Gln Gln Pro Gln Gly Val Gly Tyr Pro Pro Gln Gln
    2210                2215                2220

Gln Gln Arg Met Gln His His Met Gln Gln Met Gln Gln Gly Asn
    2225                2230                2235

Met Gly Gln Ile Gly Gln Leu Pro Gln Ala Leu Gly Ala Glu Ala
    2240                2245                2250

Gly Ala Ser Leu Gln Ala Tyr Gln Gln Arg Leu Leu Gln Gln Gln
    2255                2260                2265

Met Gly Ser Pro Val Gln Pro Asn Pro Met Ser Pro Gln Gln His
    2270                2275                2280

Met Leu Pro Asn Gln Ala Gln Ser Pro His Leu Gln Gly Gln Gln
    2285                2290                2295

Ile Pro Asn Ser Leu Ser Asn Gln Val Arg Ser Pro Gln Pro Val
    2300                2305                2310

Pro Ser Pro Arg Pro Gln Ser Gln Pro Pro His Ser Ser Pro Ser
    2315                2320                2325

Pro Arg Met Gln Pro Gln Pro Ser Pro His His Val Ser Pro Gln
    2330                2335                2340
```

```
Thr Ser  Ser Pro His Pro Gly  Leu Val Ala Ala Gln  Ala Asn Pro
    2345                 2350                 2355

Met Glu  Gln Gly His Phe Ala  Ser Pro Asp Gln Asn  Ser Met Leu
    2360                 2365                 2370

Ser Gln  Leu Ala Ser Asn Pro  Gly Met Ala Asn Leu  His Gly Ala
    2375                 2380                 2385

Ser Ala  Thr Asp Leu Gly Leu  Ser Thr Asp Asn Ser  Asp Leu Asn
    2390                 2395                 2400

Ser Asn  Leu Ser Gln Ser Thr  Leu Asp Ile His
    2405                 2410
```

<210> SEQ ID NO 9
<211> LENGTH: 777
<212> TYPE: PRT
<213> ORGANISM: Artificial Sequence
<220> FEATURE:
<223> OTHER INFORMATION: Synthetic polypeptide

<400> SEQUENCE: 9

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285
```

-continued

```
Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700
```

-continued

```
Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775
```